(12) United States Patent
Fedida et al.

(10) Patent No.: US 7,674,820 B2
(45) Date of Patent: Mar. 9, 2010

(54) ION CHANNEL MODULATING ACTIVITY I

(75) Inventors: David Fedida, Vancouver (CA); Gregory N Beatch, Vancouver (CA); Alan M Ezrin, Miami, FL (US); Peter M R Orth, Vancouver (CA); Christian Hesketh, Montreal (CA)

(73) Assignee: Cardiome Pharma Corp., Vancouver (CA)

( * ) Notice: Subject to any disclaimer, the term of this patent is extended or adjusted under 35 U.S.C. 154(b) by 1063 days.

(21) Appl. No.: 10/914,864

(22) Filed: Aug. 9, 2004

(65) Prior Publication Data

US 2005/0070552 A1 Mar. 31, 2005
US 2006/0135536 A9 Jun. 22, 2006

Related U.S. Application Data

(60) Provisional application No. 60/544,941, filed on Feb. 13, 2004, provisional application No. 60/516,486, filed on Oct. 31, 2003, provisional application No. 60/493,392, filed on Aug. 7, 2003.

(51) Int. Cl.
*A61K 31/40* (2006.01)
(52) U.S. Cl. .................................................. 514/424
(58) Field of Classification Search ................ 514/424
See application file for complete search history.

(56) References Cited

U.S. PATENT DOCUMENTS

| | | | |
|---|---|---|---|
| 2,954,380 A | 9/1960 | Shapiro et al. | |
| 3,218,328 A | 11/1965 | Shapiro et al. | |
| 4,145,435 A | 3/1979 | Szmuszkovicz | |
| 4,179,501 A | 12/1979 | Szmuszkovicz | |
| 4,598,087 A | 7/1986 | Horwell | |
| 4,656,182 A | 4/1987 | Horwell | |
| 4,663,343 A | 5/1987 | Horwell et al. | |
| 4,855,316 A | 8/1989 | Horwell et al. | |
| 4,880,800 A | 11/1989 | Wallis | |
| 4,906,655 A | 3/1990 | Horwell et al. | |
| 5,019,588 A | 5/1991 | Horwell et al. | |
| 5,051,428 A | 9/1991 | Horwell et al. | |
| 5,059,620 A | 10/1991 | Stout et al. | |
| 5,492,825 A | 2/1996 | Jan et al. | |
| 5,506,257 A | 4/1996 | MacLeod et al. | |
| 5,637,583 A | 6/1997 | MacLeod et al. | |
| 5,670,335 A | 9/1997 | Jan et al. | |
| 5,728,535 A | 3/1998 | Lester et al. | |
| 5,734,021 A | 3/1998 | Lester et al. | |
| 5,750,537 A | 5/1998 | Nomura et al. | |
| 5,817,698 A | 10/1998 | Brown et al. | |
| 5,885,984 A | 3/1999 | MacLeod et al. | |
| 6,174,879 B1 | 1/2001 | MacLeod et al. | |
| 6,180,632 B1 | 1/2001 | Myers et al. | |
| 6,210,809 B1 | 4/2001 | Okutomi et al. | |
| 6,214,809 B1 | 4/2001 | Fermini et al. | ................ 514/75 |
| 6,451,819 B2 | 9/2002 | Alanine et al. | ............... 514/326 |
| 6,521,619 B2 | 2/2003 | Link et al. | ............... 514/237.2 |
| 6,649,603 B2 | 11/2003 | Sum | ..................... 514/210.01 |
| 2005/0020481 A1 | 1/2005 | Bain et al. | ..................... 514/1 |
| 2005/0026993 A1 | 2/2005 | Beatch et al. | ............... 514/424 |

FOREIGN PATENT DOCUMENTS

| | | |
|---|---|---|
| CA | 1234808 | 4/1988 |
| CA | 1235122 | 4/1988 |
| CA | 2004575 | 6/1990 |
| CA | 2058502 | 6/1993 |
| CA | 2172513 | 3/1995 |
| CA | 2240728 | 9/1997 |
| CA | 2008391 | 12/1997 |
| CA | 2289055 | 1/1999 |
| CA | 2268590 A1 | 10/2000 |
| CA | 2132841 | 3/2001 |
| DE | 2 259 260 | 6/1974 |
| DE | 2 658 401 | 7/1978 |
| DE | 3 517 901 | 12/1985 |
| EP | 0147085 A2 | 7/1985 |
| EP | 0222533 A1 | 5/1987 |
| EP | 0147085 B1 | 3/1990 |
| EP | 0372466 A2 | 6/1990 |
| EP | 0380063 A1 | 8/1990 |
| EP | 0552386 A1 | 7/1993 |
| EP | 0720605 | 12/2001 |
| HU | 215963 B | 2/1995 |
| JP | 02-270864 | 11/1990 |

(Continued)

OTHER PUBLICATIONS

Byrn et al., Solid-State Chemistry of Drugs, Second Edition, 1999, pp. 233-247.*

(Continued)

*Primary Examiner*—Rebecca L Anderson
(74) *Attorney, Agent, or Firm*—Seed IP Law Group PLLC

(57) ABSTRACT

Methods, compositions, dosing regimes, and routes of administration for the treatment or prevention of arrhythmias. In these methods, early afterdepolarizations and prolongation of QT interval may be reduced or eliminated by administering ion channel modulating compounds to a subject in need thereof. The ion channel modulating compounds may be cycloalkylamine ether compounds, particularly cyclohexylamine ether compounds. Also described are compositions of ion channel modulating compounds and drugs which induce early afterdepolarizations, prolongation of QT interval and/or Torsades de Pointes.

8 Claims, 40 Drawing Sheets

FOREIGN PATENT DOCUMENTS

| | | |
|---|---|---|
| JP | 0380063 B1 | 7/1993 |
| WO | WO 93/19056 | 9/1993 |
| WO | WO 94/07843 | 4/1994 |
| WO | WO 94/14435 | 7/1994 |
| WO | WO 95/08544 | 3/1995 |
| WO | WO 95/28155 | 10/1995 |
| WO | WO 96/18615 | 6/1996 |
| WO | WO 96/23894 | 8/1996 |
| WO | WO 97/32857 | 9/1997 |
| WO | WO 97/49680 | 12/1997 |
| WO | WO 99/02159 | 1/1999 |
| WO | WO 99/03468 | 1/1999 |
| WO | WO 99/11252 | 3/1999 |
| WO | WO 99/16431 | 4/1999 |
| WO | WO 99/50205 | 10/1999 |
| WO | WO 99/50225 | 10/1999 |
| WO | WO 00/47547 | 8/2000 |
| WO | WO 00/51981 | 9/2000 |
| WO | WO 01/96335 | 12/2001 |
| WO | WO 03/105756 | 12/2003 |
| WO | WO 2004/008103 | 1/2004 |
| WO | WO 2004/098525 | 11/2004 |
| WO | WO 2004/099137 | 11/2004 |

OTHER PUBLICATIONS

Fenichel et al., J Cardiovasc Electrophysiol. Apr. 2004; 15(4): 475-495.*

Haverkamp et al., Cardiovascular Drugs and Therapy 16, 101-109, 2002.*

CPMP/986/96, Dec. 1997.*

Lellouche et al., Heart Rhythm 4(1); 1274-83, Oct. 2007.*

Abstract of DE 2 259 260, Derwent World Patents Index, Jun. 6, 1974.

Abstract of JP 02-270864, espacenet database, Nov. 5, 1990.

Adcock, J.J. et al., (2003) "RSD931, a novel anti-tussive agent acting on airway sensory nerves" Br J Pharm, 138:407-416.

Altria, Kevin D. et al., (2001) "Capillary Electrophoresis as a Routine Analytical Tool in Pharmaceutical Analysis" LCGC 19(9): 972-985.

Amin et al., (1996) "RPR 101821, A New Potent Cholesterol-lowering Agent: Inhibition of Squalene Synthase and 7-Dehydrocholesterol Reductase", Naunyn-Schmiedeberg's Arch Pharmacol 353:233-240.

Bain et al., (1997) "Better Antiarrhythmics? Development of Antiarrhythmic Drugs Selective for Ischaemia-Dependent Arrhythmias", Drug Development Research 42:198-210.

Barret, T. D. et al., (1996) "Glibenclamide Possesses Transient, Ischaemia Selective Class III Antiarrhythmic Actions But does not Prevent Ischaemic Arrhythmias" BPS Proceedings 116P.

Barrett, T. D. et al., (1997) "A model of myocardial ischemia for the simultaneous assessment of electrophysiological changes and arrhythmias in intact rabbits" J Pharmacol Toxicol Methods, 37:27-36.

Barrett, T.D. (2000) "Ischaemia selectivity confers efficacy for suppression of ischaemia-induced arrhythmias in rats" Eur J Pharm, 398:365-374.

Barrett, T.D. et al., (1996) "Atypical Dose Response curves for Antiarrhythmic Drugs" BPS Proceedings 115P.

Barrett, Terrance D. (1997) "Ischemia Selective Electrophysiological and antiarrhythmic actions of RSD1019 in ischemic cardiac tissue" J Mol Cell Cardiol, pp. 197.

Barrett, Terrance D. et al., (2000) "RSD 1019 suppresses ischaemia-induced monophasic action potential shortening and arrhythmias in anaesthetized rabbits" Br J Pharm, 131.405-414.

Beatch et al., (2002) "RSD1235 Selectively Prolongs Atrial Refractoriness and Terminates AF in Dogs with Electrically Remodeled Atria", Pharmacologist, 44(2) (Supplement I), A15: XIVth World Congress of Pharmacology: Meeting Abstracts.

Beatch, G. et al., "Effect of a Novel Anti-tussive Compound CP1 Against Citric Acid Induced Cough in Guinea-Pigs" Proc West Pharmacol Soc 20.

Beatch, G. et al., Electrophysiological Profile of RSD1235, A New Drug for Conversion of Atrial Fibrillation.

Beatch, G. N. et al., "RSD 1235, A Novel Atrial-Selective Antiarrhythmic Drug, Shows Rapid and Extensive Oral Absorption in Man" 12th International Congress on Cardiovascular Pharmacotherapy, May 7-10, 2003, Barcelona, Spain.

Beatch, G. N. et al., (2002) "Ventricular Fibrillation, and Uncontrolled Arrhythmia Seeking New Targets" Drug Develop Res 55: 45-52.

Beatch, G.N. et al., (1996) "Antihistamine-induced Ventricular Arrhythmias" BPS Proceedings 120P.

Beatch, G.N. et al., (1997) "Characterization of a Non-Human Primate Model of Drug-Induced Torsades De Pointes" Proc.West. Pharmacol. Soc., 40: 13-16.

Beatch, G.N. et al., (2002) "RSD1235 Selectively Prolongs Atrial Refractoriness and Terminates AF in Dogs with Electrically Remodeled Atria" PACE 24(Part II):698. Abstract 702.

Bian et al., (1998) "Effects of K-opioid receptor stimulation in the heart and the involvement of protein kinase C" Brit. J. Pharmacol. 124:600-606.

Billman, (2003) "RSD-1235 Cardiome", Current Opinion Investigational Drugs 4(3):352- 354.

Boiadjiev et al., (1996) "pH-Sensitive Exciton Chirality Chromophore..Solvatochromic Effects on Circular Dichroism Spectra", Tetrahedron: Asymmetry 7(10):2825-2832.

Bowen et al., (1992) "Characterization of the enantiomers of cis-n-[2-(3,4- Dichlorophenyl)Ethyl]-N-Methyl-2-(1-Pyrrolidinyl)Cyclohexylamine (BD737 and BD738): Novel Compounds with High Affinity, Selectivity and Biological Efficacy at Sigma Receptors" J. Pharmacol. Exp. Ther. 262(1):32-40.

Cardiome Drug Effective for Heart Patients. Press Release Sep. 3, 2002, 3 pages.

Cardiome Pharma Completes Phase I Safety Study. New Release Transmitted by CNN Newswire, Jul. 30, 2001. 2 pages.

Cardiome Pharma Corp. Healthcare (Underweight) Company Report Dec. 12, 2002. 26 pages.

Cardiome Reports Dosing of First Patient in Pivotal Phase II Study. Press Release Jan. 17, 2002. 3 pages.

Cardiome Reports Oral Absorption of RSD1235 in Humans. News Release via Canada Newswire (2002).3 pages.

Clohs, L. et al., (2002) "Validation of a capillary electrophoresis assay for assessing the metabolic stability of verapamil in human liver microsomes" J Cap Elec & Microchip Tech. 007: 113-117.

Clohs, Lilian "Capillary Electrophoresis And Its Applications In The Pharmaceutical Industry" Short Course: One Platform Fits Many Applications. CSC 2002 Short Course, 52 pages.

Clohs, Lilian "Capillary Electrophoresis as an Analytical Tool in the Drug Discovery Process" Presentation CE Symposium, Aug. 2000, 40 pages.

Clohs, Lilian "The Versatility of CE for Drug Pharmacokinetics and Metabolism Studies" Presentation CE Symposium, Aug. 2001, 46 pages.

Clohs, Lilian (2001) "Pharmacokinetics profiling of new drug candidates: a key process in drug discovery" 4(1): 6.

Clohs, Lilian et al., (2002) "CE Analysis of Propranolol in Human Serum Using Dynamic Capillary Coating" CE Currents: LCGC Europe, Reader Service 14, pp: 289-293.

Clohs, Lilian. "Bio-Analytical Applications of Capillary Electrophoresis In A Drug Discovery Setting" CSC Seminar Jun. 2002, 29 pages.

Clohs, Lilian. "CE and Drug Metabolism Studies: A Powerful Combination in Drug Discovery" CE Symposium Washington, DC, (Aug. 2002), 31 pages.

Crotti et al., (1998) "Synthesis and Ring-Opening Reactions of the Diastereoisomeric cis- and trans-Epoxides Derived from 3-(Benzyloxy)cyclopentene and 2-(Benzyloxy)-2,5-dyhydrofuran" Eur. J. Org. Chem. 8:1675-1686.

Crotti et al., "Regiochemical Control of the Ring-Opening of Epoxides by Means of Chelating Processes. Part 13. Synthesis and Ring-Opening Reactions of the Diastereoisomeric cis- and Transepoxides Derived From 3-(benzyloxy)cyclopentene and 2-(benzyloxy)-2, 5-dihydrofuran," Chemical Abstracts 129(17):662-663, abstract No. 216472k, Oct. 26, 1998.

De Costa, Brian R. (1990) "Synthesis and Evaluation of N-Substituted cis-N-Methyl-2-(1-pyrrolidinyl)cyclohexylamines as High Affinity σ Receptor Ligands. Identification of a New Class of Highly Potent and Selective σ Receptor Probes" J Med Chem, 33:3100-3110.

Doci, A. "Local Anesthetic Effects of Intradermal RSD921 In Healthy Subjects" Clin Pham & Therapeutics, 65(2): 177.

Duan, D. et al., (1993) "Potassium Channel Blocking Properties of Propafenone in Rabbit Atrial Myocytes[1]" J Pharm Exp Ther 264(3): 1113-1123.

Ezrin et al., (2002) "Safety and Pharmaccokinetics of RSD1235, a Novel Atrial Fibrillation Converting Drug, in Health Volunteers", Abstracts: 11th Int. Congress Cardiovasc. Pharmacother. 16 Abstract P297.

Ezrin, Alan M. et al., (2002) "A Dose-Ranging Study of RSD1235, A Novel Antiarrhythmic Agent, in Healthy Volunteers" Pharmacologist, 44(2) (Supplement I), A15: XIVth World Congress of Pharmacology: Meeting Abstracts.

Ezrin, Alan M. et al., (2002) "Safety and Pharmacokinetics of RSD1235, a Novel Atrial Fibrillation Converting Drug, in Healthy Volunteers" Poster Presented at Int. Soc. Of Cardiovascular Pharmacotherapy, Montreal, 2002.

Fedida, D. et al., (2002) "Kv1.5 is an Important Component of Repolarrizing $K^+$ Current in Canine Atrial Myocytes" Circulation Research Peer Review Plus Manuscript PDF, 38 pages.

Franciosi, Luigi G. et al., "Phase II Clinical Trial of RSD921 as a Local Anaesthetic in Patients Undergoing Venous Cannulation for Elective Treatment" 28th Annual ACCP Meet Abstract 32, pp. 977.

Franciosi, Sonia et al. (2001) "pH-dependent blocking actions of three novel antiarrhythmic compounds on $K^+$ and $Na^+$ currents in rat ventricular myocytes" Eur J Pharm, 425:95-107.

Franqueza, L. et al., (1998) "Effects of propafenone and 5-hydroxypropafenone on hKv1.5 channels" Br J Pharm 125:969-978.

Friess et al., (1961)"Central Activity Evoked in the Cat by Cis-Trans Isomers of 1,2-Aminocyclohexanol Dervivatives" Taxicol. Appl. Pharmacol. 3:638-653.

Grant, (1998) "Mechanisms of Atrial Fibrillation and Action of Drugs Used in its Management", Am J Cardiol 82:43N-49N.

Halfpenny, Paul R. (1990) "Highly Selective κ-Opioid Analgesics. 3. Synthesis and Structure-Activity Relationships of Novel N-[2-(1-Pyrrolidinyl)4- or -5-substituted-cyclohexyl]arylacetamide Derivatives" J Med Chem, 33:289-291.

Halfpenny, Paul R. et al., (1989) "Highly Selective κ-Opioid Analgesics. 2. Synthesis and Structure-Activity Relationships of Novel N-[(2-Aminocyclohexyl)aryl]acetamide Derivatives" J Med Chem, 32:1620-1626.

Hayes, E. S. et al., (1996) "RSD992 Enhances Erection and Copulation in Rats and Erection in Primates" Int J Impotence Res, pp. 189, (Abstract P24).

Hayes, ES. et al., (1997) "Actions of Arylpiperazines on Corpus Cavernosum Smooth Muscle In Vitro" Asia Pac J Pharmacol, 12:97-103.

Hayes, ES. et al., (1997) "Direct Actions of Arylpiperazines on Rabbit and Human Corpus Caversonal Smooth Muscle In Vitro" Asia Par J Pharmacol, Abstract S15.

Hesketh, J., et al., "Safety of RSD1235 in a rabbit purkinje fiber model", (XIVth World Congress of Phar.: Meeting Abstracts: 22.12.

Keefe, D. etal. (1981) "New Antiarrhythmic Drugs: Their Place in Therapy" Drugs 22:363-400.

Kertesz, R. et al., "The Electrophysiological and Antiarrhythmic Actions of RSD Analogs of U50,488H in Rats" Proc west Pharmacol Soc ab. 9 pages.

Lang, C. C. et al., (2000) "Clinical Evaluation of RSD921 as a Local Anaesthetic in Patients Undergoing Venous Connulation for Elective Treatment" Clin Pham & Therapeutics, pp. 142.

Lewis et al., (1995) "Enzyme inhibition during the conversion of squalene to cholesterol", Steroids 60:475-483.

Li, GR. et al., (1996) "Adrenergic Modulation of Ultrarapid Delayed Rectifier $K^+$ current in Human Atrial Myocytes" Circ. Res.78:903-915.

Malayev, A. A. et al., (1995) "Mechanism of Clofilium Block of the Human Kv1.5 Delayed Rectifier Potassium Channel" Mol Pharm 47:198-205.

Martens et al., (1989) "Einfache Synthese neuer anellierter Pyrrole", J. Synth. Org. Chem. 12:965-967.

Matyus et al., (1997) "Antiarrhythmic Agents: Current Status and Perspective", Medicinal Research Reviews 17(5):427-451.

McLarnon, J. et al., (1996) "Mixed Block of K and Na Currents by KC8851, A Structural of Tedisamil in Vitro and in Vivo Studies" BPS Proceedings 114P.

Moorman et al., (1986) "$pK_a$ Does Not Predict pH Potentiation of Sodium Channel Blockade by Lidocaine and W6211 in Guinea Pig Ventricular Myocardium[1]", The Journal of Pharmacology and Experimental Therapeutics 238(1):159-166.

Morisawa et al., "Preparation of Flourocarbocyclic Nucleosides as Antitumor Agents," *Chemical Abstracts 115*(5):904-905, abstract No. 50215n, Aug. 5, 1991.

Nakahsima, H. et al., (2002) "Angiotensin II Type I Receptor Antagonist Prevents the Promotion of Atrial Fibrillation" PACE 24(Part II):698. Abstract 701.

Nattel et al., (1998) "Effects of the novel antiarrhythmic agent azimilide on experimental atrial fibrillation and atrial electrophysiologic properties", Cardiovascular Research 37:627-635.

Nattel et al., (2001) "P2362: RSD1235: a novel antiarrhythmic agent with a unique electrophysiological profile that terminates AF in dogs", Eur. Heart J 22(Suppl):448 (Abstract P2362).

Nattel, (1998) "Experimental evidence for proarrhythmic mechanisms of antiarrhythmic drugs", Cardiovascular Research 37:567-577.

Nattel, S. et al, "The role of channel opening in transient outward current block by quinidine, flecainide, and 4-aminopyridine in human atrial myocytes," Abstract No. Tu-Pos403, p. A209.

Nishi et al., (1985) "Studies on 2-0xoquinoline Derivatives as Blood Platelet Aggregation Inhibitors. IV." Synthesis and Biological Activity of the Metabolites of 6-[4-(1-Cyclohexyl-1 H-5-tetrazolyl)butoxy]-2-oxo-1,2,3,4-tetrahydroquinoline (OPC-13013), Chem. Pharm. Bull 33(3):1140-1147.

Nortran Arrhythmia Drug Demonstrates Oral Bioavailability. New Release Transmitted by CNN Newswire, Jun. 21, 2001. 2 pages.

Orth et al., "Cyclopentane-1-amines," *Chemical Abstracts 89*(15):555, abstract No. 129113f, Oct. 9, 1978.

Orth, Peter et al., "The Novel AF Conversion Agent RSD1235 Preferentially Blocks a Late Component of the Human Heart (h1) $Na^+$ Current Active During Repolarization" EP abstracts Oct. 2003.

Plouvier, B., Synthesis and Structure Activity Relationships of a Series of 2-Aminocyclohexyl ...as Potential Ischaemia Selective Ventricular Antiarrhythmics BMPS 994.

Pugsley and Goldin (1999) "Molecular analysis of the $Na^+$ channel blocking actions of the novel class I antiarrhytic" Br J Pharm, 127:9-18.

Pugsley, M.K. et al., "A Characterization of the Antiarrhythmic and Electrophysiological Properties od RSD992, A Novel Arylpiperazine Drug" (XIVth World Congress of Pharmacology: Meeting Abstract 22.8).

Pugsley, M.K. et al., "Electropharmacology of two new class 1 agents" Heart and Stroke Annual.

Pugsley, M.K. et al., (1998) "Sodium Channel-Blocking Properties of Spiradoline, a K Receptor Agonist, are Responsible for Its Antiarrhythmic Action in the Rat" J Cardiovas Pharmacol, 32:863-974.

Pugsley, M.K. et al., (1999) "Are the arrhythmias due to myocardial ischaemia and infarction dependent upon the sympathetic system?" Cardiol Res, 43:830-831.

Ribeiro, W. et al., (2001) "Determination of RSD921 in human plasma by high-performance liquid chromatography-tandem mass spectrometry using tri-deuterated RSD921 as internal standard: application to a phase I clinical trial" J Mass Spectrom, 36:1133-1139.

Rich, T. C. et al. "Quinidine Block of the Human Cardiac hKv1.5 Channel in Inside-Out Patches" Abstract No. TU-Pos404.

Roden et al., (1996) "The Cardiac Ion Channels: Relevance to Management of Arrhythmias", Annu. Rev. Med. 47:135-148.

Roy, D. et al., (2003) "RSD1235 Rapidly and Effectively Terminates Atrial Fibrillation" Eur Heart J.

Rynbrandt, Ronald H, et al., (1971) "Cis-1-[2-(p-Anisidinomethyl)cyclohexyl]piperidine and Related Compounds Oral Hypoglycemic Agents" J Med Chem, 14(10): 985-987.

Sanguinetti M. C. (1992) "Modulation of Potassium Channels by Antiarrhythmic and Antihypertensive Drugs" Hypertension 19(3):228-236.

Singh, (1998) "Antiarrhythmic Drugs: A Reorientation in Light of Recent Developments in the Control of Disorders of Rhythm", Am J Cardiol 81(6A):3D-13D.

Singh, (2003) "Atrial Fibrillation: Epidemiologic Considerations and Rationale for Conversion and Maintenance of Sinus Rhythm", J. Cardiovasc. Pharmacol. Ther. 8(Suppl 1):S13-S26.

Snyders, D. J. et al., (1993) "A Rapidly Activating and Slowly Inactivating Potassium Channel Cloned from Human Heart" J. Gen. Physiol. 101:513-542.

Snyders, D. J. et al., (1995) "Determinants of Antiarrhythmic Drug Action Electrostatic and Hydrophobic Components of Block of the Human Cardiac hKv1.5 Channel" Circ. Res. 77 (3):575-583.

Srilatha, B. et al., (1997) "Alterations in Rabbit Corpus Cavernosal Pharmacology by High Cholesterol Diet" Asia Par J Pharmacol, Abstract S15.

Steinbeck, G. (1992) "Proarrhythmische Wirkungen von Antiarrhythmika-theoretische undKlinische Aspekte" Z Kardiol. 81: Suppl. 4,139-143.

Tong, V. et al., (2001) "Determination of an arylether antiarrhythmic and its N-dealkyl metabolite in rat plasma and hepatic microsomal incubates using liquid chromatography-tandem mass spectrometry" J Chromatog B., 759:256-266.

Valenzuela, C. et al. (1997) "Comparative effects of nonsedating histamine $H_1$ receptor antagonists, ebastine and terfenadine, on human Kv1.5 channels" Eur J Pharm 326:257-263.

Valenzuela, C. et al., (1997) "Effects of Ropivacaine on a Potassium Channel (hKv1.5) Cloned from Human Ventricle" Anesthesiology 86:718-728.

Walker, J. A. (2002) "Antiarrhythmic Drug Development—Illusion and Disillusion" Drug Develop Res 55:1-2.

Walker, M. L. et al., (1996) "Determination of an arylacetamide antiarrhythmic in rat blood and tissues using reversed-phase high-performance liquid chromatography" J Chromatog B., 675:257-263.

Walker, M.L. et al., (1996) "Increased Electrophsiological Activity in Raised K and low pH Improves Antiarrhythmic efficacy for a group of morpholinocyclohexyl Derivatives" BPS Proceedings 118P.

Walker, Michael J.A. and Guppy, Leon J. "Targeting Ischemic Ventricular Arrhythmias" Cardiac Drug Development, pp. 175-201.

Wang, Z. et al., (1995) "Effects of Flecainide, Quinidine, and 4-Aminopyridine on Transient Outward and Ultrarapid Delayed Rectifier Currents in Human Atrial Myocytes[1]" J Pharm Exp Ther.,272(1):184-196.

Wang. Z. et al., (1993) "Sustained Depolarization-Induced Outward Current in Human Atrial Myocytes" Circ. Res. 73:1061-1076.

Wat, J.Y.K. et al., "Effects of Arylbenzacetamides on Neuromuscular Preparation" Proc West Pharmacol Soc 19.

Wolf, et al. (1998) "Impact of Atrial Fibrillation on Mortality Stroke, and Medical Costs" Arch Intern Med 158: 229-234.

Wong, Judy et al., "Protein Binding Study of AA5, a New Antiarrhythmic Drug" Poster Conference August.

Wong, J. et al., "Capillary Electrophoresis Assay to Assess In Vitro Metabolic Stability of Novel Compounds in Human Liver Microsomes".

Yeola, S. W. et al., (1996) "Molecular Analysis of a Binding Site for Quinidine in a Human Cardiac Delayed Rectifier K+ Channel" Circ. Res. 78(6): 1105-1114.

Yong et al., (1997) "Low pKa Predicts Antiarrhythmic Efficacy in a Series of Aminocyclohexyl Esters" J. Mol. and Cell Cardiol. 29(6):A169.

Yong et al., (1999) "RSD 1000: A novel antiarrhythmic agent with increased potency under acidic and high-potassium conditions" J. Pharm. Exp. Ther. 289(1):236-244.

Yong, S.L. et al., (1996) "RSD1000: A Novel Antiarrhythmic Agent with an Improved Therapeutic Index" BPS Proceedings 119P.

Yong, S.L. et al., (1996) "SAR Evidence that Antiarrhythmic Activity is Unrelated to Opioid Kappa Agonist Activity" BPS Proceedings 117P.

Zhang et al., (1997)" Inhibition of [$^3$H]-U69593 binding and the cardiac effects of U50, 488H by calcium channel blockers in the rat heart" Brit. J. Pharmacol. 120:827-832.

Zolotoy, Alexander B. et al., (2003) "Physicochemical Determinants for Drug Induced Blockade of HERG Potassium Channels: Effect of Charge and Charge Shielding" Curr Med Chem 1(3): 1-17.

\* cited by examiner

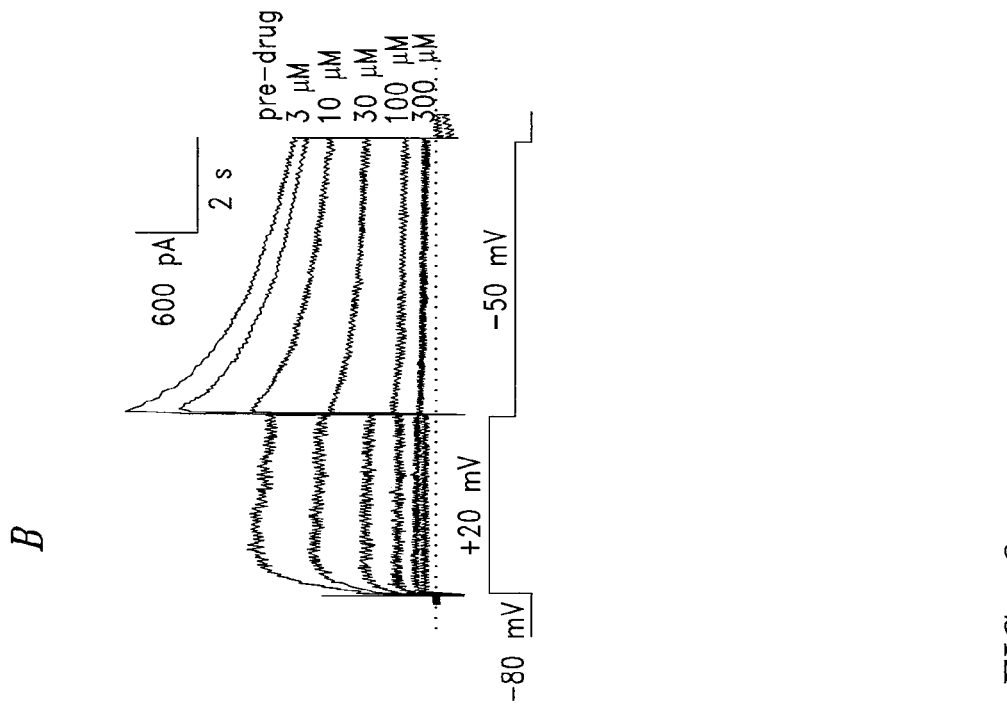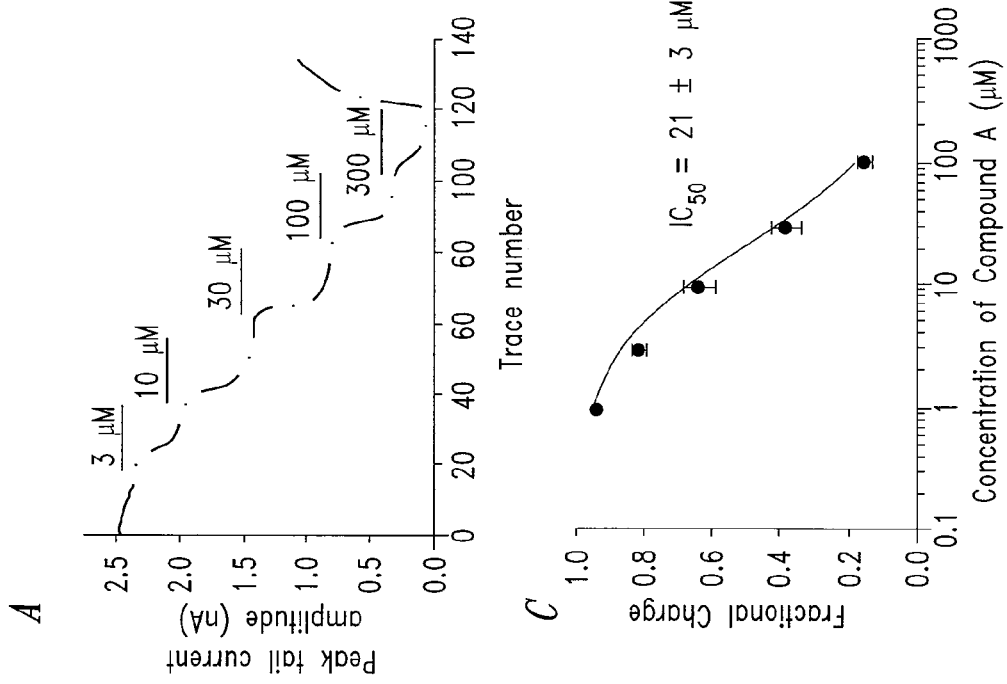
FIG. 6

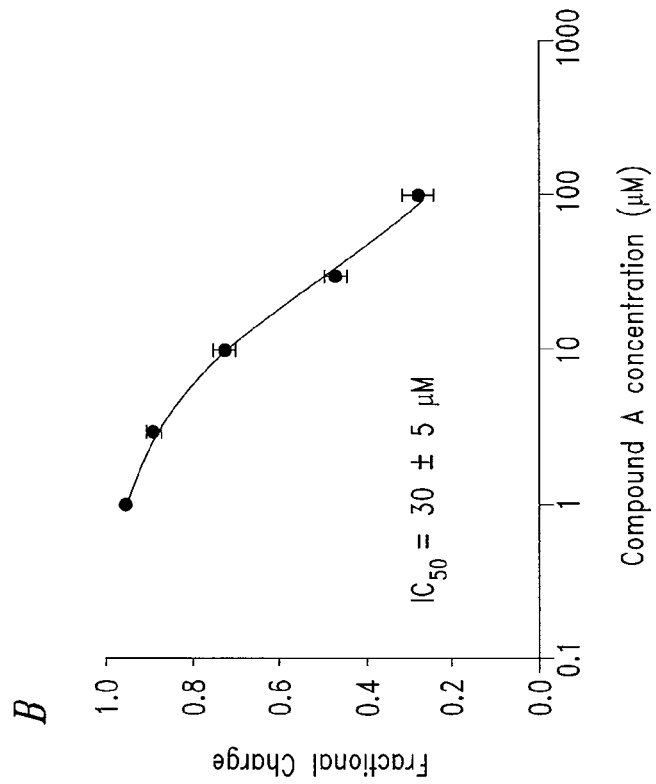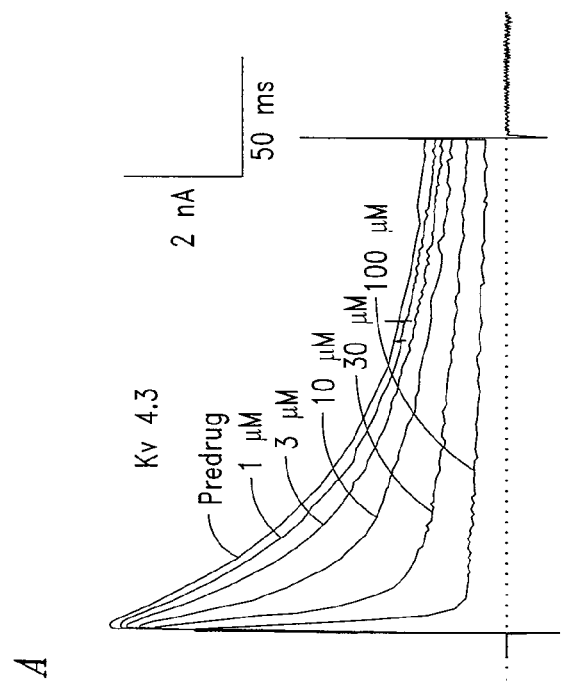
FIG. 7

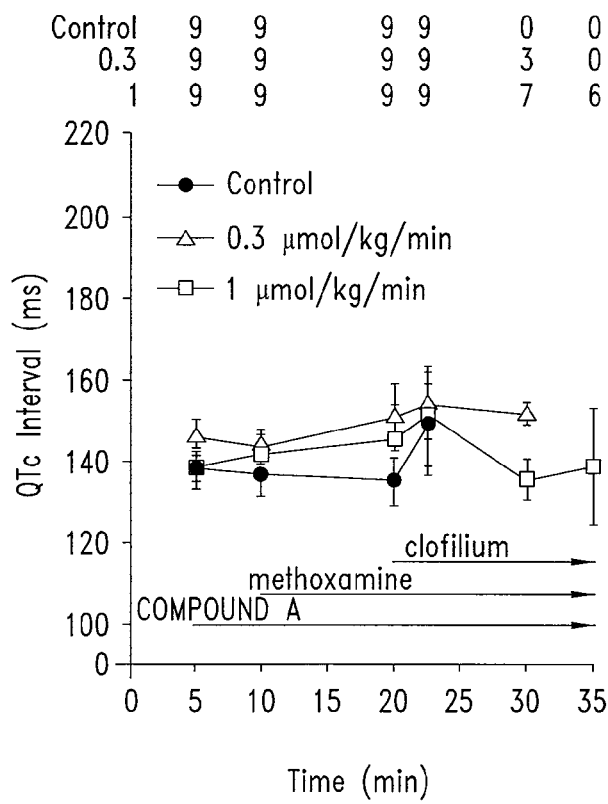
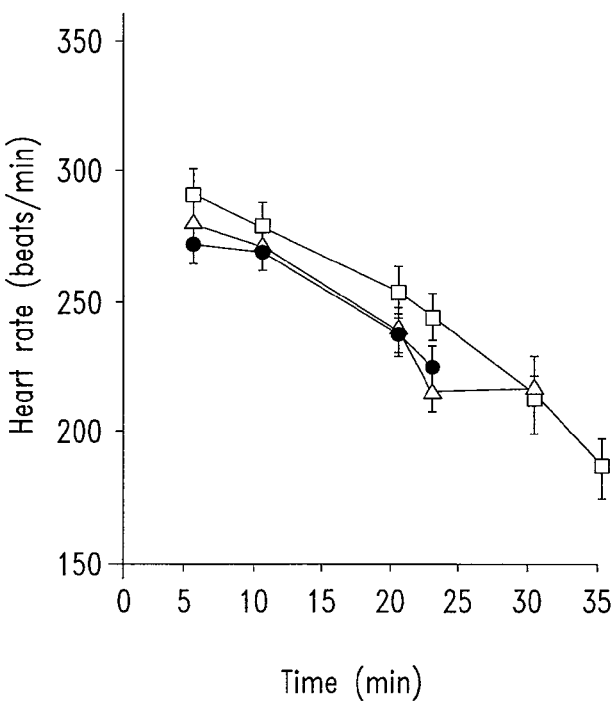
FIG. 31

Mechanism of Action

Persistent AF: goat model

AFCL increased and AF terminated in all (ventricular response rate also slowed)

| Goat | Duration AF (weeks) | Time to AF Conv (min) | AFGL start | AFGL end | Ventric CL start | Ventric CL end | QT start | QT end | QRS (%) |
|---|---|---|---|---|---|---|---|---|---|
| 9987 | 3 | 86 | 103 | 150 | 260 | 428 | 131 | 177 | 31 |
| Fancy | 16 | 73 | 112 | 158 | 290 | 438 | 190 | 181 | 10 |
| GG | 16 | 58 | 106 | 163 | 300 | 605 | 170 | 197 | 16 |
| 1856 | 3 | 44 | 108 | 140 | 314 | 530 | 156 | 180 | 8 |
| 2333 | 2 | 45 | 110 | 161 | 360 | 500 | 156 | 183 | 8 |
| 98182 | 4 | 66 | 103 | 162 | 350 | 730 | 180 | 220 | 13 |
| Mean ±SD | 7±6 | 62±6 | 105±4 | 156±10 | 304±28 | 525±96 | 163±19 | 189±16 | 15±10 |

Note:

| QTc start | QTc end |
|---|---|
| 294±36 | 260±10 |

*FIG. 39*

ION CHANNEL MODULATING ACTIVITY I

RELATED PATENTS AND PATENT APPLICATIONS

This patent application claims the priority benefit of U.S. provisional patent application 60/493,392 (filed Aug. 7, 2003), 60/544,941 (filed Feb. 13, 2004), 60/516,486 (filed Oct. 31, 2003), which are hereby incorporated by reference in their entirety.

TECHNICAL FIELD

The compounds and methods described in this patent application are ion channel modulating compounds and their uses, and include but are not limited to ion channel modulating compounds and their uses as antiarrhythmics, particularly for the treatment or prevention of atrial fibrillation, atrial flutter, Torsades de Pointes, acquired long QT-Syndrome, multifocal ventricular arrhythmias, and supraventricular arrhythmias.

BACKGROUND

Cardiac arrhythmias often occur as complications to cardiac diseases such as myocardial infarction and heart failure. In serious cases, arrhythmias can cause sudden death. Treatment of arrhythmias is complex and aspects of care, especially the decision to control the ventricular rate vs. convert the arrhythmia, remain controversial.

Class III antiarrhythmics ($I_{Kr}$ blockers) are commonly used to treat arrhythmia; however these drugs have also been shown to be proarrhythmic and cause greater lengthening in Purkinje fiber action potentials relative to those in ventricular muscle, presumably due to a greater contribution of $I_{Kr}$ in repolarization of Purkinje fibers. For example, dofetilide (10 nM) has been shown to increase the APD90 (the action potential duration at 90% repolarization) of rabbit Purkinje fibers by 83%, (basic cycle lengths, or BCL=1000 ms). Similarly, quinidine (10 µM) increased APD90 by 93% in the rabbit. In addition to drug induced dispersion of repolarization, drug induced early after depolarizations (EADs) are thought to be an important cause of Torsades de Pointes (TdP) both clinically and in animal models.

Class III agents have been shown to be proarrhythmic due to blockade of the hERG potassium channel ($I_{Kr}$ current in human ventricle). hERG channels refer to the product of expression of the human ether-a-go-go related gene, normally considered to be a potassium-conducting ion channel. It has been shown that combination therapy with quinidine (class III agent) and mexiletine (class I agent and sodium channel blocker) is more effective in the prevention of ventricular tachycardia (VT) and ventricular fibrillation (VF) in animal models and in humans. In isolated hearts, these effects have been shown to be due to sodium channel blockade. EAD generation is thought to be a major cause of TdP in humans. In addition, EADs have been shown to contribute to reinduction of atrial fibrillation (AF) following termination in isolated coronary-perfused canine right atria. Sodium channel blockers have been shown to prevent isoproterenol-induced TdP in a canine model and also abbreviate action potential duration in M-cells of the ventricular myocardium.

High densities of voltage-gated sodium channels in excitable tissues lead to a rapid membrane depolarization when excitable cells reach the threshold for sodium channel activation. The role of sodium channels in the action potential upstroke (Phase 0) has been well-characterized and block of sodium channels can affect cellular refractoriness and regulate heart rhythms. Sodium channels rapidly inactivate following initial opening during Phase 0 and during repolarization. Recovery of these inactivated channels is critical in determining the ability of a cell to generate another action potential. The period during which the cell cannot generate another action potential is known as the effective refractory period (ERP). Blockade of sodium channels can lengthen the refractory period of the cell and this activity is known to have antiarrhythmic consequences due to prolongation of the effective wavelength of the tissue, reducing the size of reentrant wavelets which the tissue can support. Blockade of sodium channels can also suppress ectopic beats which may also play a role in the genesis of fibrillatory activity in the heart. Indeed, the selective sodium channel blocker tetrodotoxin (TTX) has been shown to prevent VF in isolated rabbit hearts. Recent evidence has shown that sodium channel activity contributes not only to the action potential upstroke, but also can affect the action potential plateau (Phase 2) and repolarization (Phase 3). This sustained activity is thought to be a result of 3 separate mechanisms. The first of such mechanisms has been described as channel bursting in which the channel fails to inactivate. A second component is known as window current and occurs at potentials at which the steady-state activation and inactivation curves overlap. The third mechanism is a non-equilibrium phenomenon in which the sodium channels recover from inactivation during the repolarization phase. The sustained inward sodium current contributed by these three mechanisms can modulate repolarization during Phase 2 and Phase 3 of the action potential when the membrane potential is regulated by small amounts of both inward and outward current. Modulation of currents contributing to Phase 0, 2 and 3 of the action potential can have important roles in regulating refractoriness, action potential duration and EAD generation.

The ion channel modulating compounds described herein are atrially-selective, and block sodium channels in a frequency (or stimulation) dependent manner. Further, these ion channel modulating compounds are capable of blocking the late, early and sustained components of a sodium channel current to prevent EADs without substantially interfering with cardiac activity.

SUMMARY

Described in this patent are compositions, methods, formulations and dosage regimes for the treatment, prevention, and/or termination of arrhythmias. In particular, this patent described compositions, methods, formulations and dosage regimens for the treatment, prevention and/or termination of EADs such as EADs caused by drugs that prolong QT interval and/or trigger TdP. Compositions and methods are provided in which the proarrhythmic effects (e.g., prolonging QT interval) of a drug (such as a Class III antiarrhythmic) may be reduced or eliminated by administering an ion channel modulating compound as described herein.

Various subjects to which the ion channel compound or compounds may be administered are described in detail in the Detailed Description section. In one version of the methods, the subject is a human subject.

Various formulations, routes of administration, and dosing regimes that may be used are described in detail in the Detailed Description section. In one version of the methods, the formulation is an intravenous formulation. In one version of the methods, the formulation is an oral formulation. The formulations may include one or more ion channel modulating compounds together with other optional components. The formulations may be administered in a variety of dosing regimes, including administering one or more formulations that may or may not be administered via the same route of administration. The formulations may also be delivered by repeat dosing and by substantially continuous dosing.

Compositions of an ion channel modulating compound and a compound which prolongs QT interval are described herein.

In one version, the ion channel modulating compound is a compound that blocks an early component of a cardiac sodium channel current; wherein the ion channel modulating compound further blocks the early component of a cardiac sodium channel current approximately as much as or more than it blocks a sustained component of a cardiac sodium channel current. In some versions, the ion channel modulating compound blocks a late component of a cardiac sodium channel approximately 20% more than it blocks the early component of a cardiac sodium channel current. In one version, the ion channel modulating compound is a compound of the formula:

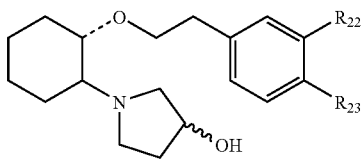

or a solvate or pharmaceutically acceptable salt thereof, wherein $R_{22}$ and $R_{23}$ are independently hydrogen, hydroxy or $C_1$-$C_6$alkoxy. In one version, the ion channel modulating compound is a monohydrochloride salt of the formula:

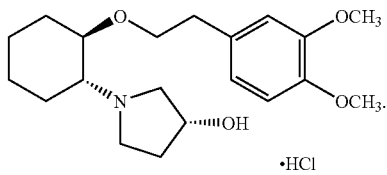

In one version, the ion channel modulating compound is a cycloalkylamine ether compound of formula

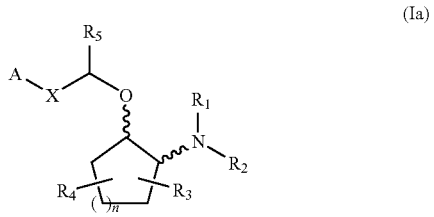

(Ia)

where n=1,2,3, or 4 and the other substituents are as defined in the Detailed Description section.

For all ion channel modulating compounds described above and elsewhere in this patent, isolated enantiomeric, diastereomeric and geometric isomers of the compounds may be used and mixtures of the compounds may be used. In addition, solvates or pharmaceutically acceptable salts of the compounds may be used.

In some versions, the compound that prolongs QT interval is an antiarrhythmic, such as a class III antiarrhythmic drug.

Examples of class III antiarrhythmic drugs include: amiodarone, sotalol, ibutilide, azimilide, clofilium, dofetilide, sematilide, d,l-sotalol, quinidine, tedisamil, procainamide, disopyramide, and dronedarone. Other compounds which prolong QT intervals are antibiotics, bronchodilators, anesthetics, anti-nausea drugs, anti-malarials, antipsychotics, appetite suppressants, decongestants, vasodilators, anti-fungals, anti-cancer drugs, antihistamines, gastrointestinal prokinetics, antispasmodics, or antidepressants. Examples of specific drugs that prolong QT interval are: albuterol, alfuzosin, amantadine, amiodarone, amitriptyline, amoxapine, ampicillin, amphetamine/dextroamphetamine, arsenic trioxide, atomoxetine, azithromycin, bepridil, chloral hydrate, chloroquine, chlorpromazine, ciprofloxacin, cisapride, clarithromycin, clomipramine, cocaine, desipramine, disopyramide, dobutamine, dofetilide, dolasetron, domperidone, dopamine, doxepin, droperidol, ephedrine, epinephrine, erythromycin, felbamate, fenfluramine, flecainide, fluconazole, fluoxetine, foscarnet, fosphenytoin, galantamine, gatifloxacin, granisetron, halofantrine, haloperidol, ibutilide, imipramine, indapamide, isoproterenol, isradipine, itraconazole, ketoconazole, levalbuterol, levofloxacin, levomethadyl, lithium, mesoridazine, metaproterenol, methadone, methylphenidate, mexiletine, midodrine, moexipril/HCTZ, moxifloxacin, nicardipine, norepinephrine, nortriptyline, octreotide, ondansetron, paroxetine, pentamidine, phentermine, phenylephrine, phenylpropanolamine, pimozide, procainamide, protriptyline, pseudoephedrine, quetiapine, quinidine, risperidone, ritodrine, salmeterol, sertraline, sibutramine, sotalol, sparfloxacin, tacrolimus, tamoxifen, telithromycin, terbutaline, thioridazine, tizanidine, trimethoprim-sulfa, trimipramine, vardenafil, venlafaxine, voriconazole, and ziprasidone. This list is not intended to be exhaustive, and other drugs which prolong QT interval are intended to be included (see, for example, Appendix I).

Methods of using compositions of ion channel modulating compounds and compounds which prolong QT interval are also described. For example, a method of treating an arrhythmia includes administering a therapeutically effective amount of a composition of an ion channel modulating compound and a compound which prolongs QT interval to a patient in need thereof.

Also described herein are compositions of ion channel modulating compounds and compounds which induce TdP. Compounds which induce TdP include antiarrhythmics such as Class III antiarrhythics. Examples of class III antiarrhythmic drugs include: amiodarone, sotalol, ibutilide, azimilide, clofilium, dofetilide, sematilide, and d,1-sotalol. Other compounds which induce TdP are antibiotics, bronchodilators, anesthetics, anti-nausea drugs, anti-malarials, antipsychotics, appetite suppressants, decongestants, vasodilaltors, anti-fungals, anti-cancer drugs, and antidepressants. Examples of specific drugs that induce TdP are: albuterol, alfuzosin, amantadine, amiodarone, amitriptyline, amoxapine, ampicillin, arsenic, atomoxetine, azithromycin, bepridil, chloral, chloroquine, chlorpromazine, ciprofloxacin, cisapride, clarithromycin, clomipramine, cocaine, disopyramide, dobutamine, dofetilide, dolasetron, domperidone, dopamine, doxepin, droperidol, ephedrine, epinephrine, erythromycin, felbamate, fenfluramine, flecainide, fluconazole, fluoxetine, foscarnet, fosphenytoin, galantamine, aatifloxacin, granisetron, halofantrine, haloperidol, ibutilide, imipramine, indapamide, isoproterenol, isradipine, itraconazole, ketoconazole, levalbuterol, levomethadyl, lithium, mesoridazine, metaproterenol, methadone, methylphenidate, midodrine, moexipril/HCTZ, moxifloxacin, nicardipine, norepinephrine, nortriptyline, octreotide, ondansetron, paroxetine, pentamidine, phentermine, phenylephrine, phenylpropanolamine, pimozide, procainamide, pseudoephedrine, quetiapine, quinidine, salmeterol, sibutramine, sotalol, tamoxifen, terbutaline, thioridazine, trimethoprim-sulfa, trimipramine, and vardenafil. This list is not intended to be exhaustive, and other drugs which induce TdP are intended to be included (see, for example, Appendix I).

Methods of using compositions of ion channel modulating compounds and compounds which induce TdP are also described. For example, a method of treating an arrhythmia includes administering a therapeutically effective amount of a composition of an ion channel modulating compound and a compound which induces TdP to a patient in need thereof.

Also described herein are methods of reducing and/or eliminating the prolongation of QT interval in a subject given a therapeutically effective amount of a drug capable of prolonging QT interval by administering to the subject a therapeutically effective amount of an ion channel modulating compound. The ion channel modulating compound may be administered before, concurrently with, or after the drug that is capable of prolonging the QT interval.

In some versions, the therapeutically effective amount of an ion channel modulating compound is an amount sufficient to block a late component of a cardiac sodium channel current approximately as much as or more than it blocks an early component of a cardiac sodium channel current, and blocks the early component of a cardiac sodium channel current approximately as much as or more than it blocks a sustained component of a cardiac sodium channel current. In some versions, the therapeutically effective amount of an ion channel modulating compound is sufficient to block a late component of a cardiac sodium channel approximately 20% more than it blocks the early component of a cardiac sodium channel current.

Also described herein are methods of reducing and/or eliminating chemically-induced TdP in a subject given a therapeutically effective amount of a drug capable of inducing TdP by administering to the subject a therapeutically effective amount of an ion channel modulating compound. The ion channel modulating compound may be administered before, concurrently with or after the drug that is capable of prolonging the QT interval.

Also described herein are methods of treating and/or preventing TdP comprising administering to a subject in need thereof an ion channel modulating compound as described herein.

Also described herein are methods of terminating and/or preventing EADs comprising administering to a subject in need thereof an ion channel modulating compound as described herein. In one version, the EADs are chemically induced. In one version, the EADs are induced by a genetic mutation in the subject, such as the genetic mutations in long-QT syndrome or Jervell and Lang-Nielson syndrome.

Other aspects of the methods, compounds and compositions provided in this patent are described in detail in the Detailed Descriptioin section.

BRIEF DESCRIPTION OF THE DRAWINGS

FIG. 6 shows a concentration-dependent inhibition of hERG channels.

FIG. 7 shows a concentration-dependent inhibition of Kv4.3 channels at 1 Hz.

FIG. 31 shows an example of the changes in QTc (corrected QT) interval and heart rate in control and COMPOUND A pre-treated animals in the chemically-induced TdP model described in FIG. 28.

FIG. 39 shows in tabular form that an ion channel modulating compound terminates AF and increases atrial fibrillation cycle length (AFCL) in goats.

DETAILED DESCRIPTION

Figure 1:
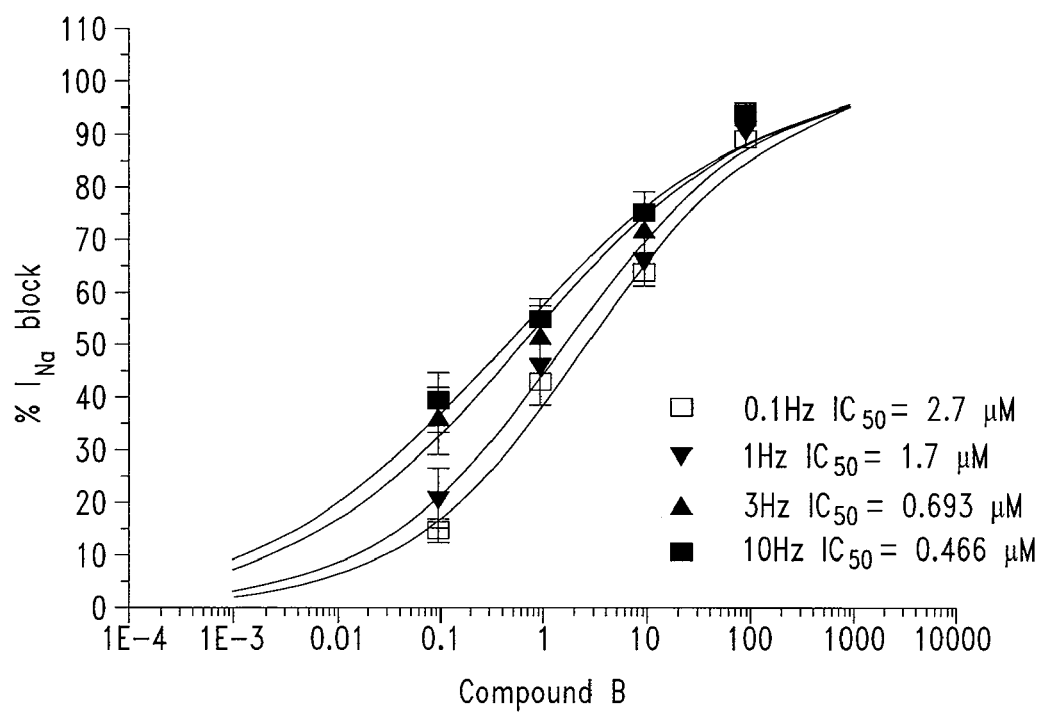
FIG. 1 illustrates rate- and concentration-dependent inhibition of sodium current ($I_{Na}$) in human atrial myocytes by COMPOUND B.

Described in this patent application are ion channel modulating compounds that may be used for treating and/or preventing a variety of diseases and conditions, including but not limited to treating, and/or preventing recurrence of atrial fibrillation or atrial flutter. The effects of ion channel modulating compounds on certain ion channel characteristics and other physiological characteristics are also described. The effect of ion channel modulating compounds to enhance, modify, suppress or eliminate the effects of other drugs (e.g., Class III antiarrhythmics) is also described.

Definitions

As used in this patent application, a "subject" may generally be any human or non-human animal that would benefit from the methods described in this application. In one version of the methods, a subject is a human subject. In some versions of the methods, a subject is a mammal. In some versions, the subject is any domestic animal, including, but not limited to dogs, and cats. In some versions, the subject is any livestock animal, including but not limited to horses, pigs, and cattle. In some versions, the subject is any zoo animal, including but not limited to Bengal tigers.

As used in this patent application, unless the context makes clear otherwise, "treatment," and similar word such as "treated," "treating" etc., is an approach for obtaining beneficial or desired results, including and preferably clinical results. Treatment can involve optionally either the amelioration of symptoms of the disease or condition, or the delaying of the progression of the disease or condition.

As used in this patent application, unless the context makes clear otherwise, "prevention," and similar word such as "prevented," "preventing" etc., is an approach for preventing the onset of a disease or condition or preventing the occurrence of the symptoms of a disease or condition, or optionally an approach for delaying the onset of a disease or condition or delaying the occurrence of the symptoms of a disease or condition. As used herein, "prevention" and similar words also includes reducing the intensity, effect, symptoms and/or burden of a disease or condition prior to onset of the disease or condition.

As used in this patent application, an "effective amount" or a "therapeutically effective amount" of a substance is that amount sufficient to affect a desired biological effect, such as beneficial results, including clinical results.

As used in this patent application, unless the context makes clear otherwise, "inhibition" and similar words such as "inhibit" of any ion channel means any decrease in current through that channel. When "inhibition" is used in the context of a specified concentration, it is determined by the $IC_{50}$. For example, an ion channel modulating compound which inhibits an ion channel at a concentration of 1 µM, the ion channel may be said to have an $IC_{50}$ of 1 µM for that ion channel modulating compound. This example is for illustrative purposes only and is in no way intended to be limiting.

As used in this patent application, unless the context makes clear otherwise, "$IC_{50}$" or "$IC_{50}$ concentration" means a drug concentration at which the specified current amplitude (peak or steady-state, or integrated current) is inhibited by 50%.

As used in this patent application, unless the context makes clear otherwise, "blocking" or "block" of an ion channel means any block or inhibition of current through that ion channel.

As used in this patent application, unless the context makes clear otherwise, "recovery time constant of inhibition" refers to a time constant at which recovery of current amplitude occurs, presumed to reflect dissociation of a drug from its binding site, as for example, a sodium channel when the stimulus rate is decreased from 10 Hz to 1 Hz.

As used in this patent application, "equivalently inhibits" and "equivalently inhibited" means equally inhibits or equally inhibited. In one version, equivalently inhibits means that there is no statistically significant difference in inhibition of currents due to application of an ion channel modulating compound. For example, the early and sustained sodium currents are equivalently inhibited if there is no statistically significant difference in the effect of an ion channel modulating compound on early and sustained sodium currents.

As used in this patent application, "rapidly associated and dissociated" means that a compound has blocking and unblocking kinetics of the 'fast-on, fast-off' form such as the 'fast-on, fast-off' kinetics defined by Carmeliet and Mubagwa (Prog. Biophys. Molec. Biol. 70, 1-72, 1998). For example, an ion channel modulating compound rapidly associates and dissociates from sodium channels where the ion channel modulating compound has 'fast-on, fast-off' kinetics as defined by Carmeliet and Mubagwa.

As used in this patent application, "rate-independent and use-independent" inhibition means inhibition that is predominantly heart rate and/or stimulus rate and use-independent such that there is no statistically significant effect of steady-state or transient changes in heart rate or stimulus rate with respect to the inhibition. For example, an ion channel modulating compound that inhibits Kv1 channels in a "rate-independent and use-independent" manner means that there is no influence of the heart rate or stimulus rate on the amount of inhibition produced by the ion channel modulating compound on Kv1 channels.

As used in this patent application, "affects atrial repolarizing currents" means "has a statistically significant effect on atrial repolarizing current amplitudes."

As used in this patent application, "prolongs atrial refractoriness" means "has a statistically significant prolonging effect on atrial refractoriness."

As used in this patent application, "has substantially no effect on ventricular tissue" means "has no statistically significant effect on normal human ventricular action potential duration or refractoriness." Any apparent difference in effect, therefore, is attributed to intrinsic variability, such as in one aspect, less than a 10% difference.

As used in this patent application, "does not substantially slow conduction" means "has no statistically significant effect on slowing conduction in the ventricles." As such, any apparent difference in effect, therefore, is attributed to intrinsic variability. In one aspect, the ion channel modulating compound has no statistically significant effect on the slowing of conduction wherein the compound produces less than a 15%, preferably less than a 10%, increase in cardiac QRS duration at physiological heart rates.

As used in this patent application, "rate-dependent inhibition" of an ion channel means that the level of inhibition of the ion channel changes with the frequency of stimulation.

Figure 8:
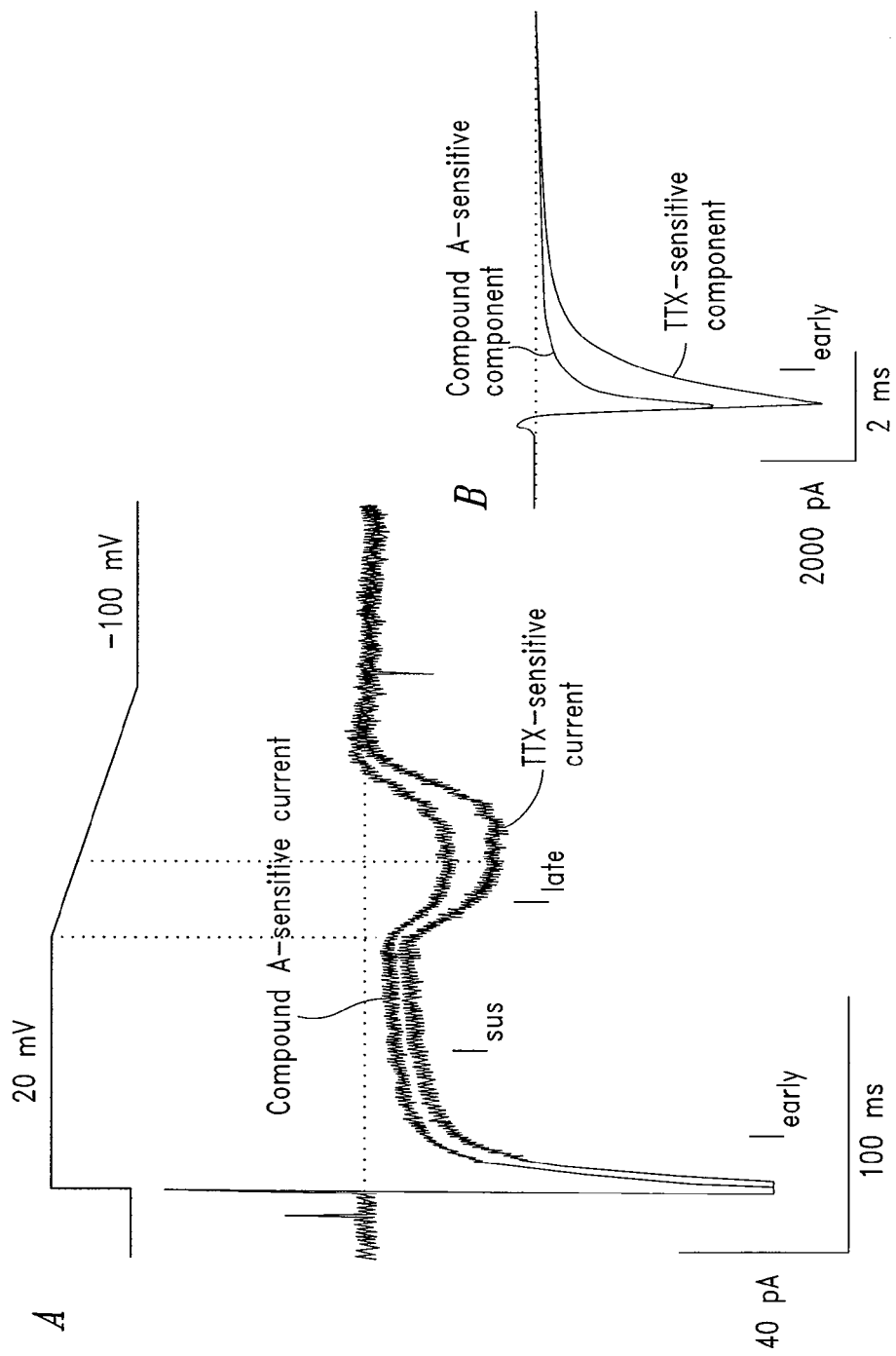
FIG. 8 shows an example of the TTX- and COMPOUND A-sensitive components of the early, sustained, and late sodium current observed during a step/ramp protocol.
Figure 9A:
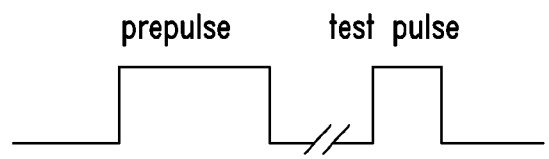
FIG. 9 illustrates a protocol to test level of inactivated state inhibition by COMPOUND C, flecainide, and lidocaine.
Figure 9B:
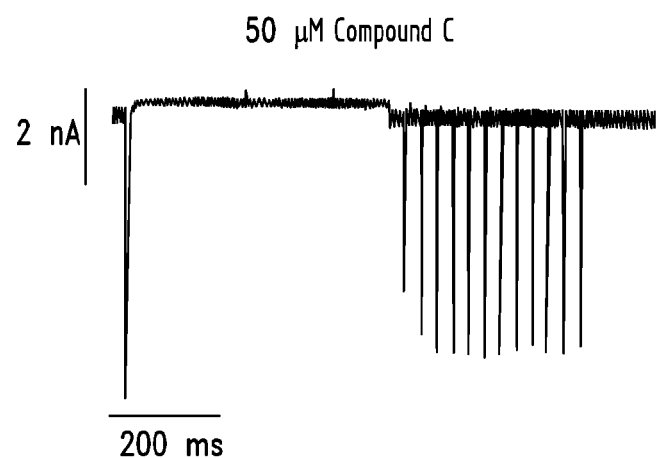
Figure 9C:
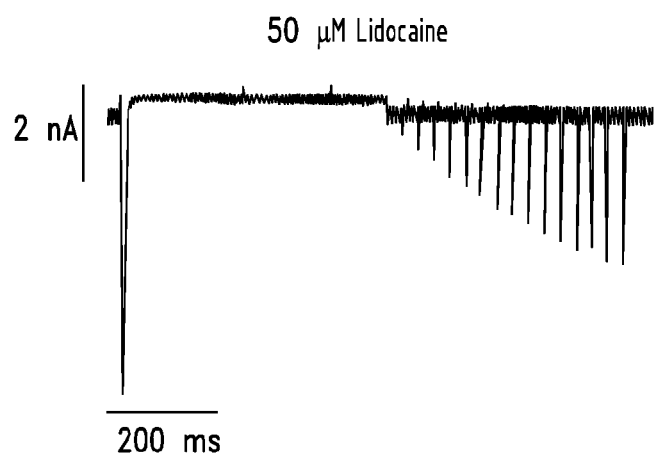
Figure 9D:
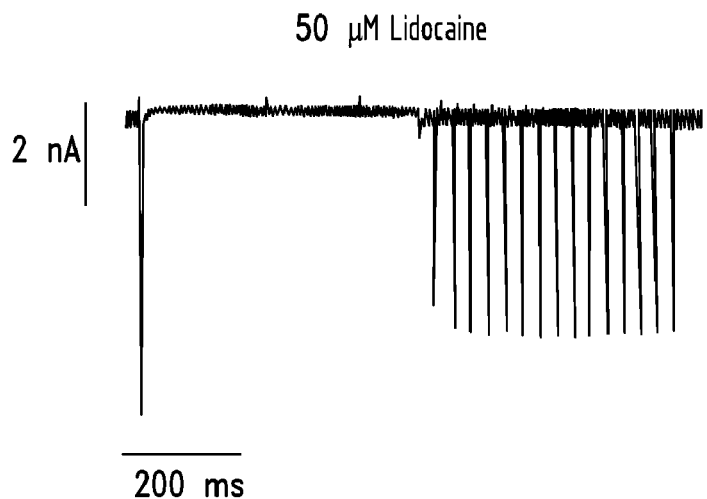
Figure 9E:
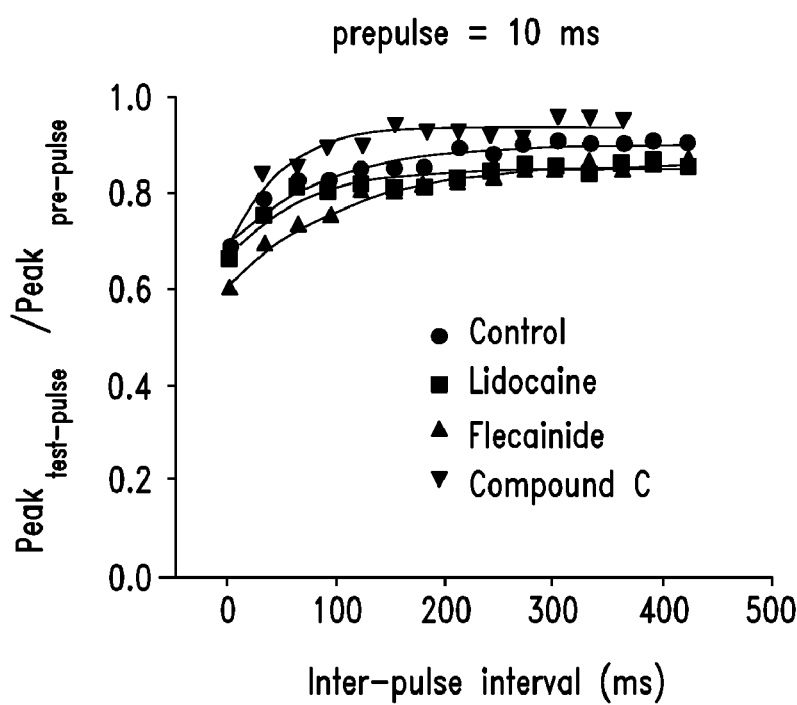
Figure 9F:
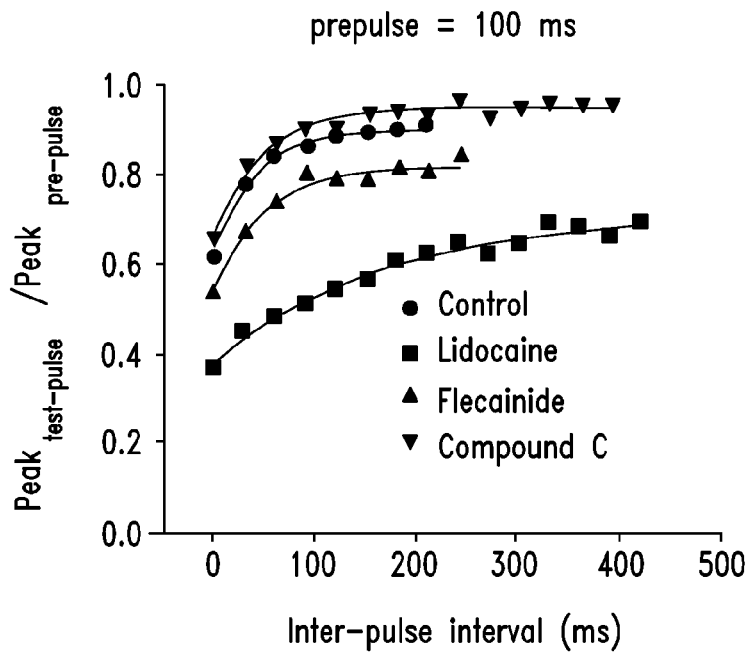
Figure 9G:
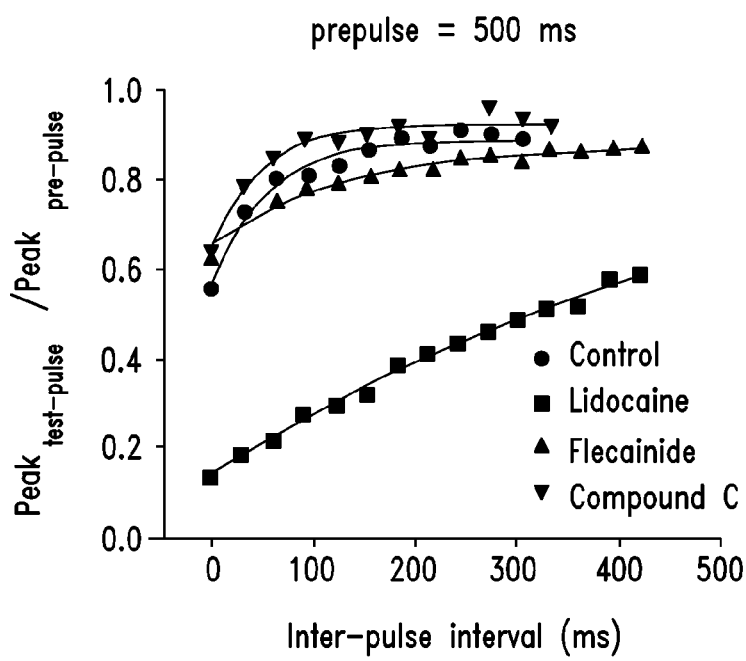

The terms 'early component,' 'late component' and 'sustained component' are used as known in the art; for example, the early, sustained and late components of a cardiac sodium channel current are as shown in FIG. 8, and as described in Example 9 and Example 18 below.

The term "QT interval" is used as is known in the art; for example, the QT interval as measured from an electrocardiogram. As used herein, unless the context makes clear otherwise, the term "prolongs" or "prolong" generally means extends or lengthens as in duration.

The term "antiarrhythmic" is used as is known in the art; for example, as a compound which prevents or alleviates irregularities in heart rate.

The term "induces" as used herein, unless the context indicates otherwise, generally means to stimulate the occurrence of.

The term "chemically induced" or "chemically induces" is used as is known in the art. As used herein, unless the context makes clear otherwise, the term "terminating" or "terminates" generally means to bring to an end or to halt.

Ion channel Modulating Compounds

Ion channel modulating compounds include but are not limited to compounds exhibiting one or more of the characteristics described in the Effect of ion channel modulating compounds on certain ion channel characteristics and other physiological characteristics section.

Specific ion channel modulating compounds that may be used are described in this section and in detail elsewhere in this patent application.

In this section are described various compounds and classes of compounds that may be used as ion channel modulating compounds in the methods, formulations, etc. described in this patent.

In this section are first described a series of specific classes of ion channel modulating compounds together with specific example compounds, followed by a general description of compounds that may be used as ion channel modulating compounds.

Specific Classes of Ion Channel Modulating Compounds and Exemplary Ion Channel Modulating Compounds Examples of specific classes of ion channel modulating compounds and exemplary ion channel modulating compounds are described below and in U.S. provisional patent application No. 60/516,248, U.S. patent application Ser. No. 10/674,684, each of which applications is incorporated herein by reference in its entirety.

In the variations described in this section on Specific Classes of Ion Channel Modulating Compounds and Exemplary Ion Channel Modulating Compounds, all enantiomeric and diastereomeric forms of the ion channel modulating compounds are intended. Pure stereoisomers, mixtures of enantiomers and/or diastereomers, and mixtures of different ion channel modulating compounds are described. Thus, the ion channel modulating compounds may occur as racemates, racemic mixtures and as individual diastereomers or enantiomers with all isomeric forms being included in the present description. A racemate or racemic mixture does not imply a 50:50 mixture of stereoisomers. Where a given structural formula or chemical name is presented for a compound it is intended that all possible solvates, pharmaceutically acceptable salts, esters, amides, complexes, chelates, stereoisomers, geometric isomers, crystalline or amorphous forms, metabolites, metabolic precursors or prodrugs of the compound are also separately described by the chemical structural formula or chemical name.

As used in this patent, unless the context make plain otherwise, the following terms are defined to have following meanings:

"Acid addition salts" refer to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Acyl" refers to branched or unbranched hydrocarbon fragments terminated by a carbonyl —(C═O)— group containing the specified number of carbon atoms. Examples include acetyl [$CH_3(C═O)$—, a $C_2$acyl] and propionyl [$CH_3CH_2(C═O)$—, a $C_3$acyl].

"Alkanoyloxy" refers to an ester substituent wherein the ether oxygen is the point of attachment to the molecule. Examples include propanoyloxy [($CH_3CH_2(C═O)$—O—, a $C_3$alkanoyloxy] and ethanoyloxy [$CH_3(C═O)$—O—, a $C_2$alkanoyloxy].

"Alkoxy" refers to an O-atom substituted by an alkyl group, for example, methoxy [—$OCH_3$, a $C_1$alkoxy].

"Alkoxyalkyl" refers to an alkylene group substituted with an alkoxy group. For example, methoxyethyl [$CH_3OCH_2CH_2$—] and ethoxymethyl ($CH_3CH_2OCH_2$—] are both $C_3$alkoxyalkyl groups.

"Alkoxycarbonyl" refers to an ester substituent wherein the carbonyl carbon is the point of attachment to the molecule. Examples include ethoxycarbonyl [$CH_3CH_2O(C═O)$—, a $C_3$alkoxycarbonyl] and methoxycarbonyl [$CH_3O(C═O)$—, a $C_2$alkoxycarbonyl].

"Alkyl" refers to a branched or unbranched hydrocarbon fragment containing the specified number of carbon atoms and having one point of attachment. Examples include n-propyl (a $C_3$alkyl), iso-propyl (also a $C_3$alkyl), and t-butyl (a $C_4$alkyl).

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group [—COOH]. Examples include carboxymethyl [HOOC—$CH_2$—, a $C_2$alkylcarboxy] and carboxyethyl [HOOC—$CH_2CH_2$—, a $C_3$alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds, where phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2$—, a $C_7$aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Heteroatom" refers to a non-carbon atom, where boron, nitrogen, oxygen, sulfur and phosphorus are preferred heteroatoms, with nitrogen, oxygen and sulfur being particularly preferred heteroatoms.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing a hydroxy (—OH) group. Examples include hydroxymethyl (—$CH_2OH$, a $C_1$hydroxyalkyl) and 1-hydroxyethyl (—$CHOHCH_3$, a $C_2$hydroxyalkyl).

"Thioalkyl" refers to a sulfur atom substituted by an alkyl group, for example thiomethyl ($CH_3S$—, a $C_1$thioalkyl).

"Modulating" in connection with the activity of an ion channel means that the activity of the ion channel may be either increased or decreased in response to administration of a compound or composition or method described herein. Thus, the ion channel may be activated, so as to transport more ions, or may be blocked, so that fewer or no ions are transported by the channel.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds derived from the combination of such compounds and an organic or inorganic acid (acid addition salts) or an organic or inorganic base (base addition salts). The compounds described herein may be used in either the free base or salt forms, with both forms being considered as being within the scope intended herein.

Aminocyclohexyl Ether Ion Channel Modulating Compounds

One class of compounds that are ion channel modulating compounds are compounds that comprise an aminocyclohexyl ether core structure having an ether oxygen atom at position 1 of a cyclohexane ring, and an amine nitrogen atom at position 2 of the cyclohexane ring. This core structure is shown below, with other positions numbered in corresponding order:

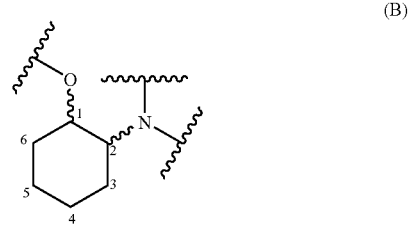

(B)

The bonds from the cyclohexane ring of (B) to the 1-oxygen and 2-nitrogen atoms in the above formula may be relatively disposed in either a cis or trans relationship. In one variation, the stereochemistry of the amine and ether substituents of the cyclohexane ring is either (R,R)-trans or (S,S)-trans. In another variation, the stereochemistry at these positions is either (R,S)-cis or (S,R)-cis.

In one variation, an ion channel modulating compound or derivative thereof as disclosed herein is not an aminocycloalkyl ester containing compound. In another variation, an ion channel modulating compound or derivative thereof as disclosed herein is not an aminocyclopentyl ester, an aminocyclohexyl ester, an aminocycloheptyl ester, or an aminocyclooctyl ester containing compound.

In one version of the aminocyclohexyl ether ion channel modulating compounds, the ion channel modulating compound is a compound of the formula:

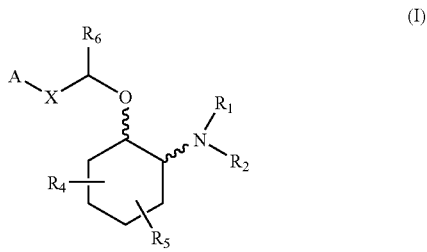

(I)

Compounds of formula (I) are aminocyclohexyl ethers. More specifically, these aminocyclohexyl ethers are substituted at position 2 of the cyclohexyl ring with an amine group —NR$_1$R$_2$. The cyclohexyl ring may also be substituted with additional substituents (designated as R$_3$ and R$_4$) as described in more detail below. Examples of specific compounds represented by formula (I) are described below.

Depending upon the selection of substituents R$_1$ and R$_2$, the compounds of formula (I) may be primary, secondary, or tertiary amines (i.e., both R$_1$ and R$_2$ are hydrogen, only one of R$_1$ and R$_2$ is hydrogen, or neither of R$_1$ and R$_2$ are hydrogen, respectively). In one embodiment, the compounds of formula (I) are tertiary amines, i.e., neither R$_1$ nor R$_2$ is hydrogen. Where the amine is tertiary, it may be a cyclic amine. Amine substituents R$_1$ and R$_2$ may be independently selected from substituents which include hydrogen, alkyl groups containing from one to eight carbon atoms (i.e., C$_1$-C$_8$alkyl), alkoxyalkyl groups containing from three to eight carbon atoms (i.e., C$_3$-C$_8$alkoxyalkyl), alkyl groups containing from one to eight carbon atoms where one of the carbon atoms is substituted with a hydroxyl group (i.e., C$_1$-C$_8$hydroxyalkyl), and aralkyl groups containing from seven to twelve carbon atoms (i.e., C$_7$-C$_{12}$aralkyl). In one version, R$_1$ and R$_2$ are independently selected from hydrogen, C$_1$-C$_8$alkyl, C$_3$-C$_8$alkoxyalkyl, C$_1$-C$_8$hydroxyalkyl, and C$_7$-C$_{12}$aralkyl. In another version, R$_1$ and R$_2$ are independently selected from C$_3$-C$_8$alkoxyalkyl, C$_1$-C$_8$hydroxyalkyl, and C$_7$-C$_{12}$aralkyl.

Alternatively, R$_1$ and R$_2$, when taken together with the nitrogen atom to which they are directly attached in formula (I), may form a ring denoted by formula (II):

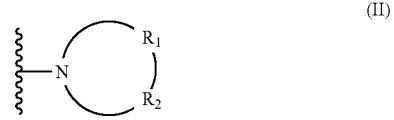

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, C$_1$-C$_3$hydroxyalkyl, oxo, C$_2$-C$_4$acyl, C$_1$-C$_3$alkyl, C$_2$-C$_4$alkylcarboxy, C$_1$-C$_3$alkoxy, C$_1$-C$_{20}$alkanoyloxy, or may be substituted to form a spiro five- or six-membered heterocyclic ring containing one or two heteroatoms selected from oxygen and sulfur (e.g., an acetal, thioacetal, ketal, or thioketal group); and any two adjacent additional carbon ring atoms may be fused to a C$_3$-C$_8$carbocyclic ring, and any one or more of the additional nitrogen ring atoms may be substituted with substituents selected from hydrogen, C$_1$-C$_6$alkyl, C$_2$-C$_4$acyl, C$_2$-C$_4$hydroxyalkyl and C$_3$-C$_8$alkoxyalkyl. Examples of substituents containing a fused ring system include the perhydroindolyl and 1,2,3,4-tetrahydroisoquinolinyl groups.

In connection with the ring of formula (II), any two adjacent ring atoms may be joined together by single or double bonds. Thus, the ring of formula (II) may be saturated or unsaturated, and an unsaturated ring may contain one, or more than one, sites of unsaturation. In other words, the ring of formula (II) may contain one or more double bonds, it being understood, however, that the unsaturated ring of formula (II) is chemically stable.

Alternatively, R$_1$ and R$_2$, when taken together with the 2-amino nitrogen of formula (I), may complete a bicyclic ring. Bicyclic rings include, for example, 3-azabicyclo[3.2.2] nonane, 2-azabicyclo[2.2.2]octane, 3-azabicyclo[3.1.0]hexane, and 3-azabicyclo[3.2.0]heptane. For these derivatives, the 2-substituents of the cyclohexyl ethers of formula (I) are the following groups: 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl.

R$_1$ and R$_2$, when taken together may contain only a single heteroatom. Preferred heteroatoms include nitrogen, oxygen and sulfur. An example of a ring in which R$_1$ and R$_2$ together include an oxygen heteroatom is the morpholinyl group. An example of a ring where R$_1$ and R$_2$ together include a second nitrogen heteroatom is the piperazinyl group.

Cyclohexane substituents R$_3$ and R$_4$ may be independently attached to ring positions 3, 4, 5 or 6 (i.e., both R$_3$ and R$_4$ may be attached to the same ring position or each attached to different ring position). R$_3$ and R$_4$ are independently selected from hydrogen, hydroxy, C$_1$-C$_6$alkyl, and C$_1$-C$_6$alkoxy, and, when both R$_3$ and R$_4$ are attached to the same cyclohexane ring atom, may together form a spiro five- or six-membered heterocyclic ring containing one or two heteroatoms selected from oxygen and sulfur. Preferred heterocyclic substituents contain either a single oxygen or a single sulfur ring atom.

Depending upon the identity of X, the ether side chain, —CH(R$_5$)—X-A, in formula (I) may take several forms. For example, a compound of formula (I) may have X as a —C(R$_6$, R$_{14}$)—Y— group, where Y may be any of a direct bond, an oxygen atom (O), a sulfur atom (S) or a C$_1$-C$_4$alkylene group. R$_6$ and R$_{14}$ are independently selected from hydrogen, C$_1$-C$_6$alkyl, aryl and benzyl, or R$_6$ and R$_{14}$, when taken together with the carbon to which they are attached, may form a spiro C$_3$-C$_5$cycloalkyl. Thus, compounds described herein include compounds of formula (I) where R$_6$ and R$_{14}$ are hydrogen and Y is a direct bond, such that X may be CH$_2$.

Alternatively, X may be an alkenylene moiety, e.g., a cis- or trans-alkenylene moiety, C(R$_{13}$)=CH, where R$_{13}$ may be any of hydrogen, C$_1$-C$_6$alkyl, C$_3$-C$_8$cycloalkyl, aryl or benzyl. For compounds of formula (I) where X is an alkenylene moiety, X is preferably a trans-alkenylene moiety.

Alternatively, X may be a direct bond. Independent of the selections for A, X and other variables, R$_5$ is selected from hydrogen, C$_1$-C$_6$alkyl, aryl and benzyl.

In one variation, X is either a —C(R$_6$,R$_{14}$)—Y— or a C(R$_{13}$)=CH group, and is not a direct bond. In another variation, the compounds exclude those compounds wherein X is a direct bond when R$_1$ and R$_2$ are hydrogen. In another variation, X is selected from a direct bond, —C(R$_6$,R$_{14}$)—Y—, and —C(R$_{13}$)=CH—, with the proviso that when X is a direct bond and A is formula (III) then at least one of R$_7$, R$_8$ and R$_9$ is not hydrogen. In another variation, the compounds exclude those compounds wherein X is a direct bond when A is formula (III) and each of R$_7$, R$_8$ and R$_9$ is hydrogen. In another variation, the compounds exclude those compounds wherein X is a direct bond when A is formula (III). In another variation, when X is a direct bond, R$_1$ and R$_2$ are H, and A is of formula (III), at least one of R$_7$, R$_8$ and R$_9$ is not hydrogen. In another variation, when X is a direct bond, R$_1$ and R$_2$ are H, and A is of formula (III), at least two of R$_7$, R$_8$ and R$_9$ are not hydrogen. In another variation, when X is a direct bond and A is formula (III) then at least one of R$_3$, R$_4$ and R$_5$ is not hydrogen. In another variation, when X is a direct bond, R$_1$ and R$_2$ are H, and A is of formula (III), at least one of R$_3$, R$_4$ and R$_5$ is not hydrogen. In another variation, when X is a direct bond and A is of formula (III), at least two of R$_3$, R$_4$ and R$_5$ are not hydrogen. In another variation, when X is a direct bond, $R_1$ and $R_2$ are H, and A is of formula (III), at least two of $R_3$, $R_4$ and $R_5$ are not hydrogen.

Ether side chain component A is generally a hydrophobic moiety. Typically, a hydrophobic moiety is comprised of non-polar chemical groups such as hydrocarbons or hydrocarbons substituted with halogens or ethers or heterocyclic groups containing nitrogen, oxygen, or sulfur ring atoms. Suitable hydrocarbons include $C_5$-$C_{12}$alkyl, $C_3$-$C_{13}$carbocyclic rings, $C_3$-$C_{13}$ cycloalkyl rings and an unsubstituted $C_3$-$C_{13}$ aryl ring. Particularly preferred cyclic hydrocarbons include selected aromatic groups such as phenyl, 1-naphthyl, 2-naphthyl, indenyl, acenaphthyl, and fluorenyl and are represented by formulae (III), (IV), (V), (VI), (VII), or (VIII), respectively.

In one variation, A is selected from the group consisting of $C_5$-$C_{12}$alkyl, a $C_3$-$C_{13}$ carbocyclic ring and ring systems selected from the formulae (III), (IV), (V), (VI), (VII) and (VIII). In one variation, A is selected from the group consisting of $C_5$-$C_{12}$alkyl, a $C_3$-$C_{13}$ aryl ring, a $C_3$-$C_{13}$ cycloalkyl ring and ring systems selected from the formulae (III), (IV), (V), (VI), (VII) and (VIII). In another variation, A is selected from the group consisting of $C_5$-$C_{12}$alkyl, a $C_3$-$C_{13}$ cycloalkyl ring, an unsubstituted $C_3$-$C_{13}$ aryl ring and ring systems selected from the formulae (III), (IV), (V), (VI), (VII) and (VIII). In one variation, when A is a $C_3$-$C_{13}$ carbocyclic ring, $R_5$ is not hydrogen. In another variation, when A is a $C_3$-$C_{13}$ carbocyclic ring, one of $R_1$ and $R_2$ is not hydrogen. In one variation, when A is a $C_3$-$C_{13}$ aryl ring, $R_5$ is not hydrogen. In another variation, when A is a $C_3$-$C_{13}$ aryl ring, one of $R_1$ and $R_2$ is not hydrogen. In another variation, when X is a direct bond and A is a $C_3$-$C_{13}$ aryl ring, then A is not an aryl ring substituted by another aryl ring. In another variation, when X is a direct bond and A is a $C_3$-$C_{13}$ carbocyclic ring, then A is not an aryl ring substituted by another aryl ring. In another variation, when $R_1$ and $R_2$ are independently selected from hydrogen or $C_1$-$C_8$alkyl, or $R_1$ and $R_2$ together with the nitrogen atom to which they are directly attached represent a phthalimido group, and A is a $C_3$-$C_{13}$ carbocyclic ring, then A is not an aryl ring which is substituted by another aryl ring. In another variation, when $R_1$ and $R_2$ are independently selected from hydrogen or $C_1$-$C_8$alkyl, or $R_1$ and $R_2$ together with the nitrogen atom to which they are directly attached represent a phthalimido group, and A is a $C_3$-$C_{13}$ aryl ring, then A is not an aryl ring which is substituted by another aryl ring.

A suitable "A" group in the formula above is a phenyl ring represented by formula (III):

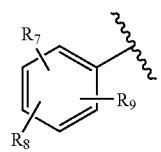

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, aryl and $N(R_{15},R_{16})$ where $R_{15}$ and $R_{16}$ are independently selected from hydrogen, acetyl, methanesulfonyl, and $C_1$-$C_6$alkyl.

For compounds of formula (I) where X is a direct bond or $CH_2$, at least one of $R_7$, $R_8$ and $R_9$ is preferably selected from amine (—$NR_{15}R_{16}$, where $R_{15}$ and $R_{16}$ are independently hydrogen, acetyl, methanesulfonyl, and $C_1$-$C_6$alkyl), bromine, chlorine, fluorine, carboxy, hydrogen, hydroxy, hydroxymethyl, nitro, trifluoromethyl, $C_2$-$C_7$alkanoyloxy, $C_1$-$C_6$alkyl, $C_1$-$C_6$alkoxy, $C_2$-$C_7$alkylcarbonyl, $C_1$-$C_6$thioalkyl or aryl groups. For compounds of formula (I) when X is CH=CH, and $R_3$ and $R_4$ are hydrogen, at least one of $R_7$, $R_8$ and $R_9$ is preferably a substituent other than hydrogen. One variation presents compounds of formula (I) where A includes phenyl groups of formula (III) such that at least one of $R_7$, $R_8$ and $R_9$ is not hydrogen, i.e., formula (III) is a phenyl group that contains at least one non-hydrogen substituent. In another variation, $R_7$, $R_8$ and $R_9$ are selected from amine (—$NR_{15}R_{16}$, where $R_{15}$ and $R_{16}$ are independently hydrogen, acetyl, methanesulfonyl, and $C_1$-$C_6$alkyl), bromine, chlorine, fluorine, carboxy, hydrogen, hydroxy, hydroxymethyl, nitro, trifluoromethyl, $C_2$-$C_7$alkanoyloxy, $C_1$-$C_6$alkyl, $C_1$-$C_6$alkoxy, $C_2$-$C_7$alkylcarbonyl and $C_1$-$C_6$thioalkyl, i.e., none of $R_7$, $R_8$ or $R_9$ is aryl. In another variation, A does not include a phenyl ring of formula (III) when X is a direct bond.

Other suitable "A" groups are 1-naphthyl groups as represented by formula (IV):

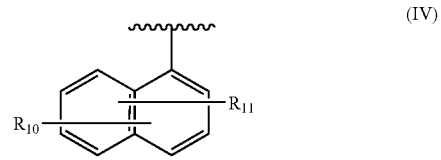

(IV)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl.

Other suitable "A" groups are 2-naphthyl group as represented by formula (V):

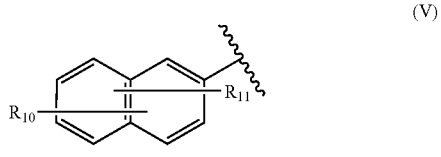

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl, as defined above.

Other suitable "A" groups are aromatic groups represented by formula (VI):

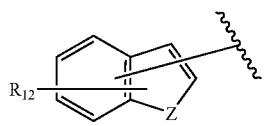

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15}, R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl.

The aryl groups of formula (VI) are derivatives of indene, indole, benzofuran, and thianaphthene when Z is methylene, nitrogen, oxygen, and sulfur, respectively. Preferred heterocyclic groups of formula (VI) include indole where Z is NH, benzofuran where Z is O, and thianaphthene where Z is S. As described below, in a preferred embodiment, Z is O, S or N—$R_{17}$, and in a particularly preferred embodiment Z is O or S.

Another suitable "A" group is acenaphthyl groups as represented by formula (VII):

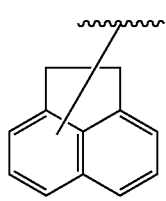

(VII)

Still another suitable "A" group is the fluorenyl group represented by formula (VIII):

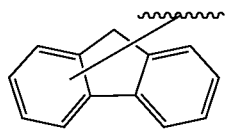

(VIII)

In some variations, ether side chain component A is an acenapthyl or fluorenyl group only when X is a direct bond or $CH_2$. In other variations, the acenaphthyl group is a 1-acenaphthyl group, and the fluorenyl group is a 9-fluorenyl group.

In a particular variation of formula (I), X is $(CH_2)$—Y. For these variations, Y is preferably a direct bond, an oxygen atom, or a sulfur atom. In another variation, Y is a direct bond or an oxygen atom. In still another variation Y is a direct bond and X is $C(R_6,R_{14})$, where $R_6$ and $R_{14}$ are as defined above. In yet another variation, X is $C(R_{13})$=CH, and $R_{13}$ is a hydrogen atom. For these variations, $R_3$ and $R_4$ may be independently attached to the cyclohexane ring at the 4- or 5-positions.

In another version of the aminocyclohexyl ether ion channel modulating compounds, the ion channel modulating compound is a compound of the formula (I), wherein: independently at each occurrence, X is selected from a direct bond, —$C(R_6,R_{14})$—Y— and —$C(R_{13})$=CH—, with the proviso that when X is a direct bond and A is formula (III) then at least one of $R_7$, $R_8$ and $R_9$ is not hydrogen;

Y is selected from a direct bond, O, S and $C_1$-$C_4$alkylene;

$R_{13}$ is selected from hydrogen, $C_1$-$C_6$alkyl, $C_3$-$C_8$cycloalkyl, aryl and benzyl;

$R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or $R_1$ and $R_2$ are independently selected from $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached in formula (I), form a ring denoted by formula (II):

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached in formula (I), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cyclohexane ring shown in formula (I) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from $C_5$-$C_{12}$alkyl, a $C_3$-$C_{13}$carbocyclic ring, and ring systems selected from formulae (III), (IV), (V), (VI), (VII) and (VIII):

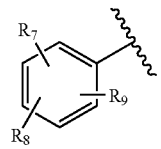
(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and $N(R_{15},R_{16})$ where $R_{15}$ and $R_{16}$ are independently selected from hydrogen, acetyl, methanesulfonyl and $C_1$-$C_6$alkyl;

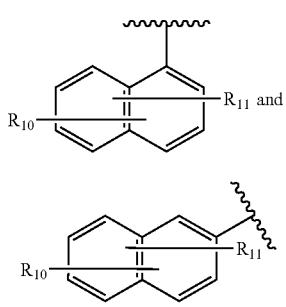
(IV)

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and, $C_1$-$C_6$alkyl;

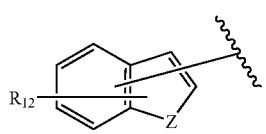
(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

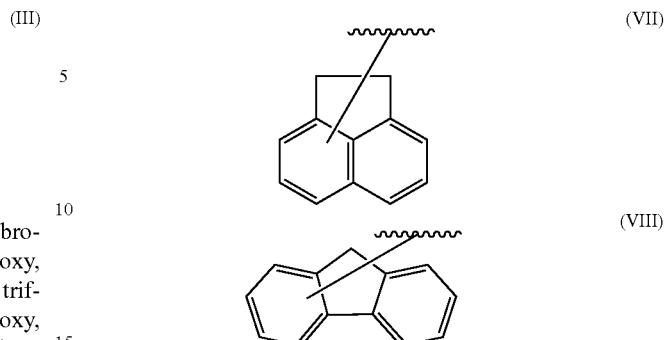
(VII)

(VIII)

including isolated enantiomeric, diastereomeric and geometric isomers thereof and solvates and/or pharmaceutically acceptable salts of any of the foregoing.

In another version of the aminocyclohexyl ether ion channel modulating compounds, the ion channel modulating compound is a compound of the formula (IX), or a solvate or pharmaceutically acceptable salt thereof:

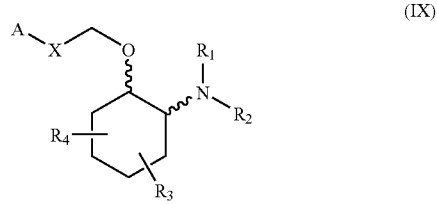
(IX)

wherein, independently at each occurrence,

X is selected from a direct bond, —CH═CH— and —C($R_6$,$R_{14}$)—Y—;

Y is selected from a direct bond, O and S; and $R_1$, $R_2$, $R_3$, $R_4$, $R_6$, $R_7$, $R_8$, $R_9$, $R_{10}$, $R_{11}$, $R_{12}$, $R_{14}$, A and Z are defined as above for compounds of formula (I).

In one variation, the compounds as recited by the formulae herein are compounds other than any one or any combination of two or more compounds selected from the group consisting of 2-benzyloxycyclohexylamine, 3-benzyloxycyclohexylamine, 4-benzyloxycyclohexylamine, 2-(4-[benzoxazol-2-yl]benzyloxy)cyclohexylamine, trans-2-(4-[4-chloro benzoyl]-benzyloxy)cyclohexylamine, 2-(4-benzooxazol-2-yl-benzyloxy)-cyclohexylamine.

In another version of the aminocyclohexyl ether ion channel modulating compounds, the ion channel modulating compound is a compound of the formula (X), or a solvate or pharmaceutically acceptable salt thereof:

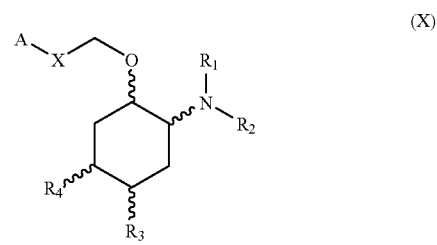
(X)

wherein, independently at each occurrence,

X is selected from a direct bond, —CH═CH— and —C(R$_6$,R$_{14}$)—Y—;

Y is selected from a direct bond, O, and S;

R$_1$, R$_2$, R$_6$ and R$_{14}$ are defined as above for compounds of formula (I);

R$_3$ and R$_4$ are independently attached to the cyclohexane ring at the 4- or 5-positions, and are independently selected from hydrogen and C$_1$-C$_6$alkoxy; and A is selected from C$_5$-C$_{12}$alkyl, C$_3$-C$_8$cycloalkyl, and any of formulae (III), (IV), (V), and (VI) as above for compounds of formula (I), wherein Z, R$_7$, R$_8$, R$_9$, R$_{10}$, R$_{11}$ and R$_{12}$ are defined as above for compounds of formula (I).

In another version of the aminocyclohexyl ether ion channel modulating compounds, the ion channel modulating compound is a compound of the formula (XI), or a solvate or pharmaceutically acceptable salt thereof:

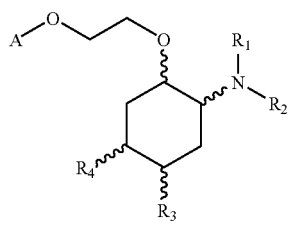

(XI)

wherein, independently at each occurrence,

R$_1$ and R$_2$ are defined as above for compounds of formula (I);

R$_3$ and R$_4$ are independently attached to the cyclohexane ring at the 4- or 5-positions, and are independently selected from hydrogen and methoxy; and A is selected from C$_5$-C$_{12}$alkyl, C$_3$-C$_8$cycloalkyl, and any of formulae (III), (IV), (V), and (VI) as above for compounds of formula (I), wherein Z, R$_7$, R$_8$, R$_9$, R$_{10}$, R$_{11}$ and R$_{12}$ are defined as above for compounds of formula (I).

In another version of the aminocyclohexyl ether ion channel modulating compounds, the ion channel modulating compound is a compound of the formula (XII), or a solvate or pharmaceutically acceptable salt thereof:

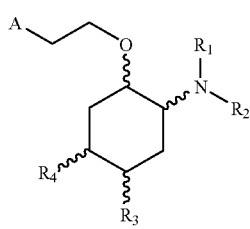

(XII)

wherein, independently at each occurrence,

R$_1$ and R$_2$ are defined as above for compounds of formula (I);

R$_3$ and R$_4$ are independently attached to the cyclohexane ring at the 4- or 5-positions, and are independently selected from hydrogen and methoxy; and A is selected from C$_5$-C$_{12}$alkyl, C$_3$-C$_8$cycloalkyl, and any of formulae (III), (IV), (V), and (VI) as above for compounds of formula (I), wherein Z, R$_7$, R$_8$, R$_9$, R$_{10}$, R$_{11}$ and R$_{12}$ are defined as above for compounds of formula (I).

In another version of the aminocyclohexyl ether ion channel modulating compounds, the ion channel modulating compound is a compound of the formula (XIII), or a solvate or pharmaceutically acceptable salt thereof:

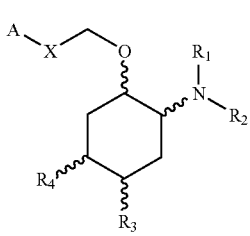

(XIII)

wherein, independently at each occurrence,

X is selected from —C(R$_6$,R$_{14}$)—Y— and —CH═CH—;

Y, R$_1$, R$_2$, R$_6$ and R$_{14}$ are defined as above for compounds of formula (I);

R$_3$ and R$_4$ are independently attached to the cyclohexane ring at the 4- or 5-positions, and are independently selected from hydrogen and methoxy; and A is selected from C$_3$-C$_8$cycloalkyl and any of formulae (III), (IV), (V), (VI), (VII) and (VIII) as above for compounds of formula (I), where R$_8$ and R$_9$ are defined as above for compounds of formula (I); R$_7$, R$_{10}$, R$_{11}$ and R$_{12}$ are hydrogen, and Z is selected from O, S and N—R$_{17}$ where R$_{17}$ is selected from hydrogen and methyl.

In another version of the aminocyclohexyl ether ion channel modulating compounds, the ion channel modulating compound is a compound of the formula (XIV), or a solvate or pharmaceutically acceptable salt thereof:

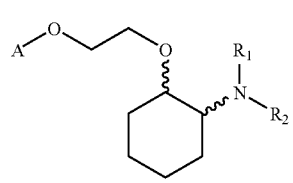

(XIV)

wherein, independently at each occurrence,

R$_1$ and R$_2$ are defined as above for compounds of formula (I);

A is selected from any of formulae (III), (IV), (V) and (VI) as above for compounds of formula (I), wherein R$_7$, R$_{10}$, R$_{11}$, and R$_{12}$, are hydrogen, R$_8$ and R$_9$ are independently selected from hydrogen, hydroxy, fluorine, chlorine, bromine, methanesulfonamido, methanoyloxy, methoxycarbonyl, nitro, sulfamyl, thiomethyl, trifluoromethyl, methyl, ethyl, methoxy, ethoxy and NH$_2$, with the proviso that at least one of R$_8$ and R$_9$ is not hydrogen; and Z is selected from O and S.

In another version of the aminocyclohexyl ether ion channel modulating compounds, the ion channel modulating compound is a compound of the formula (XV), or a solvate or pharmaceutically acceptable salt thereof:

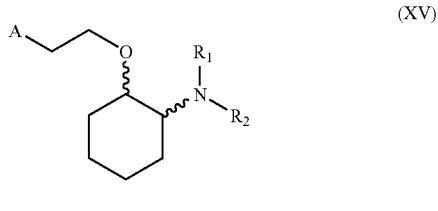

(XV)

wherein, independently at each occurrence, $R_1$ and $R_2$ are defined as above for compounds of formula (I); and A is selected from any of formulae (III), (IV), (V) and (VI) as defined above for compounds of formula (I), wherein $R_7$, $R_{10}$, $R_{11}$, and $R_{12}$, are hydrogen, $R_8$ and $R_9$ are independently selected from hydrogen, hydroxy, fluorine, chlorine, bromine, methanesulfonamido, methanoyloxy, methoxycarbonyl, nitro, sulfamyl, thiomethyl, trifluoromethyl, methyl, ethyl, methoxy, ethoxy and $NH_2$, with the proviso that at least one of $R_8$ and $R_9$ is not hydrogen; and Z is selected from O and S.

In another version of the aminocyclohexyl ether ion channel modulating compounds, the ion channel modulating compound is a compound of the formula (XVI), or a solvate or pharmaceutically acceptable salt thereof:

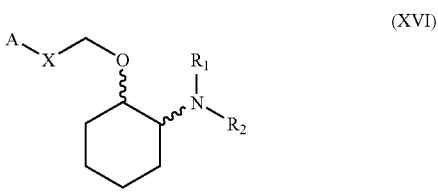

(XVI)

wherein, independently at each occurrence,

X is selected from a direct bond, trans-CH=CH—, —$CH_2$— and —$CH_2$—O—;

$R_1$ and $R_2$ are both methoxyethyl or, when taken together with the nitrogen atom to which they are attached, complete a ring selected from pyrrolidinyl, 2-ketopyrrolidinyl, 3-ketopyrrolidinyl, 2-acetoxypyrrolidinyl, 3-acetoxypyrrolidinyl, 2-hydroxypyrrolidinyl, 3-hydroxypyrrolidinyl, thiazolidinyl, piperidinyl, 2-ketopiperidinyl, 3-ketopiperidinyl, 4-ketopiperidinyl, acetylpiperazinyl, 1,4-dioxa-7-azaspiro[4.4]non-7-yl, hexahydroazepinyl, morpholinyl, N-methylpiperazinyl and 3-azabicyclo[3.2.2]nonanyl; and A is selected from cyclohexyl, monochlorophenyl, 2,6-dichlorophenyl, 3,4-dichlorophenyl, 2-bromophenyl, 2,4-dibromophenyl, 3-bromophenyl, 4-bromophenyl, 3,4-dimethoxyphenyl, 1-naphthyl, 2-naphthyl, 3-benzo(b)thiophenyl, 4-benzo(b)thiophenyl, (2-trifluoromethyl)phenyl, 2,4-di(trifluoromethyl)phenyl, and (4-trifluoromethyl)phenyl.

In another version of the aminocyclohexyl ether ion channel modulating compounds, the ion channel modulating compound is a compound of the formula (XVII), or a solvate or pharmaceutically acceptable salt thereof:

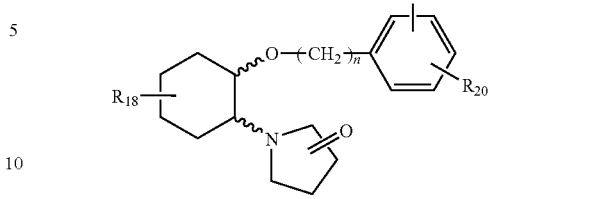

(XVII)

wherein, independently at each occurrence, n is selected from 1, 2 and 3;

$R_{18}$ is either hydrogen or methyl and is independently attached to the cyclohexane ring shown in formula (XVII) at one of the 3-, 4-, 5- or 6-positions;

$R_{19}$ is selected from a group consisting of bromine, chlorine, fluorine and hydrogen; and $R_{20}$ is selected from a group consisting of bromine, chlorine and fluorine;

including isolated enantiomeric, diastereomeric and geometric isomers thereof.

In another version of the aminocyclohexyl ether ion channel modulating compounds, the ion channel modulating compound is a compound that is a trans configuration of formula (XVII) as represented by formula (XVIII), or a solvate or pharmaceutically acceptable salt thereof:

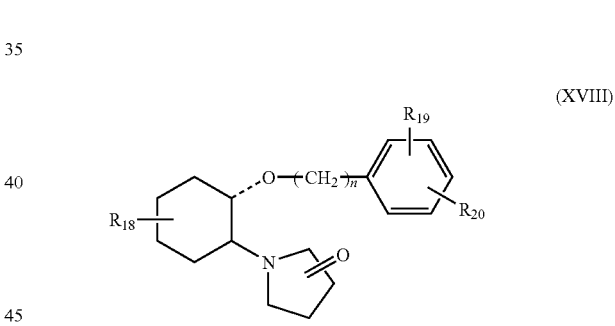

(XVIII)

wherein, independently at each occurrence, n is selected from 1, 2 and 3;

$R_{18}$ is either hydrogen or methyl and is independently attached to the cyclohexane ring shown in formula (XVII) at one of the 3-, 4-, 5- or 6-positions;

$R_{19}$ is selected from a group consisting of bromine, chlorine, fluorine and hydrogen; and $R_{20}$ is selected from a group consisting of bromine, chlorine and fluorine;

including isolated enantiomeric, diastereomeric and geometric isomers thereof.

In another version of the aminocyclohexyl ether ion channel modulating compounds, the ion channel modulating compound is a compound of the formula (IXX); or a solvate or pharmaceutically acceptable salt thereof:

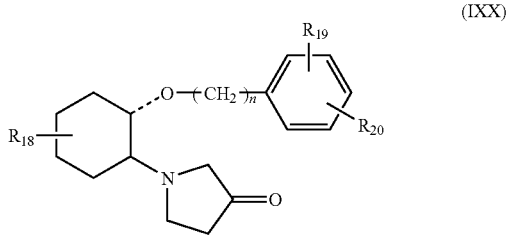

(IXX)

wherein, independently at each occurrence, n is selected from 1, 2 and 3;

$R_{18}$ is either hydrogen or methyl and is independently attached to the cyclohexane ring shown in formula (XVII) at one of the 3-, 4-, 5- or 6-positions;

$R_{19}$ is selected from a group consisting of bromine, chlorine, fluorine and hydrogen; and $R_{20}$ is selected from a group consisting of bromine, chlorine and fluorine;

including isolated enantiomeric, diastereomeric and geometric isomers thereof.

In another version of the aminocyclohexyl ether ion channel modulating compounds, the ion channel modulating compound is a compound of formula (XX), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

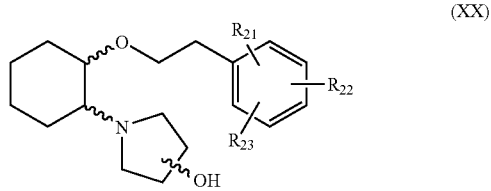

(XX)

wherein, $R_{21}$, $R_{22}$ and $R_{23}$ are independently selected from hydrogen, hydroxy and $C_1$-$C_6$alkoxy, including isolated enantiomeric, diastereomeric and geometric isomers thereof, and mixtures thereof, with the proviso that $R_{21}$, $R_{22}$ and $R_{23}$ cannot all be hydrogen.

In another version of the aminocyclohexyl ether ion channel modulating compounds, the ion channel modulating compound is a compound of formula (XX), or a solvate, pharmaceutically acceptable salt thereof, including isolated enantiomeric, diastereomeric and geometric isomers thereof, and mixtures thereof.

In another version of the aminocyclohexyl ether ion channel modulating compounds, the ion channel modulating compound is a compound of formula (XX), or a solvate, pharmaceutically acceptable salt thereof, wherein, $R_{22}$ and $R_{23}$ are independently selected from hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is a compound of formula (XX), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are independently selected from hydroxy and $C_1$-$C_6$alkoxy.

In another version of the aminocyclohexyl ether ion channel modulating compounds, the ion channel modulating compound is a compound of formula (XX), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_{21}$ is hydrogen, $R_{22}$ and $R_{23}$ are independently selected from $C_1$-$C_6$alkoxy.

In another version of the aminocyclohexyl ether ion channel modulating compounds, the ion channel modulating compound is a compound of formula (XX), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are independently selected from $C_1$-$C_6$alkoxy.

In another version of the aminocyclohexyl ether ion channel modulating compounds, the ion channel modulating compound is a compound of formula (XX), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_{21}$ is hydrogen, $R_{22}$ and $R_{23}$ are $C_1$alkoxy.

In another version of the aminocyclohexyl ether ion channel modulating compounds, the ion channel modulating compound is a compound of formula (XX), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are $C_1$alkoxy.

In another version of the aminocyclohexyl ether ion channel modulating compounds, the ion channel modulating compound is a compound of formula (XXI), or a solvate, pharmaceutically acceptable salt, ester, amide, complex, chelate, stereoisomer, stereoisomeric mixture, geometric isomer, crystalline or amorphous form,

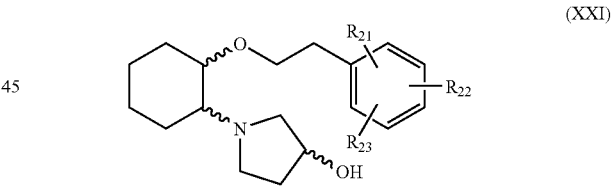

(XXI)

metabolite, metabolic precursor or prodrug thereof:

wherein, $R_{21}$, $R_{22}$ and $R_{23}$ are independently selected from hydrogen, hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is a compound of formula (XXI), or a solvate, pharmaceutically acceptable salt thereof, including isolated enantiomeric, diastereomeric and geometric isomers thereof, and mixtures thereof.

In another version of the aminocyclohexyl ether ion channel modulating compounds, the ion channel modulating compound is a compound of formula (XXI), or a solvate, pharmaceutically acceptable salt thereof, wherein, $R_{22}$ and $R_{23}$ are independently selected from hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is a compound of formula (XXI), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are independently selected from hydroxy and $C_1$-$C_6$alkoxy.

In another version of the aminocyclohexyl ether ion channel modulating compounds, the ion channel modulating compound is a compound of formula (XXI), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_{21}$ is hydrogen, $R_{22}$ and $R_{23}$ are independently selected from $C_1$-$C_6$alkoxy.

In another version of the aminocyclohexyl ether ion channel modulating compounds, the ion channel modulating compound is a compound of formula (XXI), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are independently selected from $C_1$-$C_6$alkoxy.

In another version of the aminocyclohexyl ether ion channel modulating compounds, the ion channel modulating compound is a compound of formula (XXI), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_{21}$ is hydrogen, $R_{22}$ and $R_{23}$ are $C_1$alkoxy.

In another version of the aminocyclohexyl ether ion channel modulating compounds, the ion channel modulating compound is a compound of formula (XXI), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are $C_1$alkoxy.

In another version of the aminocyclohexyl ether ion channel modulating compounds, the ion channel modulating compound is a compound of formula (XXII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

(XXII)

wherein, $R_{21}$, $R_{22}$ and $R_{23}$ are independently selected from hydrogen, hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is a compound of formula (XXII), or a solvate, pharmaceutically acceptable salt thereof, including isolated enantiomeric, diastereomeric and geometric isomers thereof, and mixtures thereof.

In another version of the aminocyclohexyl ether ion channel modulating compounds, the ion channel modulating compound is a compound of formula (XXII), or a solvate, pharmaceutically acceptable salt thereof, wherein, $R_{22}$ and $R_{23}$ are independently selected from hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is a compound of formula (XXII), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are independently selected from hydroxy and $C_1$-$C_6$alkoxy.

In another version of the aminocyclohexyl ether ion channel modulating compounds, the ion channel modulating compound is a compound of formula (XXII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_{21}$, is hydrogen, $R_{22}$ and $R_{23}$ are independently selected from $C_1$-$C_6$alkoxy.

In another version of the aminocyclohexyl ether ion channel modulating compounds, the ion channel modulating compound is a compound of formula (XXII), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are independently selected from $C_1$-$C_6$alkoxy.

In another version of the aminocyclohexyl ether ion channel modulating compounds, the ion channel modulating compound is a compound of formula (XXII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_{21}$ is hydrogen, $R_{22}$ and $R_{23}$ are $C_1$alkoxy.

In another version of the aminocyclohexyl ether ion channel modulating compounds, the ion channel modulating compound is a compound of formula (XXII), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are $C_1$alkoxy.

In another version of the aminocyclohexyl ether ion channel modulating compounds, the ion channel modulating compound is a compound of formula (XXIII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

(XXIII)

wherein, $R_{21}$, $R_{22}$ and $R_{23}$ are independently selected from hydrogen, hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is a compound of formula (XXIII), or a solvate, pharmaceutically acceptable salt thereof, wherein, $R_{22}$ and $R_{23}$ are independently selected from hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is a compound of formula (XXIII), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are independently selected from hydroxy and $C_1$-$C_6$alkoxy.

In another version of the aminocyclohexyl ether ion channel modulating compounds, the ion channel modulating compound is a compound of formula (XXIII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_{21}$ is hydrogen, $R_{22}$ and $R_{23}$ are independently selected from $C_1$-$C_6$alkoxy.

In another version of the aminocyclohexyl ether ion channel modulating compounds, the ion channel modulating compound is a compound of formula (XXIII), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are independently selected from $C_1$-$C_6$alkoxy.

In another version of the aminocyclohexyl ether ion channel modulating compounds, the ion channel modulating compound is a compound of formula (XXIII), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_{21}$ is hydrogen, $R_{22}$ and $R_{23}$ are $C_1$alkoxy.

In another version of the aminocyclohexyl ether ion channel modulating compounds, the ion channel modulating compound is a compound of formula (XXIII), or a solvate, pharmaceutically acceptable salt thereof, including isolated enantiomeric, diastereomeric and geometric isomers thereof, and mixtures thereof, wherein, $R_{21}$ is hydrogen, $R_{22}$ and $R_{23}$ are $C_1$alkoxy.

In another version of the aminocyclohexyl ether ion channel modulating compounds, the ion channel modulating compound is a compound of formula (XXIV), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof:

(XXIV)

wherein, $R_{22}$ and $R_{23}$ are independently selected from hydrogen, hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is a compound of formula (XXIV), or a solvate, pharmaceutically acceptable salt thereof, including isolated enantiomeric, diastereomeric and geometric isomers thereof, and mixtures thereof.

In another version of the aminocyclohexyl ether ion channel modulating compounds, the ion channel modulating compound is a compound of formula (XXIV), or a solvate, pharmaceutically acceptable salt thereof, wherein, $R_{22}$ and $R_{23}$ are independently selected from hydroxy and $C_1$-$C_6$alkoxy, including isolated enantiomeric, diastereomeric and geometric isomers thereof, and mixtures thereof.

In another version of the aminocyclohexyl ether ion channel modulating compounds, the ion channel modulating compound is a compound of formula (XXIV), or a solvate, pharmaceutically acceptable salt thereof, including isolated enantiomeric, diastereomeric and geometric isomers thereof, and mixtures thereof, wherein, $R_{22}$ and $R_{23}$ are independently selected from hydroxy and $C_1$-$C_3$alkoxy.

In another version of the aminocyclohexyl ether ion channel modulating compounds, the ion channel modulating compound is a compound of formula (XXIV), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_{22}$ and $R_{23}$ are independently selected from $C_1$-$C_6$alkoxy.

In another version of the aminocyclohexyl ether ion channel modulating compounds, the ion channel modulating compound is a compound of formula (XXIV), or a solvate, pharmaceutically acceptable salt thereof, including isolated enantiomeric, diastereomeric and geometric isomers thereof, and mixtures thereof, wherein, $R_{22}$ and $R_{23}$ are independently selected from $C_1$-$C_3$alkoxy.

In another version of the aminocyclohexyl ether ion channel modulating compounds, the ion channel modulating compound is a compound of formula (XXIV), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, wherein, $R_{22}$ and $R_{23}$ are $C_1$alkoxy.

In another version of the aminocyclohexyl ether ion channel modulating compounds, the ion channel modulating compound is a compound of formula (XXIV), or a solvate, pharmaceutically acceptable salt thereof, including isolated enantiomeric, diastereomeric and geometric isomers thereof, and mixtures thereof, wherein, $R_{22}$ and $R_{23}$ are $C_1$alkoxy.

In another version of the aminocyclohexyl ether ion channel modulating compounds, the ion channel modulating compound is a compound of the formula (XXV),

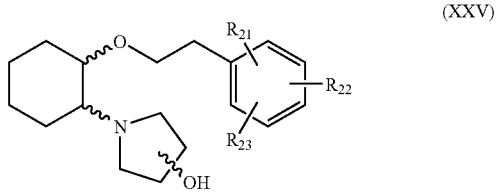

(XXV)

wherein:
$R_{21}$, $R_{22}$ and $R_{23}$ are independently selected from hydrogen, hydroxy and $C_1$-$C_6$alkoxy; or,
$R_{21}$, $R_{22}$ are independently selected from hydroxyl and $C_1$-$C_6$alkoxy and $R_{23}$ is hydrogen; or,
$R_{21}$, $R_{22}$ are both $C_1$-$C_6$alkoxy and $R_{23}$ is hydrogen; or
$R_{21}$, $R_{22}$ are both methoxy and $R_{23}$ is hydrogen; or
including isolated enantiomeric, diastereomeric and geometric isomers thereof, and mixtures thereof, with the proviso that $R_{21}$, $R_{22}$ and $R_{23}$ cannot all be hydrogen; and
∾∾∾indicates a bond that provides a R stereoisomer or a S stereoisomer at the position to which the bond is attached.

In one variation, the hydroxyl substituent is positioned at the 3 position of the pyrrolidinyl ring in (XXV). In another variation, the stereochemistry at the position of the cycloalkyl ring of (XXV) containing the nitrogen group is racemic, which may be provided for any of the variations mentioned above.

In another version of the aminocyclohexyl ether ion channel modulating compounds, the ion channel modulating compound is a compound of the formula (XXVI):

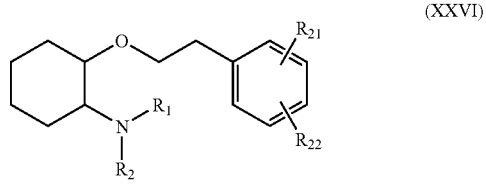

(XXVI)

wherein:
the ---- bond to the ether oxygen indicates that the ether and amine groups attached to the cyclohexyl group are in a trans configuration. and the C-1 and C-2 carbons of the cyclohexyl group may be either R,R configuration or S,S configuration;
$R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or
$R_1$ and $R_2$ are independently selected from $C_3$-$C_8$alkoxyalkyl, $C_1$-$C_8$hydroxyalkyl, and $C_7$-$C_{12}$aralkyl; or $R_1$ and $R_2$, are taken together with the nitrogen atom to which they are directly attached in formula (XXVI) to form a ring denoted by formula (II):

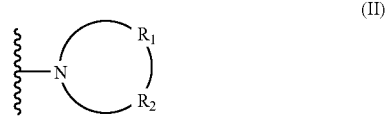

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$ are taken together to form

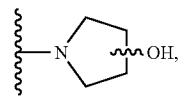

wherein the OH group may be at any position on the pyrrolidinyl ring, including the 3-position;

$R_1$ and $R_2$, when taken together with the nitrogen atom to which they are directly attached in formula (XXVI), may form a bicyclic ring system selected from 3-azabicyclo[3.2.2] nonan-3-yl, 2-azabicyclo[2.2.2]octan-2-yl, 3-azabicyclo [3.1.0]hexan-3-yl and 3-azabicyclo[3.2.0]heptan-3-yl; and $R_{21}$ and $R_{22}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and $N(R_{15},R_{16})$ where $R_{15}$ and $R_{16}$ are independently selected from hydrogen, acetyl, methanesulfonyl and $C_1$-$C_6$alkyl.

In one version of formula (XXVI), $R_{21}$, and $R_{22}$ are independently selected from hydrogen, hydroxyl and $C_1$-$C_6$alkoxy. In another version of formula (XXVI), both $R_2$, and $R_{22}$ are $C_1$-$C_6$alkoxy. In another variation, both $R_{21}$ and $R_{22}$ are methoxy. In still another variation of formula (XXVI), $R_{21}$ and $R_{22}$ are positioned at the 3 and 4 positions of the aromatic ring, wherein the position on the aromatic ring containing the alkyl chain is designated the 1 position, this variation may be combined with any other variation mentioned above.

In another version of the aminocyclohexyl ether ion channel modulating compounds, the ion channel modulating compound is of the formula shown as Compound A, or pharmaceutically acceptable salts or solvates thereof.

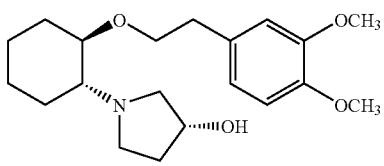

Compound A (1R,2R)-2-[(3R)-hydroxypyrrolidinyl]-1-(3,4-dimethoxyphenethoxy)cyclohexane In another version of the aminocyclohexyl ether ion channel modulating compounds, the ion channel modulating compound is a pharmaceutically acceptable salt of Compound A, such as the compound of the formula (XXVII),

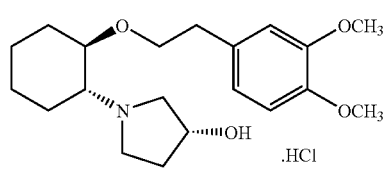

(XXVII)

(1R,2R)-2-[(3R)-hydroxypyrrolidinyl]-1-(3,4-dimethoxyphenethoxy)cyclohexane monohydrochloride.

In one variation, the ion channel modulating compound comprises a cycloalkyl ring, such as a cyclohexyl ring, wherein the cycloalkyl ring comprises two adjacent substituents, such as substituents at the 1 and 2 position of the cycloalkyl ring, wherein the two adjacent substituents are situated in trans stereochemical positions relative to one another. In one variation, one of the two adjacent substituents is an amino substituent bound to the cycloalkyl ring via a nitrogen atom and one of the two adjacent substituents is an ether substituent bound to the cycloalkyl ring via an oxygen atom.

In another version of the aminocyclohexyl ether ion channel modulating compounds, the ion channel modulating compound is a compound or any salt thereof, or any solvate thereof, or mixture comprising one or more said compounds or any salt thereof, or any solvate thereof, selected from the group consisting of:

| | |
|---|---|
| (1R,2R)-[2-(4-morpholinyl)-1-(2-naphthenethoxy)] cyclohexane or (1S,2S)-[2-(4-morpholinyl)-1-(2-naphthenethoxy)] cyclohexane or a mixture of (1R,2R)-[2-(4-morpholinyl)-1-(2-naphthenethoxy)] cyclohexane and (1S,2S)-[2-(4-morpholinyl)-1-(2-naphthenethoxy)] cyclohexane | 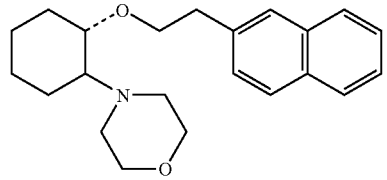 |
| (1R,2R)-[2-(4-morpholinyl)-1-(1-naphthenethoxy)] cyclohexane or (1S,2S)-[2-(4-morpholinyl)-1-(1-naphthenethoxy)] cyclohexane or a mixture of (1R,2R)-[2-(4-morpholinyl)-1-(1-naphthenethoxy)] cyclohexane and (1S,2S)-[2-(4-morpholinyl)-1-(1-naphthenethoxy)] | 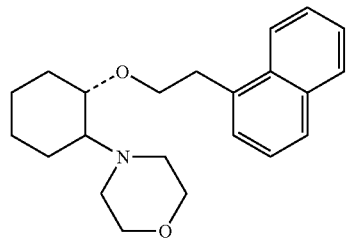 |
| (1R,2R)-[2-(4-morpholinyl)-1-(4-bromophenethoxy)] cyclohexane or (1S,2S)-[2-(4-morpholinyl)-1-(4-bromophenethoxy)] cyclohexane or a mixture of (1R,2R)-[2-(4-morpholinyl)-1-(4-bromophenethoxy)] cyclohexane and (1S,2S)-[2-(4-morpholinyl)-1-(4-bromophenethoxy)] cyclohexane | 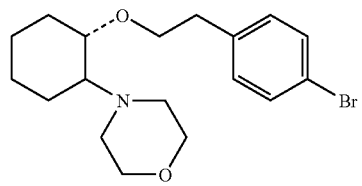 |
| (1R,2R)-[2-(4-morpholinyl)-1-[2-(2-naphthoxy)ethoxy]] cyclohexane or (1S,2S)-[2-(4-morpholinyl)-1-[2-(2-naphthoxy)ethoxy]] cyclohexane or a mixture of (1R,2R)-[2-(4-morpholinyl)-1-[2-(2-naphthoxy)ethoxy]] cyclohexane and (1S,2S)-[2-(4-morpholinyl)-1-[2-(2-naphthoxy)ethoxy]] cyclohexane | 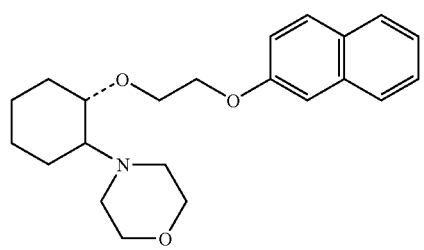 |

| | |
|---|---|
| (1R,2R)-[2-(4-morpholinyl)-1-[2-(4-bromophenoxy) ethoxy]] cyclohexane or (1S,2S)-[2-(4-morpholinyl)-1-[2-(4-bromophenoxy) ethoxy]] cyclohexane or a mixture of (1R,2R)-[2-(4-morpholinyl)-1-[2-(4-bromophenoxy) ethoxy]] cyclohexane and (1S,2S)-[2-(4-morpholinyl)-1-[2-(4-bromophenoxy) ethoxy]] cyclohexane | 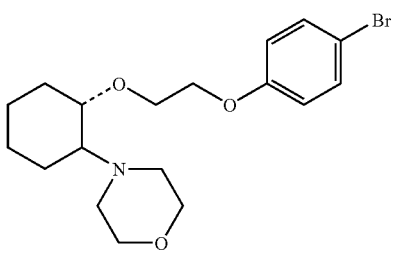 |
| (1R,2R)-[2-(4-morpholinyl)-1-(3,4-dimethoxyphen ethoxy)] cyclohexane or (1S,2S)-[2-(4-morpholinyl)-1-(3,4-dimethoxyphen ethoxy)] cyclohexane or a mixture of (1R,2R)-[2-(4-morpholinyl)-1-(3,4-dimethoxyphen ethoxy)] cyclohexane and (1S,2S)-[2-(4-morpholinyl)-1-(3,4-dimethoxyphen ethoxy)] cyclohexane | 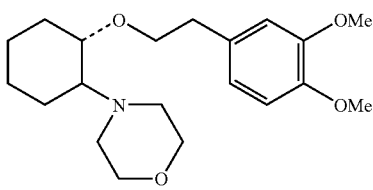 |
| (1R,2R)-[2-(1-pyrrolidinyl)-1-(1-naphthenethoxy)] cyclohexane or (1S,2S)-[2-(1-pyrrolidinyl)-1-(1-naphthenethoxy)] cyclohexane or a mixture of (1R,2R)-[2-(1-pyrrolidinyl)-1-(1-naphthenethoxy)] cyclohexane and (1S,2S)-[2-(1-pyrrolidinyl)-1-(1-naphthenethoxy)] cyclohexane | 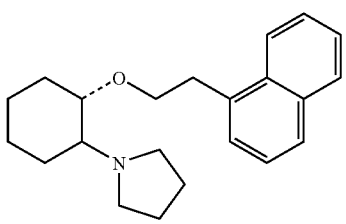 |
| (1R,2R)-[2-(4-morpholinyl)-1-(2-(benzo[b]thiophen-3-yl)] cyclohexane or (1S,2S)-[2-(4-morpholinyl)-1-(2-(benzo[b]thiophen-3-yl)] cyclohexane or a mixture of (1R,2R)-[2-(4-morpholinyl)-1-(2-(benzo[b]thiophen-3-yl)] cyclohexane and (1S,2S)-[2-(4-morpholinyl)-1-(2-(benzo[b]thiophen-3-yl)] cyclohexane | 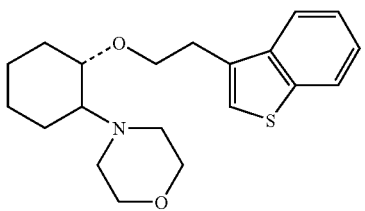 |
| (1R,2R)-[2-(4-morpholinyl)-1-(2-(benzo[b]thiophen-4-yl)] cyclohexane or (1S,2S)-[2-(4-morpholinyl)-1-(2-(benzo[b]thiophen-4-yl)] cyclohexane or a mixture of (1R,2R)-[2-(4-morpholinyl)-1-(2-(benzo[b]thiophen-4-yl)] cyclohexane and (1S,2S)-[2-(4-morpholinyl)-1-(2-(benzo[b]thiophen-4-yl)] cyclohexane | 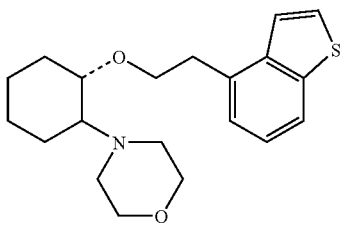 |
| (1R,2R)-[2-(4-morpholinyl)-1-(3-bromophenethoxy)] cyclohexane or (1S,2S)-[2-(4-morpholinyl)-1-(3-bromophenethoxy)] cyclohexane or a mixture of (1R,2R)-[2-(4-morpholinyl)-1-(3-bromophenethoxy)] cyclohexane and (1S,2S)-[2-(4-morpholinyl)-1-(3-bromophenethoxy)] cyclohexane | 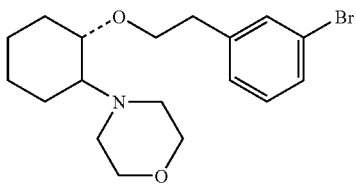 |
| (1R,2R)-[2-(4-morpholinyl)-1-(2-bromophenethoxy)] cyclohexane or (1S,2S)-[2-(4-morpholinyl)-1-(2-bromophenethoxy)] cyclohexane or (1R,2R)-[2-(4-morpholinyl)-1-(2-bromophenethoxy)] cyclohexane and (1S,2S)-[2-(4-morpholinyl)-1-(2-bromophenethoxy)] cyclohexane | 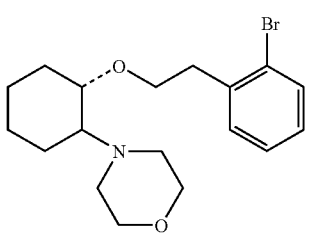 |

-continued

| | |
|---|---|
| (1R,2R)-[2-(4-morpholinyl)-1-(3-(3,4-dimethoxyphenyl) propoxy)] cyclohexane or (1S,2S)-[2-(4-morpholinyl)-1-(3-(3,4-dimethoxyphenyl) propoxy)] cyclohexane or a mixture of (1R,2R)-[2-(4-morpholinyl)-1-(3-(3,4-dimethoxyphenyl) propoxy)] cyclohexane and (1S,2S)-[2-(4-morpholinyl)-1-(3-(3,4-dimethoxyphenyl) propoxy)] cyclohexane | 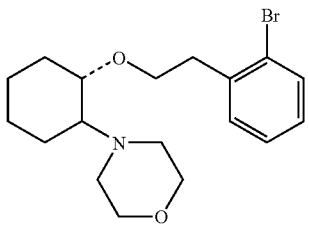 |
| (1R,2R)-[2-[bis(2-methoxyethyl)aminyl]-1-(2-naphthen ethoxy)] cyclohexane or (1S,2S)-[2-[bis(2-methoxyethyl)aminyl]-1-(2-naphthenethoxy)] cyclohexane and a mixture of (1R,2R)-[2-[bis(2-methoxyethyl)aminyl]-1-(2-naphthenethoxy)] cyclohexane and (1S,2S)-[2-[bis(2-methoxyethyl)aminyl]-1-(2-naphthenethoxy)] cyclohexane | 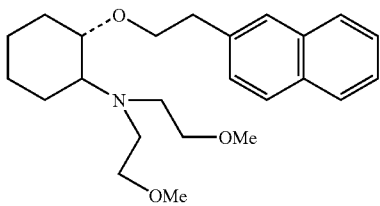 |
| (1R,2R)-2-(4-morpholinyl)-1-(3,4-dichlorophenethoxy) cyclohexane or (1S,2S)-2-(4-morpholinyl)-1(3,4 dichlorophenethoxy) cyclohexane or a mixture of (1R,2R)-2-(4-morpholinyl)-1-(3,4-dichlorophenethoxy) cyclohexane and (1S,2S)-2-(4-morpholinyl)-1-(3,4-dichlorophenethoxy) cyclohexane | 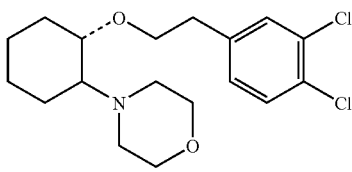 |
| (1R,2R)-2-(3-ketopyrrolidinyl)-1-(1-naphthenethoxy) cyclohexane or (1S,2S)-2-(3-ketopyrrolidinyl)-1-(1-naphthenethoxy) cyclohexane or a mixture of (1R,2R)-2-(3-ketopyrrolidinyl)-1-(1-naphthenethoxy) cyclohexane and (1S,2S)-2-(3-ketopyrrolidinyl)-1-(1-naphthenethoxy) cyclohexane | 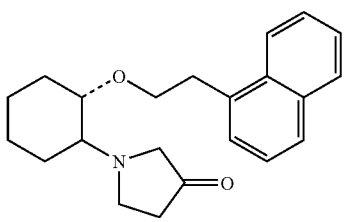 |
| (1R,2R)-2-(1-acetylpiperazinyl)-1-(2-naphthenethoxy) cyclohexane or (1S,2S)-2-(1-acetylpiperazinyl)-1-(2-naphthenethoxy) cyclohexane or a mixture of(1R,2R)-2-(1-acetylpiperazinyl)-1-(2-naphthenethoxy) cyclohexane and (1S,2S)-2-(1-acetylpiperazinyl)-1-(2-naphthenethoxy) cyclohexane | 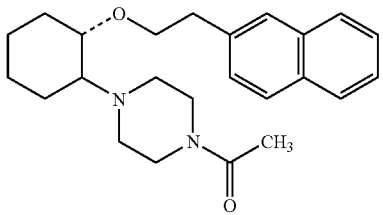 |
| (1R,2R)-2-(3-ketopyrrolidinyl)-1-(2,6-dichlorophenethoxy) cyclohexane or (1S,2S)-2-(3-ketopyrrolidinyl)-1-(2,6-dichlorophenethoxy) cyclohexane or a mixture of (1R,2R)-2-(3-ketopyrrolidinyl)-1-(2,6-dichlorophenethoxy) cyclohexane and (1S,2S)-2-(3-ketopyrrolidinyl)-1-(2,6-dichlorophenethoxy) cyclohexane | 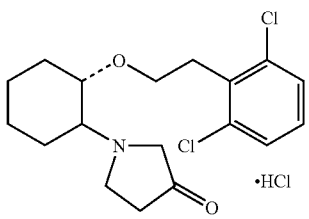 |
| (1R,2R)-2-[1,4-dioxa-7-azaspiro[4.4]non-7-yl]-1-(1-naphthenethoxy) cyclohexane or (1S,2S)-2-[1,4-dioxa-7-azaspiro [4.4]non-7-yl]-1-(1-naphthenethoxy) cyclohexane and a mixture of (1R,2R)-2-[1,4-dioxa-7-azaspiro[4.4]non-7-yl]-1-(1-naphthenethoxy) cyclohexane and (1S,2S)-2-[1,4-dioxa-7-azaspiro[4.4]non-7-yl]-1-(1-naphthenethoxy) cyclohexane | 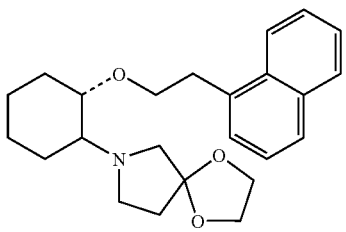 |

-continued

| | |
|---|---|
| (1R,2S)-2-(4-morpholinyl)-1-[(2-trifluoromethyl)phenethoxy] cyclohexane monohydrochloride or (1S,2R)-2-(4-morpholinyl)-1-[(2-trifluoromethyl)phenethoxy] cyclohexane monohydrochloride or a mixture of(1R,2S)-2-(4-morpholinyl)-1-[(2-trifluoromethyl)phenethoxy] cyclohexane monohydrochloride and (1S,2R)-2-(4-morpholinyl)-1-[(2-trifluoromethyl)phenethoxy] cyclohexane monohydrochloride | 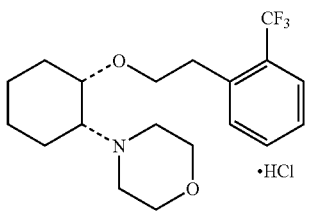 |
| (1R,2R)-2-(3-ketopyrrolidinyl)-1-[3-(cyclohexyl)propoxy] cyclohexane monohydrochloride or (1S,2S)-2-(3-ketopyrrolidinyl)-1-[3-(cyclohexyl)propoxy] cyclohexane monohydrochloride or a mixture of (1R,2R)-2-(3-ketopyrrolidinyl)-1-[3-(cyclohexyl)propoxy] cyclohexane monohydrochloride and (1S,2S)-2-(3-ketopyrrolidinyl)-1-[3-(cyclohexyl)propoxy] cyclohexane monohydrochloride | 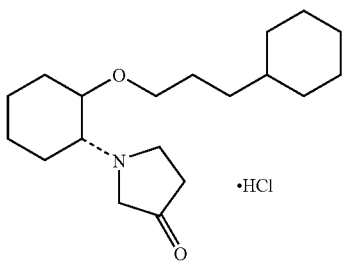 |
| (1R,2R)-2-(3-acetoxypyrrolidinyl)-1-(1-naphthenethoxy) cyclohexane monohydrochloride or (1S,2S)-2-(3-acetoxypyrrolidinyl)-1-(1-naphthenethoxy) cyclohexane monohydrochloride or a mixture of (1R,2R)-2-(3-acetoxypyrrolidinyl)-1-(1-naphthenethoxy) cyclohexane monohydrochloride and (1S,2S)-2-(3-acetoxypyrrolidinyl)-1-(1-naphthenethoxy) cyclohexane monohydrochloride | 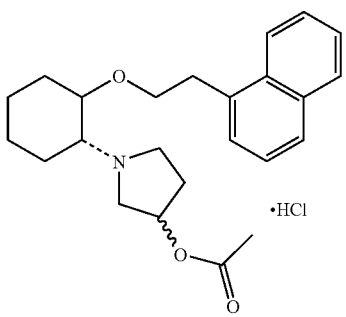 |
| (1R,2R)-2-(4-morpholinyl)-1-[(2,6-dichlorophenyl)methoxy] cyclohexane monohydrochloride or (1S,2S)-2-(4-morpholinyl)-1-[(2,6-dichlorophenyl)methoxy] cyclohexane monohydrochloride or a mixture of(1R,2R)-2-(4-morpholinyl)-1-[(2,6-dichlorophenyl)methoxy] cyclohexane monohydrochloride and (1S,2S)-2-(4-morpholinyl)-1-[(2,6-dichlorophenyl)methoxy] cyclohexane monohydrochloride | 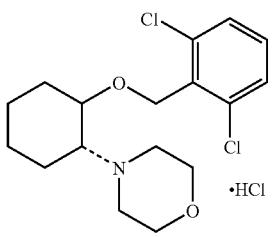 |
| (1R,2R)-2-(3-ketopyrrolidinyl)-1-[(2,6-dichlorophenyl)methoxy] cyclohexane monohydrochloride or (1S,2S)-2-(3-ketopyrrolidinyl)-1-[(2,6-dichlorophenyl)methoxy] cyclohexane monohydrochloride or a mixture of (1R,2R)-2-(3-ketopyrrolidinyl)-1-[(2,6-dichlorophenyl) methoxy] cyclohexane monohydrochloride and (1S,2S)-2-(3-ketopyrrolidinyl)-1-[(2,6-dichlorophenyl) methoxy] cyclohexane monohydrochloride | 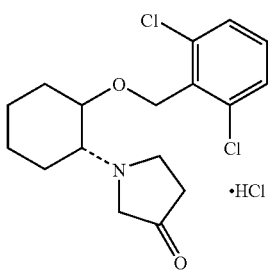 |
| (1R,2R)-2-(3-hydroxypyrrolidinyl)-1-(2,6-dichlorophenethoxy) cyclohexane monohydrochloride or (1S,2S)-2-(3-hydroxypyrrolidinyl)-1-(2,6-dichlorophenethoxy) cyclohexane monohydrochloride or a mixture of (1R,2R)-2-(3-hydroxypyrrolidinyl)-1-(2,6-dichlorophenethoxy) cyclohexane monohydrochloride and (1S,2S)-2-(3-hydroxypyrrolidinyl)-1-(2,6-dichlorophenethoxy) cyclohexane monohydrochloride, wherein the hydroxyl moiety in any of the above may be in the R or S stereochemical configuration. | 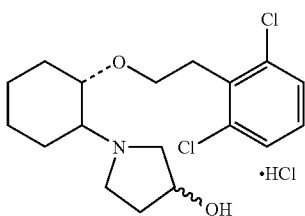 |

| | |
|---|---|
| (1R,2R)-2-(3-ketopyrrolidinyl)-1-(2,2-diphenylethoxy) cyclohexane monohydrochloride or (1S,2S)-2-(3-ketopyrrolidinyl)-1-(2,2-diphenylethoxy) cyclohexane monohydrochloride or a mixture of(1R,2R)-2-(3-ketopyrrolidinyl)-1-(2,2-diphenylethoxy) cyclohexane monohydrochloride and (1S,2S)-2-(3-ketopyrrolidinyl)-1-(2,2-diphenylethoxy) cyclohexane monohydrochloride | 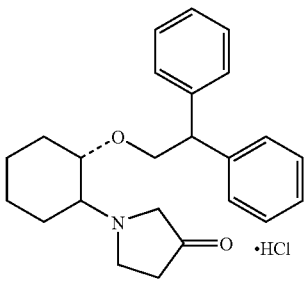 |
| (1R,2R)-2-(3-thiazolidinyl)-1-(2,6-dichlorophenethoxy) cyclohexane monohydrochloride or (1S,2S)-2-(3-thiazolidinyl)-1-(2,6-dichlorophenethoxy) cyclohexane monohydrochloride or a mixture of(1R,2R)-2-(3-thiazolidinyl)-1-(2,6-dichlorophenethoxy) cyclohexane monohydrochloride and (1S,2S)-2-(3-thiazolidinyl)-1-(2,6-dichlorophenethoxy) cyclohexane monohydrochloride | 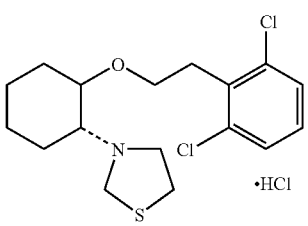 |
| (1R,2S)-2-(3-ketopyrrolidinyl)-1-(1-naphthenethoxy) cyclohexane monohydrochloride or (1S,2R)-2-(3-ketopyrrolidinyl)-1-(1-naphthenethoxy) cyclohexane monohydrochloride or a mixture of(1R,2S)-2-(3-ketopyrrolidinyl)-1-(1-naphthenethoxy) cyclohexane monohydrochloride and (1S,2R)-2-(3-ketopyrrolidinyl)-1-(1-naphthenethoxy) cyclohexane monohydrochloride | 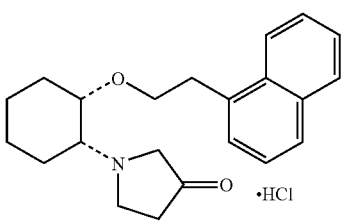 |
| (1R,2R)-2-(3-hydroxypyrrolidinyl)-1-(3,4-dimethoxyphenethoxy) cyclohexane monohydrochloride or (1S,2S)-2-(3-hydroxypyrrolidinyl)-1-(3,4-dimethoxyphenethoxy) cyclohexane monohydrochloride or a mixture of (1R,2R)-2-(3-hydroxypyrrolidinyl)-1-(3,4-dimethoxyphenethoxy) cyclohexane monohydrochloride and (1S,2S)-2-(3-hydroxypyrrolidinyl)-1-(3,4-dimethoxyphenethoxy) cyclohexane monohydrochloride, wherein the hydroxyl moiety in any of the above may be in the R or S stereochemical configuration. | 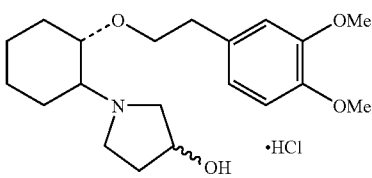 |

Also described here is a composition that includes one or more of the compounds or mixtures listed in the above table, or includes a solvate or a pharmaceutically acceptable salt of one or more of the compounds or mixtures listed in the above table. The composition may or may not include additional components. Additional components that may be used are described elsewhere in detail in this patent.

In another version of the aminocyclohexyl ether ion channel modulating compounds, the ion channel modulating compound is a compound or mixture comprising compounds, or any solvate thereof, selected from the group consisting of:

| Structure | Chemical name |
|---|---|
| | (1R,2R)-2-[(3R)/(3S)-Hydroxypyrrolidinyl]-1-(3,4-dimethoxyphenethoxy)-cyclohexane or (1S,2S)-2-[(3R)/(3S)-hydroxypyrrolidinyl]-1-(3,4-dimethoxyphenethoxy)-cyclohexane or a mixture of (1R,2R)-2-[(3R)/(3S)-hydroxypyrrolidinyl]-1-(3,4-dimethoxyphenethoxy)-cyclohexane and (1S,2S)-2-[(3R)/(3S)-hydroxypyrrolidinyl]-1-(3,4-dimethoxyphenethoxy)-cyclohexane, where the designation (3R)/(3S) indicates the stereochemistry at the 3-position may be R or S. |

-continued

| Structure | Chemical name |
|---|---|
| 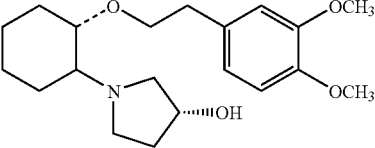 | (1R,2R)-2-[(3R)-Hydroxypyrrolidinyl]-1-(3,4-dimethoxyphenethoxy)-cyclohexane or (1S,2S)-2-[(3R)-hydroxypyrrolidinyl]-1-(3,4-dimethoxyphenethoxy)-cyclohexane and a mixture of (1R,2R)-2-[(3R)-hydroxypyrrolidinyl]-1-(3,4-dimethoxyphenethoxy)-cyclohexane and (1S,2S)-2-[(3R)-hydroxypyrrolidinyl]-1-(3,4-dimethoxyphenethoxy)-cyclohexane |
| 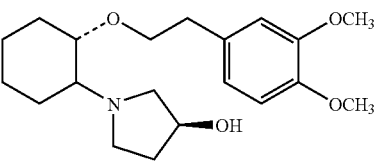 | (1R,2R)-2-[(3S)-Hydroxypyrrolidinyl]-1-(3,4-dimethoxyphenethoxy)-cyclohexane or (1S,2S)-2-[(3S)-hydroxypyrrolidinyl]-1-(3,4-dimethoxyphenethoxy)-cyclohexane and a mixture of (1R,2R)-2-[(3S)-hydroxypyrrolidinyl]-1-(3,4-dimethoxyphenethoxy)-cyclohexane and (1S,2S)-2-[(3S)-hydroxypyrrolidinyl]-1-(3,4-dimethoxyphenethoxy)-cyclohexane |
| 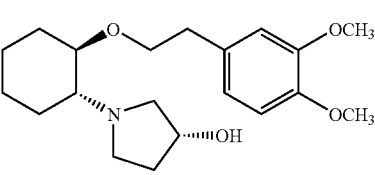 | (1R,2R)-2-[(3R)-Hydroxypyrrolidinyl]-1-(3,4-dimethoxyphenethoxy)-cyclohexane |
| 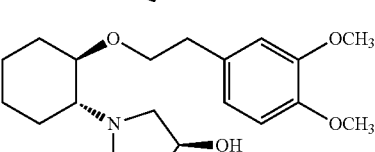 | (1R,2R)-2-[(3S)-Hydroxypyrrolidinyl]-1-(3,4-dimethoxyphenethoxy)-cyclohexane |
| 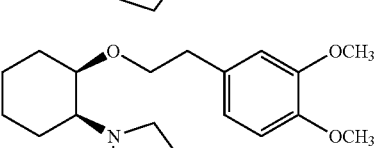 | (1R,2S)-2-[(3R)-Hydroxypyrrolidinyl]-1-(3,4-dimethoxyphenethoxy)-cyclohexane |
| 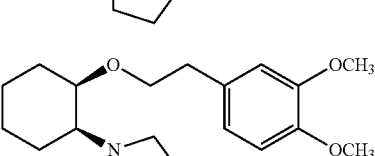 | (1R,2S)-2-[(3S)-Hydroxypyrrolidinyl]-1-(3,4-dimethoxyphenethoxy)-cyclohexane |
| 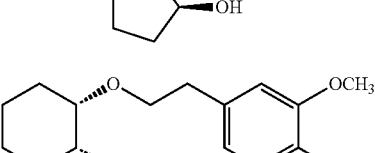 | (1S,2R)-2-[(3R)-Hydroxypyrrolidinyl]-1-(3,4-dimethoxyphenethoxy)-cyclohexane |
| 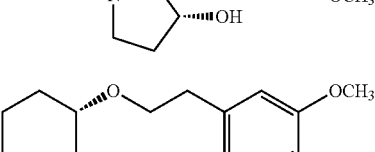 | (1S,2R)-2-[(3S)-Hydroxypyrrolidinyl]-1-(3,4-dimethoxyphenethoxy)-cyclohexane |
| 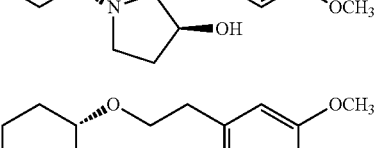 | (1S,2S)-2-[(3R)-Hydroxypyrrolidinyl]-1-(3,4-dimethoxyphenethoxy)-cyclohexane |

-continued

| Structure | Chemical name |
|---|---|
| 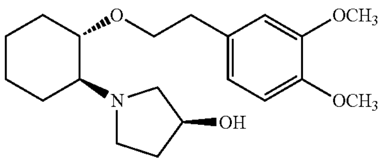 | (1S,2S)-2-[(3S)-Hydroxypyrrolidinyl]-1-(3,4-dimethoxyphenethoxy)-cyclohexane |
| 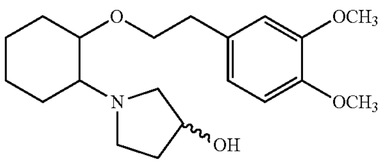 | (1R,2S)-2-[(3R)/(3S)-Hydroxypyrrolidinyl]-1-(3,4-dimethoxyphenethoxy)-cyclohexane or (1S,2R)-2-[(3R)/(3S)-hydroxypyrrolidinyl]-1-(3,4-dimethoxyphen ethoxy)-cyclohexane or a mixture of (1R,2S)-2-[(3R)/(3S)-hydroxypyrrolidinyl]-1-(3,4-dimethoxyphenethoxy)-cyclohexane and (1S,2R)-2-[(3R)/(3S)-hydroxypyrrolidinyl]-1-(3,4-dimethoxyphen ethoxy)-cyclohexane, where the designation (3R)/(3S) indicates the stereochemistry at the 3-position may be R or S. |
| 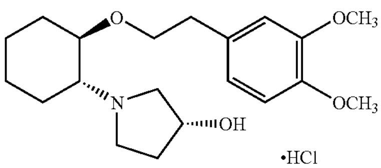 | (1R,2R)-2-[(3R)-Hydroxypyrrolidinyl]-1-(3,4-dimethoxyphenethoxy)-cyclohexane monohydrochloride |
| 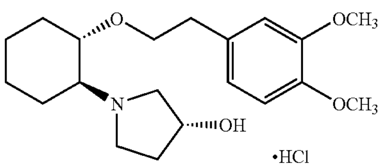 | (1S,2S)-2-[(3R)-Hydroxypyrrolidinyl]-1-(3,4-dimethoxyphenethoxy)-cyclohexane monohydrochloride |
| 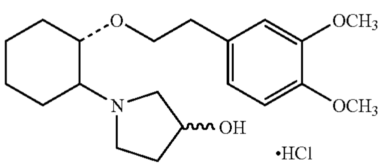 | (1R,2R)-2-[(3R)/(3S)-Hydroxypyrrolidinyl]-1-(3,4-dimethoxyphenethoxy)-cyclohexane monohydrochloride or (1S,2S)-2-[(3R)/(3S)-hydroxypyrrolidinyl]-1-(3,4-dimethoxyphenethoxy)-cyclohexane monohydrochloride or a mixture of (1R,2R)-2-[(3R)/(3S)-hydroxypyrrolidinyl]-1-(3,4-dimethoxyphenethoxy)-cyclohexane monohydrochloride and (1S,2S)-2-[(3R)/(3S)-hydroxypyrrolidinyl]-1-(3,4-dimethoxyphenethoxy)-cyclohexane monohydrochloride, where the designation (3R)/(3S) indicates the stereochemistry at the 3-position may be R or S. |
| 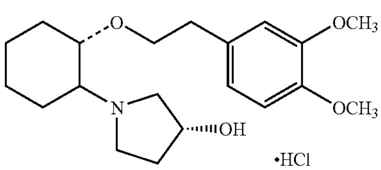 | (1R,2R)-2-[(3R)-Hydroxypyrrolidinyl]-1-(3,4-dimethoxyphenethoxy)-cyclohexane monohydrochloride or (1S,2S)-2-[(3R)-hydroxypyrrolidinyl]-1-(3,4-dimethoxyphenethoxy)-cyclohexane monohydrochloride or a mixture of (1R,2R)-2-[(3R)-hydroxypyrrolidinyl]-1-(3,4-dimethoxyphenethoxy)-cyclohexane monohydrochloride and (1S,2S)-2-[(3R)-hydroxypyrrolidinyl]-1-(3,4-dimethoxyphenethoxy)-cyclohexane monohydrochloride |
| 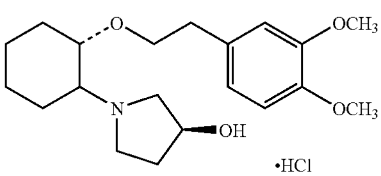 | (1R,2R)-2-[(3S)-Hydroxypyrrolidinyl]-1-(3,4-dimethoxyphenethoxy)-cyclohexane monohydrochloride or (1S,2S)-2-[(3S)-hydroxypyrrolidinyl]-1-(3,4-dimethoxyphenethoxy)-cyclohexane monohydrochloride or a mixture of (1R,2R)-2-[(3S)-hydroxypyrrolidinyl]-1-(3,4-dimethoxyphenethoxy)-cyclohexane monohydrochloride and (1S,2S)-2-[(3S)-hydroxypyrrolidinyl]-1-(3,4-dimethoxyphenethoxy)-cyclohexane monohydrochloride |
| 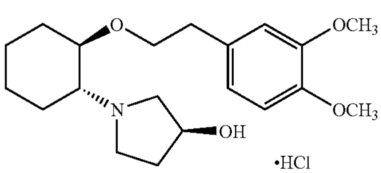 | (1R,2R)-2-[(3S)-Hydroxypyrrolidinyl]-1-(3,4-dimethoxyphenethoxy)-cyclohexane monohydrochloride |

| Structure | Chemical name |
|---|---|
| ![structure] | (1S,2S)-2-[(3S)-Hydroxypyrrolidinyl]-1-(3,4-dimethoxyphenethoxy)-cyclohexane monohydrochloride |

Also described here is a composition that includes one or more of the compounds or mixtures listed in the above table, or includes a solvate or a pharmaceutically acceptable salt of one or more of the compounds or mixtures listed in the above table. The composition may or may not include additional components. Additional components that may be used are described elsewhere in detail in this patent.

In another version of the aminocyclohexyl ether ion channel modulating compounds, the ion channel modulating compound is one of the following compounds: (1R,2R)-2-[(3R)-hydroxypyrrolidinyl]-1-(3,4-dimethoxyphenethoxy)-cyclohexane free base or any salt thereof, or any solvate thereof; (1R,2R)-2-[(3S)-hydroxypyrrolidinyl]-1-(3,4-dimethoxyphenethoxy)-cyclohexane free base or any salt thereof, or any solvate thereof; (1S,2S)-2-[(3R)-hydroxypyrrolidinyl]-1-(3,4-dimethoxyphenethoxy)-cyclohexane free base or any salt thereof, or any solvate thereof, (1S,2S)-2-[(3S)-hydroxypyrrolidinyl]-1-(3,4-dimethoxyphenethoxy)-cyclohexane free base or any salt thereof, or any solvate thereof, (1R,2R)-2-[(3R)-hydroxypyrrolidinyl]-1-(3,4-dimethoxyphenethoxy)-cyclohexane monohydrochloride, or any solvate thereof, (1R,2R)-2-[(3S)-hydroxypyrrolidinyl]-1-(3,4-dimethoxyphenethoxy)-cyclohexane monohydrochloride, or any solvate thereof, (1S,2S)-2-[(3R)-hydroxypyrrolidinyl]-1-(3,4-dimethoxyphenethoxy)-cyclohexane monohydrochloride, or any solvate thereof, or (1S,2S)-2-[(3S)-hydroxypyrrolidinyl]-1-(3,4-dimethoxyphenethoxy)-cyclohexane monohydrochloride, or any solvate thereof.

In another version of the aminocyclohexyl ether ion channel modulating compounds, the ion channel modulating compound is a protonated version of any of the aminocyclohexyl ether compounds described in this patent. That is, for each aminocyclohexyl ether compound described in this patent, the quaternary protonated amine form of the compound may also be considered as an aminocyclohexyl ether ion channel modulating compound. These quaternary protonated amine forms of the compounds may be present in the solid phase, for example in crystalline or amorphous form, and may be present in solution. These quaternary protonated amine forms of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

Aminocycloalkyl Ether Ion Channel Modulating Compounds with 5, 7, and 8 Membered Cycloalkyl Rings One class of compounds that are ion channel modulating compound comprise an aminocycloalkyl ether core structure having an ether oxygen atom at position 1 of a cycloalkyl ring, and an amine nitrogen atom at position 2 of the cycloalkyl ring. In one version the cycloalkyl ring is a 5, 7, or 8 membered ring.

In one version of the aminocycloalkyl ether ion channel modulating compounds, the ion channel modulating compound is a compound having an ether oxygen atom ((Q=O) in formula (XXVIII)) at position 1 of a cycloalkyl ring, and an amine nitrogen atom at position 2 of the cycloalkyl ring, where the cycloalkyl ring is either cyclopentyl, cycloheptyl or cyclooctyl, with other positions numbered in corresponding order as shown below in structure (C) for cyclopentane, structure (D) for cycloheptane, and structure (E) for cyclooctane:

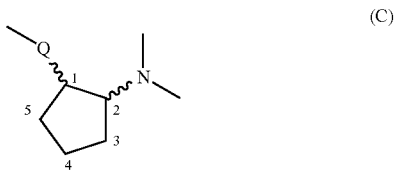

(C)

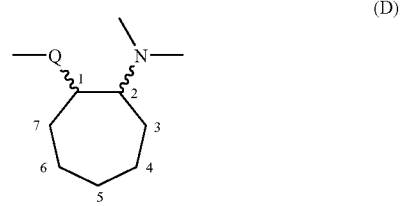

(D)

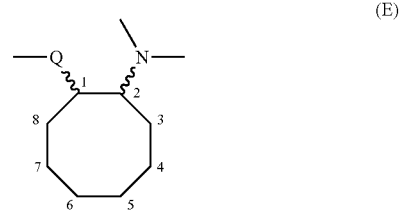

(E)

The bonds from the cycloalkyl ring to the 1-oxygen and 2-nitrogen atoms in the above formula may be relatively disposed in either a cis or trans relationship. In one version, the stereochemistry of the amine and ether substituents of the cycloalkyl ring is either (R,R)-trans or (S,S)-trans. In another version, the stereochemistry is either (R,S)-cis or (S,R)-cis.

In one version of the aminocycloalkyl ether ion channel modulating compounds, the ion channel modulating compound is a compound of formula (XXVIII):

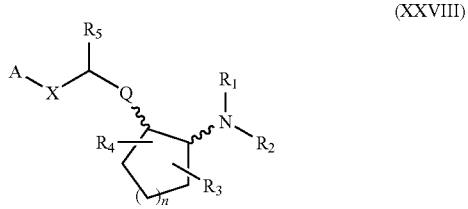

(XXVIII)

wherein the substituents A, $R_1$, $R_2$, $R_3$, $R_4$, $R_5$ and X are as described above for formula (I) and wherein Q is an ether oxygen atom (Q=O in formula (XXVIII)) and wherein n is 1, 3 or 4 such that a cyclopentyl, cycloheptyl or cyclooctyl ring is provided.

Compounds of formula (XXVIII) are cycloalkylamines such as aminocycloalkyl ethers. More specifically, these aminocycloalkyl ethers are substituted at position 2 of a cycloalkyl ring with an amine group —$NR_1R_2$. The C-1 position is an ether (Q=O in formula (XXVIII)). The cycloalkyl ring may also be substituted with additional substituents (designated as $R_3$ and $R_4$) as described in more detail below. In formula (XXVIII), n is selected from 1, 3 and 4, and represents a number of carbon atoms such that when n equals 1, the ring shown in Formula (XXVIII) is a substituted cyclopentane (i.e., a cyclopentyl group), when n equals 3, the ring shown in Formula (XXVIII) is a substituted cycloheptane (i.e., a cycloheptyl group), and when n equals 4, the ring shown in Formula (XXVIII) is a substituted cyclooctane (i.e., a cyclooctyl group). Examples of specific compounds represented by formula (XXVIII) are described below.

Depending upon the selection of substituents $R_1$ and $R_2$, the compounds of formula (XXVIII) may be primary, secondary, or tertiary amines (i.e., both $R_1$ and $R_2$ are hydrogen, only one of $R_1$ and $R_2$ is hydrogen, or neither of $R_1$ and $R_2$ are hydrogen, respectively). Where the amine is tertiary, it may be a cyclic amine. Amine substituents $R_1$ and $R_2$ may be independently selected from substituents which include hydrogen, alkyl groups containing from one to eight carbon atoms (i.e., $C_1$-$C_8$alkyl), alkoxyalkyl groups containing from three to eight carbon atoms (i.e., $C_3$-$C_8$alkoxyalkyl), alkyl groups containing from one to eight carbon atoms where one of the carbon atoms is substituted with a hydroxyl group (i.e., $C_1$-$C_8$hydroxyalkyl), and aralkyl groups containing from seven to twelve carbon atoms (i.e., $C_7$-$C_{12}$aralkyl).

Alternatively, $R_1$ and $R_2$, when taken together with the nitrogen atom to which they are directly attached in formula (XXVIII), may form a ring denoted by formula (II):

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur (e.g., an acetal, thioacetal, ketal, or thioketal group); and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl. Examples of substituents containing a fused ring system include the perhydroindolyl and 1,2,3,4-tetrahydroisoquinolinyl groups.

In connection with the ring of formula (II), any two adjacent ring atoms may be joined together by single or double bonds. Thus, the ring of formula (II) may be saturated or unsaturated, and an unsaturated ring may contain one, or more than one, sites of unsaturation. In other words, the ring of formula (II) may contain one or more double bonds, it being understood, however, that the unsaturated ring of formula (II) is chemically stable.

Alternatively, $R_1$ and $R_2$, when taken together with the 2-amino nitrogen of formula (XXVIII), may complete a bicyclic ring. Bicyclic rings include, for example, 3-azabicyclo[3.2.2]nonane, 2-azabicyclo[2.2.2]octane, 3-azabicyclo[3.1.0]hexane, and 3-azabicyclo[3.2.0]heptane. For these derivatives, the C-2 substituents of the cycloalkyl ethers of formula (I) are the following groups: 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl.

Preferably for formula (II), $R_1$ and $R_2$, when taken together, contain only a single heteroatom. Preferred heteroatoms include nitrogen, oxygen and sulfur. An example of a ring in which $R_1$ and $R_2$ together include an oxygen heteroatom is the morpholinyl group. An example of a ring where $R_1$ and $R_2$ together include a second nitrogen heteroatom is the piperazinyl group.

Cycloalkyl substituents $R_3$ and $R_4$ may be independently attached to any of the ring positions except positions 1 and 2 (e.g., both $R_3$ and $R_4$ may be attached to the same ring position or each attached to different ring positions). $R_3$ and $R_4$ are independently selected from hydrogen, hydroxy, $C_1$-$C_6$alkyl, and $C_1$-$C_6$alkoxy, and, when both $R_3$ and $R_4$ are attached to the same cycloalkyl ring atom, may together form a spiro five- or six-membered heterocyclic ring containing one or two heteroatoms selected from oxygen and sulfur. Preferred heterocyclic substituents contain either a single oxygen or a single sulfur ring atom.

Depending upon the identity of X, the ether sidechain, —$CH(R_5)$—X-A, in formula (XXVIII) may take several forms. For example, a compound of formula (XXVIII) may have X as a —$C(R_6,R_{14})$—Y— group, where Y may be any of a direct bond, an oxygen atom (O), a sulfur atom (S) or a $C_1$-$C_4$alkylene group. $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl. Thus, compounds may include compounds of formula (XXVIII) where $R_6$ and $R_{14}$ are hydrogen and Y is a direct bond, such that X may be $CH_2$.

Alternatively, X may be an alkenylene moiety, e.g., a cis-or trans-alkenylene moiety, $C(R_{13})$=CH, where $R_{13}$ may be any of hydrogen, $C_1$-$C_6$alkyl, $C_3$-$C_8$cycloalkyl, aryl or benzyl. For compounds of formula (XXVIII) where X is an alkenylene moiety, X is preferably a trans-alkenylene moiety.

Alternatively, X may be a direct bond. Independent of the selections for A, X and other variables, $R_5$ is selected from hydrogen, $C_1$-$C_6$alkyl, aryl and benzyl.

Ether side chain component A is generally a hydrophobic moiety. Typically, a hydrophobic moiety is comprised of non-polar chemical groups such as hydrocarbons or hydrocarbons substituted with halogens or ethers or heterocyclic groups containing nitrogen, oxygen, or sulfur ring atoms. Suitable hydrocarbons are $C_5$-$C_{12}$alkyl and $C_3$-$C_{13}$carbocyclic rings. Particularly preferred cyclic hydrocarbons include selected aromatic groups such as phenyl, 1-naphthyl, 2-naphthyl, indenyl, acenaphthyl, and fluorenyl and are represented by formulae (III), (IV), (V), (VI), (VII), or (VIII), respectively.

A suitable "A" group within the compounds described herein is a phenyl ring represented by formula (III):

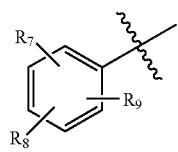

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, aryl and $N(R_{15},R_{16})$ where $R_{15}$ and $R_{16}$ are independently selected from hydrogen, acetyl, methanesulfonyl, and $C_1$-$C_6$alkyl.

For compounds of formula (XXVIII) where X is a direct bond or $CH_2$, at least one of $R_7$, $R_8$ and $R_9$ is preferably selected from amine (—$NR_{15}R_{16}$, where $R_{15}$ and $R_{16}$ are independently hydrogen, acetyl, methanesulfonyl, and $C_1$-$C_6$alkyl), bromine, chlorine, fluorine, carboxy, hydrogen, hydroxy, hydroxymethyl, nitro, trifluoromethyl, $C_2$-$C_7$alkanoyloxy, $C_1$-$C_6$alkyl, $C_1$-$C_6$alkoxy, $C_2$-$C_7$alkylcarbonyl, $C_1$-$C_6$thioalkyl or aryl groups. For compounds of formula (I) when X is CH=CH, and $R_3$ and $R_4$ are hydrogen, at least one of $R_7$, $R_8$ and $R_9$ is preferably a substituent other than hydrogen.

Other suitable "A" groups in compounds described herein are 1-naphthyl groups as represented by formula (IV):

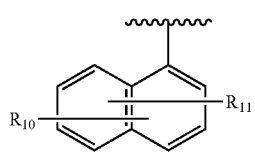

(IV)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl.

Other suitable "A" groups in compounds described herein are 2-naphthyl group as represented by formula (V):

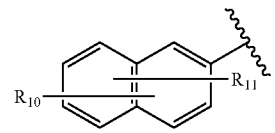

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl, as defined above.

Other suitable "A" groups in compounds described herein are aromatic groups represented by formula (VI):

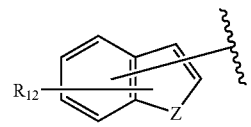

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (XXVIII) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl.

The aryl groups of formula (VI) are derivatives of indene, indole, benzofuran, and thianaphthene when Z is methylene, nitrogen, oxygen, and sulfur, respectively. Preferred heterocyclic groups of formula (VI) include indole where Z is NH, benzofuran where Z is O, and thianaphthene where Z is S. As described below, in a preferred embodiment, Z is O, S or N—$R_{17}$, and in a particularly preferred embodiment Z is O or S.

Another suitable "A" group in compounds described herein are acenaphthyl groups as represented by formula (VII):

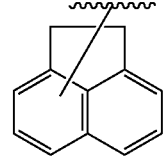

(VII)

Still another suitable "A" group in compounds described herein is the fluorenyl group represented by formula (VIII):

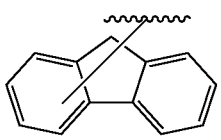

(VIII)

Preferably, ether sidechain component A is an acenapthyl or fluorenyl group only when X is a direct bond or CH$_2$. In other variations, the acenaphthyl group is a 1-acenaphthyl group, and the fluorenyl group is a 9-fluorenyl group.

In another variation of (XXVIII), X is (CH$_2$)—Y. For these variations, Y is a direct bond, an oxygen atom, or a sulfur atom. In a particular variation, Y is a direct bond or an oxygen atom. In another variation, Y is a direct bond and X is C(R$_6$, R$_{14}$), where R$_6$ and R$_{14}$ are as defined above. In another variation, X is C(R$_{13}$)=CH, and R$_{13}$ is a hydrogen atom. For these variations, R$_3$ and R$_4$ are preferably independently attached to the cycloalkyl ring at the 4- or 5-positions.

Ion channel modulating compounds of formula (XXVIII) may be provided, wherein: independently at each occurrence, n is selected from 1, 3 and 4;

Q is either O (oxygen) or S (sulfur);

X is selected from a direct bond, —C(R$_6$,R$_{14}$)—Y— and —C(R$_{13}$)=CH—;

Y is selected from a direct bond, O, S and C$_1$-C$_4$alkylene;

R$_{13}$ is selected from hydrogen, C$_1$-C$_6$alkyl, C$_3$-C$_8$cycloalkyl, aryl and benzyl;

R$_1$ and R$_2$ are independently selected from hydrogen, C$_1$-C$_8$alkyl, C$_3$-C$_8$alkoxyalkyl, C$_1$-C$_8$hydroxyalkyl, and C$_7$-C$_{12}$aralkyl; or R$_1$ and R$_2$ are independently selected from C$_3$-C$_8$alkoxyalkyl, C$_1$-C$_8$hydroxyalkyl, and C$_7$-C$_{12}$aralkyl; or R$_1$ and R$_2$ are taken together with the nitrogen atom to which they are directly attached in formula (XXVIII) to form a ring denoted by formula (II):

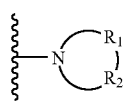

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may bear one or two substituents selected from hydrogen, hydroxyl, C$_1$-C$_3$hydroxyalkyl, oxo, C$_2$-C$_4$acyl, C$_1$-C$_3$alkyl, C$_2$-C$_4$alkylcarboxy, C$_1$-C$_3$alkoxy, C$_1$-C$_{20}$alkanoyloxy, or may form a spiro five- or six-membered heterocyclic ring containing one or two heteroatoms selected from oxygen and sulfur; and any two adjacent additional carbon ring atoms may be fused to a C$_3$-C$_8$carbocyclic ring, and any one or more of the additional nitrogen ring atoms may bear substituents selected from hydrogen, C$_1$-C$_6$alkyl, C$_2$-C$_4$acyl, C$_2$-C$_4$hydroxyalkyl and C$_3$-C$_8$alkoxyalkyl; or R$_1$ and R$_2$ are taken together with the nitrogen atom to which they are directly attached in formula (XXVIII) to form a bicyclic ring system selected from 3-azabicyclo[3.2.2] nonan-3-yl, 2-azabicyclo[2.2.2]octan-2-yl, 3-azabicyclo [3.1.0]hexan-3-yl and 3-azabicyclo[3.2.0]heptan-3-yl;

R$_3$ and R$_4$ are independently attached to the cycloalkyl ring shown in formula (XXVIII) at other than the 1 and 2 positions and are independently selected from hydrogen, hydroxyl, C$_1$-C$_6$alkyl and C$_1$-C$_6$alkoxy, and, when both R$_3$ and R$_4$ are attached to the same cycloalkyl ring atom, may together form a spiro five- or six-membered heterocyclic ring containing one or two heteroatoms selected from oxygen and sulfur;

R$_5$, R$_6$ and R$_{14}$ are independently selected from hydrogen, C$_1$-C$_6$alkyl, aryl and benzyl, or R$_6$ and R$_{14}$, when taken together with the carbon to which they are attached, may form a spiro C$_3$-C$_5$cycloalkyl;

A is selected from C$_5$-C$_{12}$alkyl, a C$_3$-C$_{13}$carbocyclic ring, and ring systems selected from formulae (III), (IV), (V), (VI), (VII) and (VIII):

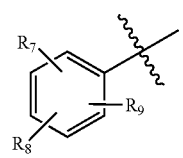

(III)

where R$_7$, R$_8$ and R$_9$ are independently selected from bromine, chlorine, fluorine, carboxy, hydrogen, hydroxy, hydroxymethyl, methanesulfonamido, nitro, sulfamyl, trifluoromethyl, C$_2$-C$_7$alkanoyloxy, C$_1$-C$_6$alkyl, C$_1$-C$_6$alkoxy, C$_2$-C$_7$alkoxycarbonyl, C$_1$-C$_6$thioalkyl, aryl and N(R$_{15}$,R$_{16}$) where R$_{15}$ and R$_{16}$ are independently selected from hydrogen, acetyl, methanesulfonyl and C$_1$-C$_6$alkyl;

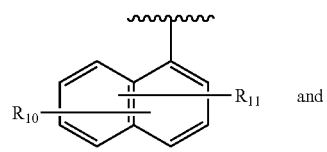

(IV) and

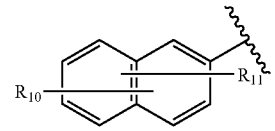

(V)

where R$_{10}$ and R$_{11}$ are independently selected from bromine, chlorine, fluorine, carboxy, hydrogen, hydroxy, hydroxymethyl, methanesulfonamido, nitro, sulfamyl, trifluoromethyl, C$_2$-C$_7$alkanoyloxy, C$_1$-C$_6$alkyl, C$_1$-C$_6$alkoxy, C$_2$-C$_7$alkoxycarbonyl, C$_1$-C$_6$thioalkyl, and N(R$_{15}$,R$_{16}$) where R$_{15}$ and R$_{16}$ are independently selected from hydrogen, acetyl, methanesulfonyl, and C$_1$-C$_6$alkyl;

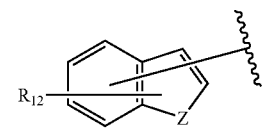

(VI)

where R$_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (XXVIII) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

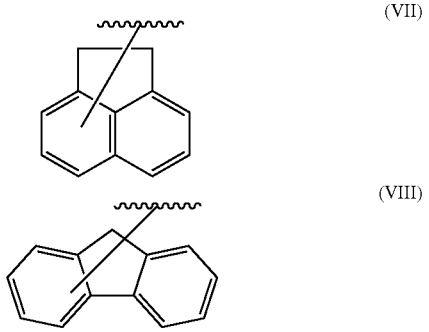

including isolated enantiomeric, diastereomeric and geometric isomers thereof;

In another version of the aminocycloalkyl ether ion channel modulating compounds, the ion channel modulating compound is one of the following compounds or mixtures of compounds.

(1R,2R)-2-(4-Morpholinyl)-1-(2-naphthalenethoxy) cyclopentane monohydrochloride or (1S,2S)-2-(4-morpholinyl)-1-(2-naphthalenethoxy) cyclopentane.HCl monohydrochloride or a mixture of (1R,2R)-2-(4-morpholinyl)-1-(2-naphthalenethoxy) cyclopentane monohydrochloride and (1S,2S)-2-(4-morpholinyl)-1-(2-naphthalenethoxy) cyclopentane monohydrochloride (1R,2R)-2-(3-Ketopyrrolidinyl)-1-(2,6-dichlorophenethoxy) cyclopentane monohydrochloride or (1S,2S)-2-(3-ketopyrrolidinyl)-1-(2,6-dichlorophen ethoxy) cyclopentane monohydrochloride or a mixture of (1R,2R)-2-(3-ketopyrrolidinyl)-1-(2,6-dichlorophenethoxy) cyclopentane monohydrochloride and (1S,2S)-2-(3-ketopyrrolidinyl)-1-(2,6-dichlorophenethoxy) cyclopentane monohydrochloride.

In a preferred embodiment, the ion channel modulating compound has the formula

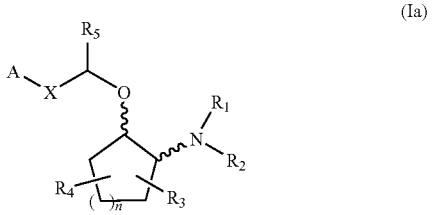

or solvates or pharmaceutically acceptable salts thereof; wherein, n=1, 2, 3, or 4;

X is a direct bond, —$C(R_6,R_{14})$—Y—, or —$C(R_{13})$=CH—, with the proviso that when X is a direct bond and A is formula (III) then at least one of $R_7$, $R_8$ and $R_9$ is not hydrogen;

Y is a direct bond, O, S, or $C_1$-$C_4$alkylene;

$R_{13}$ is hydrogen, $C_1$-$C_6$alkyl, $C_3$-$C_8$cycloalkyl, aryl, or benzyl;

$R_1$ and $R_2$ are independently hydrogen, $C_1$-$C_8$alkyl, $C_3$-$C_8$alkoxyalkyl, $C_1$-$C_8$hydroxyalkyl, or $C_7$-$C_{12}$aralkyl; or $R_1$ and $R_2$, when taken together with the nitrogen atom to which they are directly attached in formula (Ia), form a ring denoted by formula (II):

wherein the ring of formula (II) is formed from the nitrogen as shown as well as three to nine additional ring atoms independently carbon, nitrogen, oxygen, or sulfur; where any two adjacent ring atoms may be joined together by single or double bonds, and where any one or more of the additional carbon ring atoms may be substituted with one or two substituents selected from the group consisting of hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, and $C_1$-$C_{20}$alkanoyloxy, or may be substituted to form a spiro five- or six-membered heterocyclic ring containing one or two heteroatoms of oxygen or sulfur; and any two adjacent additional carbon ring atoms may be fused to a $C_3$-$C_8$carbocyclic ring, and any one or more of the additional nitrogen ring atoms may be substituted with substituents of hydrogen, $C_1$-$C_6$alkyl, $C_2$-$C_4$acyl, $C_2$-$C_4$hydroxyalkyl or $C_3$-$C_8$alkoxyalkyl; or $R_1$ and $R_2$, when taken together with the nitrogen atom to which they are directly attached in formula (Ia), may form a bicyclic ring system of 3-azabicyclo[3.2.2]nonan-3-yl, 2-azabicyclo[2.2.2]octan-2-yl, 3-azabicyclo[3.1.0]hexan-3-yl, or 3-azabicyclo[3.2.0]heptan-3-yl;

$R_3$ and $R_4$ are independently attached to the cyclohexane ring shown in formula (Ia) at the 3-, 4-, 5- or 6-positions and are independently hydrogen, hydroxy, $C_1$-$C_6$alkyl, or $C_1$-$C_6$alkoxy, and, when both $R_3$ and $R_4$ are attached to the same cyclohexane ring atom, may together form a spiro five- or six-membered heterocyclic ring containing one or two heteroatoms of oxygen or sulfur;

$R_5$, $R_6$ and $R_{14}$ are independently hydrogen, $C_1$-$C_6$alkyl, aryl or benzyl, or $R_6$ and $R_{14}$, when taken together with the carbon to which they are attached, may form a spiro $C_3$-$C_5$cycloalkyl;

A is $C_5$-$C_{12}$alkyl, a $C_3$-$C_{13}$carbocyclic ring, or ring systems comprising formulae (III), (IV), (V), (VI), (VII) or (VIII):

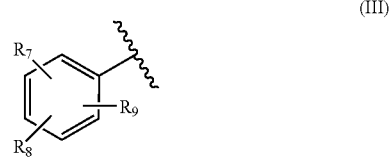

where $R_7$, $R_8$ and $R_9$ are independently bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl or $N(R_{15},R_{16})$ where $R_{15}$ and $R_{16}$ are independently hydrogen, acetyl, methanesulfonyl, or $C_1$-$C_6$alkyl;

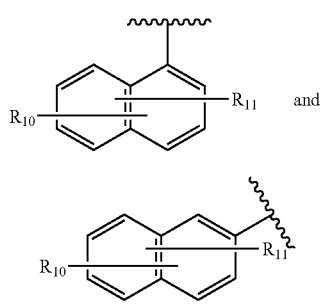

where $R_{10}$ and $R_{11}$ are independently bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, or $N(R_{15},R_{16})$ where $R_{15}$ and $R_{16}$ are independently hydrogen, acetyl, methanesulfonyl, or $C_1$-$C_6$alkyl;

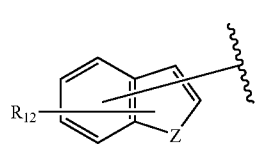

where $R_{12}$ is bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, or $N(R_{15},R_{16})$ where $R_{15}$ and $R_{16}$ are independently hydrogen, acetyl, methanesulfonyl, or $C_1$-$C_6$alkyl; and Z is CH, $CH_2$, O, N or S, where Z may be directly bonded to "X" as shown in formula (Ia) when Z is CH or N, or Z may be directly bonded to $R_{17}$ when Z is N, and $R_{17}$ is hydrogen, $C_1$-$C_6$alkyl, $C_3$-$C_8$cycloalkyl, aryl or benzyl;

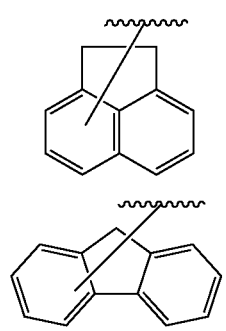

In another version of the aminocycloalkyl ether ion channel modulating compounds, the ion channel modulating compound is a protonated version of any of the aminocycloalkyl ether compounds described in this patent. That is, for each aminocycloalkyl ether compound described in this patent, the quaternary protonated amine form of the compound may also be considered as an aminocycloalkyl ether ion channel modulating compound. These quaternary protonated amine forms of the compounds may be present in the solid phase, for example in crystalline or amorphous form, and may be present in solution. These quaternary protonated amine forms of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

General Description of Ion Channel Modulating Compounds

Generally, any compound that modulates ion channel activity may be an ion channel modulating compound. A compound that modulates ion channel activity may be a compound that increases or decreases ion channel activity. An ion channel modulating compound that decreases ion channel activity may be a compound that blocks ion channel activity completely or partially.

In another version, any compound that either singly or together with one or more additional compounds selectively inhibit certain combination of cardiac ionic currents is an ion channel modulating compound. The cardiac currents may be the sodium currents and early repolarizing currents. Ion channel modulating compounds may block cardiac currents from extracellular loci. Such compounds may act on an external locus of the ion channel that is accessible from the extracellular surface. This facilitates access to the ion channel and provides rapid onset kinetics and exhibits frequency dependent blockade of currents. Such properties are all beneficial for compounds used to treat arrhythmias.

An ion channel modulating compound may selectively inhibit cardiac early repolarizing currents and cardiac sodium currents. Ion channel modulating compounds may be used to selectively inhibit cardiac early repolarizing currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation and those conditions that precede the onset of arrhythmias such as atrial fibrillation or atrial flutter. An ion channel modulating compound may be an atrial selective agent. An ion channel modulating compound may treat or prevent ventricular arrhythmia. An ion channel modulating compound block may cardiac sodium currents or cardiac early repolarizing currents. An ion channel modulating compound may inhibit multiple cardiac ionic currents. An ion channel modulating compound may be used to treat or prevent arrhythma, including ventricular or atrial arrhythmia, particularly atrial fibrillation or atrial flutter.

The ion channel modulating compounds may block the cardiac ion channels responsible for early repolarizing currents and sodium currents; and/or block cardiac early repolarizing currents and cardiac sodium currents under conditions where an arrhythmogenic substrate is present in the heart; and/or block the cardiac ion channels responsible for early repolarizing currents and sodium currents under conditions where an arrhythmogenic substrate is present in the heart; and/or block cardiac early repolarizing currents and cardiac sodium currents from extracellular loci in cardiac cells.

In one variation, the cardiac early repolarizing currents referred to above comprise ionic currents which activate rapidly after depolarization of membrane voltage and which effect repolarization of the cell. The early repolarizing currents may comprise the cardiac transient outward potassium current ($I_{tO}$) and/or the ultrarapid delay rectifier current ($I_{Kur}$). The cardiac transient outward potassium current ($I_{tO}$) and/or the ultrarapid delay rectifier current ($I_{Kur}$) may comprise at least one of the Kv4.2, Kv4.3, Kv2.1, Kv1.4 and Kv1.5 currents.

Ion channel modulating compounds may generally have any pKa, however ion channel modulating compounds typically have pKa values of between 4-9, and may have pKa values that are less than 8, including pKa values between 5-7.5. Methods to determine pKa values are well known in the art (see, e.g., Perrin, "Dissociation Constants of Organic Bases in Aqueous Solution", Butterworth, London, 1972). For ion channel modulating compounds with the specific ranges of pKa described above, the fraction of the charged (protonated) species will be increased under the pathological conditions such as cardiac arrhythmias and the presence of an arrhythmogenic substrate in the heart as described above due to the increase in cardiac milieu acidity. Where the charged form of a compound is active, its potency increases under conditions associated with an increase in cardiac milieu acidity.

Particular ion channel modulating compounds have structural characteristics that may be determined by various physical methods, such as single crystal X-ray crystallography. For instance, some ion channel modulating compounds comprise a cycloalkane ring and substituents J and K as shown below in structure T, wherein the relative positions of J and K provide a "C" shaped angle and wherein n=1, 2, 3 or 4.

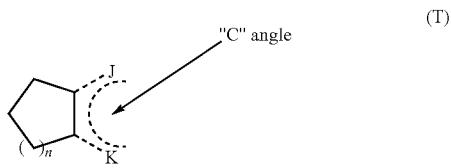

(T)

Typically, one of J and K comprises a hydrophobic moiety, such as but not limited to a moiety comprising alkyl and/or aryl moieties. In one variation, one of J and K comprises a hydrophobic aromatic moiety, which may be attached to the cycloalkane ring of structure T via an ether bond. Typically, one of J and K comprises a hydrophilic moiety, such as a heteroatom containing moiety, including but not limited to a nitrogen containing moiety that is available to form a quaternary salt and/or a hydroxyl moiety. In one variation, one of J and K comprises a nitrogen containing moiety substituted with a hydroxyl moiety or the like, such as a pyrrolidinyl moiety. In a particular variation of structure T, n=2, J comprises a aromatic moiety and K comprises a nitrogen containing moiety substituted with a hydroxyl moiety or the like. The cycloalkane ring may be optionally substituted.

In one version, the cycloalkane ring may be replaced by a structural moiety imparting rigidity to the relative positions of the J and K groups. For example if the J and K groups are attached to atoms L and M that are directly bonded to each other, any group that does not allow substantial rotation about the bond between atoms L and M can impart rigidity to the relative positions of the J and K groups. For example, the ion channel modulating compound may be a compound of formula

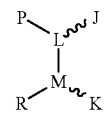

where J and K are as described above and groups P and R are moieties such that there is not substantial rotation about the L-M bond. In one example P and R taken together form a cyclic moiety that prevents substantial rotation about the L-M bond.

In one version, the ion channel modulating compound comprises an amino substituted 5, 6, 7 or 8-membered ring, which may be a 5, 6, 7, or 8-membered substituted or unsubstituted cycloalkyl ring. The amino substituted cycloalkane ring may be an aminocyclohexyl ring and may be further substituted with one or more additional moieties. In one version, the amino substituted cycloalkane ring is further substituted with an ether moiety. In some instances, the ion channel modulating compound comprises an aminocyclohexyl ring that is further substituted with an ether moiety.

In another version, the ion channel modulating compound is a protonated version of any of the ion channel modulating compounds described in this patent. That is, for each ion channel modulating compound described in this patent, the quaternary protonated amine form of the compound may also be considered as an amino ion channel modulating compound. These quaternary protonated amine forms of the compounds may be present in the solid phase, for example in crystalline or amorphous form, and may be present in solution. These quaternary protonated amine forms of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

Methods of Making Ion Channel Modulating Compounds

Methods that may be used to synthesize the ion channel modulating compounds for use in the methods, formulations etc. described in this patent application include but are not limited to the synthesis methods described in U.S. application Ser. No. 10/674,684 titled Ion Channel Modulating Compounds, in U.S. provisional application No. 60/516,248, titled Aminocyclohexyl Ether Compounds and Uses Thereof, in U.S. provisional application 60/516,486, titled Aminocyclohexyl Ether Compounds and Uses Thereof, in PCT/US03/34655 (filed Oct. 31, 2003), and WO 99/50225, each of which is incorporated herein by reference in its entirety.

Figure 14:
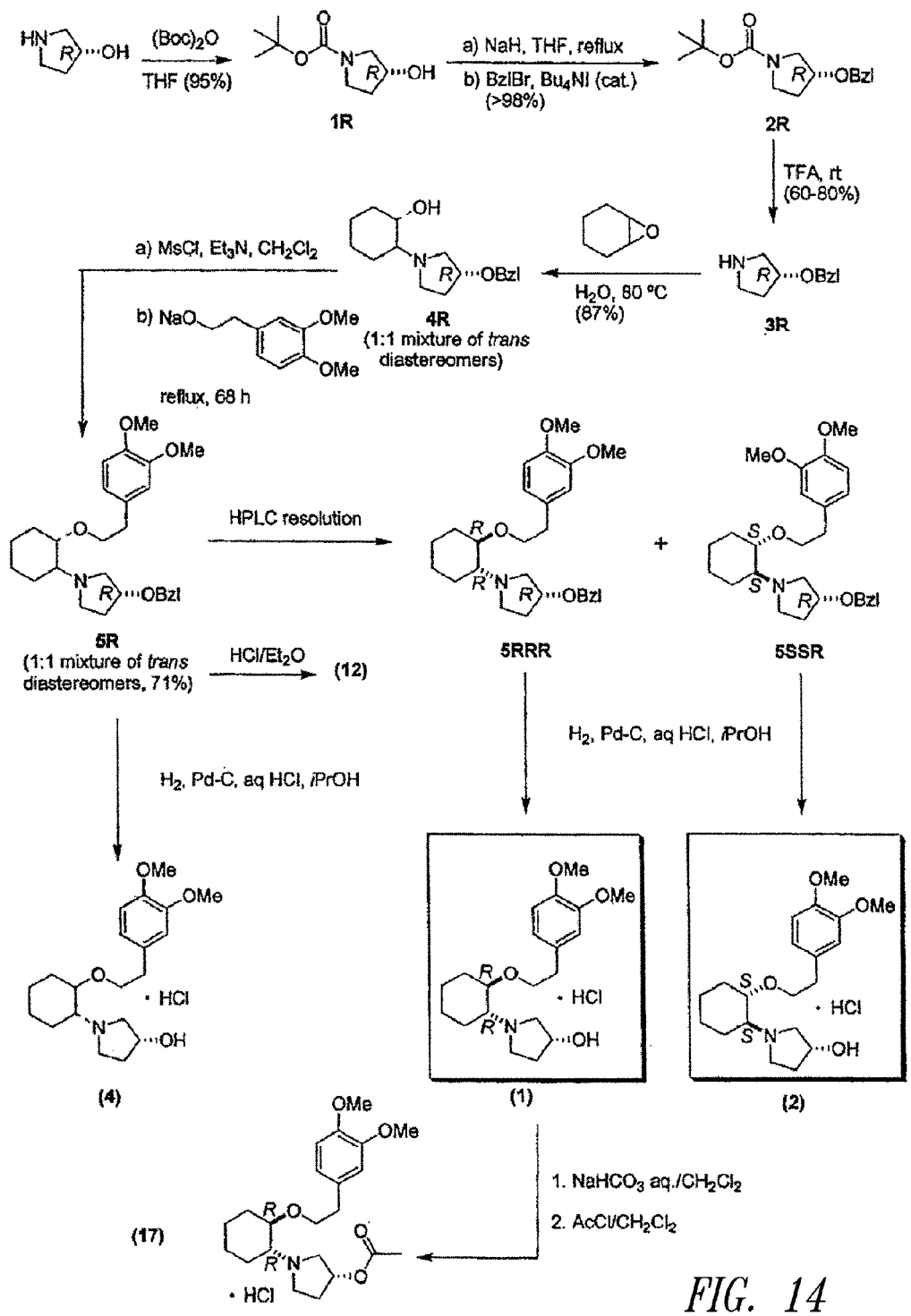
FIG. 14 illustrates an exemplary reaction scheme to synthesize an ion channel modulating compound as described herein.

In one method, illustrated in FIG. 14, compounds are prepared by a Williamson ether synthesis (Feuer, H.; Hooz, J. Methods of Formation of the Ether Linkage. In Patai, Wiley: New York, 1967; pp 445-492) between an activated form of aminoalcohol 4R with the alkoxide of 3,4-dimethoxyphenethyl alcohol in a polar solvent such as dimethoxyethane (ethylene glycol dimethyl ether) (DME) (FIG. 1) that provided the corresponding aminoether 5R in high yield. Subsequent resolution of the diastereomers such as by chromatographic separation (e.g., HPLC) to afford 5RRR and 5SSR followed by hydrogenolysis provided compound 1 and compound 2, respectively.

(1R,2R)-2-[(3S)-Hydroxypyrrolidinyl]-1-(3,4-dimethoxyphenethoxy)cyclohexane free base and the corresponding monohydrochloride (compound 6) and (1S,2S)-2-[(3S)-hydroxypyrrolidinyl]-1-(3,4-dimethoxyphenethoxy)cyclohexane free base and the corresponding monohydrochloride (compound 7) are obtained using a similar synthetic sequence but starting with 3-(S)-hydroxypyrrolidine.

Hydrogenolysis of (1R,2R)/(1S,2S)-2-[(3R)-benzyloxypyrrolidinyl]-1-(3,4-dimethoxyphenethoxy)cyclohexane (5R) provided (1R,2R)/(1S,2S)-2-[(3R)-hydroxypyrrolidinyl]-1-(3,4-dimethoxyphenethoxy)cyclohexane free base and the corresponding monohydrochloride (compound 4). Similarly, starting with 3-(S)-hydroxypyrrolidine instead of 3-(R)-hydroxypyrrolidine and following the same synthetic sequence will afford (1R,2R)/(1S,2S)-2-[(3S)-benzyloxypyrrolidinyl]-1-(3,4-dimethoxyphenethoxy)cyclohexane. The latter on hydrogenolysis will provide (1R,2R)/(1S,2S)-2-[(3S)-hydroxypyrrolidinyl]-1-(3,4-dimethoxyphenethoxy)cyclohexane free base and the corresponding monohydrochloride (compound 5). (1R,2R)/(1S,2S)-2-[(3R)1(3S)-Hydroxypyrrolidinyl]-1-(3,4-dimethoxyphenethoxy)-cyclohexane free base and the corresponding monohydrochloride (compound 3) can also be synthesized by similar process by starting with racemic 3-hydroxypyrrolidine.

Dosage Forms, Routes of Administration, and Formulations of Ion Channel Modulating Compounds Dosage forms, routes of administration, and formulations of the ion channel modulating compounds include but are not limited to those described in U.S. application Ser. No. 10/674,684, titled Ion Channel Modulating Compounds, in U.S. provisional application No. 60/516,248, titled Aminocyclohexyl Ether Compounds and Uses Thereof, and in U.S. provisional application 60/516,486, titled Aminocyclohexyl Ether Compounds and Uses Thereof, each of which are incorporated herein by reference. Any effective dosage forms, routes of administration, and formulations may generally be used with any and all other aspects described in this patent application.

The ion channel modulating compounds and formulations described herein may be formulated in a dosage form suitable for delivery via a variety of administration routes, including but not limited to oral, parenteral, mucosal, nasal, sublingual, transdermal, buccal, topical, vaginal, rectal, ocular or other administration. An ion channel modulating compounds as described herein may be in the form of an immediate and/or modified release formulation or it may be designed to release the ion channel modulating compound in a relatively fast manner in order to enable a relatively fast onset of the therapeutic effect. As used herein "compounds" and "compositions" of ion channel modulating compounds includes the ion channel modulating compounds as described herein alone or in combination with other materials.

Use of Ion Channel Modulating Compounds to Treat or Prevent Certain Diseases and Conditions Ion channel modulating compounds may be used to treat or prevent various diseases and conditions as described in this patent application. The compounds, compositions, formulations, methods, etc. described in this patent application may be used in the treatment and/or prevention of a variety of diseases and conditions, including arrhythmias such as ventricular arrhythmias (e.g., ventricular tachycardia, ventricular fibrillation, premature ventricular contractions), supraventricular arrhythmias (e.g., supraventricular tachycardia, atrial fibrillation, atrial flutter, Wolff-Parkinson-White Syndrome, atrial flutter, premature supraventricular contractions), heart block, Long QT Syndrome, and sick sinus syndrome. Other diseases or conditions that may be treated and/or prevented include but are not limited to disease of the central nervous system (CNS disorders), Lou Gehrig's disease (Amyotrophic Lateral Sclerosis), Alzheimer, AIDS-related dementia, Multiple Sclerosis (MS), convulsion, seizures, epileptic spasms, depression, insomnia, anxiety, schizophrenia, Parkinson's disease, trigeminal pain, phantom limb pain, back pain, smoke cessation, respiratory disorders, cystic fibrosis, asthma, cough, inflammation and inflammatory disorders, irritable bowel disorders, irritable bowel syndrome Crohn's disease, prostatic hyperplasia, insect bites, psoriasis, arthritis, allergies, gastrointestinal disorders, urinary incontinence, cardio-vascular disorders, arrhythmia, heart failure, hypotension, cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, alopecia, diseases or dysfunctions of ion channels and receptors, diseases of voltage-gated ion channels, paralysis. This list is illustrative of the kinds of disorders which could be treated and/or prevented as described herein, and is not intended to be either limiting or exhaustive.

The compounds, compositions and methods described herein may be used as antitoxins, anti-venoms, antivirals, antibiotics, antiparasitics, antineoplastics, antinociceptives, sedatives, anesthetics, analgesics, painkillers, antipsychotics, local anaesthetics, topical anesthetics, antiangiogenics, cardioplegias, and cardioprotectants.

Effect of Ion Channel Modulating Compounds on Certain Ion Channel Characteristics and Other Physiological Characteristics The effects of ion channel modulating compounds on certain ion channel characteristics and other physiological characteristics are described below. The effects described in this section may generally be used with any and all other aspects described in this patent application to identify ion channel modulating compounds useful for treating any of the diseases and/or conditions described herein.

In one set of methods described in this patent application, cardiac arrhythmia (such as supraventricular tachyarrhythmia, atrial fibrillation, atrial flutter, ventricular fibrillation, ventricular flutter etc.) and other diseases and/or conditions discussed herein may be treated and/or prevented using an ion channel modulating compound which exhibits two or more of the following characteristics:

1. the compound exhibits rate-dependent inhibition of a sodium channel over a physiologically and pathophysiologically significant range of heart rates;
2. the compound minimally effects cardiac QRS duration;
3. the compound exhibits voltage-dependent inhibition of sodium channels;
4. the compound inhibits Kv potassium channels with an $IC_{50}$ in the micromolar range;
5. the compound exhibits predominantly open channel inhibition of Kv1 subfamily channels;
6. the compound inhibits Kv1 channels in a non-rate and non-use-dependent manner;
7. the compound does not inhibit HERG channels, except at $IC_{50}$ concentrations greater than 1, 10, 20 µM;
8. The compound does not substantially inhibit L-type Calcium Channels, ($IC_{50}$>100 µM);
9. the compound prolongs atrial refractoriness;

10. the compound inhibits acetyl choline dependent or adenosine dependent potassium channels (Kir3 channels) with an $IC_{50}$ in the micromolar range;
11. the compound has neutral effects on ventricular repolarization;
12. the compound inhibits early, sustained and late components of sodium currents; the compound inhibits the late component of sodium current as much or more than it inhibits the early component of sodium current, and the compound inhibits the early component of sodium current as much or more than it inhibits the sustained component of sodium current, and the compound inhibits the late component of sodium current more than it inhibits the sustained component of sodium current;
13. the compound exhibits state-dependent inhibition of sodium channels;
14. the compound rapidly associates and dissociates from sodium channels;
15. the compound exhibits pathology-selective inhibition of a sodium channel, and atrial selectivity;
16. the compound affects atrial repolarization but has substantially no effect on ventricular tissue;
17. the compound affects atrial conduction but has substantially no effect on ventricular conduction;
18. the compound prolongs atrial refractoriness but has substantially no effect on ventricular refractoriness;
19. the compound prolongs atrial refractoriness and AV nodal conduction and suppresses inducible atrial tachycardia but has substantially no effect on ventricular tissues; the compound produces a selective increase in atrial ERP and prolonged AFCL in AF;
20. the compound delays conduction in the atria by inhibition of sodium channels and prolongs refractoriness in the atria via inhibition of $I_{Kur}$;
21. the compound delays conduction in the atria by inhibition of sodium channels and prolongs refractoriness in the atria via inhibition of $I_{tO}$;
22. the compound delays conduction in the atria by inhibition of sodium channels and prolongs refractoriness in the atria via inhibition of hERG;
23. the compound delays conduction in the atria by inhibition of sodium channels and prolongs refractoriness in the atria via inhibition of $I_{KACh}$;
24. the compound delays conduction in the atria by inhibition of sodium channels and prolongs refractoriness in the atria via inhibition of $I_{Kur}$ and $I_{tO}$;
25. the compound delays conduction in the atria by inhibition of sodium channels and prolongs refractoriness in the atria via inhibition of $I_{Kur}$ and hERG;
26. the compound delays conduction in the atria by inhibition of sodium channels and prolongs refractoriness in the atria via inhibition of $I_{Kur}$ and $I_{KACh}$;
27. the compound delays conduction in the atria by inhibition of sodium channels and prolongs refractoriness in the atria via inhibition of $I_{tO}$ and hERG;
28. the compound delays conduction in the atria by inhibition of sodium channels and prolongs refractoriness in the atria via inhibition of $I_{tO}$ and $I_{KACh}$;
29. the compound delays conduction in the atria by inhibition of sodium channels and prolongs refractoriness in the atria via inhibition of hERG and $I_{KACh}$;
30. the compound delays conduction in the atria by inhibition of sodium channels and prolongs refractoriness in the atria via inhibition of $I_{Kur}$, $I_{tO}$ and hERG;
31. the compound delays conduction in the atria by inhibition of sodium channels and prolongs refractoriness in the atria via inhibition of $I_{Kur}$, $I_{tO}$ and $I_{KACh}$;
32. the compound delays conduction in the atria by inhibition of sodium channels and prolongs refractoriness in the atria via inhibition of $I_{Kur}$, hERG and $I_{KACh}$;
33. the compound delays conduction in the atria by inhibition of sodium channels and prolongs refractoriness in the atria via inhibition of $I_{tO}$, hERG and $I_{KACh}$;
34. the compound delays conduction in the atria by inhibition of sodium channels and prolongs refractoriness in the atria via inhibition of $I_{Kur}$, $I_{tO}$, hERG and $I_{KACh}$;
35. the compound inhibits sodium channel activity in a frequency dependent manner, delaying conduction in the atria and inhibits $I_{tO}$ and $I_{Kur}$, prolonging refractoriness in the atria;
36. the compound does not substantially alter the conduction or the voltage time course of repolarization in ventricular muscle or Purkinje fibers In another embodiment, one set of methods described in this patent application, the diseases and conditions, with a proviso excluding cardiac arrhythmia (such as supraventricular tachyarrhythmia, atrial fibrillation, atrial flutter, ventricular fibrillation, ventricular flutter etc.) described in the patent application may be treated and/or prevented using an ion channel modulating compound which exhibits one or more of the following characteristics:

37. the compound exhibits rate-dependent inhibition of a sodium channel over a physiologically and pathophysiologically significant range of heart rates;
38. the compound minimally effects cardiac QRS duration;
39. the compound exhibits voltage-dependent inhibition of sodium channels;
40. the compound inhibits Kv potassium channels with an $IC_{50}$ in the micromolar range;
41. the compound exhibits predominantly open channel inhibition of Kv1 subfamily channels;
42. the compound inhibits Kv1 channels in a non-rate and non-use-dependent manner;
43. the compound does not inhibit hERG channels, except at $IC_{50}$ concentrations greater than 1, 10, 20 µM;
44. The compound does not substantially inhibit L-type Calcium Channels, ($IC_{50}$>100 µM);
45. the compound prolongs atrial refractoriness;
46. the compound inhibits acetyl choline dependent or adenosine dependent potassium channels (Kir3 channels) with an $IC_{50}$ in the micromolar range;
47. the compound has neutral effects on ventricular repolarization;
48. the compound inhibits early, sustained and late components of sodium currents; the compound inhibits the late component of sodium current as much or more than it inhibits the early component of sodium current and inhibits the early component of sodium current as much or more than it inhibits the sustained component of sodium current, and the compound inhibits the late component of sodium current more than it inhibits the sustained component of sodium current;
49. the compound exhibits state-dependent inhibition of sodium channels;
50. the compound rapidly associates and dissociates from sodium channels;
51. the compound exhibits pathology-selective inhibition of a sodium channel, and atrial selectivity;
52. the compound affects atrial repolarization but has substantially no effect on ventricular tissue;
53. the compound affects atrial conduction but has substantially no effect on ventricular conduction;
54. the compound prolongs atrial refractoriness but has substantially no effect on ventricular refractoriness;

55. the compound prolongs atrial refractoriness and AV nodal conduction and suppresses inducible atrial tachycardia but has substantially no effect on ventricular tissues; the compound produces a selective increase in atrial ERP and prolonged AFCL in AF;
56. the compound delays conduction in the atria by inhibition of sodium channels and prolongs refractoriness in the atria via inhibition of $I_{Kur}$;
57. the compound delays conduction in the atria by inhibition of sodium channels and prolongs refractoriness in the atria via inhibition of $I_{tO}$;
58. the compound delays conduction in the atria by inhibition of sodium channels and prolongs refractoriness in the atria via inhibition of hERG;
59. the compound delays conduction in the atria by inhibition of sodium channels and prolongs refractoriness in the atria via inhibition of $I_{KACh}$;
60. the compound delays conduction in the atria by inhibition of sodium channels and prolongs refractoriness in the atria via inhibition of $I_{Kur}$ and $I_{tO}$;
61. the compound delays conduction in the atria by inhibition of sodium channels and prolongs refractoriness in the atria via inhibition of $I_{Kur}$ and hERG;
62. the compound delays conduction in the atria by inhibition of sodium channels and prolongs refractoriness in the atria via inhibition of $I_{Kur}$ and $I_{KACh}$;
63. the compound delays conduction in the atria by inhibition of sodium channels and prolongs refractoriness in the atria via inhibition of $I_{tO}$ and hERG;
64. the compound delays conduction in the atria by inhibition of sodium channels and prolongs refractoriness in the atria via inhibition of $I_{tO}$ and $I_{KACh}$;
65. the compound delays conduction in the atria by inhibition of sodium channels and prolongs refractoriness in the atria via inhibition of hERG and $I_{KACh}$;
66. the compound delays conduction in the atria by inhibition of sodium channels and prolongs refractoriness in the atria via inhibition of $I_{Kur}$, $I_{tO}$, and hERG;
67. the compound delays conduction in the atria by inhibition of sodium channels and prolongs refractoriness in the atria via inhibition of $I_{Kur}$, $I_{tO}$ and $I_{KACh}$;
68. the compound delays conduction in the atria by inhibition of sodium channels and prolongs refractoriness in the atria via inhibition of $I_{Kur}$, hERG and $I_{KACh}$;
69. the compound delays conduction in the atria by inhibition of sodium channels and prolongs refractoriness in the atria via inhibition of $I_{tO}$, hERG and $I_{KACh}$;
70. the compound delays conduction in the atria by inhibition of sodium channels and prolongs refractoriness in the atria via inhibition of $I_{Kur}$, $I_{tO}$, hERG and $I_{KACh}$;
71. the compound inhibits sodium channel activity in a frequency dependent manner, delaying conduction in the atria and inhibits $I_{tO}$, and $I_{Kur}$, prolonging refractoriness in the atria;
72. the compound does not substantially alter the conduction or the voltage time course of repolarization in ventricular muscle or Purkinje fibers.

Described herein are ion channel modulating compounds that exhibit one or more of the above characteristics for the treatment and/or prevention of diseases and conditions except cardiac arrhythmia (such as supraventricular tachyarrhythmia, atrial fibrillation, atrial flutter, ventricular fibrillation, ventricular flutter etc.) described in the patent application. Described in this patent are ion channel modulating compounds that exhibit any combination of any number of the above characteristics for the treatment and/or prevention of diseases and conditions except cardiac arrhythmia (such as supraventricular tachyarrhythmia, atrial fibrillation, atrial flutter, ventricular fibrillation, ventricular flutter etc.) described in the patent application.

Specific methods described in this patent application include (1) a method for treating atrial arrhythmia by administering to a subject a therapeutically effective amount of an ion channel modulating compound which exhibits two or more of the above listed characteristics (#1 to 36); (2) a method for preventing atrial arrhythmia by administering to a subject in need thereof an ion channel modulating compound which exhibits two or more of the above listed characteristics (#1 to 36); (3) a method for treating and preventing atrial arrhythmia by administering to a subject in need thereof an ion channel modulating compound which exhibits two or more of the above listed characteristics (#1 to 36); (4) a method for treating atrial fibrillation or atrial flutter by administering to a subject in need thereof an ion channel modulating compound which exhibits two or more of the above listed characteristics (#1 to 36); (5) a method for preventing atrial fibrillation or atrial flutter by administering to a subject in need thereof an ion channel modulating compound which exhibits two or more of the above listed characteristics (#1 to 36); and (6) a method for treating and preventing atrial fibrillation or atrial flutter by administering to a subject in need thereof an ion channel modulating compound which exhibits two or more of the above listed characteristics (#1 to 36). Generally, any compound exhibiting two or more of the above listed characteristics (#1 to 36) may be used as an ion channel modulating compound in these methods. In one aspect, Compound A, Compound B, or Compound C is used.

Specific compounds that may be used include the compounds described in the Ion channel modulating compounds section of this patent application. Specific dosage forms, routes of administration, and formulations that may be used include the dosage forms, routes of administration, and formulations described in the Dosage forms, routes of administration and formulation of Ion channel modulating compounds section of this patent application. Specific diseases and conditions that may be targeted are described in the Uses of ion channel modulating compounds to treat or prevent certain diseases and conditions section of this patent application. Preferably the subject is a human subject.

In one version, unless the context makes plain otherwise, the ion channels on which the ion channel modulating compounds may act to exert its effects are those present in human atrial myocytes. In one version, the ion channels on which the ion channel modulating compounds act to exert an effect are voltage-gated ion channels present in human atrial myocytes.

In one version, the ion channel modulating compounds may be used for prevention of one or more diseases and conditions including but not limited to TdP, acquired long-QT syndrome, multifocal ventricular arrhythmias, supraventricular arrhythmias, and polymorphic ventricular tachycardia. The ion channel modulating compound may be used to prevent and/or treat EADs. The ion channel modulating compounds may be used by administering a therapeutically effective amount of an ion channel modulating compound to a subject in need thereof, wherein the ion channel modulating compound is a compound with any one or more of the following characteristics:

1. the ion channel modulating compound blocks at least one component of a sodium channel current. In one version, the ion channel modulating compound blocks a late component of a current through a sodium channel.
2. the ion channel modulating compound blocks a human heart sodium channel, hH1.

3. the ion channel modulating compound blocks at least one component of a sodium channel current in vivo, in vitro or in vivo and in vitro. In one version, the ion channel modulating compound blocks a late component of a sodium channel current in vivo, in vitro or in vivo and in vitro. In one version, the ion channel modulating compound blocks at least one component of a sodium channel current in vivo in human.
4. the ion channel modulating compound blocks a sodium channel current stably expressed in HEK cells.
5. the ion channel modulating compound blocks a late component of a sodium channel current approximately equivalently to the amount that it blocks an early component of a sodium channel current. In one version, the ion channel modulating compound produces a block of an early component of a sodium channel current and a block of a late component of a sodium channel current, and the difference between the block of the early component of a sodium channel current and the block of the late component of the sodium channel current is less than about five percent of the block of the late component of the sodium channel current. In one version, the difference in block is less than about ten percent of the block of the late component of the sodium channel current. In one version, the difference in block is less than about twenty percent of the block of the late component of the sodium channel current. In one version, the difference in block is less than about thirty percent of the block of the late component of the sodium channel current. In one version, the difference in block is less than about fifty percent of the block of the late component of the sodium channel current.
6. the ion channel modulating compound inhibits the late component of sodium current approximately as much as or more than it inhibits the early component of sodium current and inhibits the early component of sodium current approximately as much as or more than it inhibits the sustained component of sodium current, and the compound inhibits the late component of sodium current more than it inhibits the sustained component of sodium current. In one version, the phrase "inhibits the late component of sodium current approximately as much as or more than it inhibits the early component" (or "blocks the late component of sodium current approximately as much as or more than it blocks the early component") means that the difference between the percentage of the late component of the sodium current blocked and the percentage of the early component of the sodium current blocked is less than 25%. In one version, the difference is less than 20%. In another version, the difference is less than 15%. In one version, the sodium channel current is a cardiac sodium channel current.
7. the ion channel modulating compound inhibits the early component of a sodium channel current approximately as much as or more than it inhibits the sustained component of sodium current. In one version, the phrase "inhibits the early component of sodium current approximately as much as or more than it inhibits the sustained component" (or "blocks the early component of sodium current approximately as much as or more than it blocks the sustained component") means that the difference between the percentage of the early component of the sodium current blocked and the percentage of the sustained component of the sodium current blocked is less than 25%. In one version, the difference is less than 20%. In another version, the difference is less than 15%. In one version, the sodium channel current is a cardiac sodium channel current.
8. the ion channel modulating compound blocks a late component of a sodium channel current approximately five percent, ten percent, twenty percent, twenty-five percent, thirty percent, or fifty percent more than it blocks a sustained component of a sodium channel current.
9. the ion channel modulating compound blocks a late component of a sodium channel current in vivo within one hour after administration. In one version of the methods, the ion channel modulating compound blocks a late component of a sodium channel current within 45 minutes, 30 minutes, 25 minutes, 20 minutes, 10 minutes, 5 minutes, or 1 minute after administration.
10. the ion channel modulating compound blocks a late component of a sodium channel current in vitro within one hour after contact with the sodium channel current. In one version of the methods, the ion channel modulating compound blocks a late component of a sodium channel current within 45 minutes, 30 minutes, 25 minutes, 20 minutes, 10 minutes, 5 minutes, or 1 minute after administration.
11. the ion channel modulating compound terminates, prevents, or terminates and prevents EADs. In one version, the ion channel modulating compound prevents EADs. In one version, the ion channel modulating compound terminates EADs. In one version, the ion channel modulating compound terminates EADs in isolated rabbit Purkinje fibers. In one version, the ion channel modulating compound terminates EADs induced by dofetilide in isolated rabbit Purkinje fibers. In one version, the ion channel modulating compound terminates EADs induced by blockade of hERG (IKr) channels or by blockade of long QT syndrome type (LQTS1) channels (IKs) or by delay in the inactivation of sodium channels (e.g., ATX-II), or by augmentation of inward currents, or by prolonging the QT interval. In one version, the ion channel modulating compound terminates EADs induced by compounds which result in blockade of hERG (IKr) channels or by blockade of LQTS1 channels (IKs) or by delay in the inactivation of sodium channels (e.g., ATX-II), or by augmentation of inward currents, or by prolonging the QT interval. In one version, the ion channel modulating compound terminates EADs induced by class III antiarrhythmics, antihistamines, antimicrobials, tricyclics, or psychotopics. In one version, the ion channel modulating compound terminates EADs induced by any genetic mutation that leads to EADs. In one version, the ion channel modulating compound terminates EADs induced by long QT syndromes (LQT1-6) or by Jervell and Lange-Nielsen syndrome (JLNS). In one version, the ion channel modulating compound terminates EADs induced by any one or more of the drugs listed in Appendix I. The list of drugs in Appendix I is published by www.torsades.org through the University of Arizona Center for Education and Research on Therapeutics based on information from the FDA-approved drug labeling and the medical literature. The list is revised and updated on a regular basis by www.torsades.org. The drugs that induce EADs are not limited to those listed and may include equivalent drugs that are not now known.
12. the ion channel modulating compound terminates, prevents, or terminates and prevents TdP. In one version, the ion channel modulating compound prevents TdP. In one version, the ion channel modulating compound terminates TdP. In one version, the ion channel modulating compound terminates, prevents, or terminates and prevents TdP in a dose-dependent fashion. In one version, the ion channel modulating compound prevents TdP from being induced. In one version, the ion channel modulating compound terminates induced TdP. In one version, the ion channel modulating compound terminates chemically induced TdP. In one version, the ion channel modulating compound prevents chemically induced TdP. In one version, the ion channel modulating compound terminates TdP induced by any one or more of the drugs listed in Appendix I. The list of drugs in Appendix I is published by www.torsades.org through the University of Arizona Center for Education and Research on Therapeutics based on information from the FDA-approved drug labeling and the medical literature. In one version, the ion channel modulating compound prevents TdP from being induced by any one or more of the drugs listed in Appendix I. In one version, the ion channel modulating compound terminates TdP induced by any one or more of the following drugs: sotalol, cisapride, amiodarone, erythromycin, ibutilide, terfenidine, quinidine, clarithromycin, haloperidol, fluoxetine, digoxin, procainamide, terodiline, fluconazole, disopyramide, bepridil, furosemide, thioridozine, flecainide, loratidine. In one version, the ion channel modulating compound prevents TdP from being induced by any one or more of the following drugs: sotalol, cisapride, amiodarone, erythromycin, ibutilide, terfenidine, quinidine, clarithromycin, haloperidol, fluoxetine, digoxin, procainamide, terodiline, fluconazole, disopyramide, bepridil, furosemide, thioridozine, flecainide, loratidine. In one version, the ion channel modulating compound terminates TdP induced by an arrhythmic agent. In one version, the ion channel modulating compound prevents TdP from being induced by an arrhythmic agent. In one version, the ion channel modulating compound terminates TdP induced by clofilium. In one version, the ion channel modulating compound prevents TdP from being induced by clofilium. In one version, the ion channel modulating compound terminates chemically-induced TdP in a dose-dependent fashion. In one version, the ion channel modulating compound prevents chemically-induced TdP from being induced, in a dose-dependent fashion. In one version, the ion channel modulating compound substantially terminates, prevents or terminates and prevents TdP at infusion rates less than 100 µmol/kg/min, at infusion rates less than 10 µmol/kg/min, at infusion rates less than 1 µmol/kg/min, at infusion rates less than 0.1 µmol/kg/min. In one version, the ion channel modulating compound delays or prevents the onset of TdP at infusion rates less than 100 µmol/kg/min, at infusion rates less than 10 µmol/kg/min, at infusion rates less than 1 µmol/kg/min, at infusion rates less than 0.1 µmol/kg/min. In one version, the ion channel modulating compound reduces the effect of TdP when compared to the untreated state at infusion rates less than 100 µmol/kg/min, at infusion rates less than 10 µmol/kg/min, at infusion rates less than 1 µmol/kg/min, at infusion rates less than 0.1 µmol/kg/min.

In one version of the methods, the method is used for treating, preventing, or treating and preventing an arrhythmia, particularly acquired long-QT syndrome, multifocal ventricular arrhythmias or supraventricular arrhythmias. In one version of the methods, the method is used for treating, preventing, or treating and preventing one or more of TdP, and polymorphic ventricular tachycardia.

Rate-Dependent Inhibition of Sodium Channels

Figure 2:
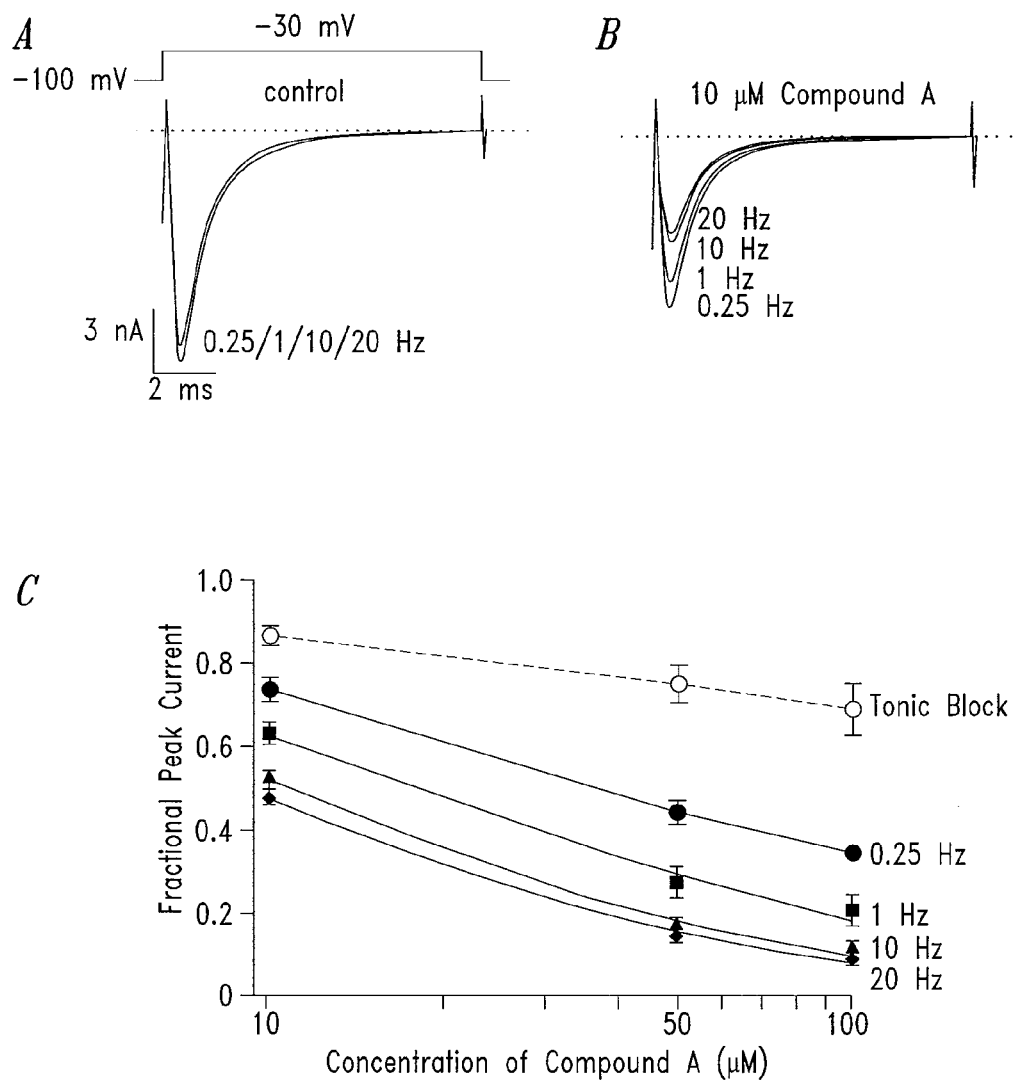
FIG. 2 shows a concentration- and frequency-dependent inhibition of hH1 sodium channels by COMPOUND A.

The diseases and conditions described in this patent application, and specifically atrial fibrillation or atrial flutter, may be treated and/or prevented using an ion channel modulating compound which exhibits a rate-dependent inhibition of sodium channels over a physiologically and pathophysiologically significant range of heart rates. As used in this patent application, unless the context makes clear otherwise, A "and/or" B means A or B, or A and B. In one version, the ion channel modulating compound exhibits a rate-dependent inhibition in the range of about a 2-fold to about a 100-fold (2×-100×) rate-dependent increase in the inhibition of sodium channels as the frequency of activation of the sodium channel increases from about 0.25 Hz to about 20 Hz. In one version, the ion channel modulating compound exhibits a rate-dependent increase in inhibition in the range of about a 5-fold to about a 10-fold rate-dependent increase in the inhibition of sodium channels as the frequency of activation of the sodium channel increases from 0.25 to 20 Hz (as shown in FIGS. 1 and 2). As a nonlimiting example, in human atrial myocytes, at 22° C., the ion channel modulating compound may exhibit an $IC_{50}$ of >2 µM at 0.1 Hz and <0.5 µM at 10 Hz (FIG. 1).

As used in this patent application, unless the context makes clear otherwise, a physiological heart rate means a beating rate that falls within the accepted normal distribution for a healthy individual of that age, and a pathophysiologically significant range of heart rates includes, for example, those which occur during atrial fibrillation or atrial flutter, or other disorders of heart rhythm.

Minimal Effect on QRS Duration

The diseases and conditions described in this patent application, and specifically atrial fibrillation or atrial flutter, may be treated and/or prevented using an ion channel modulating compound which does not substantially increase the QRS duration of a heart. As used in this patent application, unless the context makes clear otherwise, "QRS duration" means the interval of the QRS wave, for example, from an ECG.

In one version, the ion channel modulating compound produces less than a 15% increase in QRS duration at therapeutic concentrations. In one version, the ion channel modulating compound produces less than a 10% increase in QRS duration at therapeutic concentrations (as shown in Example 2, below).

Voltage-Dependent Inhibition of Sodium Channels

As used in this patent application, unless the context makes clear otherwise, "voltage-dependent inhibition" refers to a change in the level of inhibition of an ion channel when the ion channel is activated after being held at different resting potentials. Voltage-dependent ion channel inhibition may be different than "state-dependence of inhibition".

Figure 3:
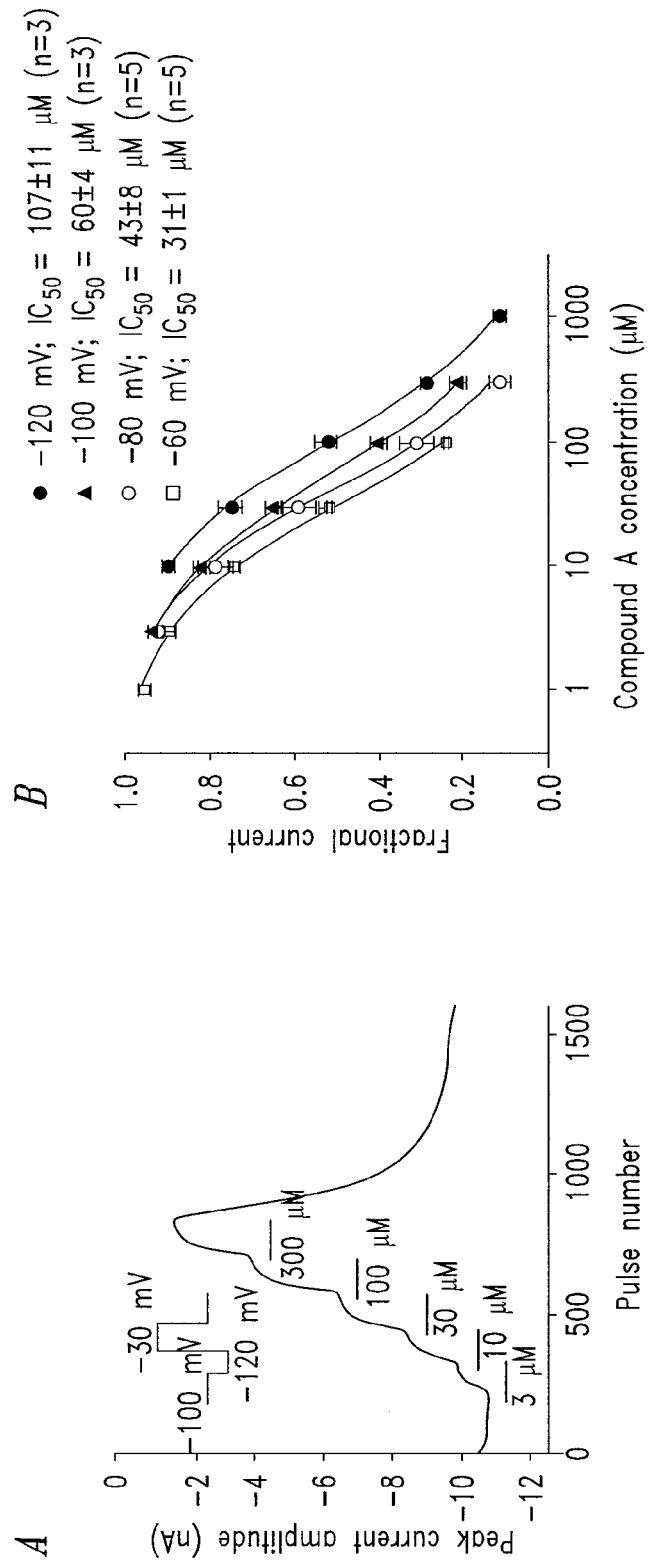
FIG. 3 shows a voltage-dependent block of hH1 by COMPOUND A.

The diseases and conditions described in this patent application, and specifically atrial fibrillation or atrial flutter, may be treated and/or prevented using an ion channel modulating compound that demonstrates a voltage-dependent inhibition of sodium channels. In one version, the voltage-dependent inhibition is demonstrated in that the $IC_{50}$ of the ion channel modulating compound is decreased by about 10× when the potential that cells are held at prior to step depolarization to −30 mV (at 1 Hz) is changed from about −120 mV to about −60 mV. In one version, the voltage-dependent inhibition of sodium channels is demonstrated in that the $IC_{50}$ of the ion channel modulating compound is decreased by about 4× when the potential that cells are held at prior to step depolarization to −30 mV (at 1 Hz) is changed from about −120 mV ($IC_{50}$ of approximately 107 μM in HEK cells expressing hH1) to about −60 mV ($IC_{50}$ of approximately 31 μM in HEK cells expressing hH1) (FIG. 3).

Failure to Inhibit Calcium Channels

The diseases and conditions described in this patent application, and specifically atrial fibrillation or atrial flutter, may be treated and/or prevented using an ion channel modulating compound which does not substantially inhibit calcium currents at therapeutic concentrations. In one version, the ion channel modulating compound does not inhibit L-type calcium channels at therapeutic concentrations. In one version, the ion channel modulating compound inhibits L-type calcium channels with an $IC_{50}$ greater than 200 μM.

Figure 4:
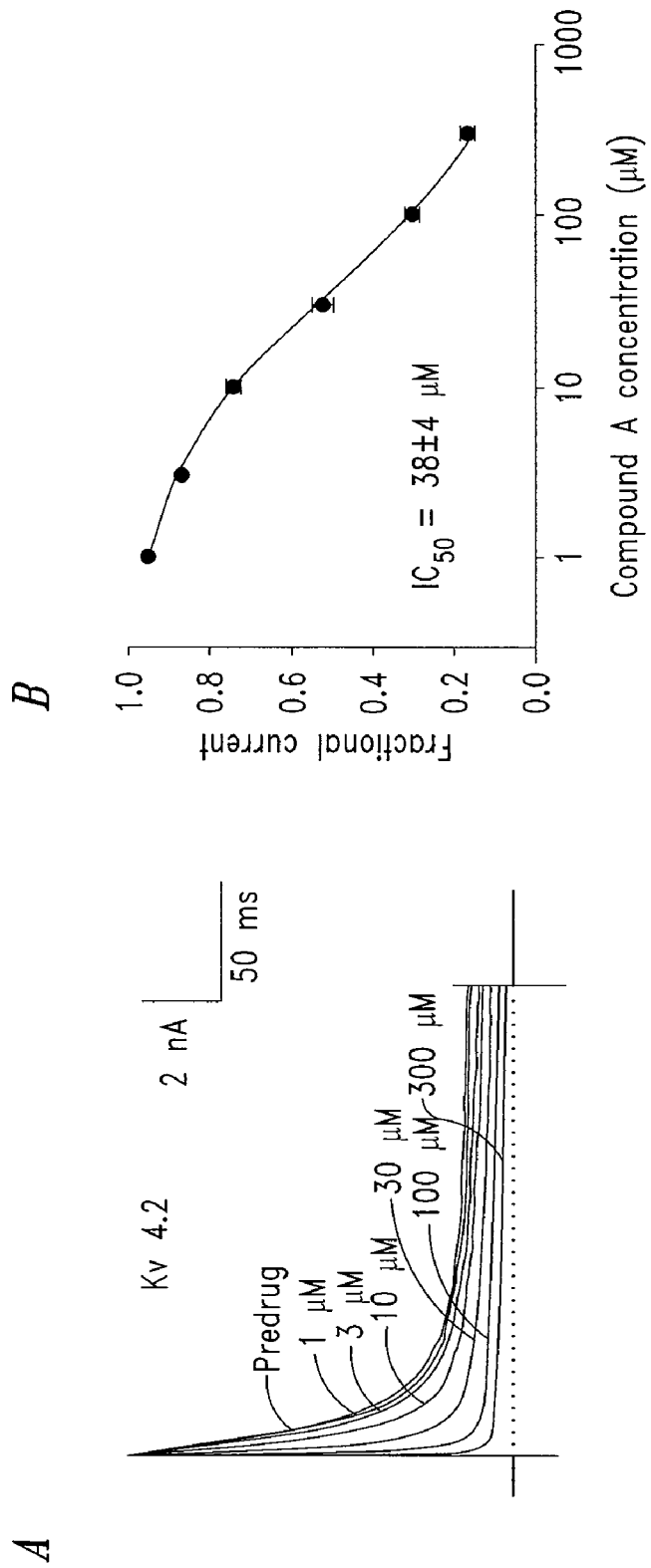
FIG. 4 shows a concentration-dependent inhibition of Kv4.2 at 1 Hz.

Inhibition of Kv Potassium Channels with $IC_{50}$ Values in the Micromolar Range The diseases and conditions described in this patent application, and specifically atrial fibrillation or atrial flutter, may be treated and/or prevented using an ion channel modulating compound which inhibits Kv1 channels at concentrations between about at least 2 μM and about 1000 μM and inhibits Kv2 and Kv4 channels at concentrations between about 0.1 μM and about 1000 μM. In one version, the ion channel modulating compound is a compound which does not inhibit Kv channels, expressed heterologously in human embryonic kidney cells (HEK) with an $IC_{50}$ of about 8 μM, but does inhibit Kv channels expressed in HEK cells with an $IC_{50}$ between about 8 μM and about 100 μM (as shown in FIGS. 4 and 5).

As used in this patent application, unless the context makes clear otherwise, "Kv" channels may include any member of the subfamilies of potassium channels that are comprised of four subunits of six-transmembrane domains. In one embodiment, Kv1.5 is inhibited by an ion channel modulating compound with an $IC_{50}$ of between 10 and 50 μM. In one embodiment, Kv1.5 is inhibited by an ion channel modulating compound with an $IC_{50}$ of approximately 13±1 μM. In one embodiment, Kv1.5, expressed in HEK cells, is inhibited by an ion channel modulating compound with an $IC_{50}$ of approximately 13±1 μM (as shown in FIG. 5) and Kv4 subfamily members are inhibited with an $IC_{50}$ of about 10 μM or greater (FIG. 4). In one embodiment, Kv1.5, expressed in HEK cells, is inhibited by an ion channel modulating compound with an $IC_{50}$ of approximately 13±1 μM (as shown in FIG. 5) and Kv4 subfamily members are inhibited with an $IC_{50}$ of about 30 μM or greater (as shown in FIGS. 4 and 7).

Open Channel Inhibition of Kv1

Figure 5:
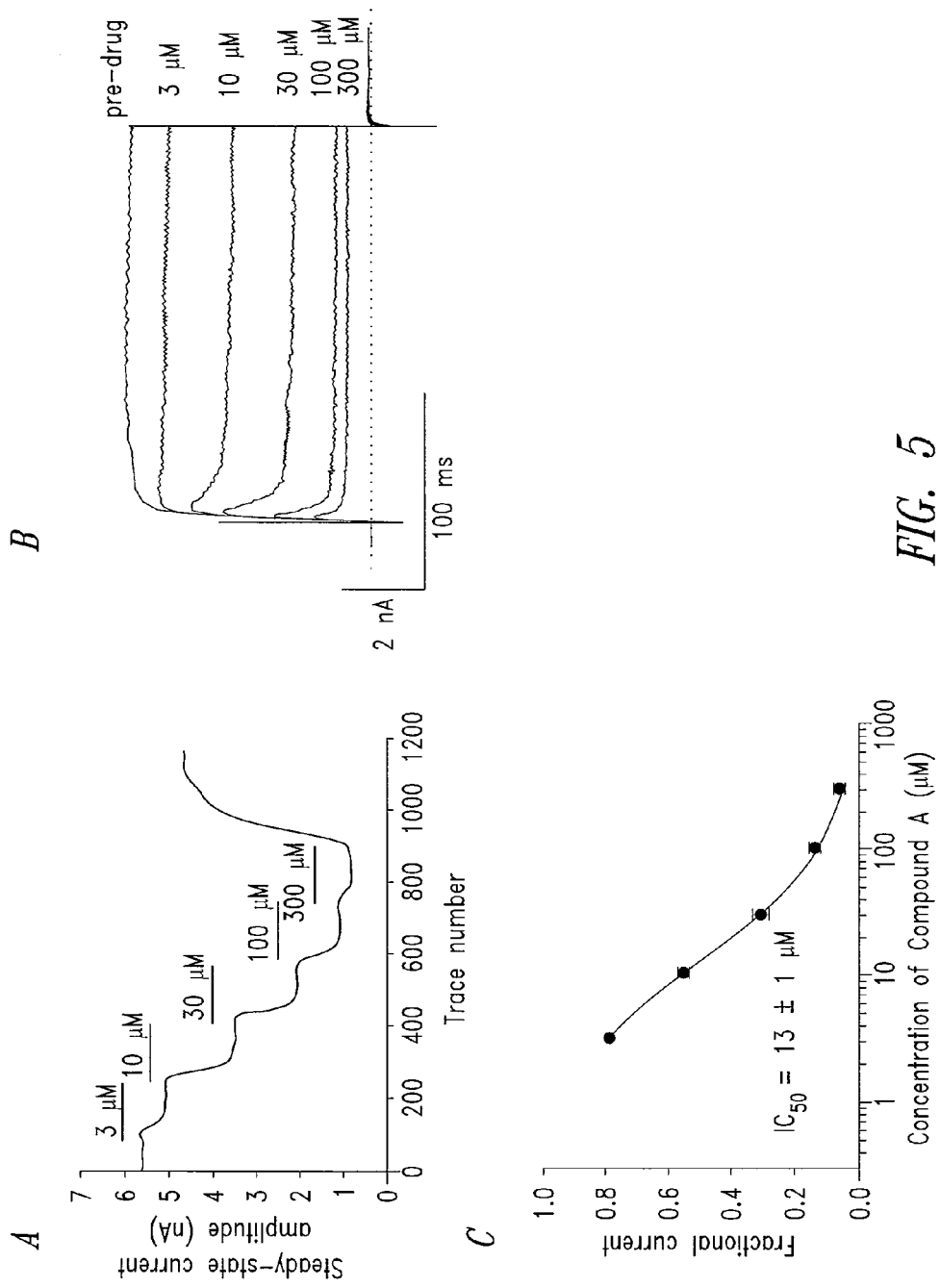
FIG. 5 shows the concentration-dependent inhibition of Kv1.5 channels by COMPOUND A at 1 Hz.

The diseases and conditions described in this patent application, and specifically atrial fibrillation or atrial flutter, may be treated and/or prevented using an ion channel modulating compound which inhibits Kv1 channels predominantly as an open channel blocker (as shown in FIG. 5). In one version, the ion channel modulating compound is a compound that is predominantly an open Kv1 channel blocker that exhibits substantially no rate-dependence (FIG. 12) or use-dependence (FIG. 13) in inhibiting the channel when it is activated at a frequency between approximately 0.1 and 20 Hz. In one version, the ion channel modulating compound inhibits Kv1.5 as an open channel blocker.

Inhibition of hERG Channels

The diseases and conditions described in this patent application, and specifically atrial fibrillation or atrial flutter, may be treated and/or prevented using an ion channel modulating compound which does not inhibit hERG channels except at micromolar concentrations. In one version, the ion channel modulating compound is a compound which inhibits hERG channels at $IC_{50}$ concentrations of greater than about 1 μM and less than about 100 μM. In one version, the ion channel modulating compound is a compound which inhibits hERG channels at $IC_{50}$ concentrations of greater than about 10 μM and less than about 50 μM. In one version, the ion channel modulating compound is a compound which inhibits hERG channels at $IC_{50}$ concentrations of greater than about 10 μM and less than about 25 μM (as seen in FIG. 6).

Equivalent Block of hERG and Kv1.5 in HEK Cells

The diseases and conditions described in this patent application, and specifically atrial fibrillation or atrial flutter, may be treated and/or prevented using an ion channel modulating compound for which the inhibition of hERG and the inhibition of Kv1.5 are about the same in HEK cells heterologously expressing these channels. In one version, the ion channel modulating compound is a compound for which inhibition (measured by $IC_{50}$) of hERG is approximately equivalent to inhibition (measured by $IC_{50}$) of Kv1.5 in HEK cells expressing these channels (FIGS. 5 and 6).

Preferential Block of hERG and Kv1.5 Over Kv4.2 and Kv4.3 in HEK Cells

The diseases and conditions described in this patent application, and specifically atrial fibrillation or atrial flutter, may be treated and/or prevented using an ion channel modulating compound which inhibits hERG and Kv1.5 preferentially over Kv4.2 and Kv4.3 in HEK cells heterologously expressing these channels. As used in this patent application, unless the context makes clear otherwise, preferential inhibition means that the $IC_{50}$ concentration at which the ion channel modulating compound inhibits one channel is less than the $IC_{50}$ concentration at which the ion channel modulating compound inhibits another (the non-preferential) channel.

In one version, the ion channel modulating compound is a compound for which inhibition (measured by $IC_{50}$) of hERG is between about 1× and 20× the potency for inhibition of Kv4.3 in HEK cells expressing these channels, and for which inhibition (measured by $IC_{50}$) of Kv1.5 is between about 1× and 20× the potency for inhibition of Kv4.3 in HEK cells expressing these channels. In one version, the ion channel modulating compound is a compound for which inhibition (measured by $IC_{50}$) of hERG is between about 1× and 8× the potency for inhibition of Kv4.3 in HEK cells expressing these channels, and for which inhibition (measured by $IC_{50}$) of Kv1.5 is between about 1× and 8× the potency for inhibition of Kv4.3 in HEK cells expressing these channels. In one version, the ion channel modulating compound is a compound for which inhibition (measured by $IC_{50}$) of hERG is between about 1× and 4× the potency for inhibition of Kv4.3 in HEK cells expressing these channels, and for which inhibition (measured by $IC_{50}$) of Kv1.5 is between about 1× and 4× the potency for inhibition of Kv4.3 in HEK cells expressing these channels (FIG. 7). In this last example the inhibition of Kv1.5 and of hERG are about equivalent (FIGS. 5 and 6).

In one version, the ion channel modulating compound is a compound for which inhibition (measured by $IC_{50}$) of hERG is approximately equivalent to the potency for inhibition of Kv4.3 in HEK cells expressing these channels, and for which inhibition (measured by $IC_{50}$) of Kv1.5 is approximately equivalent to the potency for inhibition of Kv4.3 in HEK cells expressing these channels.

Prolonged Atrial Refractoriness

The diseases and conditions described in this patent application, and specifically atrial fibrillation or atrial flutter, may be treated and/or prevented using an ion channel modulating compound which prolongs atrial refractoriness. In one version, the ion channel modulating compound is a compound which prolongs the atrial refractoriness in human atria by preferentially inhibiting $I_{Kur}$ (Kv1.5) or $I_{tO}$ (Kv4.3) or sodium channels (hH1). In one version, the ion channel modulating compound is a compound which prolongs the atrial refractoriness by inhibiting both $I_{Kur}$ (Kv1.5) and sodium channels (hH1). In one version, the ion channel modulating compound is a compound which prolongs the atrial refractoriness by inhibiting both $I_{Kur}$ (Kv1.5) and $I_{tO}$ (Kv4.3). In one version, the ion channel modulating compound is a compound which prolongs the atrial refractoriness by inhibiting both $I_{tO}$ (Kv4.3) and sodium channels (hH1). In one version, the ion channel modulating compound is a compound which prolongs the atrial refractoriness by inhibiting $I_{Kur}$ (Kv1.5), and $I_{tO}$ (Kv4.3), and sodium channels (hH1).

Figure 11:
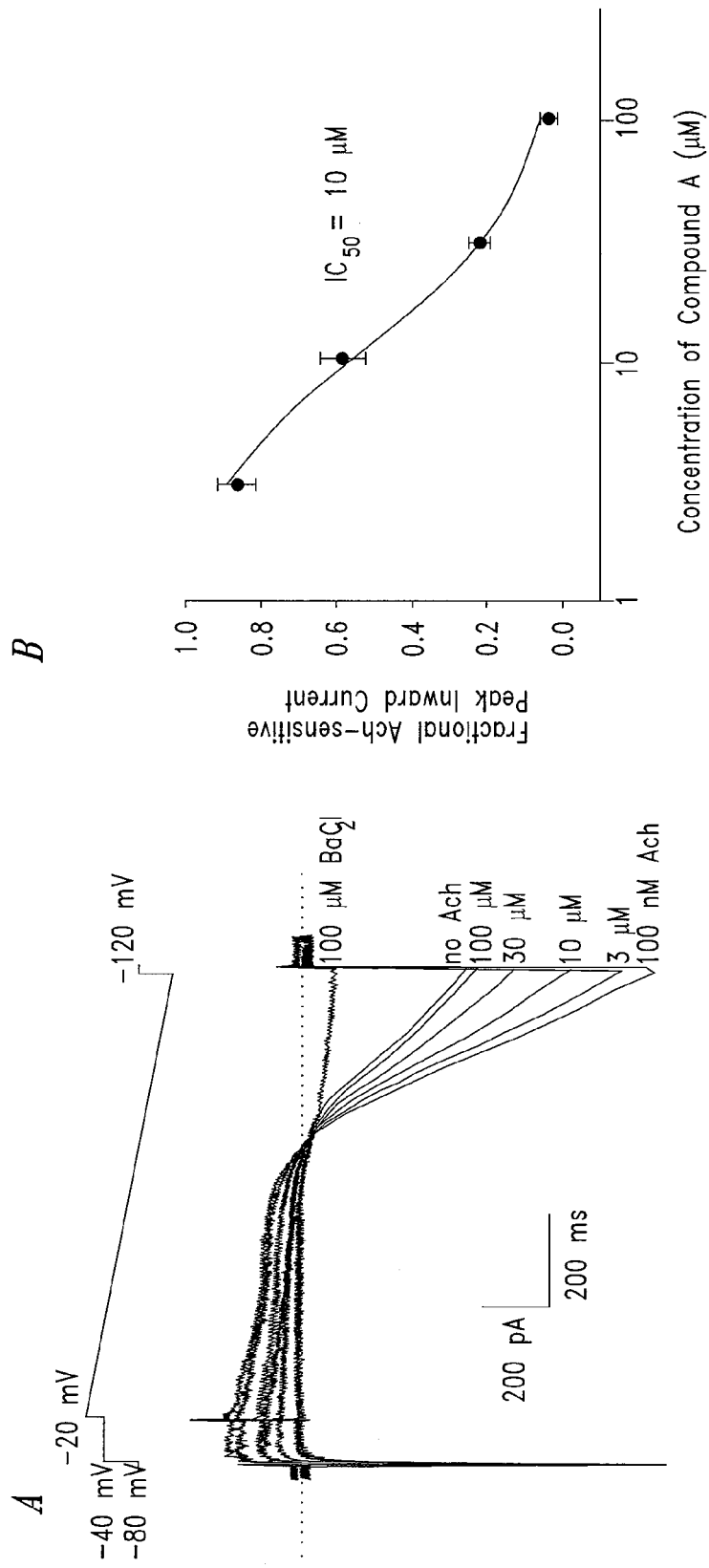
FIG. 11 illustrates concentration-dependent block of $I_{KACh}$ by COMPOUND A in isolated guinea pig atrial myocytes at 0.1 Hz.

Inhibition of Acetyl Choline Dependent or Adenosine Dependent Potassium Channels (Kir3) with an $IC_{50}$ in the Micromolar Range The diseases and conditions described in this patent application, and specifically atrial fibrillation or atrial flutter, may be treated and/or prevented using an ion channel modulating compound which inhibits Kir3 channels such as those which give rise to acetyl choline dependent potassium current $IK_{ACh}$, at concentrations between about 0.1 µM and about 1000 µM. In one version, the ion channel modulating compound is a compound which does not inhibit $IK_{ACh}$ in guinea pig atrial cells with an $IC_{50}$ of less than about 1 µM, but does inhibit $IK_{ACh}$ in guinea pig atrial cells with an $IC_{50}$ between about 1 µM and about 50 µM (FIG. 11).

As used in this patent application, unless the context makes clear otherwise, "Kir3" channels may include any member of the subfamilies of potassium channels that are activated by acetyl choline or adenosine interaction with its associated receptor. In one embodiment, Kir3 or $IK_{ACh}$ is inhibited by an ion channel modulating compound with an $IC_{50}$ of between 1 and 50 µM (at 1 Hz). In one embodiment, Kir3 or $IK_{ACh}$ is inhibited by an ion channel modulating compound with an $IC_{50}$ of approximately 10 µM (at 1 Hz). In one embodiment, $IK_{ACh}$ in guinea pig atrial cells is inhibited by an ion channel modulating compound with an $IC_{50}$ of approximately 10 µM (at 1 Hz, FIG. 11), and Kv1 and Kv4 subfamily members are also inhibited with an $IC_{50}$ of about 10 µM or greater (FIGS. 4 and 5).

Neutral Effect on Ventricular Repolarization

The diseases and conditions described in this patent application, and specifically atrial fibrillation or atrial flutter, may be treated and/or prevented using an ion channel modulating compound which has a neutral effect on ventricular repolarization. In one version, the ion channel modulating compound is a compound which has a neutral effect on human ventricular repolarization in that the ion channel modulating compound inhibits sodium current, including late sodium current, at similar concentrations and/or higher potency than it inhibits the hERG channels. In one version, the ion channel modulating compound is a compound which inhibits sodium channels (hH1) expressed in HEK cells with an $IC_{50}$ between 10-50 µM and which also inhibits hERG channels with an $IC_{50}$ greater than 10 µM.

Equivalent Inhibition of Early and Sustained Sodium Currents

The diseases and conditions described in this patent application, and specifically atrial fibrillation or atrial flutter, may be treated and/or prevented using an ion channel modulating compound which inhibits both the early and the late sodium currents in approximately equivalent magnitude. In one version, the ion channel modulating compound is a compound which inhibits both the early and the late sodium currents expressed in HEK cells in approximately equal magnitude (FIG. 8).

State-dependent Inhibition of Sodium Channels

The diseases and conditions described in this patent application, and specifically atrial fibrillation or atrial flutter, may be treated and/or prevented using an ion channel modulating compound which exhibits a state-dependent inhibition of the sodium channels. In one version, the ion channel modulating compound is a compound which exhibits a state-dependent inhibition that affects sodium channels in the activated state more than in the closed state. In one version, the ion channel modulating compound is a compound that causes inhibition of activated and closed hH1 sodium channels expressed in HEK cells with an activated:closed potency ratio (proportion of activated channel inhibition relative to proportion of closed channel inhibition, as proportions of total inhibition) of between about 10:1 and 1:1. Activated channels include those that are both open and also inactivated. In one version the ion channel modulating compound is a compound that causes inhibition of activated and closed hH1 sodium channels expressed in HEK cells with an activated:closed potency ratio between about 10:1 and 1:1 when pulsed from a holding potential between about −120 to −60 mV, to potentials that will open the channels. As used in this patent application, unless the context makes clear otherwise, "pulse" or "pulsed" refers to a voltage clamp step of a defined amplitude in mV. In one version, the ion channel modulating compound is a compound that, when used at about its $IC_{50}$, causes inhibition of activated and closed hH1 sodium channels expressed in HEK cells with an activated:closed potency ratio of about 2:1 when pulsed from about −100 mV to about −30 mV at about 10 Hz.

In one version, the ion channel modulating compound is a compound that causes inhibition of sodium channels in the open-state to a greater extent than the inactivated-state. In one version, the ion channel modulating compound is a compound that causes inhibition of sodium channels in the open-state with an open:inactivated potency ratio (proportion of open channel inhibition relative to proportion of inactivated channel inhibition, as proportions of total inhibition) of between about 100:1 and 5:1. In one version, the ion channel modulating compound is a compound that causes inhibition of sodium channels in the open-state with an with an open:inactivated potency ratio of greater than about 10:1 when pulsed from about −80 mV to about −30 mV for about 200 milliseconds (see FIG. 9).

Rapid Association and Dissociation from Sodium Channels

The diseases and conditions described in this patent application, and specifically atrial fibrillation or atrial flutter, may be treated and/or prevented using an ion channel modulating compound which rapidly associates and dissociates from sodium channels. In one version, the ion channel modulating compound is a compound which rapidly associates and dissociates from sodium channels at approximately the $IC_{50}$ concentration that the ion channel modulating compound inhibits the sodium channel. The rapid association of the compound may be exemplified by its minor effect on the time to peak of the inward sodium current. The rapid dissociation of the compound may be inferred from the minor effect on the relaxation phase of the macroscopic inward sodium current, the overall inhibiting effect therefore appearing as 'a scaling down' of the current waveform. Minor effect includes not having any effect, or having less than 15%, 10% or 5% effect.

In further experiments, rapid dissociation was assessed by applying continuous 1 Hz stimulation after a 10 Hz conditioning train in the presence of 10 μM COMPOUND C and measuring the time constants of recovery of early sodium currents. The mean time constant of recovery (τ1) was 0.19±0.05 s and this accounted for 76.6% of the total current recovery. The conclusion of this experiment is that almost complete sodium current recovery from block by COMPOUND C will occur in less than 1.5 s.

Figure 10:
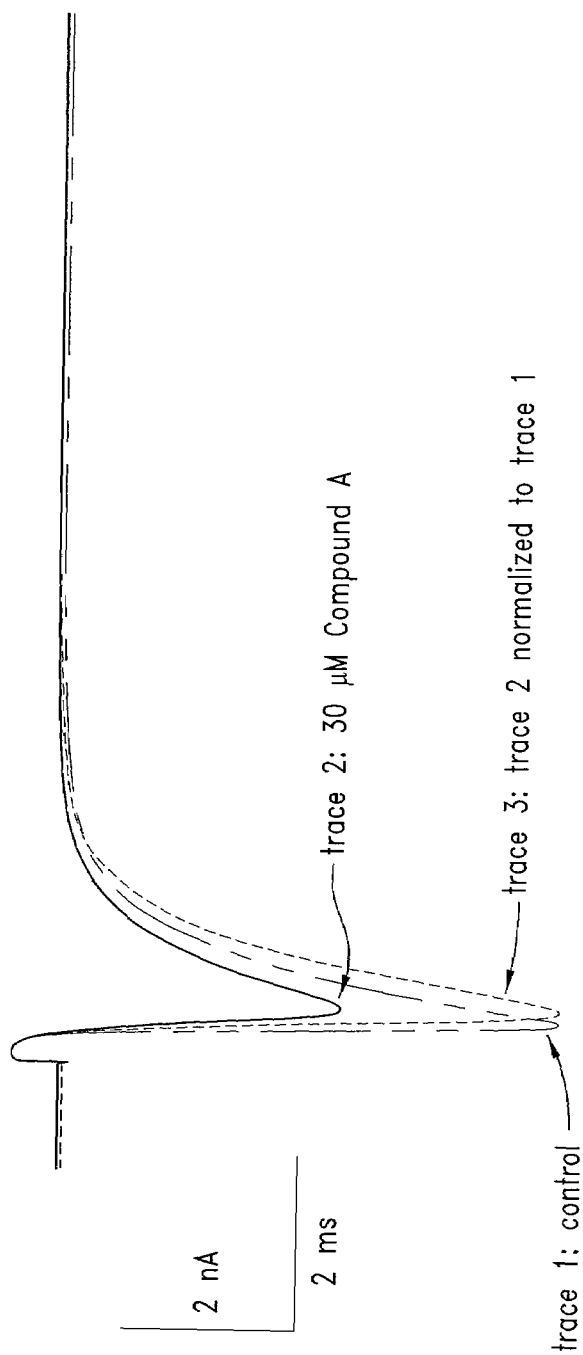
FIG. 10 illustrates hH1 sodium current traces exemplifying minor changes in waveform kinetics in the presence of COMPOUND A.

As used in this patent application, unless the context makes clear otherwise, "rapid association and dissociation" includes the characteristics of "fast on/fast off" inhibition of sodium currents (FIG. 10).

Pathology-selective Inhibition of a Sodium Channel, and Atrial Selectivity

The diseases and conditions described in this patent application, and specifically atrial fibrillation or atrial flutter, may be treated and/or prevented using an ion channel modulating compound which demonstrates a pathology-selective inhibition of sodium channels. In one version, the ion channel modulating compound is a compound which brings about inhibition of sodium channels during a pathology that causes a depolarization of the membrane potential (i.e. a voltage-dependence of inhibition). In one version voltage-dependence of inhibition is demonstrated by between about a 1-fold and a 50-fold decrease in $IC_{50}$ for a resting potential change from about −120 to about −60 mV. In one version this voltage-dependence of inhibition is demonstrated by between about a 3-fold and a 20-fold decrease in $IC_{50}$ for a resting potential change from about −120 to about −60 mV.

Combinations of Ion Channel Modulating Compounds and Other Drugs

The ion channel modulating compounds described in this patent application can be provided for treating and/or preventing a variety of diseases and conditions in combination with other drugs including, but not limited to cardio-vascular agents, beta-blockers, ACE inhibitors, antihypertensives, diuretics, antipsychotics, anticoagulants (antiplatelets), antidepressants, inotropes, Ca sensitizers, Ca channel blockers, adrenergic blocking agents, angiotensin II receptor antagonists, xanthine oxidase inhibitors (XOIs), natriuretic peptides, metabolic modulators, lipid/cholesterol modulating agents, anti-inflammatory agents, vasodilators, anti-convulsants, antioxidants, antilipids, digitalis glycosides, rate control drugs, antihistamines, antisaspmodics, antibiotics, anti-rejection drugs, immunomodulators, chemotherapeutics, and antiarrhythmics.

Diseases and conditions that may be treated and/or prevented using the combinations described in this section include but not limited to (1) treating arrhythmia (2) preventing arrhythmia, (3) preventing reoccurrence of arrhythmia (4) treating and preventing recurrence of arrhythmia, (5) treating atrial fibrillation, (6) preventing recurrence of atrial fibrillation, (7) treating and preventing recurrence of atrial fibrillation, (8) treating atrial flutter, (9) preventing of atrial flutter, and (10) treating and preventing of atrial flutter.

As used herein "combination" refers to any mixture or permutation of ion channel modulating compound and another drug or drugs. Unless the context makes clear otherwise, "combination" may include simultaneous or sequentially delivery of an ion channel modulating compound with another drug or drugs. Unless the context makes clear otherwise, "combination" may include dosage forms of an ion channel modulating compound with another drug or drugs. Unless the context makes clear otherwise, "combination" may include routes of administration of an ion channel modulating compound with another drug or drugs. Unless the context makes clear otherwise, "combination" may include formulations of an ion channel modulating compound with another drug or drugs. Dosage forms, routes of administration and formulations include but not limited to those described in the section entitled Dosage forms, routes of administration, and formulation of ion channel modulating compounds.

Typically, beta blockers block the beta adrenergic receptors, either selectively or nonselectively. Examples of beta blocker which may be provided in combination with the ion channel modulating compounds described herein include, but are not limited to Acebutolol (Acebutolol Hydrochloride, Sectral), Atenolol (Tenormin, Tenoretic), Betaxolol (Kerlone), Bisoprolol (Zebeta, Ziac), Cartelol (Cartrol), Carvedilol (Coreg), Esmolol (Brevibloc), Labetolol (Normodyne, Trandate, Labetolol HCl), Metoprolol (Lopressor, Lopressor HCl, Toprol, Toprol XL), Nadolol (Corgard, Corzide), Bendroflumethiazide (Corzide), Triamterene (Dyazide), Hydrochlorothiazide (Dyazide), Penbutolol (Levatol, Penbutolol Sulfate), Pindolol (Visken), Propranolol (Inderal, Inderide, Innopran, Betchron, Propanolol), Sotalol (Betapace, Sotalol), Timolol (Blocadren, Timolide, Timoptic), Oxprenolol, Moprolol, Carazolol, Alprenolol, Bunolol. This list is not exhaustive, and additional beta blockers known in the art are also contemplated.

In one example, COMPOUND A is used in combination with one or more of the above listed beta blockers. The COMPOUND A and another drug may be administered at the same time, or at different times. COMPOUND A and another drug may be administered via the same route or by different routes of administration. COMPOUND A and another drug may be administered in one formulation or in different formulations.

Angiotensin converting enzyme inhibitors (ACE inhibitors) reduce peripheral vascular resistance via blockage of the angiotensin converting enzyme, reducing myocardial oxygen consumption. Examples of ACE inhibitors which may be provided in combination with the ion channel modulating compounds described herein include, but are not limited to Quinapril (Accupril, Accuretic), Perindopril (Aceon, Perindopril Erbumine), Ramipril (Altace), Captopril (Capoten, Capozide), Benazepril (Lotensin, Benazepril HCl, Lotensin HCl, Lotrel), Trandolapril (Mavik, Tarka), Fosinopril (Monopril, Fosinopril Sodium), Lisinopril (Prinivil, Zestril, Prinizide, Prinzide, Zestoretic), Moexipril (Univasc, Moexipril HCl, Uniretic), Enalapril (Vasotec, Lexxel, Teczem, Vaseretic), Enalaprilat, Ziac (Hydrochlorothiazide and Bisoprolol fumarate), Zebeta. This list is not exhaustive, and additional ACE inhibitors known in the art are also contemplated.

In one example, COMPOUND A is used in combination with one or more of the above listed ACE inhibitors. The COMPOUND A and another drug may be administered at the same time, or at different times. COMPOUND A and another drug may be administered via the same route or by different routes of administration. COMPOUND A and another drug may be administered in one formulation or in different formulations.

Examples of antihypertensives which may be provided in combination with the ion channel modulating compounds described herein include, but are not limited to Sulfonamide Diuretics (Hydrochlorothiazide, Chlorthalidone, Furosemide, Mefruside, Indapamide), $K^+$-Retaining Diuretics (Amiloride Triamterene), Inhibitors of the Sympathetic Nervous System, Drugs with Primarily Central Actions (Methyldopa, Clonidine, Guanfacine, Guanabenz), Drugs with Primarily Peripheral Action (Amine Depleting and Adrenergic Neuron Blocking Agents such as Reserpine, Guanethidine and/or a-Adrenoceptor Antagonists such as: Prazosin, Indoramin, Urapidil, and/or b-Adrenoceptor Antagonists such as: Propranolol, Metoprolol, Nadolol, Pindolol, Timolol, Acebutolol, Labetalol), Smooth Muscle Relaxants ($Ca^{2+}$ Channel Antagonists and Vasodilators), Bidil (isosorbide dinitrate hydralizine combination). This list is not exhaustive, and additional antihypertensives known in the art are also contemplated. In one example, COMPOUND A is used in combination with one or more of the above listed antihypertensives. The COMPOUND A and an antihypertensive may be administered at the same time, or at different times. COMPOUND A and an antihypertensive may be administered via the same route or by different routes of administration. COMPOUND A and an antihypertensive may be administered in one formulation or in different formulations.

Examples of antipsychotics which may be provided in combination with the ion channel modulating compounds described herein include, but are not limited to Thioridazine (Melleril, Aldazine), Pimozide, Clozapine, Haloperidol (Haldol), Risperidone (Risperdal), Olanzapine, Quetiapine, Ziprasidone, Aripiprazole, Sulpride, Chlorpromazine (Thorazine). This list is not exhaustive, and additional antipsychotics known in the art are also contemplated.

In one example, COMPOUND A is used in combination with one or more of the above listed antipsychotics. The COMPOUND A and an antipsychotic may be administered at the same time, or at different times. COMPOUND A and an antipsychotic may be administered via the same route or by different routes of administration. COMPOUND A and an antipsychotic may be administered in one formulation or in different formulations.

Examples of anticonvulsants which may be provided in combination with the ion channel modulating compounds described herein include, but are not limited to Barbiturates: Mephobarbital (Mebaral), Pentobarbital (Nembutal), Phenobarbital (Luminol, Solfoton); Benzodiazepines: Chlorazepate (Tranxene), Clonazepam (Klonopin), Diazepam (Valium); GABA Analogues: Gabapentin (Neurontin), Tiagabine (Gabitril); Hydantoins: Ethotoin (Peganone), Fosphentyoin (Mesantoin), Phenyloin (Dilantin, Diphenylhydantoin); Oxazolidinediones: Trimethadione (Tridione); Phenyltriazines: Lamotrigine (Lamictal); Succinimides: Ethosuximide (Zarontin),Methsuximide (Celontin), Phensuximide (Milontin); and miscellaneous anticonvulsants: Acetazolamide (Diamox), Carbamazepine (Carbatrol, Tegretol), Felbamate (Felbatol), Levetiracetam (Keppra), Oxcarbazepine (Trileptal), Primidone (Mysoline), Topiramate (Topamax), Valproic acid (Depakene, Depakote), Zonisamide (Zonegran). This list is not exhaustive and additional anticonvulsants known in the art are also contemplated.

In one example, COMPOUND A is used in combination with one or more of the above listed anticonvulsants. The COMPOUND A and an anticonvulsant may be administered at the same time, or at different times. COMPOUND A and an anticonvulsant may be administered via the same route or by different routes of administration. COMPOUND A and an anticonvulsant may be administered in one formulation or in different formulations.

Examples of antioxidants which may be provided in combination with the ion channel modulating compounds described herein include, but are not limited to vitamin C, vitamin E, beta-carotene, lutein, lycopene, vitamin B2, coenzyme Q10, cysteine as well as herbs, such as bilberry, turmeric (curcumin), grape seed or pine bark extracts, and ginkgo. This list is not exhaustive and additional antioxidants known in the art are also contemplated.

In one example, COMPOUND A is used in combination with one or more of the above listed antioxidants. The COMPOUND A and an antioxidant may be administered at the same time, or at different times. COMPOUND A and an antioxidant may be administered via the same route or by different routes of administration. COMPOUND A and an antioxidant may be administered in one formulation or in different formulations.

Examples of anticoagulants (antiplatelets) which may be provided in combination with the ion channel modulating compounds described herein include, but are not limited to Heparin (Bivalirudin), Coumadin (Warfarin), Miradon (Anisindione), Sintrom (Acenocoumarol), Warfilone, Dicumarol, Ardeparin, Dalteparin, Danaparoid, Enoxaparin, Ximelagatran, Eptifibatide, Aspirin (acetylsalicylic acid, ASA), Clopidogrel (Plavix), Dipyridamole (Aggrenox, Persantine), Ticlopidine (Ticlid), Abciximab (ReoPro), platelet GPIIb-IIIa blockers. This list is not exhaustive and additional anticoagulants (antiplatelets) known in the art are also contemplated.

In one example, COMPOUND A is used in combination with one or more of the above listed anticoagulants. The COMPOUND A and an anticoagulant may be administered at the same time, or at different times. COMPOUND A and an anticoagulant may be administered via the same route or by different routes of administration. COMPOUND A and an anticoagulant may be administered in one formulation or in different formulations.

Examples of antidepressants which may be provided in combination with the ion channel modulating compounds described herein include, but are not limited to Amitriptyline (Tryptizol), Clomipramine (Anafranil), Citalopram (Cipramil), Dothepin (Prothiaden), Doxepin (Sinequan), Fluoxetine (Prozac), Imipramine (Tofranil), Lofepramine (Gamanil), Mirtazapine (Zispin), Nortriptyline (Allegron), Paroxetine (Paxil, Seroxat), Reboxitine (Edronax), Sertraline (Lustral), Trazodone (Molipaxin), Venlafaxine (Efexor), Amoxapine, Bupropion, Desipramine, Escitalopram Oxalate, Fluvoxamine, Imipramine, Isocarboxazid, Maprotiline, Phenelzine, Protriptylin, Tranylcypromine, Trimipramine, Venlafaxine. This list is not exhaustive and additional antidepressants known in the art are also contemplated.

In one example, COMPOUND A is used in combination with one or more of the above listed antidepressants. The COMPOUND A and an antidepressant may be administered at the same time, or at different times. COMPOUND A and an antidepressant may be administered via the same route or by different routes of administration. COMPOUND A and an antidepressant may be administered in one formulation or in different formulations.

Examples of inotropes which may be provided in combination with the ion channel modulating compounds described herein include, but are not limited to Dobutamine, Dopamine, Epinephrine, Norepinephrine, Milrinone (Primacor), Amrinone (Inocor), Adrenaline, Dopexamine, Ephedrine, Salbutamol, Methoxamine, Isophrenaline, Metaraminol, Phenylephrine, Noradrenaline, Adenosine, Digitalis, Amrinone, Digitoxin, Digoxin, Enoximone, Piroximione. This list is not exhaustive and additional inotropes known in the art are also contemplated.

In one example, COMPOUND A is used in combination with one or more of the above listed inotropes. The COMPOUND A and an inotrope may be administered at the same time, or at different times. COMPOUND A and an inotrope may be administered via the same route or by different routes of administration. COMPOUND A and an inotrope may be administered in one formulation or in different formulations.

Examples of calcium sensitizers which may be provided in combination with the ion channel modulating compounds described herein include, but are not limited to Levosimendan, thiadiazinone derivatives such as EMD 53998, CGP 48506. This list is not exhaustive and additional calcium sensitizers known in the art are also contemplated.

In one example, COMPOUND A is used in combination with one or more of the above listed calcium sensitizers. The COMPOUND A and a calcium sensitizer may be administered at the same time, or at different times. COMPOUND A and a calcium sensitizer may be administered via the same route or by different routes of administration. COMPOUND A and a calcium sensitizer may be administered in one formulation or in different formulations.

Examples of calcium channel blockers which may be provided in combination with the ion channel modulating compounds described herein include, but are not limited to Nitrendipine, Nifedipine (Procardia, Procardia XL, Adalat, Adalat CC), Diltiazem (Cardizem), and Verapamil (Calan, Isoptin), Nicardipine, Bepridil (Vascor), Mibefradil (Posicor), Felodipine (Plendil, Renedil), Flunarizine (Sibelium), Isradipine (DynaCirc), Nimodipine (Nimotop), Amlodipine (Norvasc). This list is not exhaustive and additional calcium channel blockers known in the art are also contemplated.

In one example, COMPOUND A is used in combination with one or more of the above listed calcium channel blockers. The COMPOUND A and a calcium channel blocker may be administered at the same time, or at different times. COMPOUND A and a calcium channel blocker may be administered via the same route or by different routes of administration. COMPOUND A and a calcium channel blocker may be administered in one formulation or in different formulations.

Examples of adrenergic blocking agents which may be provided in combination with the ion channel modulating compounds described herein include, but are not limited to reserpine, guanethidine, Alpha 1-Adrenergic antagonists (prazosin) In one example, COMPOUND A is used in combination with one or more of the above listed adrenergic blocking agents. The COMPOUND A and an adrenergic blocking agent may be administered at the same time, or at different times. COMPOUND A and an adrenergic blocking agent may be administered via the same route or by different routes of administration. COMPOUND A and an adrenergic blocking agent may be administered in one formulation or in different formulations.

Examples of angiotensin II antagonists which may be provided in combination with the ion channel modulating compounds described herein include, but are not limited to Losartan (Cozaar), Valsartan (Diovan), Irbesartan (Avapro), Candesartan (Atacand), Telmisartan (Micardis), Eprosartan, Tasosartan, Zolarsartan, Lisinopril, Atenolol, Bendroflu-azide, Saralasin. This list is not exhaustive and additional angiotensin II antagonists known in the art are also contemplated.

In one example, COMPOUND A is used in combination with one or more of the above listed angiotensin II antagonists. The COMPOUND A and an angiotensin II antagonist may be administered at the same time, or at different times. COMPOUND A and an angiotensin II antagonist may be administered via the same route or by different routes of administration. COMPOUND A and an angiotensin II antagonist may be administered in one formulation or in different formulations.

Examples of xanthine oxidase inhibitors which may be provided in combination with the ion channel modulating compounds described herein include, but are not limited to oxypurinol, allopurinol (Zyloprim, Purinol), febuxostat (TEI-6720; TMX-67). Furthermore, any pharmaceutically acceptable XOI may be provided in combination. Examples of suitable classes of compounds from which a XO inhibitor may be selected may be found in the patent documents listed below and the patents and publications referenced therein, all of which are incorporated by reference herein. The nature and synthesis of the compounds referenced are taught in those patents.

Examples of suitable classes of compounds from which a XOI may be selected include: U.S. Pat. Nos. 5,674,887, 5,272,151, 5,212,201, 4,495,195, 4,346,094, 4,281,005, 4,241,064, 4,179,512, 4,058,614, 4,024,253, 4,021,556, 3,920,652, 3,907,799, 3,892,858, 3,892,738, 3,890,313, 3,624,205, 3,474,098, 2,868,803, 6,191,136, 6,569,862, WO0200210 (PCT/US01/20457), European 429,038, phenylethenyl esters of phenylpropenoic acid; PCT Publication WO9113623, C5-monosubstituted barbiturates; Czechoslovakia 264505, salts of N-acetyl-p-aminosalicylic acid; German 3912092, heterocyclic compounds with more than one hetero atom, such as aminotriazolopyridoquinazolinone; Japanese 02245198, phenol compounds such as sodium salicylate; European 269859, pyrazolotriazines; European 274654, heterocylotriazinones such as 7-phenylisothiazolo[4,5-d]-1,2,3-triazin-4(3H)-one; Netherlands 8602382, catechol derivatives such as 4-(+)-methylthiocatechol; German 3632841, similar to the above; German 3632824, bicyclic catechol derivatives; Japanese 59219229, indoles, such as 1-formyl-4-hydroxy-9H-pyrido[3,4-b]indole; U.S. Pat. No. 4,336,257, 2-(4-pyridyl)-5-chlorobenzimidazole, 1H-imidazo[4,5-b]pyridines, and imidazo[4,5-c]pyridines; European 28660, pyrazolobenzotriazine derivatives; Japanese 55055185, compounds derived from extraction of picrasma quassioides; German 2941449, pyridolindoles isolated according to the above patent; U.S. Pat. No. 4,110,456, imidazoles, including sulfamoylimidazoles; U.S. Pat. No. 4,021,556, pyrazolopyrimidines, pyrazolopyrimidinols and pyrazolopyrimidinediols; U.S. Pat. No. 4,032,522, trifluoromethylimidazoles; U.S. Pat. No. 3,988,324, heterocyclobenzo-thiadiazinesulfonamides; Japanese 51054576, hydroxy or acyloxyalkylaminobenzothiadiazines; U.S. Pat. No. 3,960,854, 7-mercapto (or thio) benzothiadiazine-1,1-dioxides; U.S. Pat. No. 3,969,518, 3-haloalkylbenzothiadiazine-1,1-dioxides; U.S. Pat. No. 3,951,966, heterocycle-substituted benzothiodiazines; Japanese 51006992, dihydrothiazoloadenines; Japanese 51006993, imidazoadenines and pyrimidinoadenines; French 2262977, formylaminoallylidenehydrazines, substituted with aryl groups; French 2262976, formamidrazones, substituted with aryl groups; German 2410650, formamidrazones, isonicotinyl pyrimidinones and the like; German 2410579, orotic acid hydrazide, and the corresponding nicotinic and isonicotinic acid derivative; German 2509130, acryloylformamidrazones, pyrimidinones and the like; German 2410653, acylpyrazolo-carboxamides; German 2508934, formylcarbamoylpyrazoles substituted with heterocyclic and carbocyclic aryl groups; German 2410611, nicotinic acid hydrazide, azapentadienylidene; German 2509094, aminoazapentadienylidene hydrazine; German 2509049, morpholinoacryloyl-formamidrazones substituted with various aryl groups; German 2509175, substituted 2-hydrazonomethyl-3-hydroxy-4-aza-2,4-pentadiene-nitriles; U.S. Pat. No. 3,892,858, 7-alkylsulfonyl-substituted-benzothiadiazine 1,1-dioxides; German 2410614, heterocyclic N-acyl-N'-3-amino-2-cyanoacryloyl) formamidrazones; U.S. Pat. No. 3,907,799, imidazopyrimidinediols; Japanese 50004039, salicylanilides; British 1403974, dioxo-6,6-azopurine; Japanese 49072298, 9-substituted palmatine derivatives; German 2457127, haloimidazoles substituted with pyridyl and the like; Japanese 49127943, 4-(2-hydroxybenzamido)-salicylic acids; German 2418467, hydroxybenzanilides; Japanese 49048664, hydroxyalkyl imidazoles; U.S. Pat. No. 3,816,625, 7-alkylsulfonyl-substituted benzothiadiazine-1,1-dioxides; U.S. Pat. No. 3,816,626, 3-pyridyl-1,2,4-benzothiadiazine-1,1-dioxides; U.S. Pat. No. 3,816,631, 6-sulfamoyl-7-substituted-(3H)quinazolinones; German 2356690, pyrazolo[3,4-d]pyrimidine N-oxides; German 2344757, 2-cyanopyrimidine-4(1H)ones; German 2351126, 6-sulfamoyl-4(3H)-quinazolinones; German 2343702, 4-mercapto-1H-pyrazolo[3,4-d]pyrimidine; German 2344733, 3-chloro-2-(hydrazonomethyl)-4-aza-2,4-pentadienenitriles; German 2344738, 2-hydrazonomethyl-3-hydroxy-aza-2,4-pentadienenitriles; German 2224379, 7-βD-ribofuranosyl-4,6-dihydroxypyrazolo[3,4-d]pyrimidine; German 2318784, N-(2,4-dihydroxybenzoyl)-4-aminosalicylic acids; Japanese 48067491, formyluracils; German 2313573, 7-mercapto-1,2,4-benzothiadiazine 1,1-dioxide; German 2313636, benzothiadiazines substituted with heterocyclic groups; German 1966640, 4-hydroxypyrazolo[3,4-d]pyrimidines; French 2143577, 3-(2-chlorobenzoylamino)-benzoic acid derivatives; German 2255247, 5-(5-indanyloxy)tetrazoles; German 2236987, pyrazolo[1,5-a]pyrimidines; French 2109005, 4-(2-quinoxalinyl)-phenoxyacetic acid derivatives; French 2081360, 2,5-disubstituted imidazoles; German 2147794, 1,2,4-triazoles substituted with heterocyclic and other aryl groups; German 1814082, allopurinol and oxypurinol; German 1927136, 1-D-ribosylallopurinol; French 4777, 4-mercaptopyrazolo[3,4-d]pyriridine; French 1480652, 4-oxo-5-alkylpyrazolo[3,4-d]pyrimidines. This list is not exhaustive and additional XOIs known in the art are also contemplated.

In one example, COMPOUND A is used in combination with one or more of the above listed xanthine oxidase inhibitors. COMPOUND A and a xanthine oxidase inhibitor may be administered at the same time, or at different times. COMPOUND A and a xanthine oxidase inhibitor may be administered via the same route or by different routes of administration. COMPOUND A and a xanthine oxidase inhibitor may be administered in one formulation or in different formulations.

The natriuretic peptide system includes A-type or atrial natriuretic peptide (ANP), B-type or brain natriuretic peptide (BNP), C-type natriuretic peptide (CNP) and D-type natriuretic peptide (DNP). These similarly-structured peptides exert a wide range of effects on the kidney, heart and central nervous system. The A- and B-type natriuretic peptides are secreted predominantly from storage granules in the myocardium of the atria and ventricles of the human heart, respectively, and the main trigger for their secretion is the stretching of the cardiac chambers regulated by ventricular wall tension. Both ANP and BNP have profound natriuretic, diuretic and vasodilatory effects on the body. An important feature of these natriuretic peptides is their interaction with other neurohormonal systems. In contrast with loop diuretics and many vasodilators, natriuretic peptides cause inhibition rather than stimulation of the renin-angiotensin-aldosterone system. For example, ANP directly antagonizes the renin-angiotensin-aldosterone system by inhibiting renin secretion, reducing ACE activity, and inhibiting aldosterone release from the adrenal glands. Both ANP and BNP also inhibit the release of endothelins, which are potent vasoconstrictors that originate in the vascular endothelium, while ANP appears to reduce the levels of circulating catecholamines. They may also be able to reduce cardiac ischemia and modulate vascular growth.

Examples of natriuretic peptides which may be provided in combination with the ion channel modulating compounds described herein include, but are not limited to ANP and BNP such as Nesiritide (Natrecor, recombinant B-type brain natriuretic peptide). This list is not exhaustive, and additional natriuretic peptides known in the art are also contemplated.

In one example, COMPOUND A is used in combination with one or more of the above listed natriuretic peptides. COMPOUND A and a natriuretic peptide may be administered at the same time, or at different times. COMPOUND A and a natriuretic peptide may be administered via the same route or by different routes of administration. COMPOUND A and a natriuretic peptide may be administered in one formulation or in different formulations.

Examples of metabolic modulators, which may be provided in combination with the ion channel modulating compounds described herein include, but are not limited to partial fatty acid beta-oxidation (pFOX) inhibitors such as trimetazidine and ranolazine; inhibitors of the mitochondrial camitine palmitoyltransferase-1 (CPT-1) such as etomoxir, oxfenicine and perhexiline; pyruvate dehydrogenase (PDH) activators such as dichloroacetate and carnitine. This list is not exhaustive and additional metabolic modulators known in the art are also contemplated.

In one example, COMPOUND A is used in combination with one or more of the above listed metabolic modulators. COMPOUND A and a metabolic modulator may be administered at the same time, or at different times. COMPOUND A and a metabolic modulator may be administered via the same route or by different routes of administration. COMPOUND A and a metabolic modulator may be administered in one formulation or in different formulations.

Examples of lipid/cholesterol modulating agents which may be provided in combination with the ion channel modulating compounds described herein include, but are not limited to statins (atorvastatin, pravastatin, simvastatin, lovastatin), hypercholesterolemia-treating agents. This list is not exhaustive and additional lipid/cholesterol modulating agents known in the art are also contemplated. In one example, COMPOUND A is used in combination with one or more of the above listed lipid/cholesterol modulating agents. COMPOUND A and a lipid/cholesterol modulating agent may be administered at the same time, or at different times. COMPOUND A and a lipid/cholesterol modulating agent may be administered via the same route or by different routes of administration. COMPOUND A and a lipid/cholesterol modulating agent may be administered in one formulation or in different formulations.

Examples of anti-inflammatory agents which may be provided in combination with the ion channel modulating compounds described herein include, but are not limited to glucocorticoids (GCs), non-steroidal anti-inflammatory drugs (NSAIDs) such as aspirin, diclofenac, naproxen, indomethacin and ibuprofen, selective COX-2 inhibitors such as celecoxib, rofecoxib, etoricoxib. This list is not exhaustive and additional anti-inflammatory agents known in the art are also contemplated. In one example, COMPOUND A is used in combination with one or more of the above listed anti-inflammatory agents. COMPOUND A and an anti-inflammatory agent may be administered at the same time, or at different times. COMPOUND A and a anti-inflammatory agent may be administered via the same route or by different routes of administration. COMPOUND A and an anti-inflammatory agent may be administered in one formulation or in different formulations.

Examples of vasodilators which may be provided in combination with the ion channel modulating compounds described herein include, but are not limited to Hydralazine (Apresoline), Diazoxide, Minoxidil (Loniten), Sodium Nitroprusside, Nitroprusside, Diazozide, Ifenprodil Tartrate, Dilazep Dihydrochloride, Cilostazol, Dipyridamole, Isosorbide Dinitrate, Isosorbide Mononitrate, Nitroglycerin, Sildenafil, vardenafil, tadalafil (Cialis), alprostadil, Papaverine. This list is not exhaustive and additional vasodilators known in the art are also contemplated.

In one example, COMPOUND A is used in combination with one or more of the above listed vasodilators. COMPOUND A and a vasodilator may be administered at the same time, or at different times. COMPOUND A and a vasodilator may be administered via the same route or by different routes of administration. COMPOUND A and a vasodilator may be administered in one formulation or in different formulations.

Examples of diuretics which may be provided in combination with the ion channel modulating compounds described herein include, but are not limited to thiazides and related agents (hydrochlorothiazide, chlorthalindone, methyclothiazide, hydroflumethiazide, metolazone, chlorothiazide, methyclothiazide, quinethazone, chlorthalidone, trichlormethiazide, bendroflumethiazide, polythiazide), loop agents (bumetamide, torsemide, ethacrynic acid, furosemide), potassium-sparing agents (amiloride, spironolactone, triamterine), Indacrinone, Muzolimine. This list is not exhaustive and additional diuretics known in the art are also contemplated. In one example, COMPOUND A is used in combination with one or more of the above listed diuretics. COMPOUND A and a diuretic may be administered at the same time, or at different times. COMPOUND A and a diuretic may be administered via the same route or by different routes of administration. COMPOUND A and a diuretic may be administered in one formulation or in different formulations.

Examples of additional sympatholytic agents which may be provided in combination with the ion channel modulating compounds described herein include, but are not limited to clonidine, methyldopa(Aldomet), Guanabenz (Wytensin), Guanfacine (Tenex), Dihydroergotamine Mesylate, Ergotamine Tartrate, Caffine, reserpine, Propranolol (Inderal), Labetalol (Normodyne, Trandate). This list is not exhaustive and additional sympatholytic agents known in the art are also contemplated. In one example, COMPOUND A is used in combination with one or more of the above listed sympatholytic agents. COMPOUND A and a sympatholytic agent may be administered at the same time, or at different times. COMPOUND A and a sympatholytic agent may be administered via the same route or by different routes of administration. COMPOUND A and a sympatholytic agent may be administered in one formulation or in different formulations.

Other examples of antiarrhythmic agents which may be provided in combination with the ion channel modulating compounds described herein include, but are not limited to ANP, Adenosine (Adenosine triphosphate, Adenosine, Adenocard, Adenosine Phosphate), Amiodarone HCl (Amiodarone, Cordarone, Pacerone), Azimilide, Bretylium (Bretylium Tosylate, Bretylol, Bretylium Tosylate/Dextrose), Diusopyramide (Norpace, Diisopyramide Phosphate), Encainide HCl (Enkaid, Encainide), Esmolol HCl (Brevibloc), Propranolol (Inderide, Propranolol HCl), Flecainide (Tambocor, Flecainide Acetate), Lidocaine (Nulicaine, Lidocaine HCl Viscous, Lidocaine HCl/Dextrose, Xylocalne), Mexilitine (Mexitil, Mexilitine HCl), Moricizine (Ethmozine, Moricizine HCl), Procainamide (Pro-2, Procan SR, Procan, Procanbid, Pronestyl), Propanfenone (Rythmol, Propafenone), Proparacaine (Kainair), Tocaininde (Tonocard), Quinidine (Cardioquin, Quinagulate, Quinidex, Cin-Quin, Duraquin, Quinora, Sk-Quinidine Sulfate, Quinatime, Quinalan, Quinaglute, Quinidex Extentab, Quinidine Sulfate, Quinidine Gluconate), Dofetilide (Tikosyn), Ibutilide (Corvert), Sotolol (Betapace). This list is not exhaustive and additional antiarrhythmic agents known in the art are also contemplated.

The ion channel modulating compounds described herein (including COMPOUND A) can be combined with one or more class III antiarrhythmic drugs. Class III antiarrhythmics may include: amiodarone, sotalol, ibutilide, azimilide, clofilium, dofetilide, sematilide, and d,1-sotalol. These class III antiarrhythmics prolong QT interval.

In one example, COMPOUND A is used in combination with one or more of the above listed antiarrhythmic agents. The COMPOUND A and an antiarrhythmic agent may be administered at the same time, or at different times. COMPOUND A and an antiarrhythmic agent may be administered via the same route or by different routes of administration. COMPOUND A and an antiarrhythmic agent may be administered in one formulation or in different formulations. As described, the ion channel modulating compounds described herein may be combined with other drugs, including other antiarrhythmic drugs such as Class III antiarrhythmic drugs. In one version, the ion channel modulating compounds (for example, COMPOUND A) may be safely coadministered with Class III antiarrhythmic drugs. Example 19 illustrates co-administration of COMPOUND A with a Class III antiarrhythmic drug.

EXAMPLES

In the examples below, ion channel modulating compounds used are designated COMPOUND A, COMPOUND B and COMPOUND C, and ion channel modulating compounds may be referred to as "Atrial Selective Antiarrhythmic Agents," "Atrial Selective Agents," or other similar terms. COMPOUND A is:

Compund: COMPOUND A

Chemical name:(1R,2R)-2-[(3R)- hydroxypyrrolidinyl]-1-(3,4- dimethoxyphenethoxy)cyclohexane monohydrochloride Molecular formula:$C_{20}H_{31}NO_4.HCl$ FW:385.93 g/mol

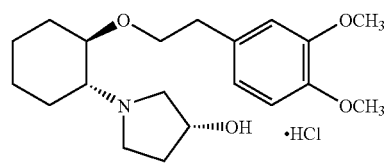

COMPOUND A refers to the R,R,R diastereomer of 2-[hydroxypyrrolidinyl]-1-(3,4-dimethoxyphenethoxy)cyclohexane monohydrochloride. COMPOUND B refers to a mixture of the R,R,R and S,S,R diastereomers of 2-[hydroxypyrrolidinyl]-1-(3,4-dimethoxyphenethoxy)cyclohexane monohydrochloride, and COMPOUND C refers to a mixture of the R,R,R, S,S,R, R,R,S, and S,S,S diastereomers of 2-[hydroxypyrrolidinyl]-1-(3,4-dimethoxyphenethoxy)cyclohexane monohydrochloride.

Example 1

An Example of a Compound Showing a Rate-Dependent Inhibition of $I_{Na}$

FIG. 1 shows a rate- and concentration-dependent inhibition of sodium current ($I_{Na}$) in human atrial myocytes by COMPOUND B. Human myocytes were obtained from specimens of human right atrial appendage obtained during surgery from hearts of patients undergoing cardiopulmonary bypass. Cells were isolated and whole-cell voltage-clamped. Experiments were performed at 22±1° C. $I_{Na}$ was elicited by a pulse to −20 mV from a holding potential of −70 mV (pulse duration was 40 ms. Peak inward current was measured in control and in the presence of 0.1, 1, 10, and 100 µM COMPOUND B. Symbols are mean±SE (n=4) and data was fit with a Hill equation.

A second example used HEK293 cells stably expressing human heart (hH1) sodium channels that were whole-cell patch clamped to measure currents. Concentration and rate-dependent inhibition of hH1 channels by COMPOUND A was tested by applying depolarizing pulses at 0.25, 1, 10, or 20 Hz in control or in the presence of 10, 50, or 100 µM (FIG. 2).

Inhibition by COMPOUND A was found to be concentration- and rate-dependent When pulse trains were applied at 20 and 10 Hz, the $IC_{50}$ values were 9±0.7 µM (Hill coefficient=0.92±0.06) and 11±1.1 µM (Hill coefficient=0.91±0.08) respectively. At reduced rates, 1 and 0.25 Hz, COMPOUND A was a less potent inhibiter producing half-maximal current inhibition at 19±2.3 µM (Hill coefficient=0.81±0.10) and 42±2.8 µM (Hill coefficient=0.70±0.05) respectively. Rate-independent hH1 channel inhibition was determined by measuring the peak sodium current for the first depolarization after a 1 minute rest in COMPOUND A and dividing by the control peak current. COMPOUND A produced tonic inhibition of hH1 channels with an $IC_{50}$ value of 800±24 µM (Hill coefficient=0.42±0.004).

FIG. 2 shows a concentration- and frequency-dependent inhibition of hH1 sodium channels by COMPOUND A. Cells were depolarized from −100 mV to −30 mV for 10 ms at rates of 0.25 Hz, 1 Hz, 10 Hz or 20 Hz. Pulses were performed in control or in the presence of COMPOUND A. Steady-state current traces were superimposed in FIG. 2A (control) and 2B (10 µM COMPOUND A). Reduction in peak current at the test potential of −30 mV was normalized to control current at each frequency and then plotted against the concentration of COMPOUND A as shown in FIG. 2C (filled symbols). To measure the tonic inhibition, peak sodium current for the first depolarization after rest in COMPOUND A for 1 minute was divided by the control peak sodium current, and this value was plotted against the concentrations of COMPOUND A (open symbols). Data were averaged from 4-6 cells for each point.

Example 2

An Example Showing a Minimal Effect on Cardiac QRS Duration in Human Volunteers is Shown by the Table Below

| | | EFFECT OF COMPOUND A ON QRS DURATION IN HUMAN VOLUNTEERS (10 MIN AFTER INFUSION) | | | | | | | |
|---|---|---|---|---|---|---|---|---|---|
| Measurement | Summary Statistic | 0.1 mg/kg | 0.25 mg/kg | 0.5 mg/kg | 1.0 mg/kg | 2.0 mg/kg | 4.0 mg/kg | 5.0 mg/kg | Placebo |
| QRS (ms) | Mean | 89.0 | 89.0 | 85.3 | 89.8 | 93.8 | 97.5 | 94.3 | 91.0 |
| | S.D. | . | . | 4.2 | 5.2 | 9.8 | 1.7 | 6.3 | 5.1 |

Example 3

An Example Showing a Voltage-Dependent Inhibition of Sodium Channels

FIG. 3 shows a voltage-dependent block of hH1 by COMPOUND A. Panel A shows a single experiment for which hH1 current amplitude is plotted for each recorded trace in response to escalating concentrations of Compound A when pulsed from a holding potential of −100 mV. Dose-response curves (FIG. 3, panel B) show that at holding potentials of −60 mV, −80 mV, −100 mV, and −120 mV the $IC_{50}$ values were 31±1 µM (Hill coefficient=0.92±0.06; n=5), 43±8 µM (Hill coefficient=0.98±0.03; n=5), 60±4 µM (Hill coefficient=0.85±0.06; n=3) and 107±11 µM (Hill coefficient=0.89±0.03; n=3). Cells were held at either −120 mV, −100 mV, −80 mV, and −60 mV and stepped to −30 mV for 6 ms (1 Hz). Cells held at −60, −80 and −100 mV received a 2 ms pulse to −120 mV to relieve channel inactivation prior to the −30 mV step.

Example 4

An Example Showing an Inhibition of Potassium Channels at Micromolar Concentrations FIG. 4 shows a concentration-dependent inhibition of Kv4.2 at 1 Hz. Currents were recorded at 1 Hz with depolarizations of 40 ms duration from −80 mV to +60 mV. Panel A shows Kv4.2 currents, after reaching the steady state, from a single cell in control and in the presence of 1, 3, 10, 30, 100 and 300 µM COMPOUND A. Reduction in steady-state current integral (relative to control) at the test potential of +60 mV was plotted against the concentration of COMPOUND A (panel B). Data were averaged from 6 cells. Solid lines were fitted to the data using a Hill equation. The $IC_{50}$ value was 38±4 µM, and the Hill coefficient was 0.84±0.06.

Example 5

An Example Showing an Open-Channel Inhibition of Kv1.5

HEK 293 cells stably expressing Kv1.5 channels were whole-cell patch clamped to measure currents. Inhibition of Kv1.5 channels was tested using a range of concentrations of COMPOUND A from 3 to a maximum of 300 µM (FIG. 5). Cells were held at −80 mV and pulsed to +60 mV for 200 ms at 1 Hz.

The presence of COMPOUND A caused a more pronounced decline in the steady-state current amplitude than the early current (FIG. 5B) indicating that the channel is preferentially inhibited in the open state. Inhibition of Kv1.5 channels with COMPOUND A occurred with an $IC_{50}$ value of 13±1.0 µM (Hill coefficient=0.92±0.05; n=6).

FIG. 5 shows the concentration-dependent inhibition of Kv1.5 channels by COMPOUND A at 1 Hz. FIG. 5A illustrates the decline in steady-state current amplitude in the presence of escalating concentrations of COMPOUND A. FIG. 5B shows full current traces (leak subtracted) recorded in the presence of 3, 10, 30, 100, and 300 µM (same cell as in A). Cells were held at −80 mV and stepped at 1 Hz to +60 mV for 200 ms. FIG. 5C shows a dose-response curve obtained by averaging data from 6 separate experiments. $IC_{50}$=13±1.0 µM and Hill coefficient=0.92±0.05.

Example 6

An Example Showing an Inhibition of hERG Channels at Concentrations Greater than 1, 10, 20 µM HEK 293 cells stably expressing hERG channels were whole-cell patch clamped to measure currents. Peak hERG tail-current amplitude was measured in control and in 3, 10, 30, 100, and 300 µM COMPOUND A (FIG. 6A) using the voltage protocol illustrated in FIG. 6B every 15 seconds. Cells were held at −80 mV and stepped to +20 mV for 4 s followed by a step to −50 mV for 4 s.

FIG. 6 shows a concentration-dependent inhibition of hERG channels. In FIG. 6A, the decline in peak hERG tail current amplitude in the presence of escalating concentrations of COMPOUND A. Data are from a single experiment and are not leak subtracted. In FIG. 6B, full current traces (leak subtracted) in the presence of 1, 3, 10, 30, 100, 300 µM (same cell as A). Cells were depolarized from a holding potential of −80 mV to +20 mV for 4 s and stepped back to −50 mV for 5 s, with an inter-pulse interval of 15 s. FIG. 6C shows a dose-response curve obtained by averaging data from 6 separate experiments. $IC_{50}$=21±3 and Hill coefficient=0.96±0.04.

Example 7

An Example of Preferential Block of hERG and/or Kv1.5 Over Kv4.3 in HEK Cells

HEK cells stably expressing Kv4.3 channels were whole-cell patch clamped to measure currents. Current inhibition was tested at a range from 3-300 µM COMPOUND A (FIG. 7). The decline in steady-state integrated current was measured at each concentration.

COMPOUND A is approximately 1.5-3 times more potent for hERG and/or Kv1.5 channels than for Kv4.3 channels.

FIG. 7 shows a concentration-dependent inhibition of Kv4.3 channels at 1 Hz. Currents were recorded at 1 Hz with depolarizations of 40 ms duration from −80 mV to +60 mV. Panel A shows Kv4.3 currents, after reaching the steady state, in a single cell (control) and at 1, 3, 10, 30 and 100 µM COMPOUND A. Reduction in steady-state current integral (relative to control) at the test potential of +60 mV was plotted against the concentration of COMPOUND A (panel B). Data were averaged from 6 cells. The $IC_{50}$ value was 30±5 µM.

Example 8

An Example of Prolonged Atrial Refractoriness, Atrial Selectivity, and Neutral Ventricular Effect in Humans All currently available antiarrhythmic drugs used for atrial arrhythmias act on ventricular, as well as atrial tissues, thus predisposing to proarrhythmia. Atrial selective agents mainly affect atrial action potential repolarization only; COMPOUND A is an investigational drug that inhibits $K^+$ channels important in human atrial repolarization and can terminate acute atrial fibrillation in humans (at cumulative doses of 5 mg/kg). COMPOUND A had a neutral effect on ventricular repolarization.

Two (2) mg/kg iv COMPOUND A was administered over 10 min, followed by 0.5 mg/kg/h for 35 min, to 10 patients following electrophysiologic study (8 also had RF ablation). At baseline and 25 min after the start of drug infusion, atrial, ventricular and AV nodal refractory periods at various cycle lengths (AERP600, 400, 300 msec and VERP600, 400 msec and WCL, respectively) and conduction times in the atrium, AV node, and ventricle were measured. All patients had normal hearts and were free of cardioactive drugs.

Subjects were 52±12 years of age, 60% male. Heart rate and blood pressure were unaffected.

TABLE 2

Results

| | AERP600 | AERP400 | AERP300 | VERP600 | VERP400 | WCL |
|---|---|---|---|---|---|---|
| Baseline | 206 ± 32 | 188 ± 31 | 180 ± 31 | 251 ± 19 | 224 ± 20 | 396 ± 113 |
| COMPOUND A | 220 ± 34* | 195 ± 24 | 181 ± 16 | 248 ± 22 | 227 ± 16 | 388 ± 94 |

All measures are in msec.
*P < 0.02

AH intervals were prolonged from 115±42 to 161±144 msec (p<0.05); QT intervals did not change significantly at 600 msec (365±27 to 361±26 msec) or 400 msec atrial pacing (328±29 to 325±9 msec). Intraatrial, His-Purkinje and intraventricular conduction (QRS duration) intervals were unaffected by COMPOUND A. Five patients had a total of 9 episodes of transient atrial tachycardia (CL 272±48.9 msec) at baseline, lasting 26.1±19.0 sec, induced with $A_1A_2$ or A burst pacing; after COMPOUND A, 3 patients had 1 episode each (4.4±4.3 sec). No patient had any adverse effect.

At the relatively low dose studied, COMPOUND A prolongs atrial refractoriness and AV nodal conduction and suppresses inducible atrial tachycardia, without effect on ventricular tissue or AV nodal refractoriness.

Example 9

An Example Showing Inhibition of Early and Sustained Sodium Currents hH1 sodium channels were stably expressed in HEK cells. K$^+$ in internal and external physiological solutions were replaced with Cs$^+$ to eliminate endogenous K$^+$ current and to maximize sodium current ($I_{Na}$) measurements. In whole-cell configuration, cells were voltage clamped using the protocol illustrated in FIG. 8. Total $I_{Na}$ (TTX-sensitive current) was measured by subtracting the current recorded in the presence of 30 µM TTX from the control current (absence of drug). COMPOUND A-sensitive currents were measured by subtracting the current recorded in the presence of 30 µM COMPOUND A from the control current.

Components of the TTX-sensitive current are evident in FIG. 8. An early inward current, $I_{early}$, results from stepping the cell from −100 mV to +20 mV. As the voltage is ramped back to −100 mV, a late inward current, $I_{late}$, develops. $I_{late}$ reaches its peak at voltages within the range of half repolarization, between −20 mV and −40 mV. A sustained current ($I_{sus}$) can be measured from the current during the constant portion of the voltage step. In 6 experiments, 30 µM COMPOUND A inhibited $I_{early}$ 61±4% and $I_{late}$ 70±4%. COMPOUND A inhibits the late component of sodium current active during depolarization approximately equipotently to (or slightly more than) the early sodium current.

FIG. 8 shows an example of the TTX- and COMPOUND A-sensitive components of the early and late sodium current observed during a step/ramp protocol. In FIG. 8A, COMPOUND A- and TTX-sensitive currents obtained by digitally subtracting the current obtained in the presence of either 30 µM COMPOUND A or COMPOUND A plus 30 µM TTX respectively from the current obtained pre-drug. In FIG. 8B, the COMPOUND A- and TTX-sensitive $I_{early}$ current traces that are off-scale in A. Current traces in A and B are averages of 45 raw traces.

Example 10

An Example Showing a State-Dependent Inhibition of Sodium Channels (FIG. 9)

HEK cells stably expressing hH1 channels were whole-cell patch clamped to measure currents. Inactivated state inhibition of hH1 sodium channel current by COMPOUND C (50 µM), lidocaine (50 µM) and flecainide (5 µM) was examined by delivering depolarizing prepulses from −100 mV to −30 mV for varying durations (10, 100, 500 ms) followed by a single test pulse to the same voltage at varying time intervals.

Lidocaine, a predominantly inactivated-state blocker, produced enhanced inhibition when prepulses of longer duration were applied. Such maneuvers increase channel inactivation and enhanced hH1 inhibition by lidocaine. By comparison, COMPOUND C did not inhibit hH1 channels to a greater extent when longer prepulses were applied. Similar results were obtained with flecainide, an activated-state blocker (FIG. 9D), suggesting that COMPOUND C preferentially inhibits the activated channel.

FIG. 9 illustrates a protocol to test level of inactivated state inhibition by COMPOUND C, flecainide, and lidocaine. In the presence of 50 µM COMPOUND C, 50 µM lidocaine, or 5 µM flecainide, pre-pulses of varying length (−100 mV to −30 mV) were applied: 10, 100, or 500 ms. Following a prepulse, a single test pulse was applied at varying time intervals. Peak current amplitude resulting from the test pulse is plotted as a function of interval between prepulse and test pulse. Inhibition by COMPOUND C is not enhanced by longer prepulses indicating that it does not inhibit hH1 channels in the inactivated state.

Example 11

An Example Showing Rapid Association and Dissociation from Sodium Channels

FIG. 10 shows that hH1 sodium current traces exemplify minor changes in waveform kinetics in the presence of COMPOUND A. Steady-state current traces were recorded in control (trace 1) and in the presence of 30 µM COMPOUND A (trace 2). Currents were generated using the same protocol as in FIG. 9. To compare the time to peak and current relaxation kinetics under each condition, trace 2 was normalized to trace 1. The resulting normalized waveform is trace 3. Note the time to peak and relaxation kinetics in trace 3 are largely unchanged from trace 1 and therefore trace 2 simply represents a 'scaling down' of the control current waveform.

Example 12

Inhibition of Acetyl Choline Dependent or Adenosine Dependent Potassium Channels (Kir3) at Micromolar Concentrations Kir3 or $IK_{ACh}$ was inhibited by COMPOUND A with an IC$_{50}$ of between 1 and 50 µM (at 0.1 Hz). $IK_{ACh}$ in guinea pig atrial cells was inhibited by COMPOUND A with an IC$_{50}$ of approximately 10 µM (at 0.1 Hz, FIG. 11).

FIG. 11 illustrates a concentration-dependent block of $I_{KACh}$ by COMPOUND A in isolated guinea pig atrial myocytes at 0.1 Hz. FIG. 11A shows current traces from one cell before ACh perfusion, after 100 nM ACh perfusion, application of increasing concentrations of COMPOUND A (3, 10, 30, 100 µM), washout of all compounds, and application of 100 µM BaCl$_2$ plus 100 nM ACh. Ventricular myocytes were depolarized at 0.1 Hz from a holding potential of −80 mV to −40 mV for 100 ms followed by a voltage ramp from −20 mV to −120 mV over 1 s. FIG. 11B shows reduction in peak $I_{KACh}$ current (relative to control current in the presence and absence of ACh) at the end of the ramp was plotted against the concentration of COMPOUND A. Solid lines were fit to the data using a Hill equation. The IC$_{50}$ for inward current (measured at −120 mV) was 10 µM and the Hill coefficient was 1.3. Data shown are mean±SEM (n=6).

Example 13

An Example Showing an Acute Reversal of Electrical Remodeling and Cardioversion of Persistent AF in the Goat Inhibition of $I_{Kur}$ and $I_{tO}$ can prolong the atrial refractory period (RP) after electrical remodeling (ER). The aminocyclohexyl ether antiarrhythmic, COMPOUND A, is a mixed $I_{Na}/I_{Kur}/I_{tO}$ blocker. An investigation of the in vivo electrophysiological mechanisms of COMPOUND A in ER atria and its efficacy for cardioversion in a persistent AF model was carried out.

Electrical remodeling (ER) was induced by repetitive induction of AF over 48 h in 6 instrumented, conscious goats, and then the effects of COMPOUND A (0.2 mg/kg/h i.v.), were evaluated on atrial refractory period (RP), window of inducibility (WOI) and AF duration. In a separate series of 6 goats, the effects of COMPOUND A on persistent AF (2-16 weeks) were evaluated.

COMPOUND A reversed ER in remodeled atria (48 h AF): COMPOUND A prolonged left atrial RP at 300 ms CL from 110±14 to 136±27 ms. Similar effects were seen at the right atrium and Bachmann's bundle. COMPOUND A decreased the median AF duration from 120 to 70 s. Lower and upper limits of vulnerability increased similar to RP, thus WOI remained unchanged (39±9 ms at baseline and 44±29 ms after drug).

In the goats with persistent AF, COMPOUND A prolonged atrial fibrillation cycle length (AFCL) from 107±4 to 156±10 ms (p<0.001) and slowed the ventricular response rate from 327±30 to 539±114 ms (p<0.01). In keeping with the slowed ventricular rate, QT-time was 176±12 ms at baseline and 190±16 ms (p=N.S.) at cardioversion. QRS increased 14±9% at this time. COMPOUND A cardioverted AF in all 6 goats after 62±16 min infusion.

FIG. 39 shows the effect of persistent AF (2-16 weeks) in goats in tabular form. COMPOUND A terminated AF and increased atrial fibrillation cycle length (AFCL) in goats (n=6). COMPOUND A prolonged AFCL from 105±4 to 156±10 ms and slowed the ventricular response rate from 304±28 to 525±96 ms. In keeping with the slowed ventricular rate, QT-time was 163±19 ms at baseline and 189±16 ms at cardioversion. QRS increased 15±10% at this time. COMPOUND A cardioverted AF in all 6 goats after 62±6 min infusion.

Figure 33:
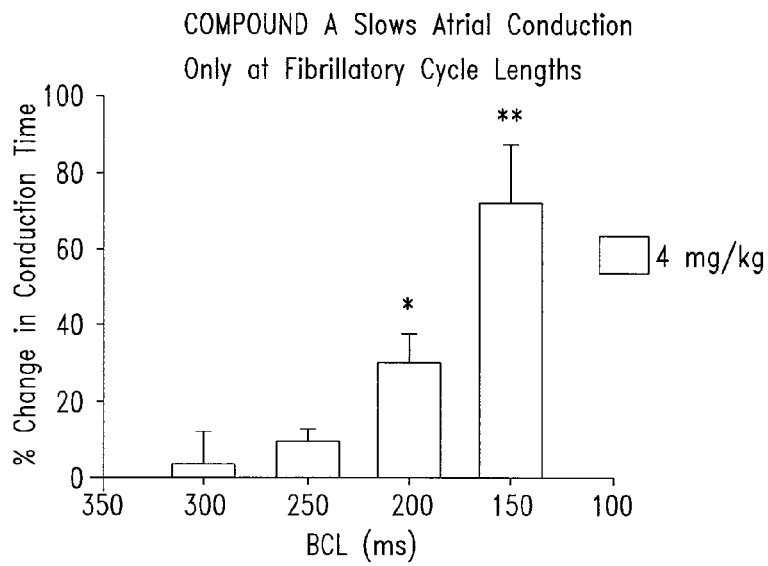
FIG. 33 shows slowing of atrial conduction by COMPOUND A only at fibrillatory cycle lengths
Figure 34:
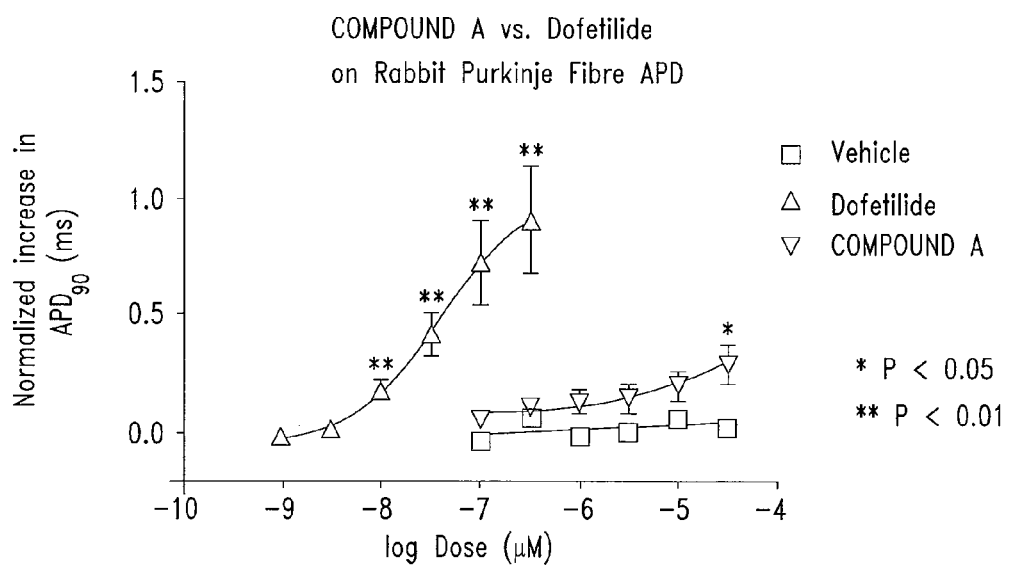
FIG. 34 shows effect of an ion channel modulating compound on Rabbit Purkinje fiber action potential duration compared to dofetilide and vehicle.
Figure 35:
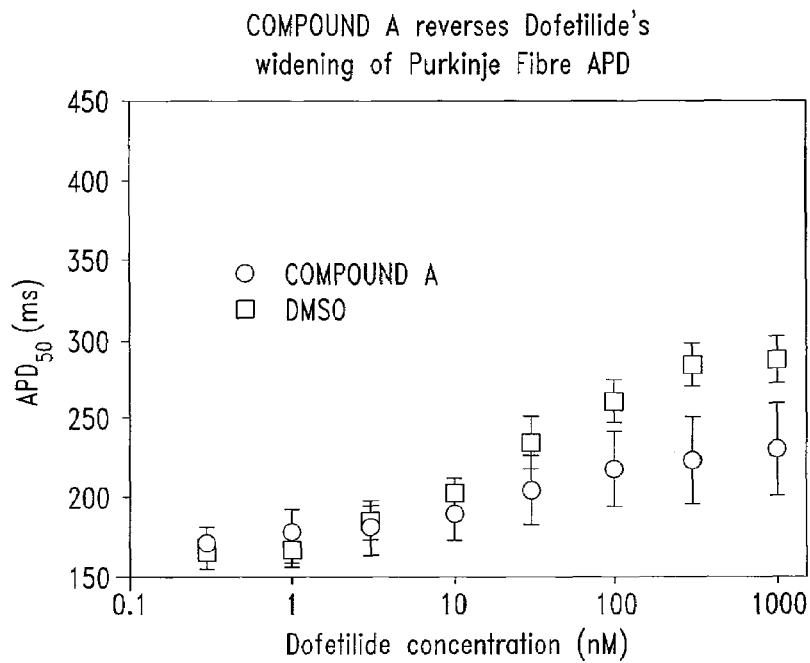
FIG. 35 shows the reversal of dofetilide-induced widening of action potential duration by an ion channel modulating compound
Figure 36:
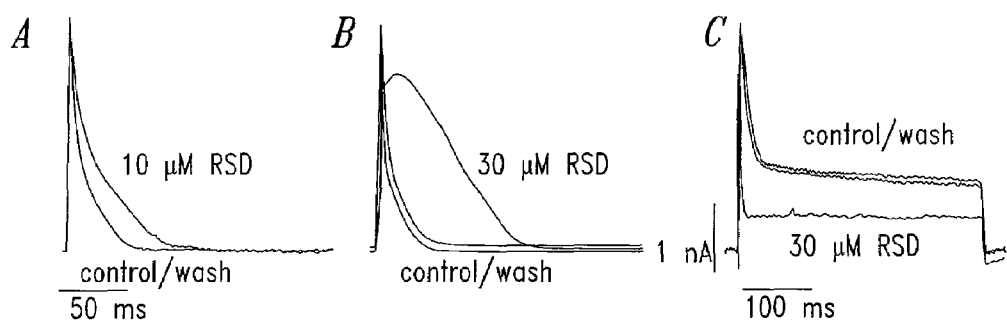
FIG. 36 shows block of Ito and $I_{sus}$ by an ion channel modulating compound resulting in prolonging action potential duration in the rat ventricular myocyte. Note that the rat has an abnormally short ventricular action potential that is intended to be representative of human atrium, and is not intended to be a model of effects on human or primate ventricle.
Figure 37:
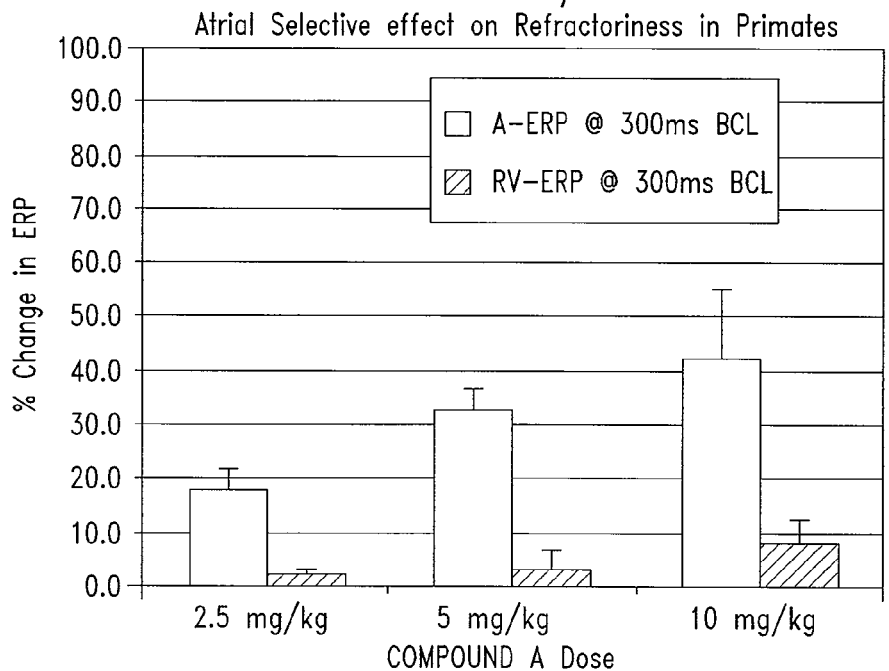
FIG. 37 shows atrial selectivity of an ion channel modulating compound (COMPOUND A) in primates.
Figure 38:
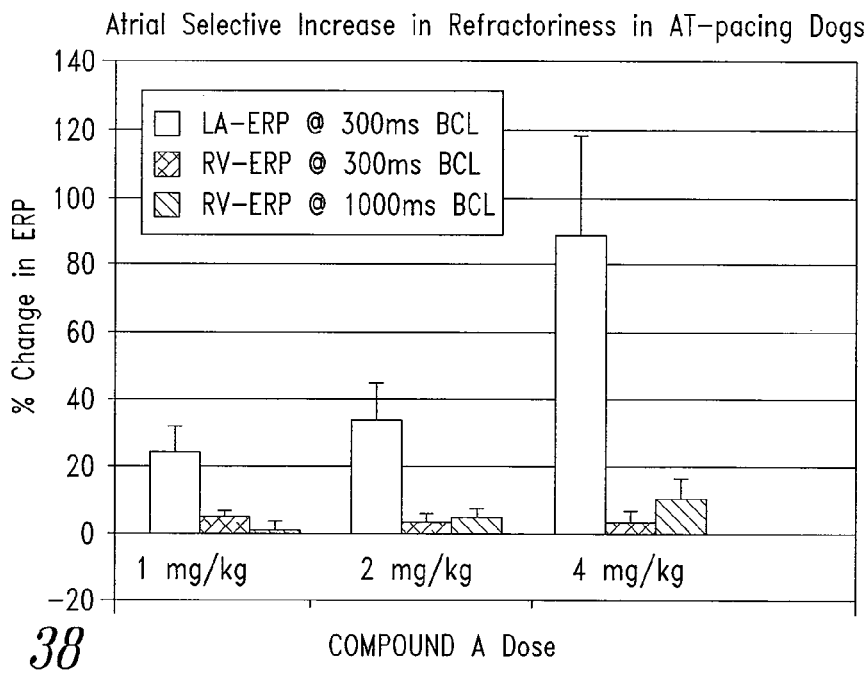
FIG. 38 shows the atrial selectivity of an ion channel modulating compound in electrically remodeled dogs.

As a comparison, FIGS. 33 to 38 show the effect of COMPOUND A on dog, primate and rabbit. For example, FIG. 33 shows that COMPOUND A slows atrial conduction only at fibrilatory cycle lengths. The percent change in conduction time is shown for different basic cycle lengths (BCL). FIG. 34 shows that COMPOUND A has a substantial dose-dependent effect on rabbit Purkinje fiber APD, particularly compared to dofetilide. Similarly, FIG. 35 shows that COMPOUND A reverses the effect of the dofetilide widening of Purkinje fiber APD compared to vehicle (DMSO). FIG. 36 shows that COMPOUND A prolongs APD in the rat by, in part, blocking $I_{tO}$ and $I_{sus}$. This species is relevant to human atrial action potentials and is not meant to be representative in any form of effects on human or primate ventricular repolarization. FIGS. 37 and 38 show the atrial selectivity of COMPOUND A in both primates (FIG. 37) and dogs (FIG. 38). At 300 ms BCL, increasing doses of COMPOUND A resulted in increasing atrial, but not ventricular, effects. COMPOUND A reversed electrical remodeling as evidenced by selective increases in ER atria RP and prolonged AFCL in persistent AF. These effects resulted in cardioversion of persistent AF (2-16 weeks) in goats.

Example 14

An Example Showing a Lack of Rate- and Use-Dependence on Kv1.5

HEK 293 cells stably expressing Kv1.5 channels were whole-cell patch clamped to measure currents. Rate- and use-dependent inhibition of Kv1.5 channels by COMPOUND A was tested by applying depolarizing pulses at 0.25, 1, 10, or 20 Hz in control or in the presence of 5 μM COMPOUND A (FIG. 13).

Figure 12:
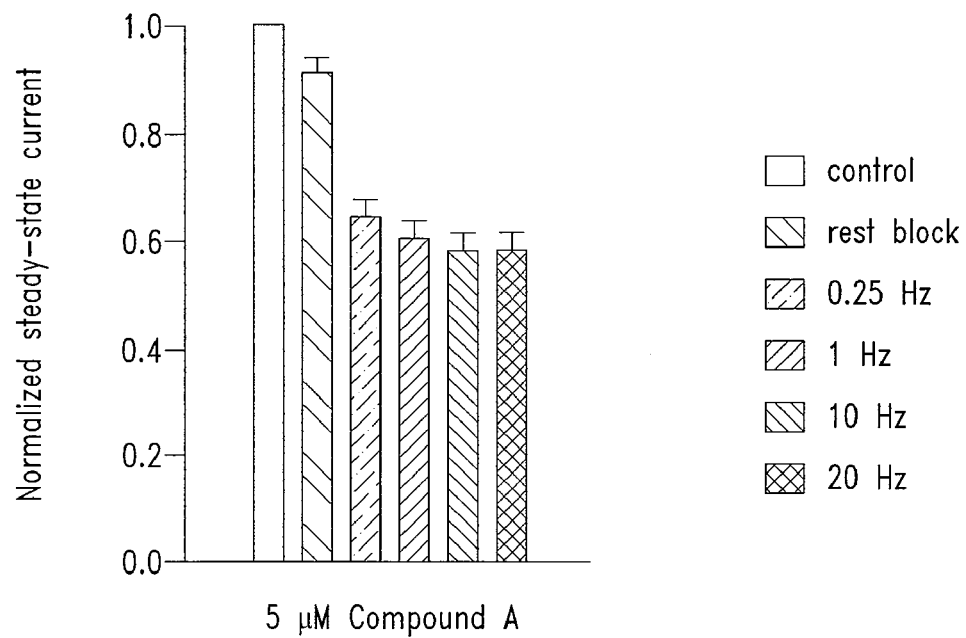
FIG. 12 shows a lack of rate-dependent inhibition of Kv1.5 by COMPOUND A.
Figure 13A:
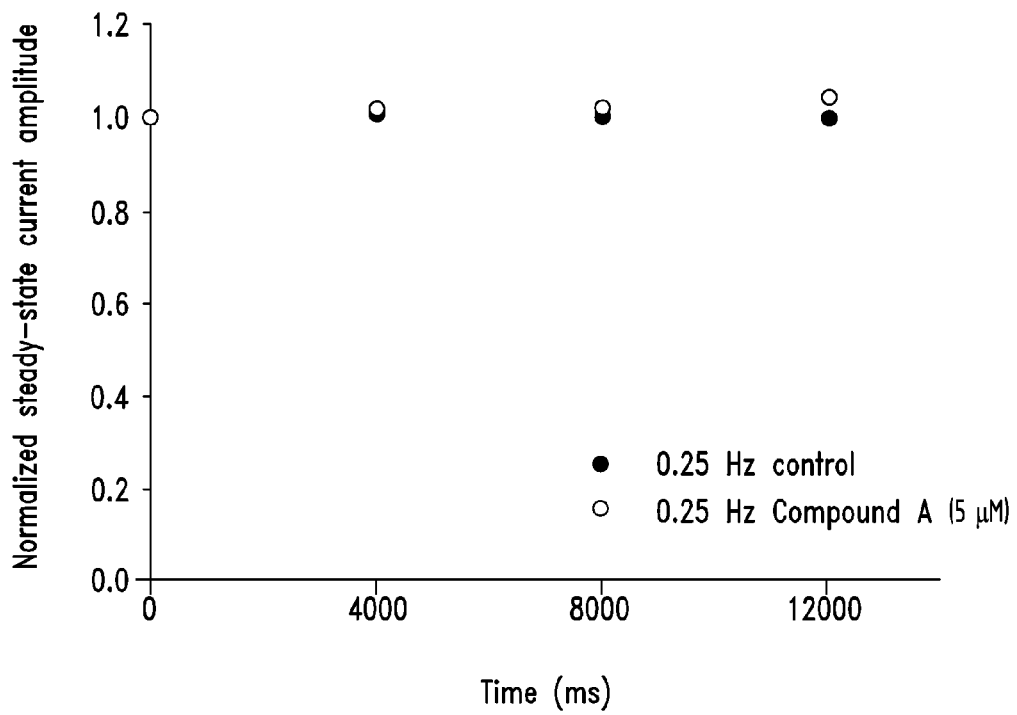
FIG. 13 shows a lack of use-dependent inhibition of Kv1.5 by COMPOUND A.
Figure 13B:
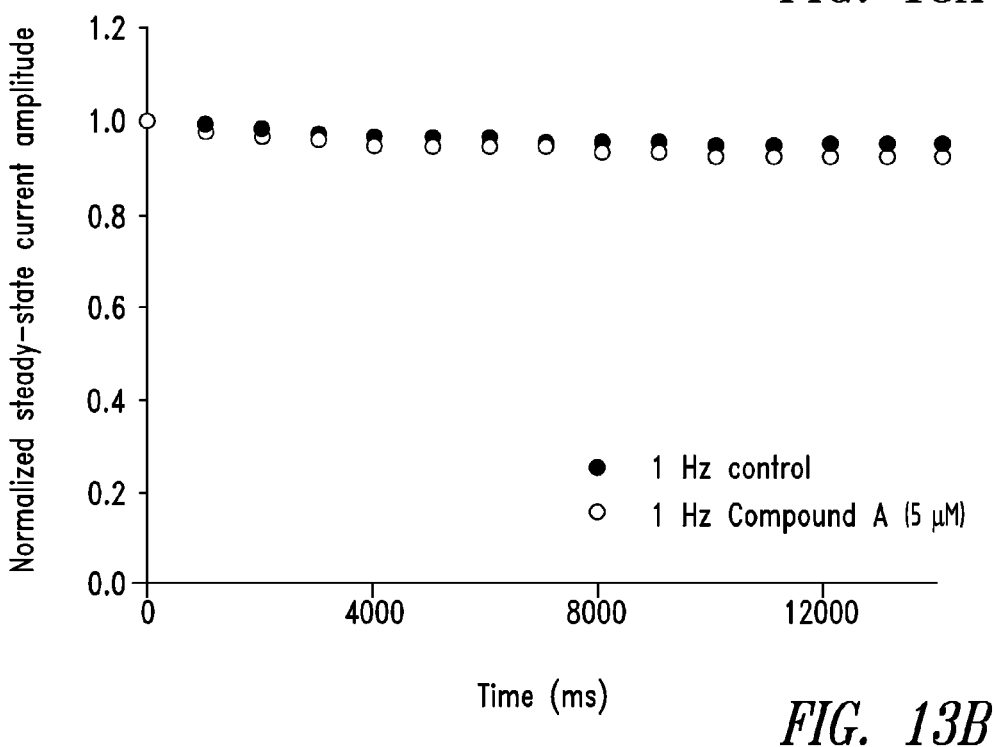
Figure 13C:
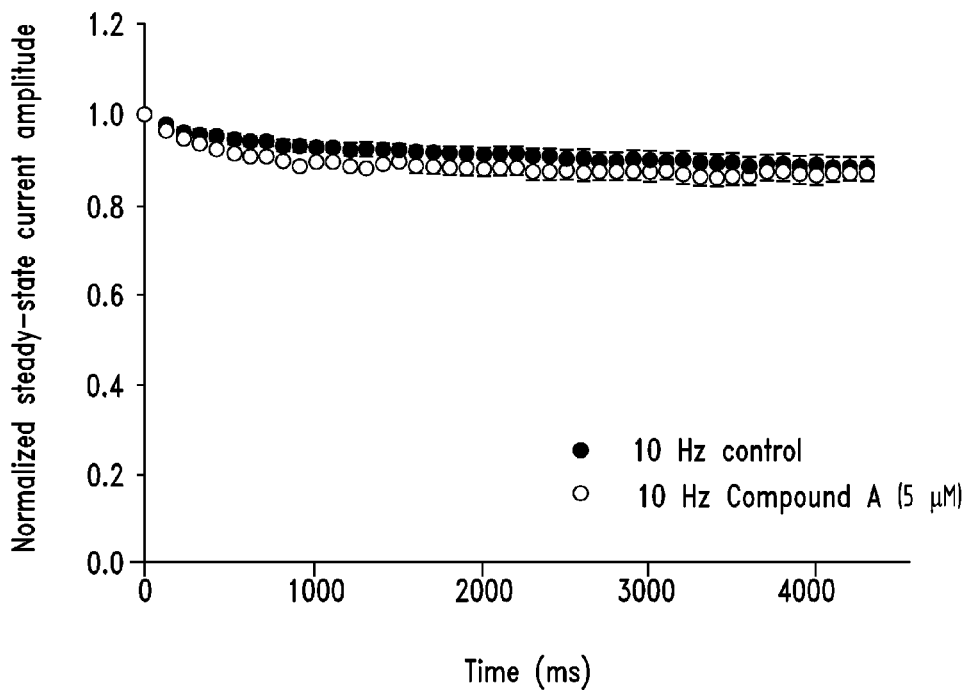
Figure 13D:
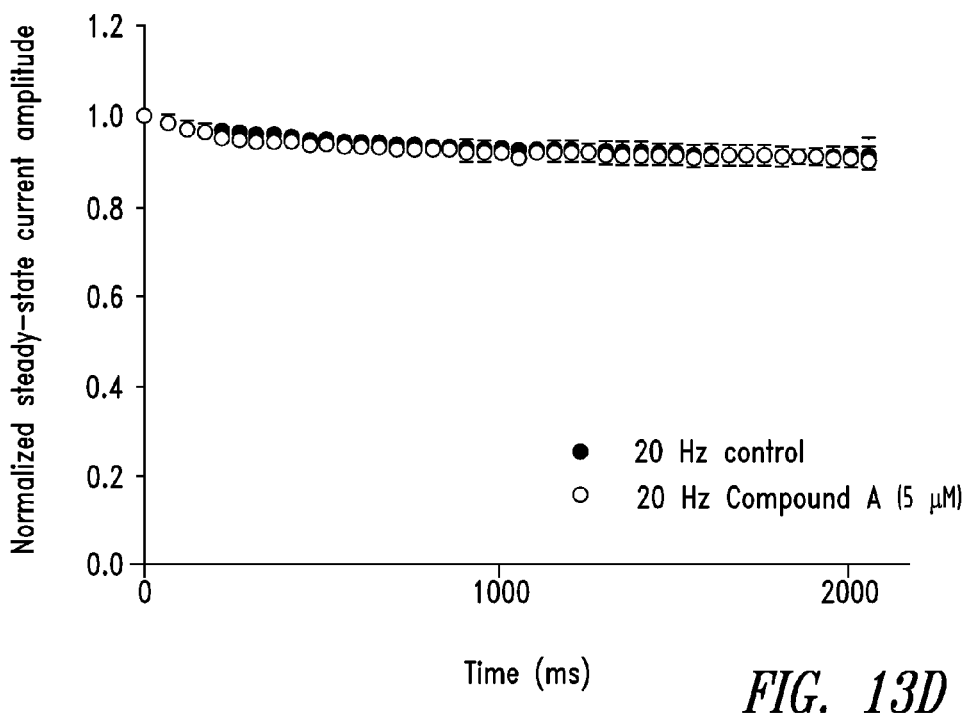

As illustrated in FIG. 12, little resting inhibition was apparent with COMPOUND A. When the rate was then increased in a stepwise fashion to 0.25, 1, 10 and 20 Hz, little steady-state rate-dependent current reduction could be observed (grey bars). To test the use-dependence of COMPOUND A on Kv1.5, the current traces during changes of rate were examined and steady-state current amplitude was plotted as a function of time (FIG. 13). Here currents can be seen when the pulse rate was changed from rest to 0.25 Hz, then to 1, 10 and 20 Hz. Note that there was no excess current reduction in the presence of COMPOUND A (open circles) over that seen in control (filled circles) when the rates were changed. This suggests that COMPOUND A is not use-dependent on Kv1.5.

FIG. 12 shows a lack of rate-dependent inhibition of Kv1.5 by COMPOUND A. Pulse trains consisted of depolarizations of 40 ms duration from −80 mV to +60 mV applied at 0.25 Hz, 1 Hz, 10 Hz or 20 Hz in the presence of 5 μM COMPOUND A. Pulses were applied until the current levels reached steady-state. Reduction in peak current at the test potential of +60 mV was normalized to control current at each frequency. To measure resting inhibition, the peak Kv1.5 current during the first depolarization after rest in drug was divided by the control peak Kv1.5 current.

FIG. 13 shows a lack of use-dependent inhibition of Kv1.5 by COMPOUND A. In each experiment, Kv1.5-expressing HEK 293 cells were stimulated from rest in control solutions (closed circles) at 0.25 Hz (A). Subsequently, the rate was increased to 1 Hz (B), then 10 Hz (C), and lastly 20 Hz (D). The stimulation sequence was then repeated in the presence of 5 μM COMPOUND A (open circles). Steady-state current amplitude was normalized to that in the first pulse and data from 4 separate cells were averaged. Most often error bars fell within the points. No significant differences were found between currents in the steady-state at the different rates. Thus, COMPOUND A is not rate- or use-dependent on Kv1.5 channels.

Example 15

Treatment of Acute Atrial Fibrillation

This was a randomized, double-blind, step-dose, placebo-controlled, parallel group study. Fifty-six patients with atrial fibrillation of 3 to 72 h duration were randomized to one of two COMPOUND A dose groups or to placebo. The two COMPOUND A groups were RSD-1 (0.5 mg/kg followed by 1.0 mg/kg) or RSD-2 (2.0 mg/kg followed by 3.0 mg/kg), doses given by intravenous infusion over 10 min. The primary endpoint was termination of atrial fibrillation during a 10-min infusion or the subsequent 30-min. Secondary endpoints included the number of patients in sinus rhythm at 0.5, 1 and 24 h post-infusion and time to conversion to sinus rhythm. RSD-2 dose showed significant differences over placebo in: 1) termination of atrial fibrillation within 30-min 61% vs. 5%; p=0.0003); 2) patients in sinus rhythm at 30 min post-dose (56% vs. 5%; p=0.0008); 3) patients in sinus rhythm 1 h post-dose (53% vs. 5%; p 0.0014), and 4) median time to achieve conversion (14 vs. 162 min; p=0.016). COMPOUND A converted acute atrial fibrillation to sinus rhythm.

COMPOUND A is a mixed frequency-dependent $Na^+$ and atria-preferential $K^+$ channel blocker. In animal models of AF, COMPOUND A is effective in terminating and preventing relapse of AF. COMPOUND A selectively prolongs atrial refractory periods without significant effects on ventricular refractoriness or QT intervals.

Patients in this study had to have a rhythm of sustained atrial fibrillation (AF) with a duration of 3 to 72 h at the time of randomization. Patients were randomized to one of three groups and in each group received up to two 10-min intravenous infusions, separated by 30 min. Infusions were placebo followed by placebo, 0.5 mg/kg followed by 1.0 mg/kg COMPOUND A, or 2.0 mg followed by 3.0 mg COMPOUND A. The second dose in each group was administered only if AF was present 30 min after completion of the first dose. Doses for patients weighing>113 kg were capped as if the patient weight was 113 kg.

A Holter rhythm strip continuously monitored ECG, vital signs (blood pressure and heart rate, BP and HR, respectively) and $O_2$ saturation were recorded every 2 min from the start of infusion to 5 min after, as well as at 15, 30, 60, 120, 240, 360, and 480 min and at discharge and one-week follow-up. Twelve-lead ECGs were obtained before dosing and every minute during infusion to 5 min after, as well as at 15, 30, 60, 120, 240, 360, and 480 min and at discharge, 24 h and one-week follow-up, and at the time of arrhythmia termination or significant rhythm changes. Venous blood samples were drawn for COMPOUND A plasma concentrations at 0, 15, 30, 120, 240, 480 min discharge and at AF termination or significant adverse events.

Fifty-five patients were evaluated for efficacy. Data are presented as mean±SD, median with interquartile range (IQR), all tests were performed as two sided and 95% confidence interval (CI) were produced; $p<0.05$ was considered statistically significant unless stated otherwise. Analysis of the relationship between termination of AF and treatment was performed using a chi-square analysis. In cases of small cell frequencies, the Fisher's exact test was used. A Cochran-Armitage test statistic with table scores was used to test the ascending dose evaluation of efficacy.

The time to conversion from the start of the first infusion was analyzed by the Cox regression method of event time analysis and one-way ANOVA. Assessment of the significance of time point values and mean change from baseline to each follow-up reading of ECG intervals (QRS, QT, QTc), BP, and HR were made within dose groups using paired t tests, and comparisons among dose groups were made using a one-way ANOVA.

Demographic characteristics for all patients in the study are shown in table 3.

Baseline clinical characteristics were similar across groups except that patients in the placebo group tended to more frequently report AF in the past than in the COMPOUND A dosed groups.

Figure 15:
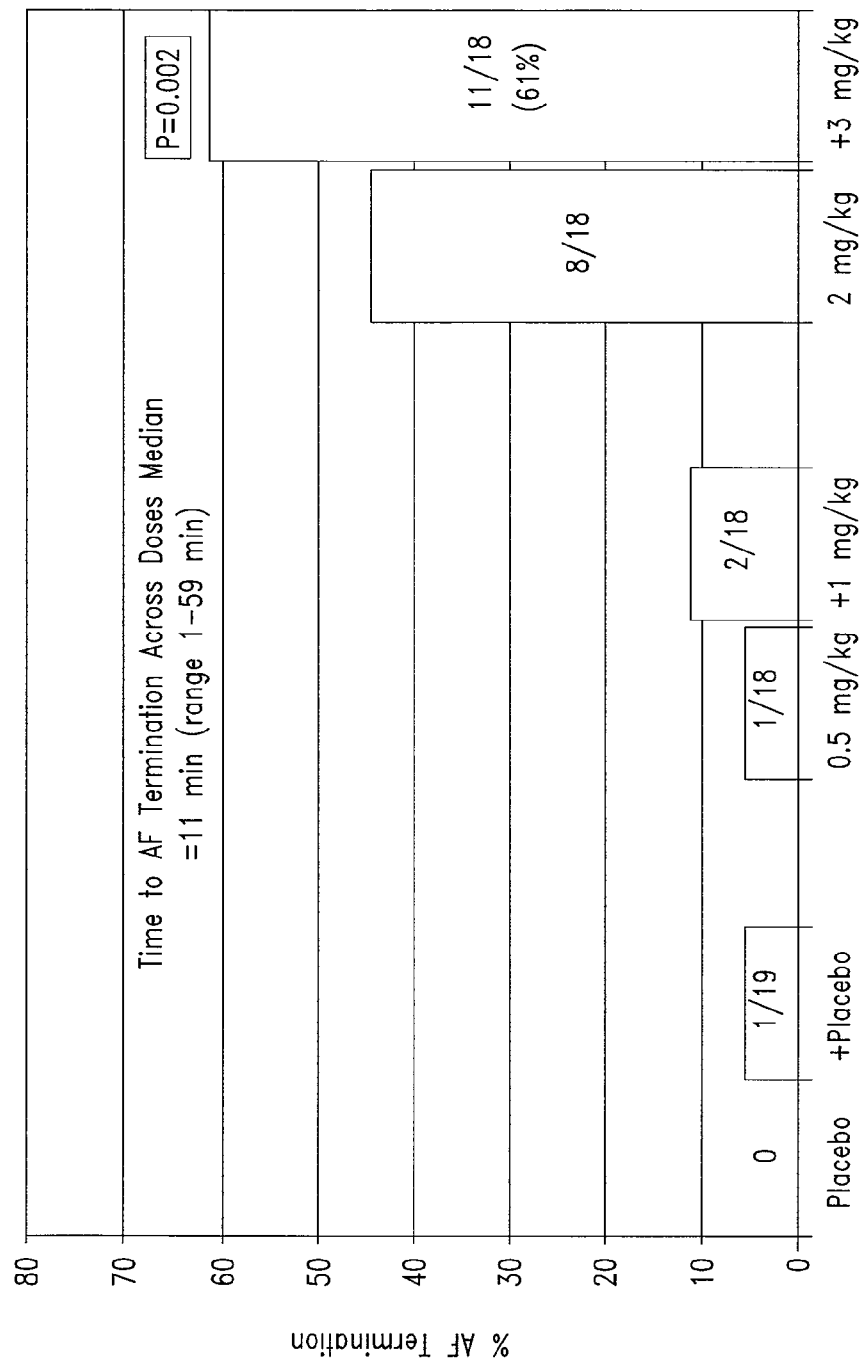
FIG. 15 Cumulative percentage of patients terminating atrial fibrillation (AF) after infusions of placebo, 0.5 and 1 mg/kg COMPOUND A or 2.0 and 3.0 mg/kg COMPOUND A, in patients with recent onset AF.

FIG. 15 shows conversion efficacy, including cumulative percentage of patients terminating atrial fibrillation (AF) after infusions of placebo, 0.5 and 1 mg/kg COMPOUND A or 2.0 and 3.0 mg/kg COMPOUND A, in patients with recent onset AF. Efficacy was significantly higher after 2+3 mg/kg COMPOUND A than after placebo ($p=0.0003$) and was significantly different between the two COMPOUND A ($p=0.0018$) dosing regimens. The median time for termination of AF was 11 min from the start of the first infusion in the COMPOUND A treatment groups.

The cumulative AF termination within 30 min of infusion was 61% (11 of 18 patients) after 2+3 mg/kg COMPOUND A infusion, 11% (2 of 18 patients) after 0.5+1.0 mg/kg COMPOUND A and 5% (1 of 19 patients) after placebo+placebo. Paired comparisons indicated a statistically significant difference ($p=0.0003$) between placebo and the RSD-2 group. There was no significant difference in the success rates between the RSD-1 group and placebo. Of the 11 AF terminations in the RSD-2 group, eight terminated on the first infusion.

The number of patients in sinus rhythm at 30-min post-infusion was 56% (10 of 18 patients) in the RSD-2 group, 11% (2 of 18 patients) in the RSD-1 group and 5% (1 of 19 patients) in the placebo group. The number of patients in sinus rhythm at 1 h post infusion was 53% (9 of 17 patients) in the RSD-2 group, 11% (2 of 18 patients) in the RSD-1 group, and 5% (1 of 19 patients) in the placebo group. Patients in sinus rhythm (excluding those electrically cardioverted) at 24 h post infusion was 79% (11 of 14 patients) in the RSD-2, 56% (5 of 9 patients) in the RSD-1 compared to 50% (5 of 10 patients) in the placebo group. Only the difference between RSD-2 and placebo was statistically significant at 30 min ($p=0.008$) and at 1 h ($p=0.0014$).

The median time to conversion to sinus rhythm from the start of the first infusion in the eleven responders in the RSD-2

TABLE 3

Demographic Characteristics for Patients in Each Study Group

| | | Placebo (n = 20) | COMPOUND A (0.5 and 1.0 mg/kg) (n = 18) | COMPOUND A (2.0 and 3.0 mg/kg) (n = 18) |
|---|---|---|---|---|
| Gender, n(%) | Male | 14(70.0) | 10(56) | 10(56) |
| Age(yrs) | Median (range) | 64.0(35-83) | 67.4(24-85) | 60.8(25-88) |
| Duration of AF(h) | Median (range) | 13.3(5.1-59.4) | 11.5(5.7-67.2) | 19.5(5.1-70.4) |
| Previous AF history, n(%) | | 75% | 61% | 44% |
| Lone AF(%) | | 35% | 28% | 39% |
| Hypertension(%) | | 45% | 72% | 56% |
| Diabetes(%) | | 25% | 28% | 17% |
| Concomitant $\beta_1$-blocker(%) | | 75% | 61% | 67% |
| Concomitant ACE-I(%) | | 30% | 28% | 22% |
| Concomitant Dilt/verap(%) | | 30%b | 22% | 33% |
| Concomitant digitalis(%) | | 30% | 22% | 11% |

ACE-I = angiotensin converting enzyme-I;
Dilt/verap = diltiazem/verapamil.

group was 14 min (range, 3 to 871 min; p=0.016) compared to the five spontaneous responders in the placebo group with a median time of 162 min (range, 58 to 1119 min). The median time to conversion to sinus rhythm from the start of the first infusion in the five eventual responders in the RSD-1 group was 166 min (range, 1 to 332 min; p=0.886 vs. placebo).

The median time to termination of AF was 11 min after start of the first infusion (range, 3 to 58 min) in the RSD-2 group. In fact, all the responders in this group reached primary end-point during drug infusion or within 10 min of the last infusion. One of the eleven responders in this group converted from AF into atrial flutter and subsequently converted to sinus rhythm 14.5 h later.

Table 4 shows the ECG effects of COMPOUND A. Infusion of COMPOUND A did not significantly prolong QTc or QRS intervals compared to placebo. There was no difference in QT and QTc intervals between placebo (389±31 ms and 414±16 ms) and RSD-2 treatment (366±28 ms and 427±19 ms) using the first available ECG records after conversion to sinus rhythm.

TABLE 4

QTc and QRS Intervals and HR Values for Patients in Each Study Group

| Time Period | Placebo | COMPOUND A (0.5 and 1.0 mg/kg) | COMPOUND A (2.0 and 3.0 mg/kg) | P Value |
|---|---|---|---|---|
| QTC(MSEC) | | | | |
| Predrug baseline(n) | 20 | 16 | 17 | |
| mean ± SD | 424 ± 6 | 417 ± 6 | 434 ± 7 | 0.233 |
| End infusion 1(n) | 19 | 17 | 17 | |
| mean ± SD | 430 ± 5 | 419 ± 6 | 449 ± 9 | 0.066 |
| End infusion 2(n) | 16 | 17 | 11 | |
| mean ± SD | 436 ± 8 | 414 ± 11 | 447 ± 17 | 0.691 |
| QRS(MSEC) | | | | |
| Predrug baseline(n) | 20 | 17 | 18 | |
| mean ± SD | 87 ± 2 | 83 ± 3 | 86 ± 3 | 0.823 |
| End infusion 1(n) | 19 | 17 | 17 | |
| mean ± SD | 89 ± 2 | 86 ± 3 | 95 ± 3 | 0.150 |
| End infusion 2(n) | 16 | 17 | 11 | |
| mean ± SD | 88 ± 2 | 90 ± 6 | 99 ± 5 | 0.120 |
| HEART RATE(BPM) | | | | |
| Predrug baseline(n) | 20 | 16 | 17 | |
| mean ± SD | 112 ± 6 | 101 ± 6 | 108 ± 6 | 0.585 |
| End infusion 1(n) | 19 | 17 | 17 | |
| mean ± SD | 115 ± 6 | 104 ± 7 | 98 ± 5 | 0.045 |
| End infusion 2(n) | 16 | 17 | 11 | |
| mean ± SD | 109 ± 6 | 107 ± 6 | 104 ± 6 | 0.601 |

There were no statistically significant differences in ECG intervals after infusion between groups. Heart rate was decreased after 2 mg/kg COMPOUND A (p<0.05), reflecting the number of patients who converted to sinus rhythm in this group. There were no clinically significant changes from baseline in systolic blood pressure, and there were no changes in blood pressures that were substantially different from those seen in the placebo group. There were two significant cases of hypotension reported in the placebo group and one mild case of transient hypotension in the RSD-2 group. Clinically significant treatment-related decreases in mean heart rate from baseline (mean: 106 beats per min) occurred in patients administered the RSD-2 dose, starting at $T_1$=15 min (mean: 90 beats per min). This likely reflected the conversion of several patients to normal sinus rhythm.

A total of thirty-nine patients experienced 122 adverse events over the course of the study, with a similar incidence of events among the three treatment groups. The majority of adverse events were of mild or moderate intensity. There were four mild adverse events that occurred in two patients considered either definitely or probably related to study drug. Both patients were in the RSD-2 dose group: one patient reported paraesthesia, and one patient reported paraesthesia, nausea, and hypotension.

The most common adverse events experienced in this study were cardiac disorders, reported by seven patients (35.0%) in the placebo group, four patients (22.2%) in the RSD-1 group, and three patients (16.7%) in the RSD-2 group. In addition to the serious adverse events discussed below, the cardiac disorders in the placebo group included two patients with non-sustained ventricular tachycardia and a patient with ventricular premature beats. Ventricular premature beats were also seen in two patients and sinus bradycardia in one patient of the low dose group. Ventricular premature beats were seen in two patients and sinus bradycardia in another patient in the RSD-2 group. Other adverse events occurring with a similar frequency among treatment groups were nervous system disorders, general disorders and infections.

Serious adverse events were reported in five patients (four in the placebo group and one in the RSD-1 group). A transient cerebral ischemic attack occurred 1 day after conversion in a placebo treated patient with a therapeutic international normalized ratio (INR) at the time of conversion. Severe bradycardia and hypotension immediately following conversion occurred in one patient, pulmonary edema in another patient and recurrent AF in the fourth placebo patient. One patient in the RSD-1 group experienced ventricular fibrillation, which was attributed to an asynchronous discharge during an electrical cardioversion attempt performed 1 h after receiving the second infusion.

Within the study period (24 h) electrical cardioversion was attempted in nine of 19 (47%) placebo treated, nine of 18 (50%) RSD-1 treated and four of 18 (22%) RSD-2 treated patients and was successful in eight (89%), nine (100%) and four (100%) patients, respectively.

Figure 16:
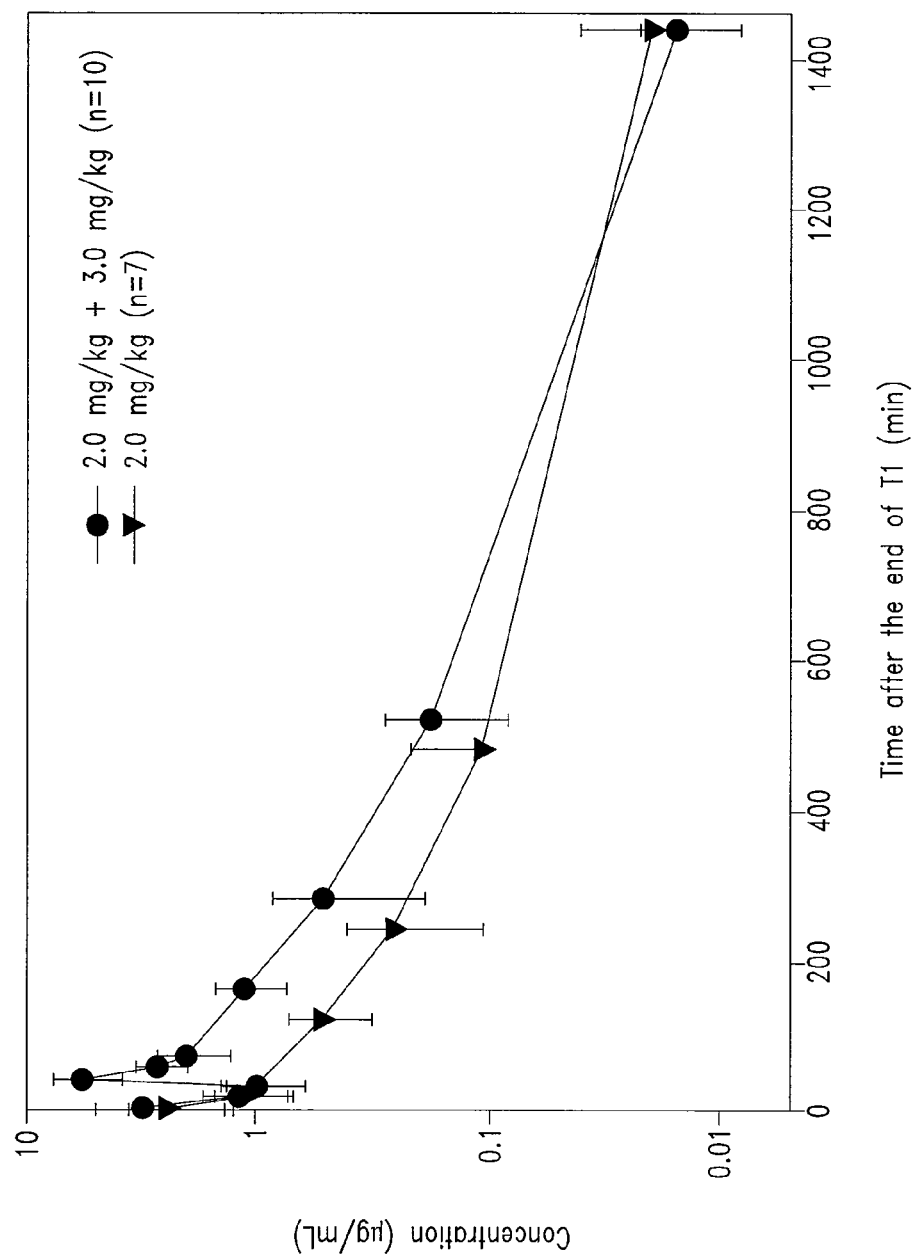
FIG. 16 Plasma concentrations of COMPOUND A after infusion in patients dosed at 2 mg/kg i.v. and those additionally dosed at 3 mg/kg i.v.

FIG. 16 shows a pharmacokinetic analysis of the data for COMPOUND A, and shows plasma concentrations of COMPOUND A after infusion in patients dosed at 2 mg/kg i.v. (filled inverted triangles) and those additionally dosed at 3 mg/kg i.v. (filled circles). COMPOUND A doses were infused over 10 min as indicated in the text. Initially a 2 mg/kg infusion was given and if required an additional 3 mg/kg was infused 30 min later in the RSD-2 group. Time is shown relative to the end of the first infusion (T1).

Mean peak COMPOUND A plasma levels were 5.8 µg/mL (range: 4.0 to 8.6 µg/mL) in the patients that received both the 2.0 and 3.0 mg/kg infusions of COMPOUND A and 1.9 µg/mL (range: 0.1 to 3.4 µg/mL) in those that received both 0.5 and 1.0 mg/kg COMPOUND A. Maximum plasma levels were seen at the end of the second infusion. Plasma drug levels at 24 h post-infusion were below the limit of detection (5 ng/mL) in the majority of patients who received RSD-1. Similarly, negligible plasma levels were seen at 24 h in the RSD-2 group; mean plasma levels were 0.017 µg/mL (range: <0.005 to 0.028 µg/mL). In those patients that received only the 2 mg/kg infusion, mean peak plasma levels at the end of infusion were 2.6 µg/mL (range: 1.4 to 4.5 µg/mL). The median plasma level at the time of AF conversion in these patients was 1.3 µg/mL (range: 1.1 to 3.5 µg/mL). The mean terminal elimination half life in these patients was 3.1 h (range: 1.7 to 5.4 h).

This study demonstrated that the upper dose of COMPOUND A (2+3 mg/kg) rapidly and effectively terminated AF compared to lower dose COMPOUND A and placebo. There were no serious adverse events associated with COM- POUND A, and observed SAEs were more common in the placebo group. In contrast to other antiarrhythmic drugs used for conversion of acute AF, there were no instances of drug related proarrhythmia. While these initial findings will require confirmation in larger scale clinical trials, this safety profile coupled with an efficacious and rapid onset confirms that COMPOUND A is a promising new agent for the medical conversion of acute AF.

COMPOUND A shows a higher net efficacy (61% to 5%=56%) for conversion of recent onset AF within 2 h of exposure.

This randomized controlled trial provides evidence for the efficacy of this atrial specific, $Na^+/K^+$ channel blocking agent for the treatment of AF. Intravenous COMPOUND A (2+3 mg/kg) was effective in rapidly terminating AF and was not associated with any drug induced proarrhythmia or any serious adverse event.

Example 16

Termination of EADs and Prevention of TdP in a Rabbit Model

COMPOUND A is an atrial fibrillation converting agent that exhibited mixed sodium and potassium channel blocking activity (Nav1.5, Kv1.5, Kv4.3, HERG $IC_{50}$ values: 33, 9, 30, 20 µM). COMPOUND A (30 µM) attenuated the action potential duration (APD) prolonging effects induced by dofetilide (300 nM) in rabbit Purkinje fibers, while COMPOUND A alone had no significant effect on APD. Class III agents induce EADs. However, COMPOUND A terminated EADs due to Class III agents in an in vivo rabbit model of drug-induced TdP. EADs were induced in isolated rabbit Purkinje fibers and in all experiments (n=7), 30 µM COMPOUND A terminated EADs induced with 300 nM dofetilide, as did 100 µM lidocaine (n=2). COMPOUND A was tested and found to suppress drug-induced TdP in an in vivo rabbit model. In 7 of 9 control animals TdP was induced by a 25 min infusion of the alpha-adrenergic agonist methoxamine (20 µg/kg/min), to which the Class III antiarrhythmic agent clofilium (300 nmol/kg/min) was added after 10 min. COMPOUND A, infused at 0.1, 0.3, or 1 µmol/kg/min for 5 min before starting methoxamine and continued throughout the study period reduced TdP incidence from 7/9 animals at 0.1, to 6/9 at 0.3, and to 1/9 at 1 µmol/kg/min COMPOUND A (p<0.05 at this dose compared to controls). Duration of TdP was also reduced in a dose-related fashion. The suppression of both EADs and TdP in the rabbit models illustrates that COMPOUND A may be safely coadministered with Class III antiarrhythmic drugs and that COMPOUND A may suppress the ventricular arrhythmias induced by these drugs.

Further examples of the effect of ion-channel modulating compounds on TdP are included in U.S. provisional application 60/544,941, titled MIXED ION CHANNEL BLOCKADE FOR THERAPEUTIC USE, filed Feb. 13, 2004 and incorporated by reference herein in its entirety.

Example 17

Block of a Late Component of the Human Heart (hH1) $Na^+$ Current Active During Repolarization COMPOUND A exhibits frequency-dependent blockade of $I_{Na}$ critical to its antiarrhythmic actions. In rabbit Purkinje fibers, in vitro tissue sensitive to agents that prolong repolarization, 30 µM COMPOUND A only minimally prolonged AP duration. In fact, COMPOUND A significantly attenuated the AP prolongation induced by the class III agent, dofetilide (300 nM). COMPOUND A lacks $I_{Ca}$ blockade at this concentration, and has little effect on AP shape. The present study tested termination of EADs induced by dofetilide in isolated rabbit Purkinje fibers using COMPOUND A. COMPOUND A blocks a late component of $I_{Na}$ that likely contributes to EAD genesis.

Figure 17:
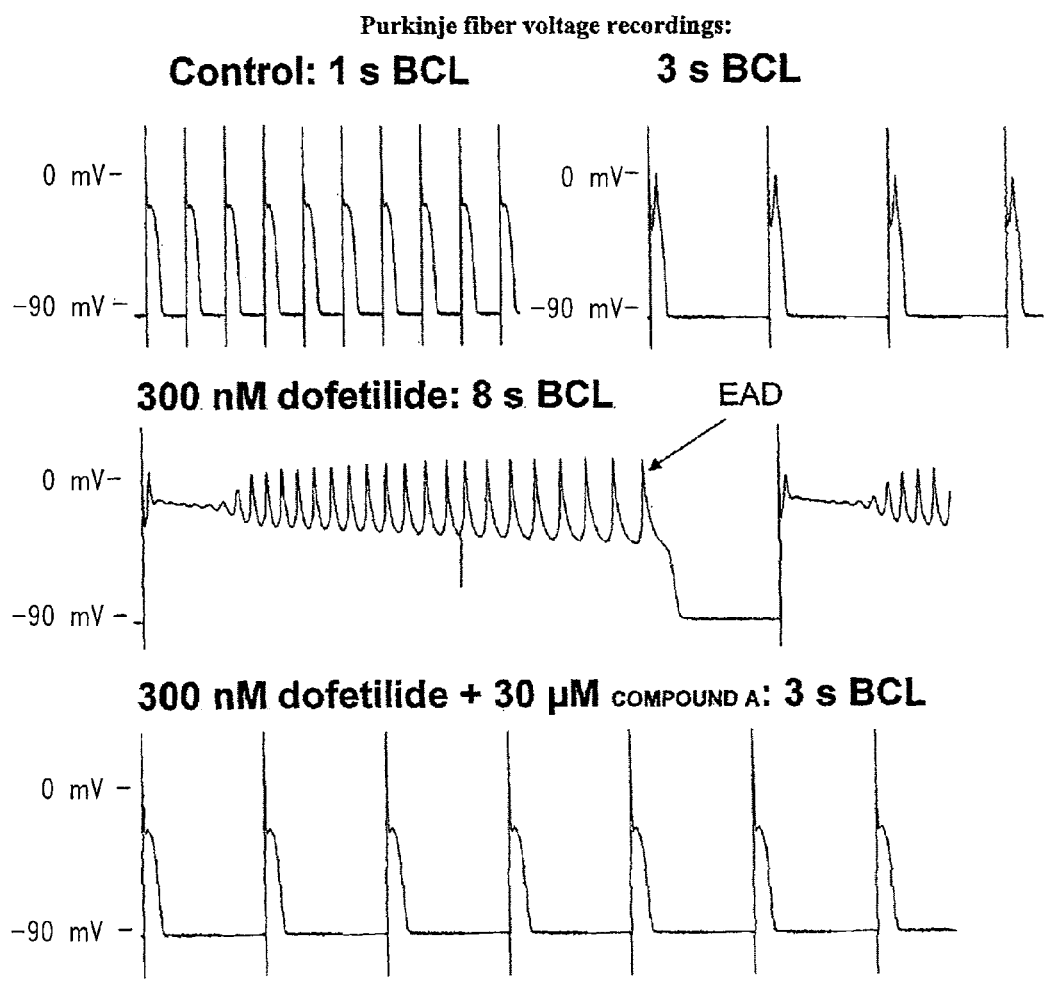
FIG. 17 shows action potentials and EADs induced in an isolated rabbit Purkinje fiber preparation.
Figure 18:
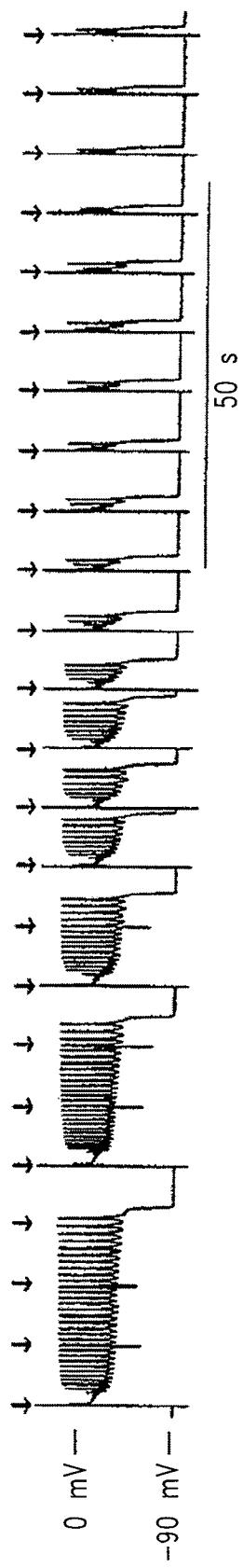
FIG. 18 shows late stage EAD suppression by COMPOUND A.

Intracellular voltage recordings were determined as follows:
  hearts were excised from female New Zealand white rabbits 2-2.5 kg
  a single cut was made along the septum to expose the endocardial surface of the left ventricle and the intervening Purkinje fibers
  a strand of Purkinje fibers was selected and excised from the ventricular tissue and placed in a tissue bath, bubbled with 95% $O_2$/5% $CO_2$
  stable impalements were made with a floating sharp electrode (10-20 Mohms)
  stock solutions of dofetilide, lidocaine and COMPOUND A were dissolved in DMSO
Current recordings were determined as follows:
  hH1 ($Na^+$) were stably expressed in HEK cells
  in physiological solutions $K^+$ was replaced with $Cs^+$
  in whole-cell configuration, cells were voltage clamped using the illustrated protocol
  total INa (TTX-sensitive current) was measured by subtracting the current recorded in the presence of 30 µM TTX from the control current
  COMPOUND A and lidocaine-sensitive current was measured by subtracting the current recorded in the presence of 30 µM COMPOUND A or 30 µM lidocaine from the control current
  stock solutions of lidocaine and COMPOUND A were dissolved in de-ionized H2O FIG. 17 shows action potentials and EADs induced in an isolated rabbit Purkinje fiber preparation. COMPOUND A (30 µM) terminates EADs induced by dofetilide (300 nM) (n=7).
  Stable EADs in isolated rabbit Purkinje fibers were induced in the presence of 300 nM dofetilide
  Superfusion of 30 µM COMPOUND A+300 nM dofetilide terminated all EADs in 7 of 7 experiments
  Mean time to EAD termination after addition of in the presence of COMPOUND A to dofetilide-containing perfusate was 35±7.8 minutes
  Addition of 100 µM lidocaine also terminated dofetilide-induced (300 nM) EADs FIG. 18 shows late stage EAD suppression by COMPOUND A. EADs were induced in the presence of 300 nM dofetilide and suppressed with the addition of 30 µM COMPOUND A to 300 nM dofetilide solution. Trace begins 10 mins after COMPOUND A addition. PF was stimulated every 8 s (arrows). In this experiment, complete EAD termination occurred in 16.8 minutes.

Figure 19:
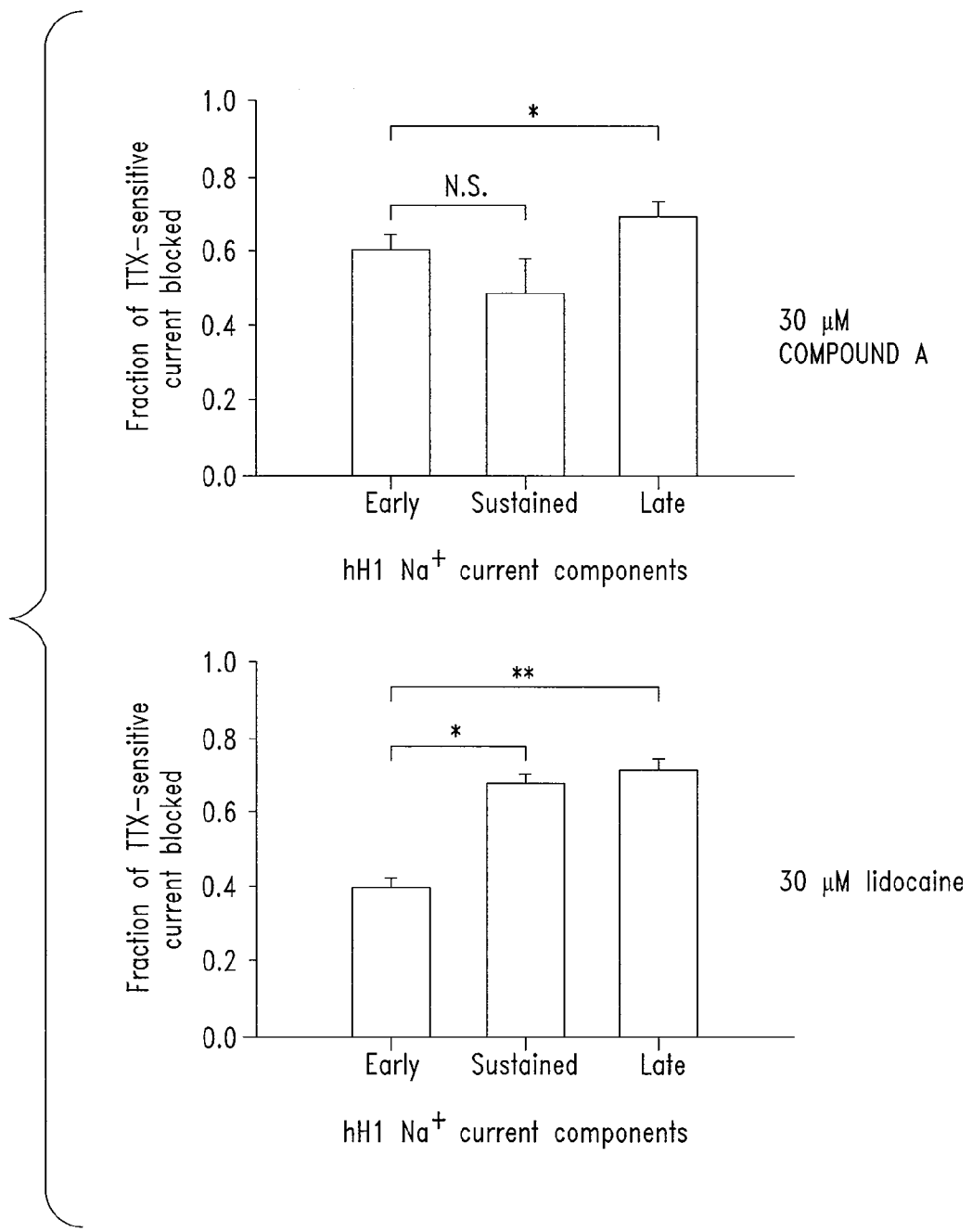
FIG. 19 shows the fraction of each component of the TTX-sensitive current blocked by 30 μM lidocaine and 30 μM COMPOUND A.

FIG. 19 shows the fraction of each component of the TTX-sensitive current blocked by 30 µM lidocaine and 30 µM COMPOUND A. Asterisks denote statistical significance (p<0.05) (n=6 for top graph). Top graph is the effect of 30 µM COMPOUND A and the bottom graph is the effect of 30 µM lidocine. The bottom graph shows the fraction of the early, sustained, and late TTX-sensitive currents blocked by 30 µM lidocaine. In 4 experiments, 30 µM lidocaine blocked 41±2.7% of the TTX-sensitive early transient current ($I_{early(TTX)}$), 70±2.5% of the TTX-sensitive sustained current ($I_{sus(TTX)}$), and 73±2.8% of the TTX-sensitive late current ($I_{late(TTX)}$). The observation that lidocaine blocks $I_{sus(TTX)}$ and $I_{late(TTX)}$ more than $I_{early(TTX)}$ is statistically significant (paired t-test; *p=0.00014, **p=0.000037, respectively). Results are expressed as the mean±S.E.M. (n=4).

COMPOUND A (30 μM) terminates EADs induced by dofetilide (300 nM) in rabbit Purkinje fibers. Further, COMPOUND A blocks a late component of $I_{Na}$ that may participate in EAD initiation.

Example 18

Block of Early, Sustained and Late Sodium Current in HEK-293 Cells Expressing the Human Heart Sodium Channel (hH1)

The sustained and late tetrodotoxin (TTX)-sensitive Na$^+$ current were measured using whole-cell patch clamp of HEK cells expressing human heart sodium channels (hH1). Cells were stimulated with a step/ramp voltage protocol that approximated the voltages reached during the plateau and repolarizing phases of the action potential in order to measure the early, sustained and late sodium current components. Thirty (30) μM of COMPOUND A inhibited all components of the TTX-sensitive current: early ($I_{early(TTX)}$), sustained ($I_{sus(TTX)}$), and late ($I_{late(TTX)}$).

COMPOUND A significantly attenuates dofetilide-induced prolongation of the rabbit Purkinje fiber action potential at voltages halfway to complete repolarization (APD$_{50}$). Block of L-type calcium current in guinea pig atrial myocytes is minimal at 30 μM of COMPOUND A. Lidocaine (a Na$^+$ channel blocker) also reverses dofetilide-induced APD$_{50}$ prolongation. In addition to attenuating dofetilide-induced APD$_{50}$ prolongation, 30 μM COMPOUND A also terminates dofetilide-induced early afterdepolarizations (EADs) in isolated rabbit Purkinje fibers.

The effect of COMPOUND A and lidocaine on the early, sustained, and late components of Na$^+$ current using a step/ramp protocol to generate the currents in HEK cells expressing the hH1 Na$^+$ channel were examined. COMPOUND A was able to effectively block the late components of $I_{Na}$, which occur at voltages approximating APD$_{50}$.

Drugs used. TTX was purchased from Calbiochem and lidocaine (lot # 116H0611) from Sigma. Tables 5 and 6 show components of experimental solutions.

TABLE 5

Constituents of Cs$^+$-containing external solution (10 L)

| Reagent | Concentration | Supplier | Cat. # | Lot # |
|---|---|---|---|---|
| NaCl | 130 mM | Sigma | S9888 | 032K1230 |
| Dextrose | 10 mM | Sigma | BP350-1 | 000199A |
| HEPES | 10 mM | Sigma | H3375 | 032K5464 |
| MgCl$_2$ | 1 mM | Sigma | M9272 | 129H0036 |
| CsCl | 5 mM | Sigma | C3011 | 11K0316 |
| CaCl$_2$ (anhydrous) | 1 mM | Sigma | C2661 | 99H0057 | pH corrected to 7.4 with NaOH

TABLE 6

Constituents of Cs$^+$-containing internal solution (500 mL)

| Reagent | Concentration | Supplier | Cat. # | Lot # |
|---|---|---|---|---|
| CsCl | 130 mM | Sigma | C3011 | 11K0316 |
| DiNa$^+$ATP | 4 mM | Fischer | A3377 | 12K1163 |
| MgCl$_2$·6H$_2$O | 1 mM | Sigma | M9272 | 129H0036 |

TABLE 6-continued

Constituents of Cs$^+$-containing internal solution (500 mL)

| Reagent | Concentration | Supplier | Cat. # | Lot # |
|---|---|---|---|---|
| HEPES | 5 mM | Sigma | H3375 | 032K5464 |
| EGTA | 10 mM | Sigma | E3889 | 58H5434 | pH corrected to 7.2 with NaOH

Stock Solution Vehicle was de-ionized water. A 10 mM stock solution of COMPOUND A was prepared by the dissolution of 22.4 mg of compound in 5.8 mL of de-ionized water. Stock solution was stored at −20° C. 10 mM stock solutions of tetrodotoxin (Calbiochem) were prepared by dissolving 1 mg in 313 μL of de-ionized water. Stock solutions were stored −20° C. Lidocaine was stored as a 10 mM stock solution at −20° C. Stock solutions were prepared by dissolving 13.54 mg in 5 mL de-ionized water.

The recordings were obtained by whole-cell patch-clamp from HEK-293 cells expressing hH1Na. Constituents of internal solution were: CsCl (130 mM), DiNa$^+$ATP (4 mM), MgCl$_2$·6H$_2$O (1 mM), HEPES (5 mM), EGTA (10 mM). Constituents of external solution were: NaCl (130 mM), Dextrose (10 mM), HEPES (10 mM), MgCl$_2$ (1 mM), CsCl (5 mM), CaCl$_2$ (anhydrous) (1 mM). Recordings were taken by:

1. After achieving whole-cell configuration with a series resistance of<10 MΩ (preferably <6 MΩ), the cell was held at −80 mV for 5-10 minutes (up to 30 minutes) to achieve a stable leak and allow for sufficient dialysis of the intracellular pipette solution. During this time the solution flow was kept off.
2. Clampex 8.2 software was configured to allow viewing of the sustained and late currents while also recording and plotting, in real-time, the peak of the early transient current that will be off scale on the signal display. Following equilibration, solution was allowed to flow and 50-100 traces of control recordings were obtained during which time the peak of the early transient current were kept stable. The voltage protocol used was: hold 25 ms @−100 mV, step from −100 mV to +20 mV, hold 100 ms @+20 mV, ramp from +20 mV to −100 mV over 100 ms.
3. When the early current peak amplitude has been stable for 100-150 traces, add COMPOUND A at the concentration desired. Again, when the early current amplitude has shown stability for 100-150 traces add 30 μM TTX. Washout after 100-150 traces in which the early current is stable.

Exclusion/Inclusion Criteria were: only cells in which the unaveraged leak does not vary more than 20 pA were accepted, experiments in which the current is not stable were excluded, experiments in which there is little or no obvious inward current (sag) during the negative ramp were excluded, series resistance had to be <10 MΩ, experiments that do not subtract correctly (likely a result of unstable current or leak) were excluded (i.e., experiments where capacitance or resistance artifacts changed, resulting in significant artifacts post-subtraction that varied in magnitude, causing artifacts that did not subtract and adversely altered current subtraction were excluded).

After achieving the whole-cell configuration, the cell was left to equilibrate for 5 to 10 minutes at a holding potential of −80 mV. This equilibration period allowed complete dialysis of the intracellular solution with the internal pipette solution and was critical to achieve stable electrophysiological signals. Since the sustained and late currents were small (<60 pA), changes in leak current during the recording could distort our measurements and the subsequent digital subtraction.

Holding the cell at −80 mV for 5-10 minutes before running the voltage protocol resulted in recordings with stable leak current and undistorted currents of interest. 30-150 control traces (1 Hz) were obtained using the step/ramp voltage clamp protocol illustrated in FIG. 20. Trace averaging occurred post hoc. Cells were then perfused with a Na$^+$ channel blocking drug, either 30 µM COMPOUND A or 30 µM lidocaine. 30 µM TTX was applied when the amplitude of the peak early current had become stable for approximately 30-150 traces. Following 30-150 traces of complete block, both drugs were washed out. By using Clampex 8.2 acquisition software, the peak early current amplitude (−2000 to −8000 pA) was plotted while allowing the experimenter to simultaneously observe the raw traces of sustained and late current portions (−50 to −150 pA).

Figure 20A:
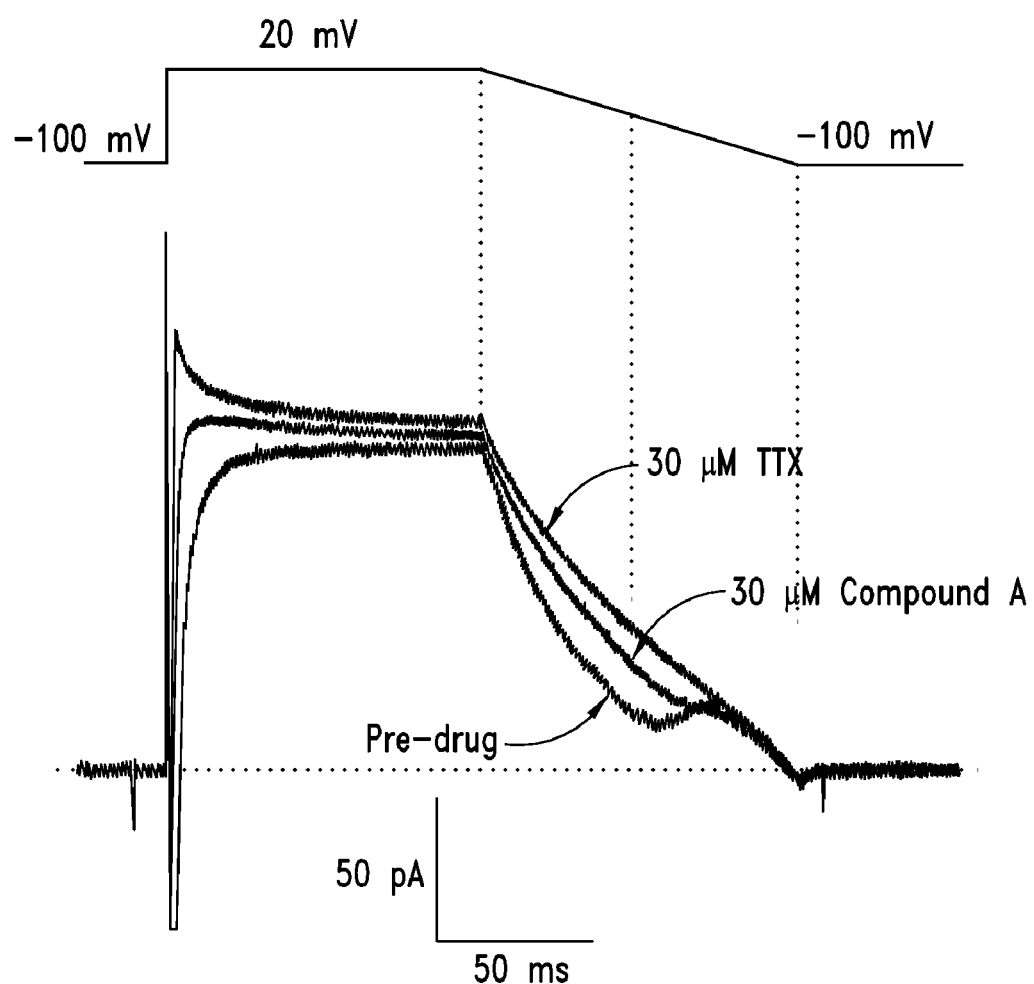
FIG. 20 shows unsubtracted current traces obtained from HEK293 cells expressing hH1 $Na^+$ channels before and during exposure to 30 μM COMPOUND A and COMPOUND A plus 30 μM TTX.

Analysis involved digital subtraction to identify the COMPOUND A-, lidocaine- and TTX-sensitive currents. 30-150 consecutive traces were averaged before drug addition, following perfusion with either COMPOUND A or lidocaine and following 30 µM TTX perfusion. Trace averaging significantly improved the signal-to-noise ratio. Thus, each analysis file contained 3 current traces: pre-drug, after perfusion with either COMPOUND A or lidocaine, and current in the presence of TTX (see FIG. 20). The COMPOUND A-, lidocaine-, and TTX-sensitive traces were obtained by digitally subtracting the averaged trace in the presence of drug from the pre-drug averaged trace (FIGS. 20 and 21).

A step/ramp voltage protocol (FIG. 20) similar to Clancy et al. (Clancy C E, Tateyama M, Liu H, Wehrens X H, Kass R S., Non-equilibrium gating in cardiac Na$^+$ channels: an original mechanism of arrhythmia. Circulation. 2003 May 6;107(17): 2233-7, herein incorporated by reference in its entirety) was used to uncover the sustained and non-equilibrium portion of the hH1Na current. Resting and voltage-gated potassium currents were blocked during these recordings by replacing K$^+$ with Cs$^+$ in both internal and external solutions. 30 µM COMPOUND A reliably blocked the unsubtracted $I_{early}$ by approximately half and 30 µM TTX blocked this current completely (FIG. 20C). During the negative ramp that simulates the repolarization phase, this protocol reliably caused a "sag" in the current trace (FIG. 20A). Addition of 30 µM COMPOUND A caused this "sag" to partly diminish.

Figure 20B:
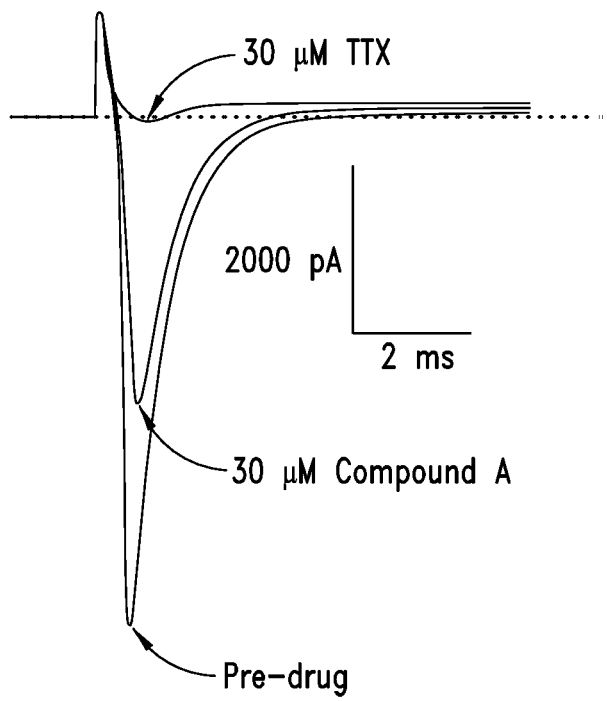
Figure 20C:
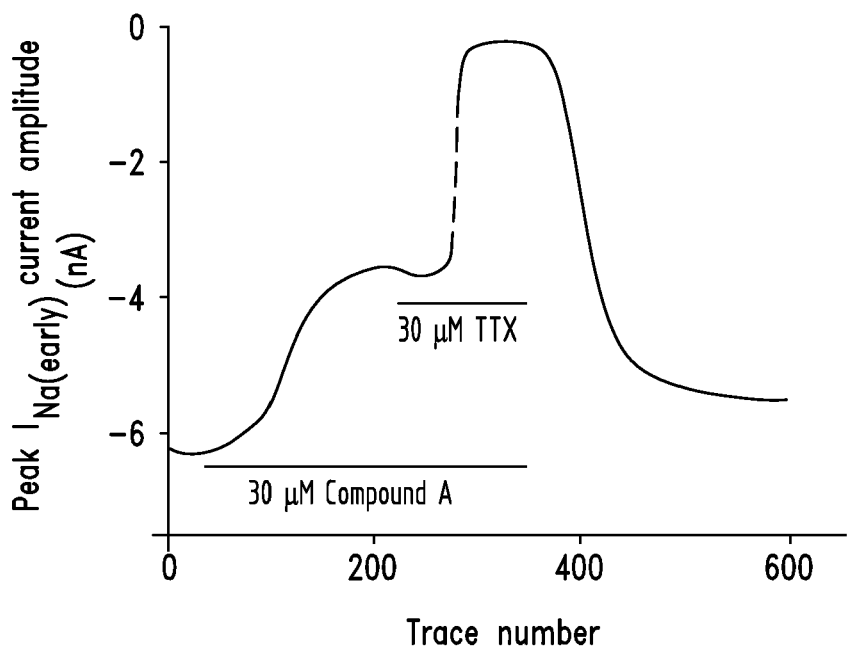
Figure 21:
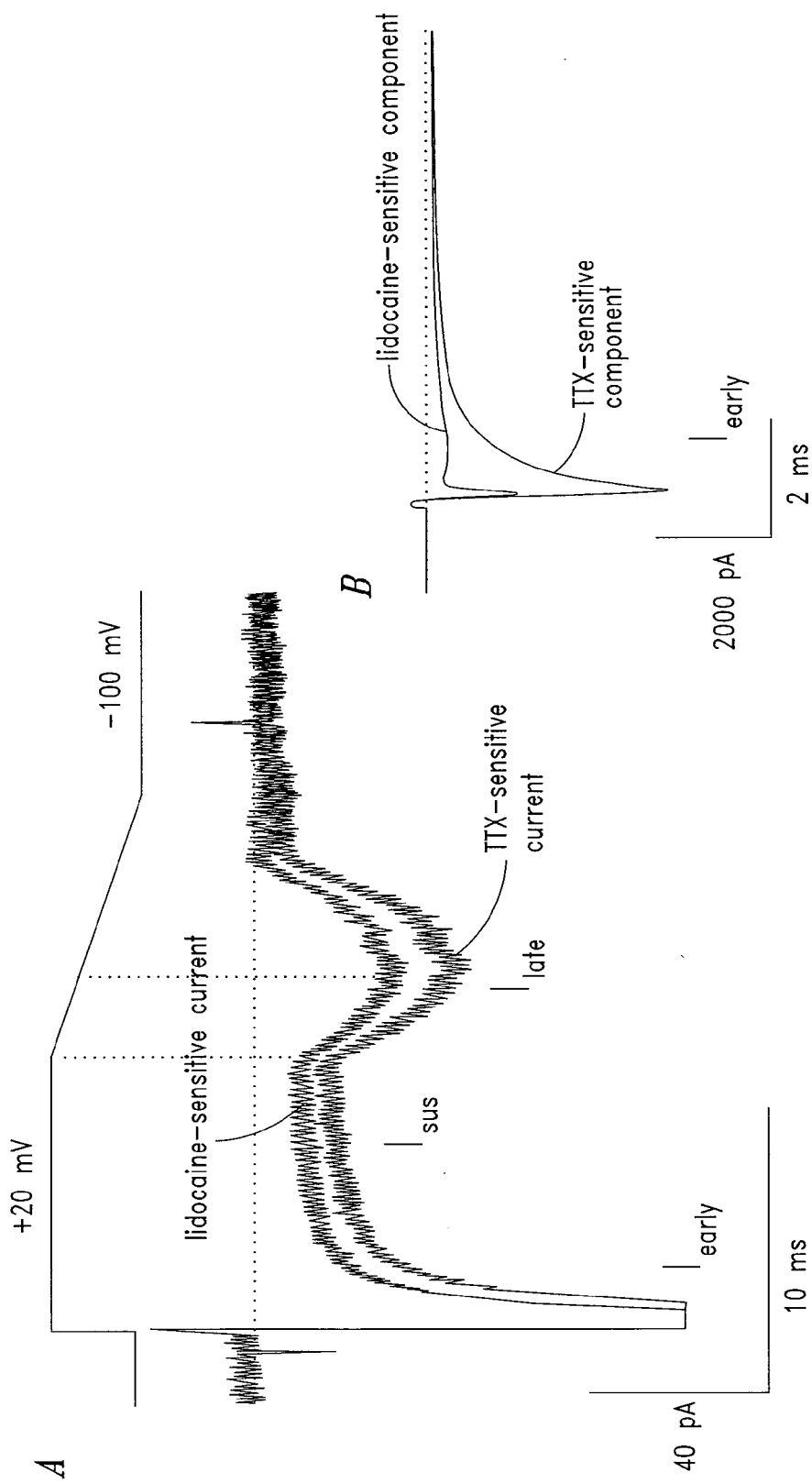
FIG. 21 shows an example of the TTX- and lidocaine-sensitive components of the early, sustained, and late sodium current observed during a step/ramp protocol.

FIG. 20 shows unsubtracted current traces obtained from HEK293 cells expressing hH1 Na$^+$ channels before and during exposure to 30 µM COMPOUND A and COMPOUND A plus 30 µM TTX. FIG. 20A (upper trace) shows the voltage protocol involves a 100 ms step depolarization from −100 mV to +20 mV and is followed by a 100 ms ramp from +20 mV back down to −100 mV. The lower trace shows averaged current traces following leak subtraction. FIG. 20B shows the early transient current ($I_{early}$) that is off-scale in 20A. FIG. 20C shows a plot of the unsubtracted peak amplitude of $I_{early}$. 30 µM COMPOUND A was followed by 30 µM TTX plus 30 µM COMPOUND A and complete washout.

Additional perfusion of 30 µM TTX almost entirely removed the non-linearity in the current trace. FIG. 8 shows examples of TTX- and COMPOUND A-sensitive current traces obtained by digital subtraction.

Three components of the TTX-sensitive current are evident. An early inward current, $I_{early(TTX)}$, results from stepping the cell from −100 mV to +20 mV. During the plateau phase of the protocol, a sustained inward current, $I_{sus(TTX)}$, is present. As the voltage is ramped back to −100 mV, a late inward current, $I_{late(TTX)}$, develops. $I_{late(TTX)}$ reaches its peak at voltages within the range of half repolarization, between −20 mV and −40 mV.

In 6 experiments, 30 µM COMPOUND A blocked 61±4% of $I_{early(TTX)}$, 50±9% of $I_{sus(TTX)}$, and 70±4% of $I_{late(TTX)}$ (FIGS. 8 & 19 top graph). 30 µM COMPOUND A proportionately blocked ~9% more of the late TTX-sensitive current than $I_{early(TTX)}$ and this is statistically significant (paired t-test; p=0.005). The difference between the proportion of $I_{sus(TTX)}$ and $I_{early(TTX)}$ blocked is not statistically significant (paired t-test; p>0.1).

The ability of another Na$^+$ channel blocker that reverses dofetilide-induced EADs, lidocaine, to block the components of Na$^+$ current during a step/ramp protocol was also examined. 30 µM lidocaine blocked $I_{early(TTX)}$ 41±2.7%, $I_{sus(TTX)}$ 70±2.5% and $I_{late(TTX)}$ 73±2.8% (FIGS. 21 & 19 bottom graph). Block of both $I_{sus(TTX)}$ and $I_{late(TTX)}$ was significantly greater than block of $I_{early(TTX)}$ (paired t-test; p=0.00014 and p=0.000037 respectively). FIG. 21 shows an example of the TTX- and lidocaine-sensitive components of the early, sustained, and late sodium current observed during a step/ramp protocol. In FIG. 21A, lidocaine- and TTX-sensitive currents are obtained by digitally subtracting the current obtained in the presence of either 30 µM lidocaine or lidocaine plus 30 µM TTX respectively from the current obtained pre-drug. FIG. 21B shows the lidocaine- and TTX-sensitive early current traces that are off-scale in 21A. Current traces in 21A and 21B are averages of 30 raw traces.

COMPOUND A does not prolong QT-interval in man. To investigate $I_{Na}$ activity during phases 2 and 3, a protocol that approximated the time-course and voltages of the action potential during these phases was used. Using this protocol, 3 TTX-sensitive components of $I_{Na}$ were identified: a fast early current ($I_{early(TTX)}$) occurring rapidly after depolarization, a sustained current ($I_{sus(TTX)}$) active during the plateau, and a late current ($I_{late(TTX)}$) that occurred during repolarization. $I_{late(TTX)}$ occurred near APD$_{50}$ potentials. 30 µM COMPOUND A or 30 µM lidocaine significantly inhibited $I_{late(TX)}$. COMPOUND A, like lidocaine, is particularly effective at promoting repolarization at the time and potentials near APD$_{50}$.

In HEK-293 cells expressing hH1Na channels, 30 µM COMPOUND A or 30 µM lidocaine reduced all TTX-sensitive current components present during a step/ramp voltage protocol. The results also indicate that COMPOUND A and lidocaine reduce the late current component, and that this inhibition occurs at voltages near APD$_{50}$.

Example 19

Use of Rabbit Purkinje Fibers to Screen for Proarrhythmic Activity

This example relates to the use of aminocyclohexyl ether compounds to modulate class III-induced action potential prolongation and generation of triggered activity (EADs and TdP). Class III agents are proarrhythmic. Combination therapy with quinidine (a class III agent) and mexiletine (a class I agent and sodium channel blocker) is more effective in the prevention of ventricular tachycardia (VT) and ventricular fibrillation (VF) in animal models and in humans. EAD generation is thought to be a major cause of TdP in humans.

The present example concerns the perfusion of aminocyclohexyl ether compounds (e.g., COMPOUND A) at concentrations sufficient to block sodium current either before or during perfusion with proarrhythmic agents (e.g., dofetilide or other class III agents) in order to attenuate action potential prolongation and/or EAD generation which are known to have proarrhythmic consequences. Sodium channel blockade by aminocyclohexyl ether compounds (e.g., COMPOUND A) can prevent induction of AF or VF as well as terminate triggered activity which is thought to lead to fatal VF. The example herein relates to the effects of aminocyclohexyl ether compounds (e.g., COMPOUND A) in rabbit Purkinje fibers, but the principles and methods can likely be extended to treatment of acquired long-QT syndrome, muti-focal ventricular arrhythmias (TdP) or prevention of AF induction in humans.

Action Potential duration measurements: female, white New Zealand rabbits weighing between 2.5 and 3.5 kg were anaesthetized with a sufficient dose of pentobarbital to create a stuporous state and the animals were sacrificed with a blow to the head. A midline thoracotomy was performed and the heart was excised as practised by those skilled in the art. The right and left atrium were removed and the heart was opened through an incision along the left side of the septum in order to expose the endocardial surface of the left ventricle. The heart was transferred to a 10 mL tissue bath and Purkinje fibers exposed for microelectrode recording. The heart was perfused with standard bicarbonate buffered Krebs' solution known to those skilled in the art. An electrode was pulled from thin-walled filamented borosilicate glass capillary tubes having a resistance of 10 to 30 megaohms when filled with 3 M KCl. The electrode was attached to headstage mounted on an Axoclamp 2A amplifier (or a similar amplifier known to those skilled in the art). The microelectrode was brought down upon an exposed Purkinje fiber using a micromanipulator and the position was adjusted until the electrode penetrated a single Purkinje cell. The Purkinje fiber network was stimulated using a biphasic stimulation pulse and subsequent action potentials were recorded for analysis. Extracellular solutions containing aminocyclohexyl ether compounds (e.g., COMPOUND A) and/or proarrhythmic agents (e.g., dofetilide or other class III agents) were then perfused to discern changes in action potential duration. A dose response relationship was obtained using ascending concentrations of aminocyclohexyl ether compounds (e.g., COMPOUND A) (0.3 to 30 $\mu$M) and this treatment was then followed by concomitant perfusion with 300 nM proarrhythmic agents (e.g., dofetilide or other class III agents) and 30 $\mu$M aminocyclohexyl ether compounds (e.g., COMPOUND A). In a separate preparation, a dose-response relationship was obtained using ascending concentrations of proarrhythmic agents (e.g., dofetilide or other class III agents) (10 nM to 300 nM) and this treatment was followed by concomitant perfusion with 300 nM proarrhythmic agents (e.g., dofetilide or other class III agents) and 30 $\mu$M aminocyclohexyl ether compounds (e.g., COMPOUND A). A final study was undertaken in which ascending concentrations of proarrhythmic agents (e.g., dofetilide or other class III agents) were paired with DMSO vehicle control, 30 $\mu$M aminocyclohexyl ether compounds (e.g., COMPOUND A) or 100 $\mu$M lidocaine, the identity of which was blinded to the experimenter.

Effective Refractory Period (ERP) measurements: in the same preparations as described above, ERP was determined following each treatment arm. An S1-S2 protocol was used as known by those skilled in the art. Briefly, 15 S1 pulses were delivered at a frequency of 1 Hz and this train was followed by an S2 pulse following a variable interval. The interval was set to be greater than the refractory period and it was reduced in 10 ms increments until an S2 response could no longer by elicited. The shortest duration which could generate an S2 response was termed the ERP.

Early-after-depolarization (EAD) measurements: the left ventricle of a rabbit heart was exposed as described previously. A Purkinje fiber was located within the Purkinje fiber network having dimensions of approximately 2 mm length and 0.5 mm width. The fiber was excised from the heart using fine cutting tools along with a small amount of ventricular tissue attached at either end of the fiber. The fiber was transferred to a 5 mL tissue bath and perfused and penetrated as described above. Stable action potentials were obtained for a period not less than 30 minutes and then 300 nM proarrhythmic agent (e.g., dofetilide or other class III agents) was perfused in order to generate EADs. EADs were characterized as depolarizations which disrupt the normal course of Purkinje fiber repolarization. Stable EADs were obtained for a period of not less than 30 minutes and then 30 $\mu$M aminocyclohexyl ether compounds (e.g., COMPOUND A) was perfused concomitantly with 300 nM proarrhythmic agent (e.g., dofetilide or other class III agents). EADs were monitored for termination over a period not exceeding 60 minutes.

Figure 22A:
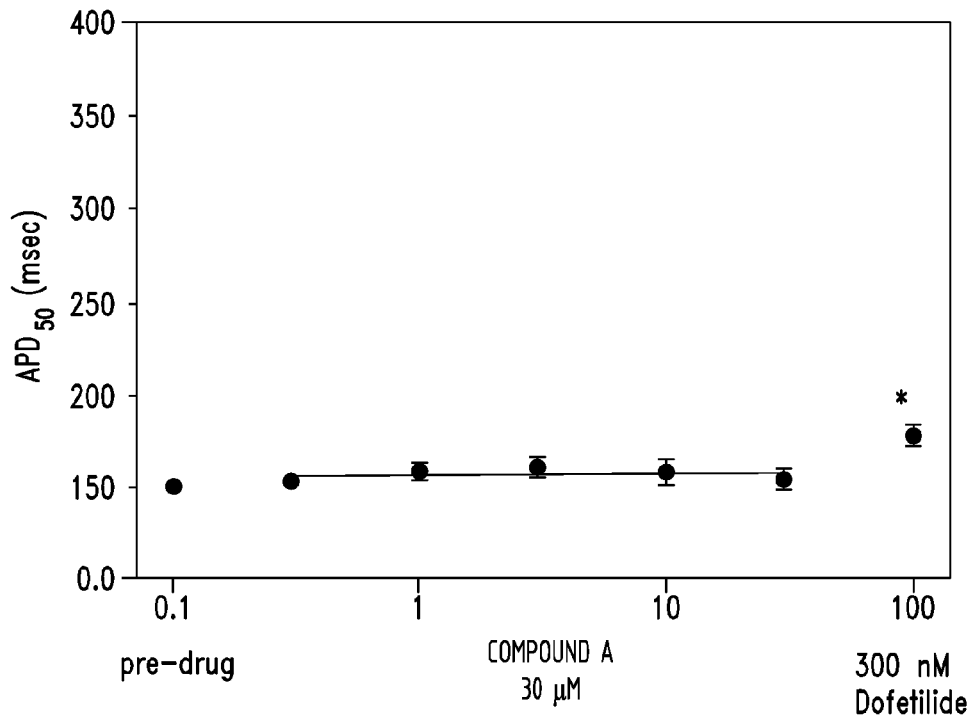
FIG. 22A and FIG. 22B show $APD_{50}$.
Figure 22B:
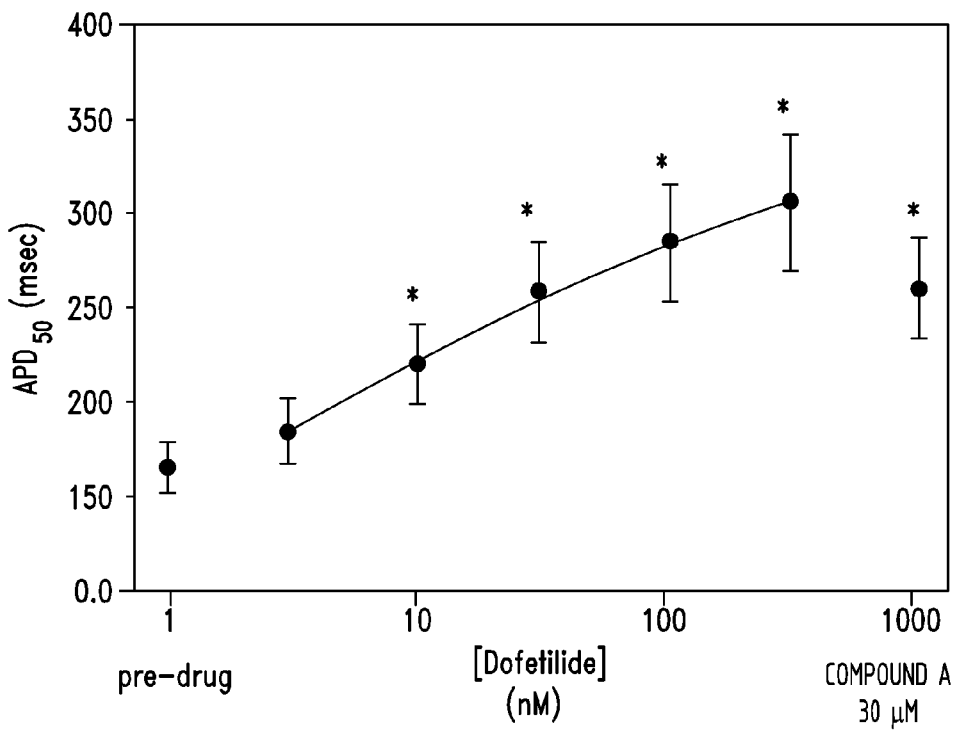
Figure 22C:
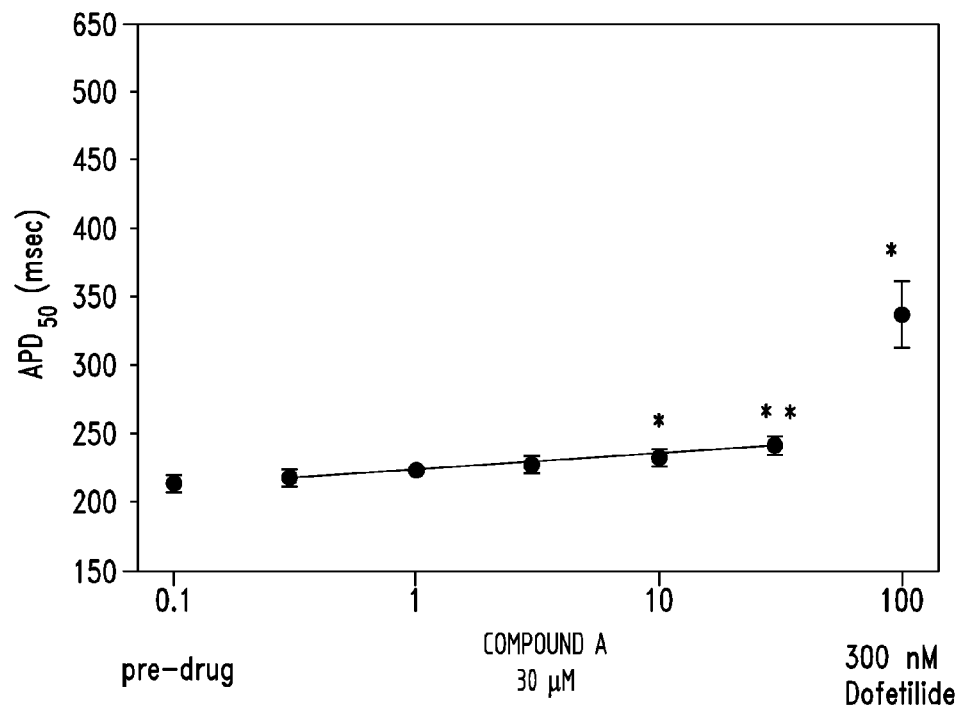
FIG. 22C and FIG. 22D show $APD_{90}$ in the presence of escalating concentrations of COMPOUND A (FIG. 22A & FIG. 22C) or dofetilide (FIG. 22B & FIG. 22D) followed by perfusion with COMPOUND A (30 μM) and dofetilide (300 nM).
Figure 22D:
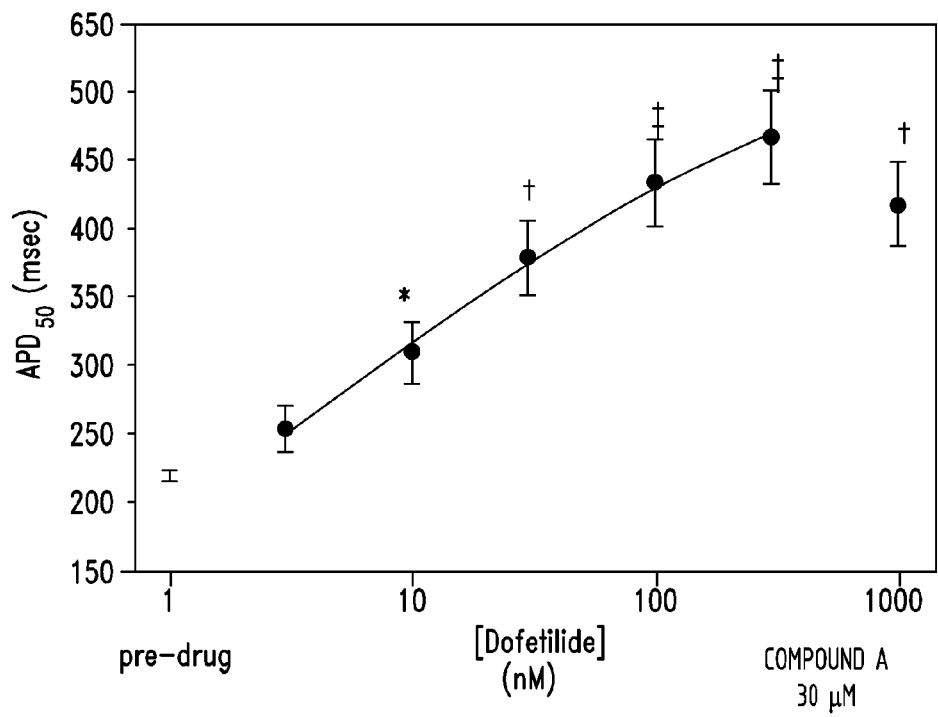

The initial experiments explored the effect of a single concentration of COMPOUND A (30 $\mu$M) following ascending concentrations of dofetilide and vice versa (single concentration of dofetilide was 300 nM). FIG. 22 illustrates the changes in action potential duration following these various treatments. The change in APD50 during COMPOUND A treatment was not significant (p>0.05), however immediately following perfusion with 30 $\mu$M COMPOUND A, concomitant perfusion of 30 $\mu$M COMPOUND A and 300 nM dofetilide induced a 20% increase in APD50 (p<0.01) (FIG. 22A). This effect of the combination of COMPOUND A and dofetilide was much less than the increase observed with 300 nM dofetilide alone which produced approximately a 100% increase in APD50 (p<0.01) (FIG. 22B). Subsequent treatment with 300 nM dofetilide and 30 $\mu$M COMPOUND A produced a reduction in APD50 to 70% of the APD50 for dofetilide alone (FIG. 22B). It appears that pretreatment with ascending concentrations of COMPOUND A (FIG. 22A) reduced the effect of dofetilide more than acute treatment (FIG. 22B). Similar, but less pronounced effects upon APD90 were observed (FIGS. 22C & 22D). COMPOUND A alone produced only mild increases in the PF APD90 at concentrations up to 30 $\mu$M (FIG. 22C). Concomitant treatment with 300 nM dofetilide and 30 $\mu$M COMPOUND A induced a 60% increase in APD90 (FIG. 22C) which was less than the 105% increase in APD90 caused by 300 nM dofetilide alone (FIG. 22D). Similar to the effects observed on APD50, COMPOUND A treatment following dofetilide pretreatment did not reduce the effects of dofetilide upon APD90 (105% increase) as much as dofetilide treatment following COMPOUND A pretreatment (60% increase) (FIG. 22D). In FIG. 22, the stimulation frequency was 1 Hz and results are expressed as the mean ±S.E.M., (n=4). *p<0.05, **p<0.01, †p<0.001, ‡p<0.0001 relative to predrug values.

Figure 23:
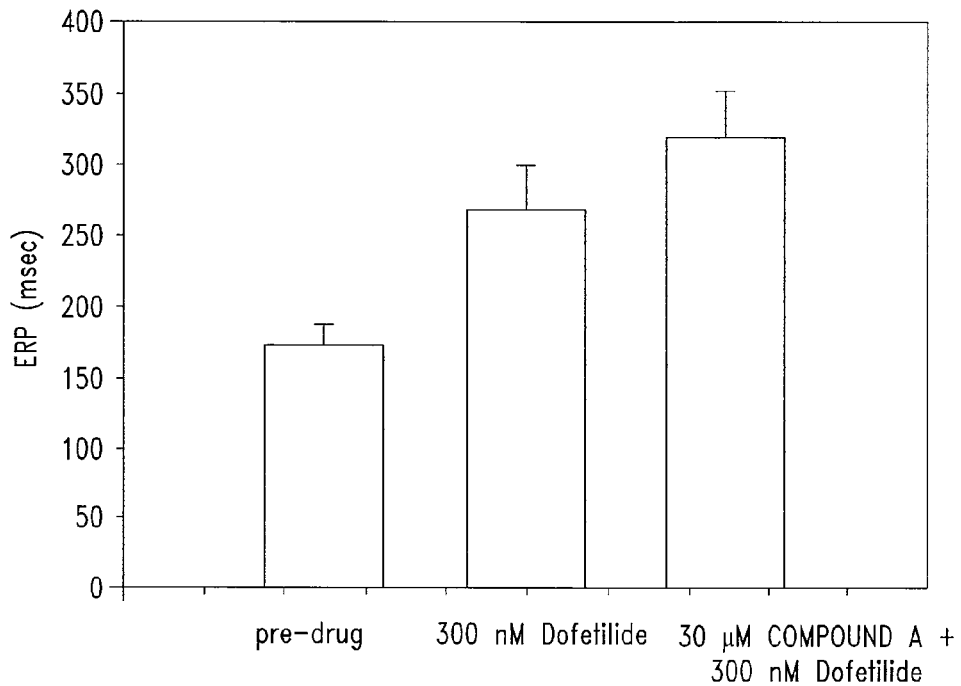
FIG. 23 shows ERP values obtained in the presence of dofetilide or a combination of dofetilide and COMPOUND A.
Figure 24:
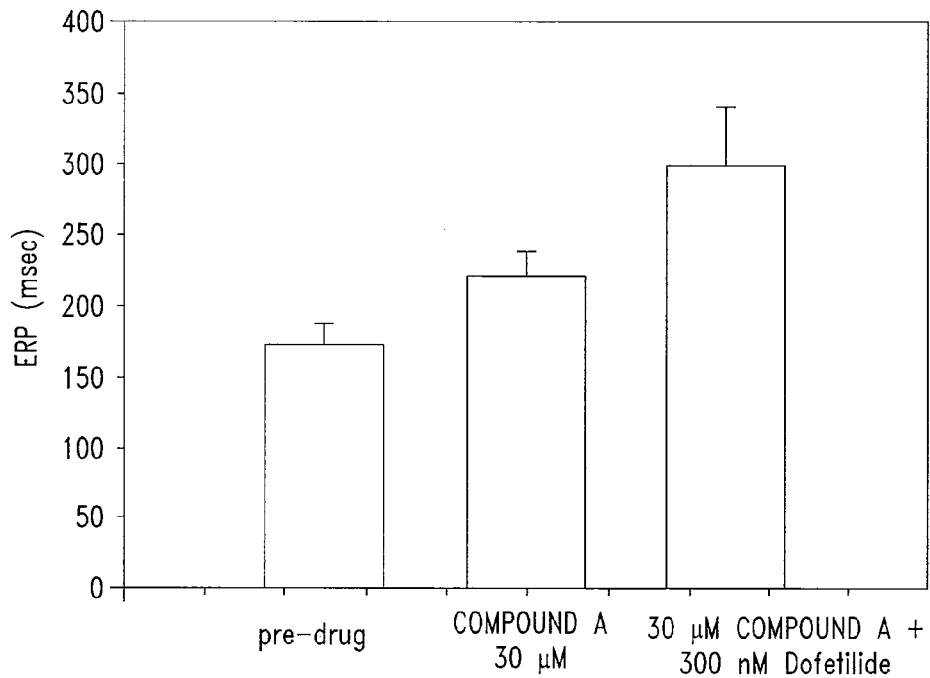
FIG. 24 shows ERP values obtained in the presence of COMPOUND A or a combination of COMPOUND A and dofetilide.

Whereas COMPOUND A tended to mildly attenuate the prolongation of APD50 and APD90 induced by dofetilide (FIGS. 22B & 22D), COMPOUND A tended to prolong the PF ERP produced by dofetilide (FIG. 23). In addition, whereas pretreatment with COMPOUND A significantly reduced the subsequent effect of dofetilide upon APD90 and APD50, COMPOUND A pretreatment did not attenuate ERP prolongation induced by dofetilide (FIGS. 23 and 24). FIG. 23 shows ERP values obtained in the presence of dofetilide or a combination of dofetilide and COMPOUND A. The S1-S1 interval was 1 second and 8 S1 pulses preceded the S2 pulse. Data are expressed as mean values ±S.E.M., n=4. *p<0.05 and **p<0.01 relative to predrug.

FIG. 24 shows ERP values obtained in the presence of COMPOUND A or a combination of COMPOUND A and dofetilide. The S1-S1 interval was 1 second and 8 S1 pulses preceded the S2 pulse. Data are expressed as mean values ±S.E.M., n=4. *p<0.05 relative to predrug.

Figure 25:
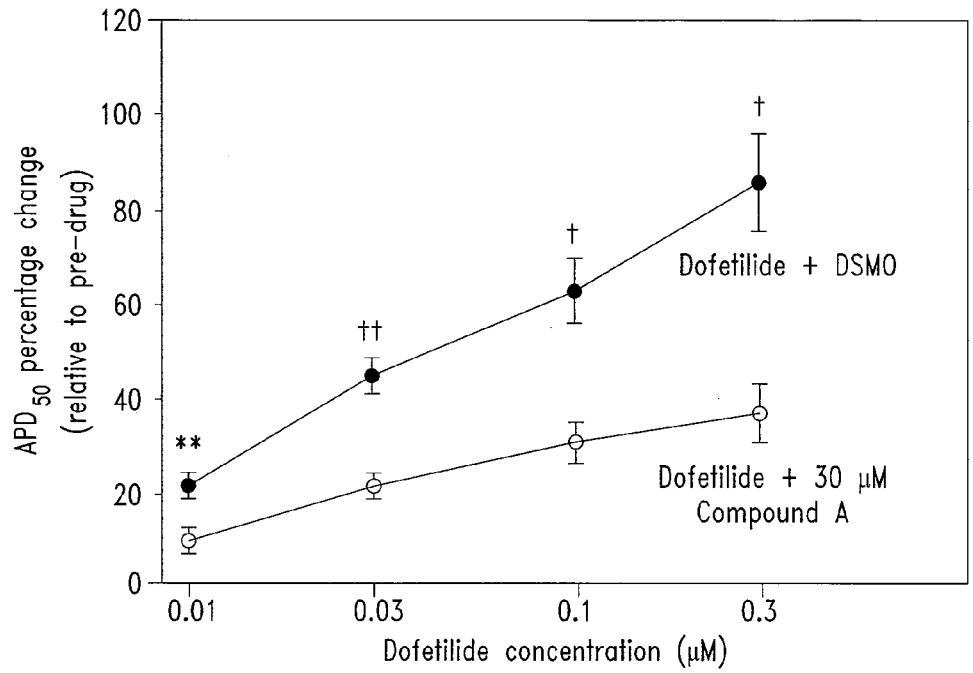
FIG. 25 shows the percent increases in APD50 when Purkinje fibers were co-treated with dofetilide and either 30 μM COMPOUND A or DMSO control.
Figure 26:
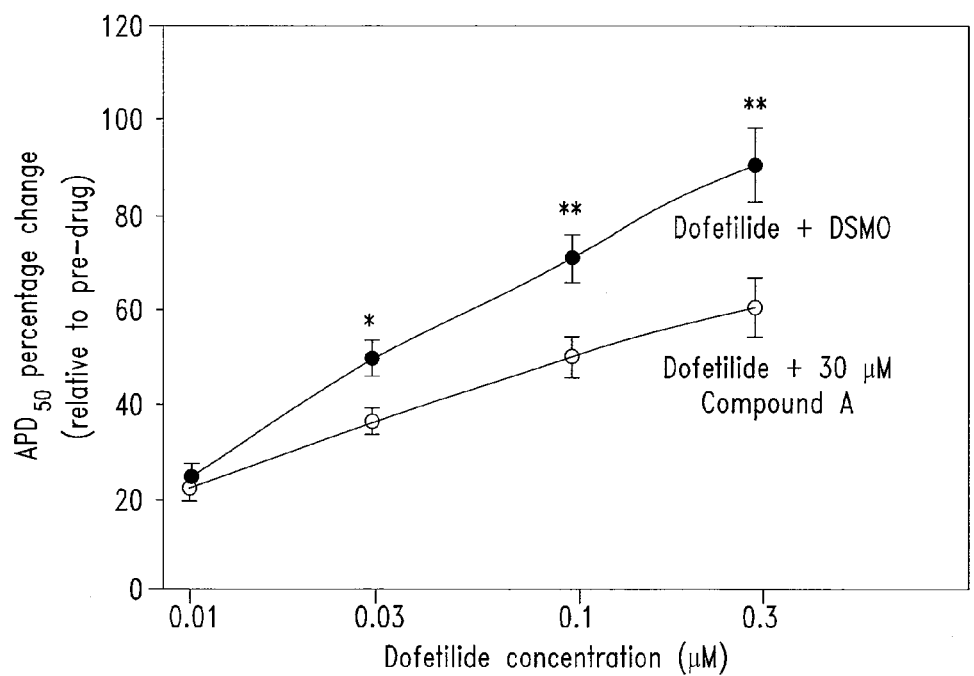
FIG. 26 shows the percent increases in APD90 when Purkinje fibers were co-treated with dofetilide and either 30 μM COMPOUND A or DMSO control.

The second set of experiments illustrated in FIGS. 25 & 26 explored the effects of concomitant COMPOUND A/dofetilide treatment over the entire dose range of dofetilide (10 to 300 nM). Blinded to the experimenter, either 30 µM COMPOUND A or DMSO was perfused with dofetilide. Concomitant treatment with 30 µM COMPOUND A significantly blunted the effects of dofetilide upon APD50 (FIG. 25) and APD90 (FIG. 26) when compared to the vehicle control (DMSO). The percentage increase in APD50 induced by 300 nM dofetilide in the presence of DMSO or 30 µM COMPOUND A was 86 and 37% respectively while the increase in APD90 was 92% and 61% respectively. There was no significant depression of Vmax in the presence of dofetilide and COMPOUND A relative to dofetilide and DMSO (205 ±37 V/s and 253±48 V/s respectively, n=10, p=0.44).

FIG. 25 shows the percent increases in APD50 when Purkinje fibers were co-treated with dofetilide and either 30 µM COMPOUND A or DMSO control. The stimulation frequency was 1 Hz. Results are expressed as the mean ±S.E.M. (n=10). **$p<0.01$, †$p<0.001$ and ††$p<0.0001$ for COMPOUND A cotreatment relative to vehicle control. FIG. 26 shows the percent increases in APD90 when Purkinje fibers were co-treated with dofetilide and either 30 µM COMPOUND A or DMSO control. The stimulation frequency was 1 Hz. Results are expressed as the mean ±S.E.M. (n=10). *$p<0.05$, **$p<0.01$ for COMPOUND A cotreatment relative to vehicle control.

Figure 27:
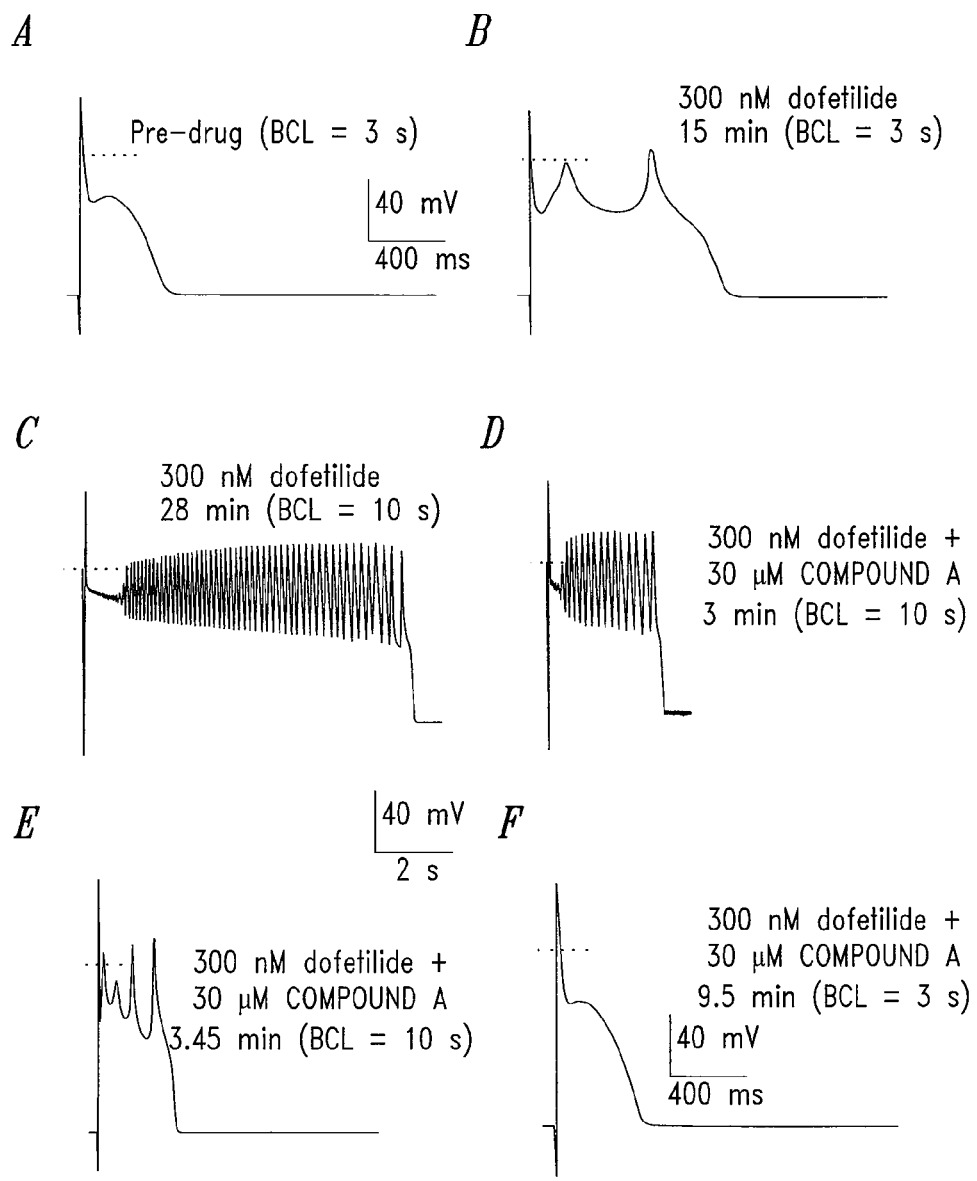
FIG. 27 shows the termination of dofetilide-induced EADs by COMPOUND A in isolated Purkinje fibers.

The reduction in dofetilide-induced APD50 prolongation in the presence of 30 µM COMPOUND A suggests that 30 µM COMPOUND A may be effective in the termination of dofetilide-induced early-after-depolarizations (EADs) in isolated rabbit Purkinje fibers. Preliminary data (FIG. 27) show dofetilide induced EADs (27B & 27C) in an isolated Purkinje fiber preparation. Stable EADs are obtained after approximately 30 minutes of perfusion with 300 nM dofetilide. Subsequent perfusion with 30 µM COMPOUND A and 300 nM dofetilide produces a time-dependent reduction in the number of early-depolarizations (27D & 27E) and after approximately 10 minutes of COMPOUND A perfusion, complete abolishment of any EAD activity (27F). The termination of EADs by 30 µM COMPOUND A was seen in 4 of 4 preparations studied. FIG. 27 shows the termination of dofetilide-induced EADs by COMPOUND A in isolated Purkinje fibers. Cycle length and treatment conditions are indicated in the text of each panel. Panels 27A, 27B and 27F are on a more expanded time base than panels 27C, 27D and 27E (see scale bars). Zero millivolts is indicated by the dotted line in each panel.

Example 20

Antiarrhythmic Actions Against Chemically-Induced TdP (Carlsson Model) in Anaesthetized Rabbits The effect of pretreatment with COMPOUND A on prevention of chemically-induced arrhythmias in a rabbit TdP model and to determine the effect of acute infusions of COMPOUND A on termination of chemically-induced arrhythmias was determined. TdP is induced by infusion of the class III drug clofilium in conjunction with methoxamine (Carlsson Model).

TdP is chemically induced in anaesthetised rabbits (Carlsson Model). Briefly, continuous infusion of COMPOUND A was administered prior to continuous infusion of methoxamine and followed by clofilium. The incidence of TdP (the number of animals in which TdP occurred) was compared to experiments in which COMPOUND A was not infused.

The following procedure was used: (1) Female NZW rabbits were weighed and anaesthetised initially with 35 mg/kg sodium pentobarbital via ear vein (60 mg/mL) using a sterile 23G ¾ needle. Additional doses (in increments of 0.2-0.3 mL) were used if required to attain and maintain sufficient anaesthesia as determined by abolishment of eyelid reflex. Care was taken not to over anaesthetize as this could cause respiratory and cardiac arrest. (2) The anaesthetised rabbit was placed on a rabbit restraining board in the supine position and limbs were tied down. (3) The fur in the neck and inguinal region were wetted with water and trimmed down to the skin with scissors to facilitate dissection. Fur was placed in a water-filled beaker to prevent fur from becoming airborne. (4) The left or right femoral artery was cannulated with PE 50 tubing and attached to a pressure transducer to monitor blood pressure. (5) The right and left jugular veins were cannulated using PE-90 tubing for drug delivery via an infusion pump. (6) The left or right femoral vein was cannulated using PE-50 tubing for drug delivery via an infusion pump. (7) ECG leads were attached as follows: the ground lead was inserted subcutaneously into the femoral vein region; one lead was inserted subcutaneously near the apex of the heart and the third lead was placed in the open surgical area near the right jugular vein. (8) Control recordings of ECG and blood pressure were taken for 5 minutes to observe pre-drug effects. Recordings were continued throughout the entire experiment. (9) Arterial $K^+$ concentration was measured with the handheld I-STAT blood-gas analyzer prior to infusion of arrhythmogenic agent and at the end of the experiment. (10) After 5 minutes, the COMPOUND A was infused at the desired rate and concentration. Infusion was continued throughout the experiment. (11) After a further 5 minutes, methoxamine was administered at 20 µg/kg/min via the femoral vein. Methoxamine infusion was also continued throughout the experiment. (12) 10 minutes following the start of methoxamine infusion, clofilium was infused via a jugular vein. (13) In COMPOUND A-pretreated animals and controls, recording continued for 15 minutes regardless of whether TdP is seen or not. (14) A blood sample was collected when the experimental endpoint was reached, immediately after the infusion pumps were stopped. (15) To test the effect of acute infusion of COMPOUND A, immediately following first bout of TdP (characterized by the classic polymorphic VT with clear twisting about the isoelectric point), animals were infused continuously with COMPOUND A. All other infusions continued concomitantly with COMPOUND A for 5 minutes at which time the experimental endpoint was reached.

Figure 28:
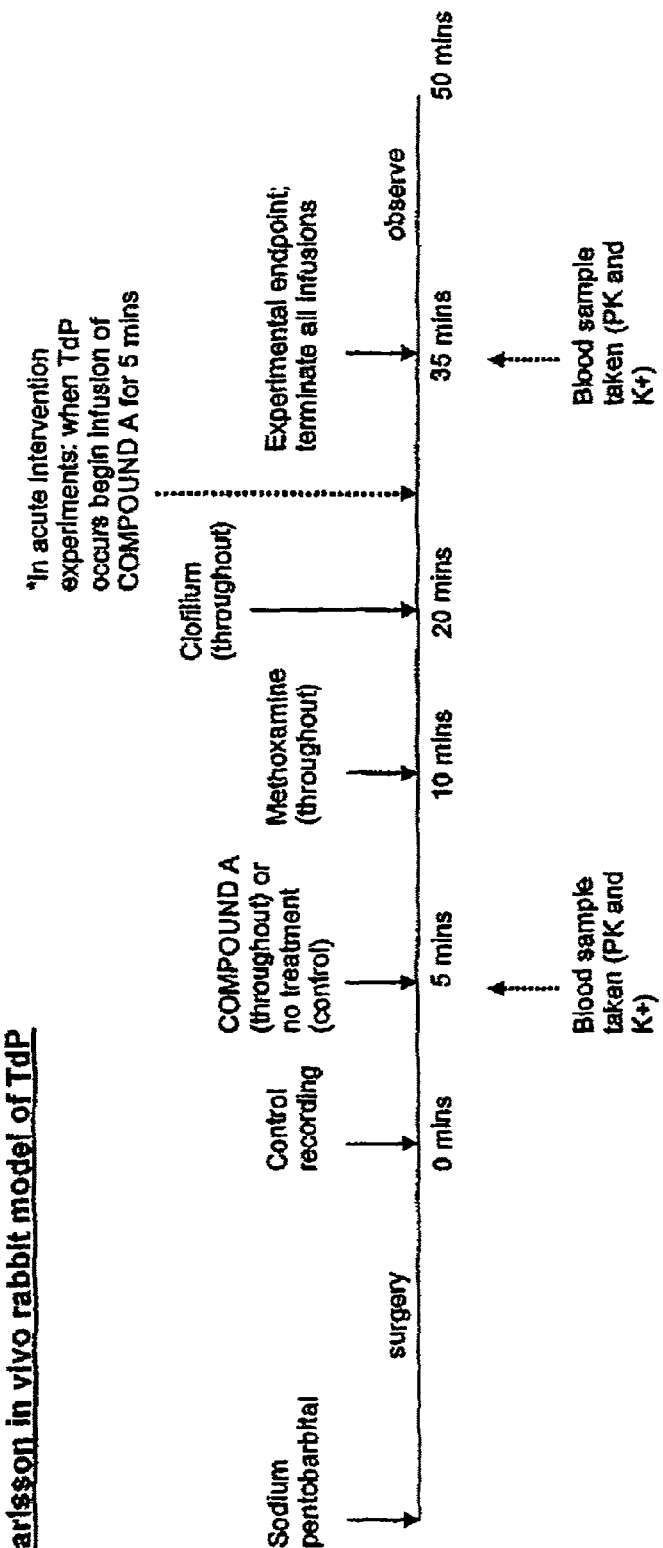
FIG. 28 shows a timeline of the method for testing the effects of COMPOUND A on chemically-induced TdP in anaesthetized rabbits.

FIG. 28 shows an outline of the method used in these experiments, as outlined above. COMPOUND A was applied and examined as described. To analyze the data, the parameters measured are (1) incidence of TdP (2) duration of TdP episodes (3) arterial $K^+$ concentration, (4) PR, QRS and QTc intervals during normal sinus rhythm (until arrhythmias begin and determination is no longer possible), (5) BP, and (6) HR.

Prevention of TdP by Compound A.

Figure 29:
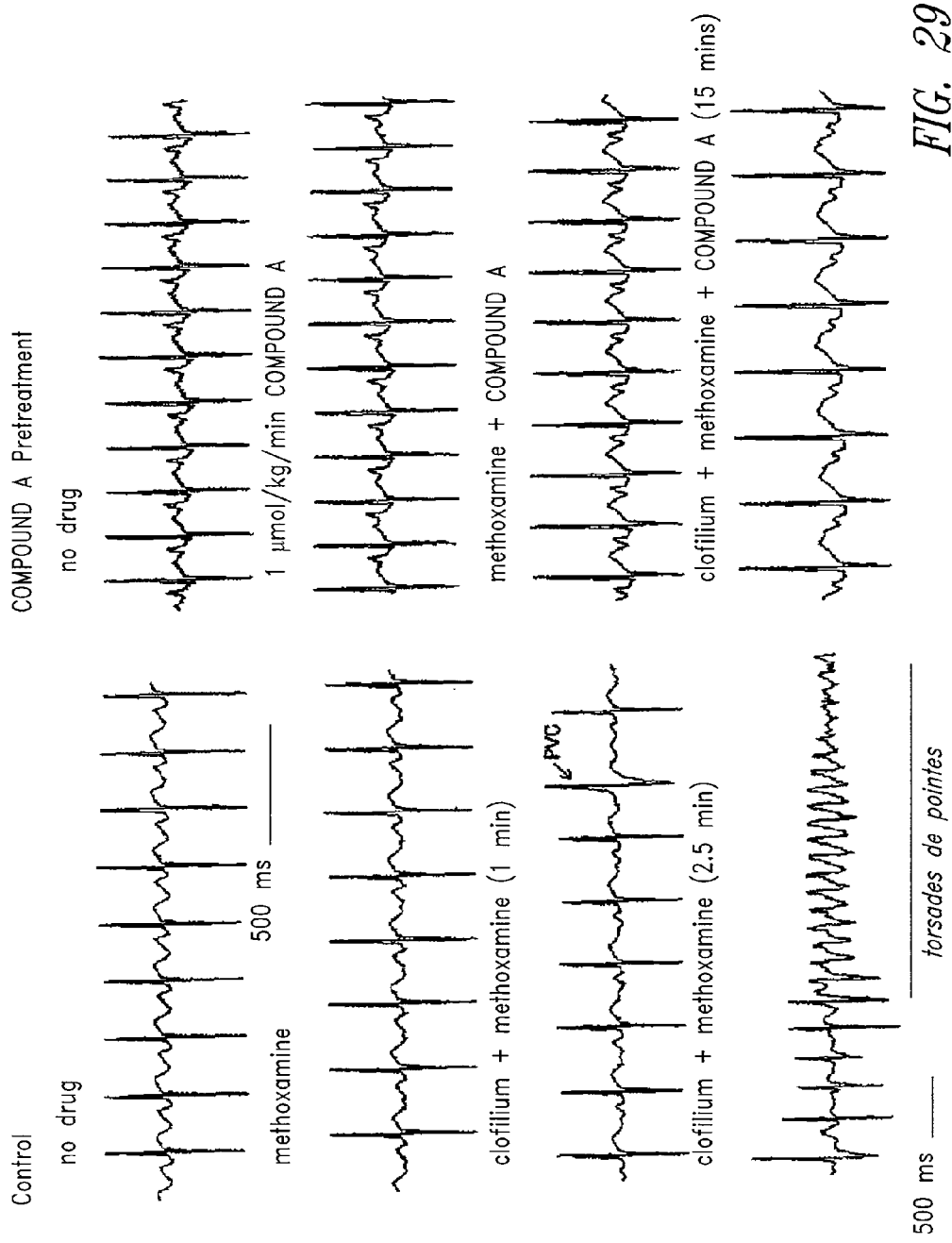
FIG. 29 shows control traces with TdP induced by clofilium infusion using the method of FIG. 28 and prevention of TdP induction by COMPOUND A.

Rabbits treated with the alpha 1-adrenergic agonist methoxamine and the class III agent clofilium consistently experienced QT prolongation, bradycardia, pre-ventricular contractions (PVCs) (FIG. 29) and, in 7 of 9 animals, TdP. In these control animals, TdP occurred on average 7.0±1.3 min after starting clofilium infusion, at a cumulative dose of 1.4±0.2 mg/kg clofilium. The first PVC was observed 3.3±0.5 min after starting clofilium infusion and no arrhythmias were observed with infusion of methoxamine alone.

Figure 30:
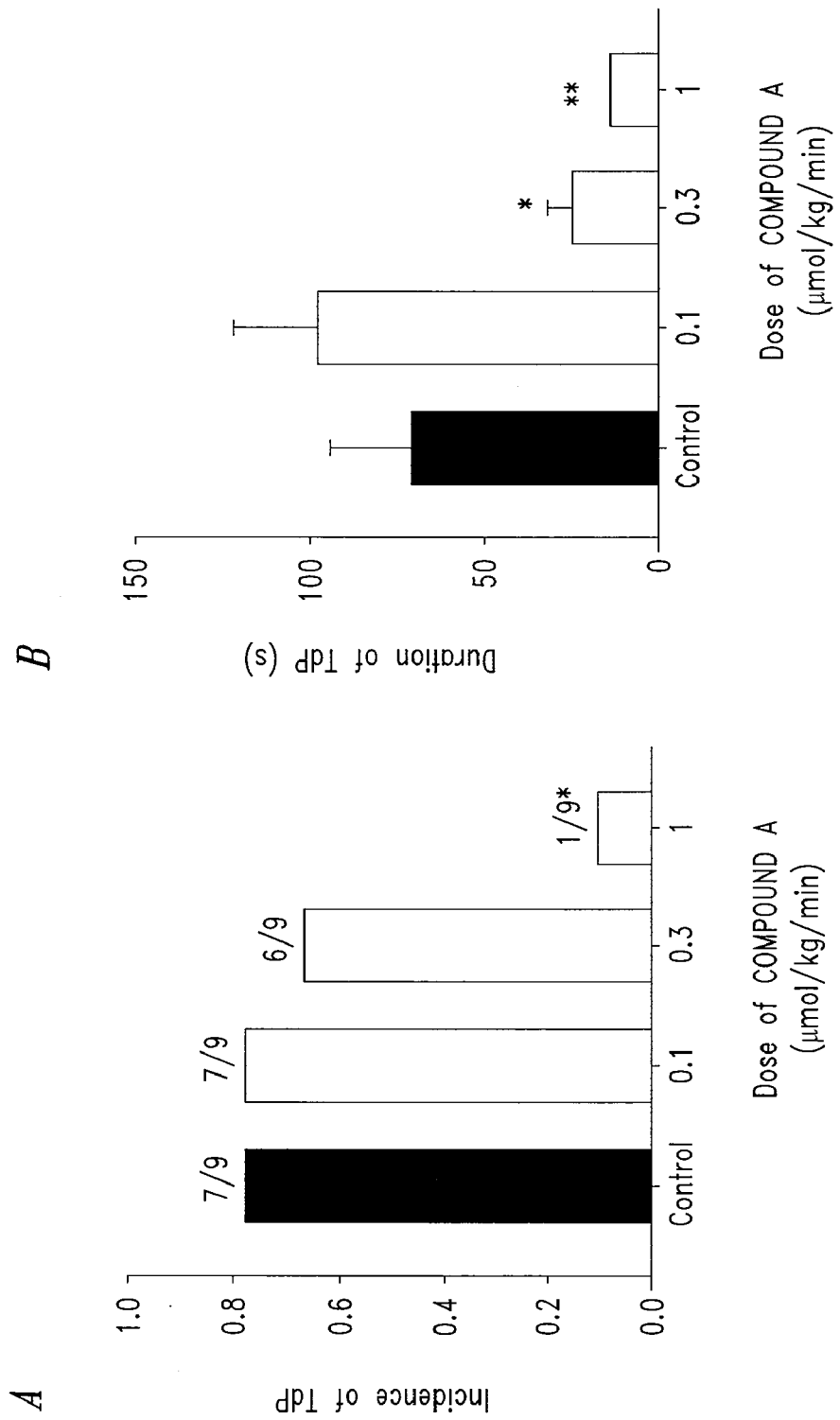
FIG. 30 shows the effect of COMPOUND A on the incidence of TdP and duration of episodes of TdP under the TdP induction model of FIG. 28.

When continuous infusion of COMPOUND A was started before methoxamine and clofilium were added to the infusion regimen, the time to first PVC increased slightly and TdP inducibility declined in a dose-dependent fashion (FIG. 30). In addition, the overall severity and frequency of arrhythmias was reduced in these pre-treated animals. Doses of 1 μmol/kg/min COMPOUND A reduced the incidence of TdP to 1 of 9 animals (p<0.05). Lower dose pretreatment with COMPOUND A (0.1 and 0.3 μmol/kg/min) did not significantly affect the incidence of TdP. Time to first PVC was delayed with escalating doses from 3.0±0.9 min at 1 μmol/kg/min, to 5.5±2.1 min 0.3 μmol/kg/min, but decreased slightly at 1 μmol/kg/min to 4.3±0.8 min. Since TdP occurred in runs that often self-terminated, the effects of COMPOUND A on the duration of the episodes of TdP during 15 min of clofilium infusion were also examined. In control and COMPOUND A pretreated animals the mean summed duration of TdP episodes per animal was significantly reduced from 64±28 s in controls (n=9) to 14±0 s (n=9; p<0.001) at a dose of 1 μmol/kg/min COMPOUND A (FIG. 30B). At 0.3 μmol/kg/min COMPOUND A, a dose that did not reduce the overall incidence of clofilium-induced TdP, the duration was reduced to 25±8 s (n=9; p<0.05). The effect of 1 μMol/kg/min, was not significantly different from control (98±24 s, n=9; p>0.1). It is also noteworthy that COMPOUND A and methoxamine, co-administered for 5 min, induced no arrhythmias, further supporting the hypothesis that COMPOUND A does not induce TdP in this model.

As prolongation of QTc interval by clofilium is the trigger for TdP, a potential mechanism for TdP prevention is suppression of QTc prolongation. QTc was measured 2.5 minutes after starting clofilium infusion in rabbits receiving methoxamine and clofilium and in rabbits pre-treated with COMPOUND A (0.3 and 1 μmol/kg/min). In controls, an increase in arrhythmias after this time prevented accurate ECG interval measurement. Rabbits pretreated with 1 μMol/kg/min COMPOUND A exhibited a 7±6% increase in QTc interval (from that measured just before clofilium infusion) compared to a 20±11% increase without any pretreatment (FIG. 31). This trend suggests that COMPOUND A may reduce the QTc prolongation induced by class III drugs.

Acute Termination of TdP by Compound A.

Figure 32A:
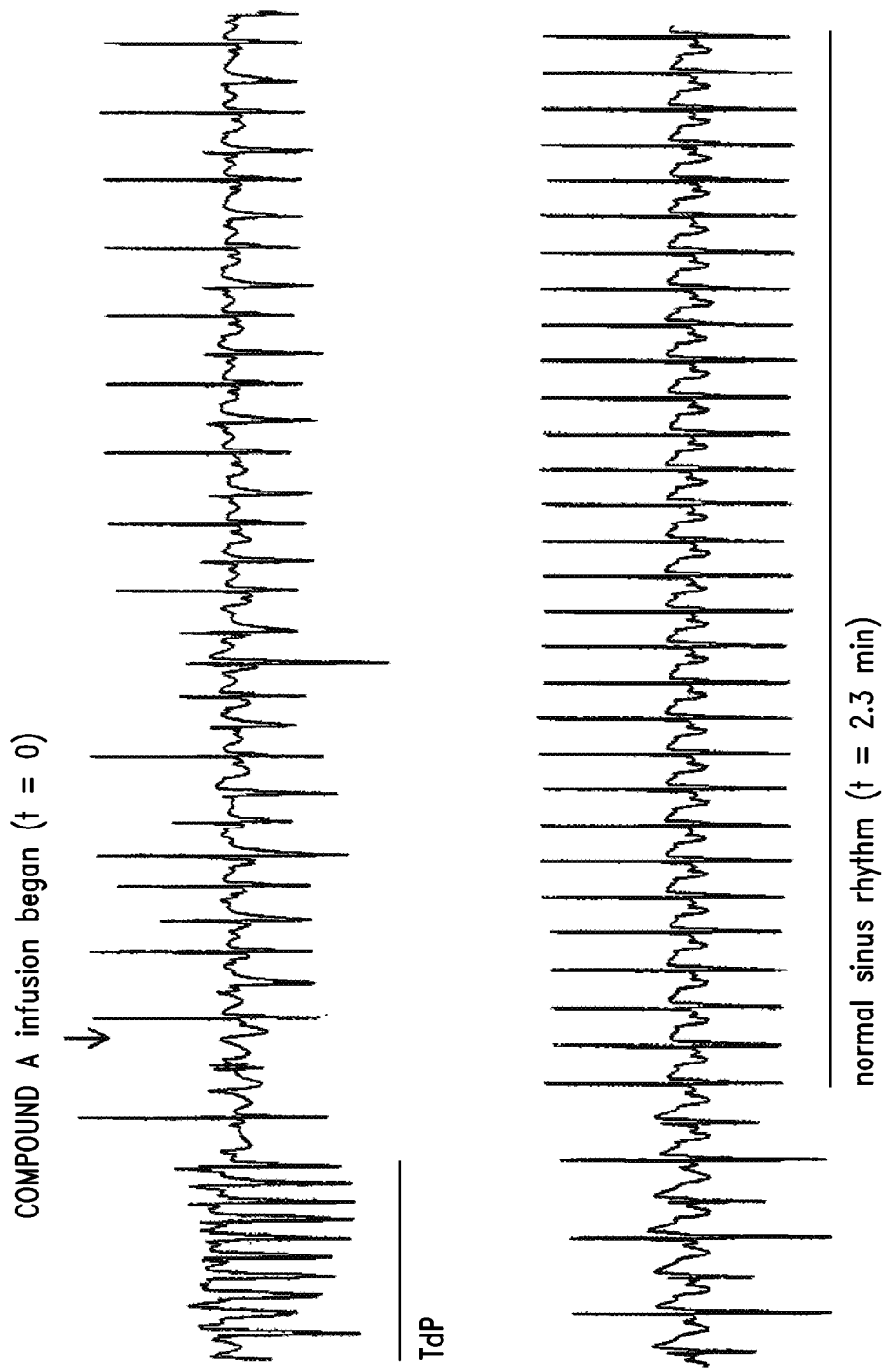
FIG. 32 shows an example of the effect of COMPOUND A on electrocardiogram (ECG) waveforms and duration of TdP during acute termination of TdP as described in the chemically-induced TdP model described in FIG. 28.
Figure 32B:
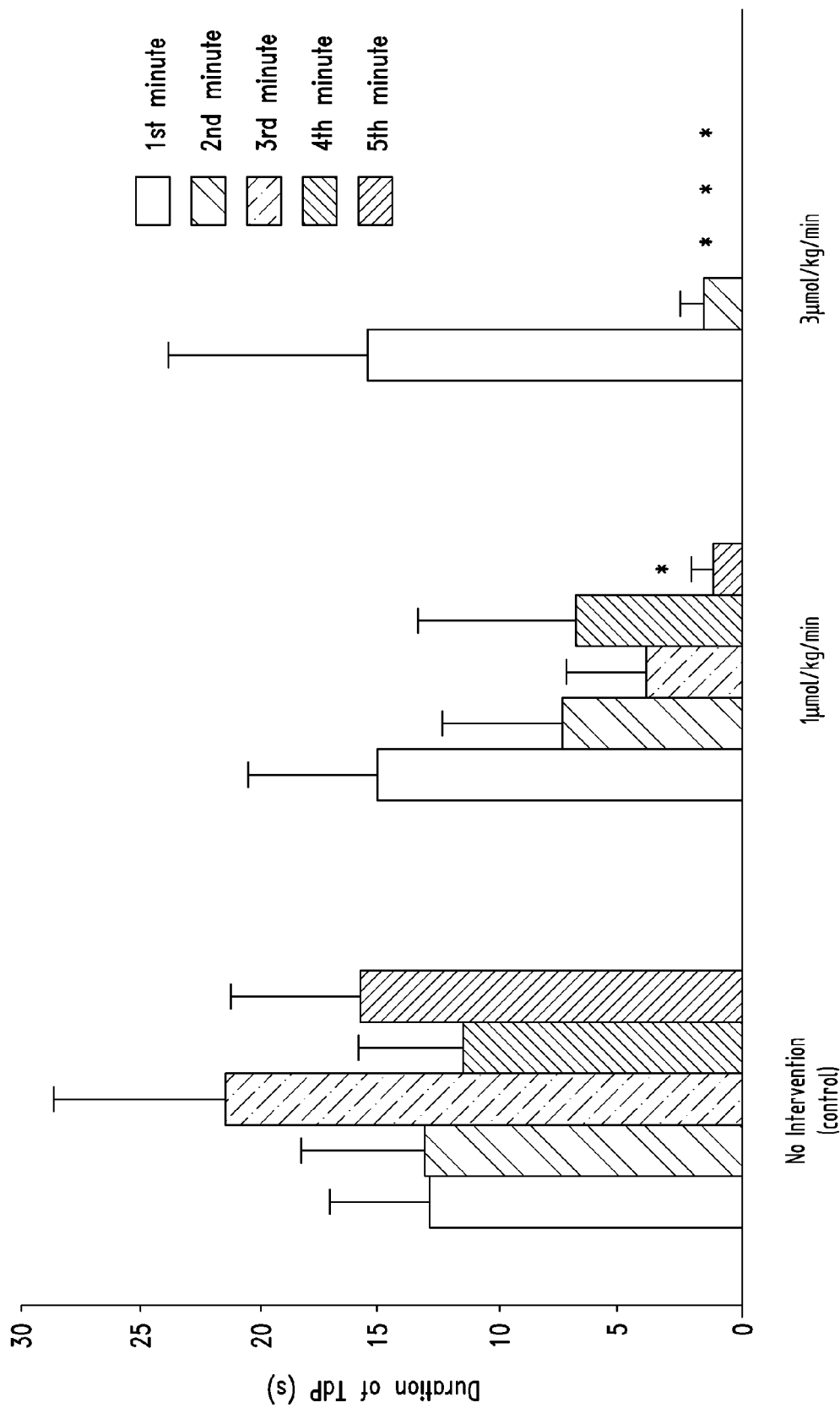

In animals treated with only methoxamine and clofilium, acute infusions of COMPOUND A reduced the overall duration of TdP in a dose-dependent manner. Doses of 1 or 3 μmol/kg/min COMPOUND A were infused over 5 min (corresponding to cumulative doses of 1.2 or 5.8 mg/kg) immediately after the first episode of TdP. 3 mg/kg COMPOUND A reduced overall duration of TdP from 81±21 s in control (n=10) to 17±9 s (p<0.05) and restored normal sinus rhythm in all animals by the end of the 5 min infusion (n=9) as exemplified by the ECG tracings in FIG. 32A. The lower dose of COMPOUND A, 1.2 mg/kg, reduced TdP duration to 35±15 s and restored normal sinus rhythm in 2 of 9 animals. The decline in TdP duration after COMPOUND A infusion began was dependent on infusion duration (FIG. 32B). With cumulative doses of 1.2 or 5.8 mg/kg COMPOUND A, there was no effect on TdP duration in the first minute of infusion. However, in the 3rd to 5th minute, TdP duration significantly declined at the higher dose, while at the lower dose TdP decreased only in the 5th minute compared to control at the same infusion duration. The effect of acute infusions of COMPOUND A on QTc was examined. QTc was measured 2 min after starting clofilium infusion and at the end of the 5 min infusion of COMPOUND A and no difference was observed (p>0.05, data not shown).

With continuous background infusions of COMPOUND A, TdP inducibility, the duration of runs of TdP, and the overall severity of arrhythmias decreased in a dose-dependent fashion. Continuous infusions of COMPOUND A administered after TdP induction suppressed TdP and restored normal sinus rhythm in a dose-dependent fashion. These data suggest that COMPOUND A may be safely co-administered with class III antiarrhythmics and indeed that COMPOUND A may be an effective treatment for TdP induced by drugs that prolong ventricular repolarization. These data also suggest that human polymorphisms that result in long QT (LQT) syndromes, such as LQT2 (hERG polymorphism) and LQT3 ($Na^+$ channel polymorphism), in which patients experience greatly increased susceptibility to TdP, may also be effectively treated with COMPOUND A.

APPENDIX I

TABLE 7

Drugs that prolong the QT interval and/or induce TdP

| Generic Name (Brand Name) | Drug Class/Clinical Usage | Comments | List |
|---|---|---|---|
| Albuterol (Ventolin ®) | Bronchodilator/Asthma | | 3 |
| Albuterol (Proventil ®) | Bronchodilator/Asthma | | 3 |
| Alfuzosin (Uroxatral ®) | Alpha1-blocker/Benign prostatic hyperplasia | | 2 |
| Amantadine (Symmetrel ®) | Dopaminergic/Anti-viral/Anti-infective/Parkinson's Disease | | 2 |
| Amiodarone (Pacerone ®) | Anti-arrhythmic/abnormal heart rhythm | Females > Males, TdP risk regarded as low | 1 |
| Amiodarone (Cordarone ®) | Anti-arrhythmic/abnormal heart rhythm | Females > Males, TdP risk regarded as low | 1 |
| Amitriptyline (Elavil ®) | Tricyclic Antidepressant/depression | | 4 |
| Amoxapine (Asendin ®) | Tricyclic Antidepressant/depression | | 4 |
| Ampicillin (Omnipen ®) | Antibiotic/infection | | 4 |
| Ampicillin (Principen ®) | Antibiotic/infection | | 4 |
| Amphetamine/ dextroamphetamine (Adderall ®) | Attention Deficite Disorder | | |
| Arsenic trioxide (Trisenox ®) | Anti-cancer/Leukemia | | 1 |

TABLE 7-continued

Drugs that prolong the QT interval and/or induce TdP

| Generic Name (Brand Name) | Drug Class/Clinical Usage | Comments | List |
|---|---|---|---|
| Atomoxetine (Strattera ®) | norepinephrine reuptake inhibitor/ADHD | | 3 |
| Azithromycin (Zithromax ®) | Antibiotic/bacterial infection | | 2 |
| Bepridil (Vascor ®) | Anti-anginal/heart pain | Females > Males | 1 |
| Chloral hydrate (Noctec ®) | Sedative/sedation/insomnia | | 2 |
| Chloroquine (Arelan ®) | Anti-malarial/malaria infection | | 1 |
| Chlorpromazine (Thorazine ®) | Anti-psychotic/Anti-emetic/schizophrenia/nausea | | 1 |
| Ciprofloxacin (Cipro ®) | Antibiotic/bacterial infection | | 4 |
| Cisapride (Propulsid ®) | GI stimulant/heartburn | Restricted availability; Females > Males. | 1 |
| Clarithromycin (Biaxin ®) | Antibiotic/bacterial infection | | 1 |
| Clomipramine (Anafranil ®) | Tricyclic Antidepressant/depression | | 4 |
| Cocaine (Cocaine) | Local anesthetic/ | | 3 |
| Desipramine (Pertofrane ®) | Tricyclic Antidepressant/depression | | 4 |
| Disopyramide (Norpace ®) | Anti-arrhythmic/abnormal heart rhythm | Females > Males | 1 |
| Dobutamine (Dobutrex ®) | Catecholamine/heart failure and shock | | 3 |
| Dofetilide (Tikosyn ®) | Anti-arrhythmic/abnormal heart rhythm | | 1 |
| Dolasetron (Anzemet ®) | Anti-nausea/nausea, vomiting | | 2 |
| Domperidone (Motilium ®) | Anti-nausea/nausea | | 1 |
| Dopamine (Intropine ®) | Anti-arrhythmic/abnormal heart rhythm | | 3 |
| Doxepin (Sinequan ®) | Tricyclic Antidepressant/depression | | 4 |
| Droperidol (Inapsine ®) | Sedative; Anti-nausea/anesthesia adjunct, nausea | | 1 |
| Ephedrine (Broncholate ®) | Bronchodilator, decongestant/Allergies, sinusitis, asthma | | 3 |
| Ephedrine (Rynatuss ®) | Bronchodilator, decongestant/Allergies, sinusitis, asthma | | 3 |
| Epinephrine (Bronkaid ®) | catecholamine, vasoconstrictor/anaphylaxis, allergic reactions | | 3 |
| Epinephrine (Primatene ®) | catecholamine, vasoconstrictor/anaphylaxis, allergic reactions | | 3 |
| Erythromycin (E.E.S. ®) | Anitibiotic; GI stimulant/bacterial infection; increase GI motility | Females > Males | 1 |
| Erythromycin (Erythrocin ®) | Antibiotic; GI stimulant/bacterial infection; increase GI motility | Females > Males | 1 |
| Felbamate (Felbatrol ®) | Anti-convulsant/seizure | | 2 |
| Fenfluramine (Pondimin ®) | Appetite suppressant/dieting, weight loss | | 3 |
| Flecainide (Tambocor ®) | Anti-arrhythmic/abnormal heart rhythm | | 2 |
| Fluconazole (Diflucan ®) | Anti-fungal/fungal infection | | 4 |
| Fluoxetine (Prozac ®) | Anti-depressant/depression | | 4 |
| Fluoxetine (Sarafem ®) | Anti-depressant/depression | | 4 |
| Foscarnet (Foscavir ®) | Anti-viral/HIV infection | | 2 |
| Fosphenytoin (Cerebyx ®) | Anti-convulsant/seizure | | 2 |
| Galantamine (Reminyl ®) | Cholinesterase inhibitor/Dementia, Alzheimer's | | 4 |
| Gatifloxacin (Tequin ®) | Antibiotic/bacterial infection | | 2 |
| Granisetron (Kytril ®) | Anti-nausea/nausea and vomiting | | 2 |
| Halofantrine (Halfan ®) | Anti-malarial/malaria infection | Females > Males | 1 |
| Haloperidol (Haldol ®) | Anti-psychotic/schizophrenia, agitation | | 1 |
| Ibutilide (Corvert ®) | Anti-arrhythmic/abnormal heart rhythm | Females > Males | 1 |
| Imipramine (Norfranil ®) | Tricyclic Antidepressant/depression | | 4 |
| Indapamide (Lozol ®) | Diuretic/stimulate urine & salt loss | | 2 |
| Isoproterenol (Isupres ®) | Catecholamine/allergic reaction | | 3 |
| Isoproterenol (Medihaler-Iso ®) | Catecholamine/allergic reaction | | 3 |
| Isradipine (Dynacirc ®) | Anti-hypertensive/high blood pressure | | 2 |

TABLE 7-continued

Drugs that prolong the QT interval and/or induce TdP

| Generic Name (Brand Name) | Drug Class/Clinical Usage | Comments | List |
|---|---|---|---|
| Itraconazole (Sporanox ®) | Anti-fungal/fungal infection | | 4 |
| Ketoconazole (Nizoral ®) | Anti-fungal/fungal infection | | 4 |
| Levalbuterol (Xopenex ®) | Bronchodilator/asthma | | 3 |
| Levofloxacin (Levaquin ®) | Antibiotic/bacterial infection | | 2 |
| Levomethadyl (Orlaam ®) | Opiate agonist/pain control, narcotic dependence | | 1 |
| Lithium (Eskalith ®) | Anti-mania/bipolar disorder | | 2 |
| Lithium (Lithobid ®) | Anti-mania/bipolar disorder | | 2 |
| Mesoridazine (Serentil ®) | Anti-psychotic/schizophrenia | | 1 |
| Metaproterenol (Alupent ®) | Bronchodilator/asthma | | 3 |
| Metaproterenol (Metaprel ®) | Bronchodilator/asthma | | 3 |
| Methadone (Dolophine ®) | Opiate agonist/pain control, narcotic dependence | Females > Males | 1 |
| Methadone (Methadose ®) | Opiate agonist/pain control, narcotic dependence | Females > Males | 1 |
| Methylphenidate (Ritalin ®) | CNS stimulant/ADHD | | 3 |
| Mexiletine (Mexitil ®) | Anti-arrhythmic/Abnormal heart rhythm | | 4 |
| Midodrine (ProAmatine ®) | Vasoconstrictor/low blood pressure, fainting | | 3 |
| Moexipril/HCTZ (Uniretic ®) | Anti-hypertensive/high blood pressure | | 2 |
| Moxifloxacin (Avelox ®) | Antibiotic/bacterial infection | | 2 |
| Nicardipine (Cardene ®) | Anti-hypertensive/high blood pressure | | 2 |
| Norepinephrine (Levophed ®) | Vasconstrictor, Inotrope/shock, low blood pressure | | 3 |
| Nortriptyline (Pamelor ®) | Tricyclic Antidepressant/depression | | 4 |
| Octreotide (Sandostatin ®) | Endocrine/acromegaly, carcinoid diarrhea | | 2 |
| Ondansetron (Zofran ®) | Anti-emetic/nausea and vomiting | | 2 |
| Paroxetine (Paxil ®) | Anti-depressant/depression | | 4 |
| Pentamidine (NebuPent ®) | Anti-infective/pneumocystis pneumonia | Females > Males | 1 |
| Pentamidine (Pentam ®) | Anti-infective/pneumocystis pneumonia | Females > Males | 1 |
| Phentermine (Fastin ®) | Appetite suppressant/dieting, weight loss | | 3 |
| Phentermine (Adipex ®) | Appetite suppressant/dieting, weight loss | | 3 |
| Phenylephrine (Neosynephrine ®) | Vasoconstrictor, decongestant/low blood pressure, allergies, sinusitis, asthma | | 3 |
| Phenylpropanolamine (Dexatrim ®) | Decongestant/allergies, sinusitis, asthma | | 3 |
| Phenylpropanolamine (Acutrim ®) | Decongestant/allergies, sinusitis, asthma | | 3 |
| Pimozide (Orap ®) | Anti-psychotic/Tourette's tics | Females > Males | 1 |
| Procainamide (Pronestyl ®) | Anti-arrhythmic/abnormal heart rhythm | | 1 |
| Procainamide (Procan ®) | Anti-arrhythmic/abnormal heart rhythm | | 1 |
| Protriptyline (Vivactil ®) | Tricyclic Antidepressant/depression | | 4 |
| Pseudoephedrine (PediaCare ®) | Decongestant/allergies, sinusitis, asthma | | 3 |
| Pseudoephedrine (Sudafed ®) | Decongestant/allergies, sinusitis, asthma | | 3 |
| Quetiapine (Seroquel ®) | Anti-psychotic/schizophrenia | | 2 |
| Quinidine (Quinaglute ®) | Anti-arrhythmic/abnormal heart rhythm | Females > Males | 1 |
| Quinidine (Cardioquin ®) | Anti-arrhythmic/abnormal heart rhythm | Females > Males | 1 |
| Risperidone (Risperdal ®) | Anti-psychotic/schizophrenia | | 2 |
| Ritodrine (Yutopar ®) | Uterine relaxant/prevent premature labor | | 3 |
| Salmeterol (Serevent ®) | Sympathomimetic/asthma, COPD | | 2 |
| Sertraline (Zoloft ®) | Anti-depressant/depression | | 4 |
| Sibutramine (Meridia ®) | Appetitie suppressant/dieting, weight loss | | 3 |
| Sotalol (Betapace ®) | Anti-arrhythmic/abnormal heart rhythm | Females > Males | 1 |
| Sparfloxacin (Zagam ®) | Antibiotic/bacterial infection | | 1 |

TABLE 7-continued

Drugs that prolong the QT interval and/or induce TdP

| Generic Name (Brand Name) | Drug Class/Clinical Usage | Comments | List |
|---|---|---|---|
| Tacrolimus (Prograf®) | Immunosuppressant/Immune suppression | | 2 |
| Tamoxifen (Nolvadex®) | Anti-cancer/breast cancer | | 2 |
| Telithromycin (Ketek®) | Antibiotic/bacterial infection | | 2 |
| Terbutaline (Brethine®) | Bronchodilator/asthma | | 3 |
| Thioridazine (Mellaril®) | Anti-psychotic/schizophrenia | | 1 |
| Tizanidine (Zanaflex®) | Muscle relaxant/ | | 2 |
| Trimethoprim-Sulfa (Sulfa®) | Antibiotic/bacterial infection | | 4 |
| Trimethoprim-Sulfa (Bactrim®) | Antibiotic/bacterial infection | | 4 |
| Trimipramine (Surmontil®) | Tricyclic Antidepressant/depression | | 4 |
| Vardenafil (Levitra®) | phosphodiesterase inhibitor/vasodilator | | 2 |
| Venlafaxine (Effexor®) | Anti-depressant/depression | | 2 |
| Voriconazole (VFend®) | Anti-fungal/anti-fungal | | 2 |
| Ziprasidone (Geodon®) | Anti-psychotic/schizophrenia | | 2 |

A note about Brand Names: Drugs are listed with up to 2 common brand names. There are many more brand names for some of the common drugs, such as pseudoephedrine and erythromycin. It is also important to look at the list of active drugs in medicines that contain a combination of drugs such as Zyrtec-D®, which contains pseudoephedrine.
Source: www.torsades.org
KEY
Females > Males: Substantial evidence indicates a greater risk (usually > two-fold) of TdP in women.
Drug List 1: Drugs that are generally accepted by authorities to have a risk of causing TdP.
Drug List 2: Drugs that in some reports may be associated with TdP but at this time lack substantial evidence for causing TdP.
Drug List 3: Drugs to be avoided for use in patients with diagnosed or suspected congenital long QT syndrome. (Drugs on Lists 1 and 2 are also included here)
Drug List 4: Drugs that, in some reports, have been weakly associated with TdP but that, when used in usual dosages, are unlikely to be a risk for TdP.

A note about Brand Names: Drugs are listed with up to 2 common brand names. There are many more brand names for some of the common drugs, such as pseudoephedrine and erythromycin. It is also important to look at the list of active drugs in medicines that contain a combination of drugs such as Zyrtec-D®, which contains pseudoephedrine.

Source:www.torsades.org

Key

Females>Males: Substantial evidence indicates a greater risk (usually>two-fold) of TdP in women.

Drug List 1: Drugs that are generally accepted by authorities to have a risk of causing TdP.

Drug List 2: Drugs that in some reports may be associated with TdP but at this time lack substantial evidence for causing TdP.

Drug List 3: Drugs to be avoided for use in patients with diagnosed or suspected congenital long QT syndrome. (Drugs on Lists 1 and 2 are also included here)

Drug List 4: Drugs that, in some reports, have been weakly associated with TdP but that, when used in usual dosages, are unlikely to be a risk for TdP.

We claim:

1. A method of reducing the incidence of chemically-induced Torsades de Pointes comprising administering to a subject in need thereof an effective amount of an ion channel modulating compound of formula:

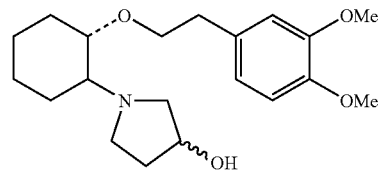

as an isolated enantiomeric or diastereomeric isomer or as a mixture thereof, or as a pharmaceutically acceptable salt thereof; wherein the ion channel modulating compound is administered to the subject in combination with a chemical capable of inducing Torsades de Pointes.

2. The method of claim 1 wherein the ion channel modulating compound comprises a monohydrochloride salt of the formula:

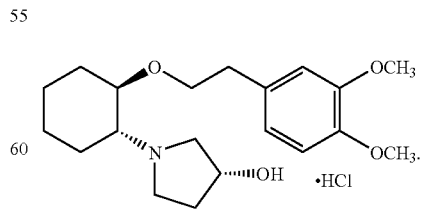

3. The method of claim 1 wherein the ion channel modulating compound has the formula:

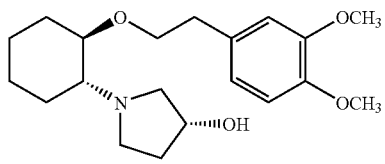

or a pharmaceutically acceptable salt thereof.

4. The method of claim 1 wherein the chemical is an antiarrhythmic.

5. The method of claim 4 wherein the antiarrhythmic is a class III artiarrhythmic.

6. The method of claim 5 wherein the class III antiarrhythmic is selected from the group consisting of: amiodarone, sotalol, ibutilide, azimilide, clofilium, dofetilide, sematilide, d,1-sotalol, quinidine, tedisamil, procainamide, disopyramide, and dronedarone.

7. The method of claim 1 wherein the chemical is an antibiotic, a bronchodilator, an anesthetic, an anti-nausea drug, an anti-malarial, an antipsychotic, an appetite suppressant, a decongestant, a vasodilator, an anti-fungal, an anti-cancer drug, an antihistamine, a gastrointestinal prokinetic, an antispasmodic, or an antidepressant.

8. The method of claim 7 wherein the chemical is selected from the group consisting of: albuterol, alfuzosin, amantadine, amiodarone, amitriptyline, amoxapine, ampicillin, amphetamine/dextroamphetamine, arsenic trioxide, atomoxetine, azithromycin, bepridil, chloral hydrate, chloroquine, chlorpromazine, ciprofloxacin, cisapride, clarithromycin, clomipramine, cocaine, desipramine, disopyramide, dobutamine, dofetilide, dolasetron, domperidone, dopamine, doxepin, droperidol, ephedrine, epinephrine, erythromycin, felbamate, fenfluramine, flecainide, fluconazole, fluoxetine, foscarnet, fosphenytoin, galantamine, gatifloxacin, granisetron, halofantrine, haloperidol, ibutilide, imipramine, indapamide, isoproterenol, isradipine, itraconazole, ketoconazole, levalbuterol, levofloxacin, levomethadyl, lithium, mesoridazine, metaproterenol, methadone, methylphenidate, mexiletine, midodrine, moexipril/HCTZ, moxifloxacin, nicardipine, norepinephrine, nortriptyline, octreotide, ondansetron, paroxetine, pentamidine, phentermine, phenylephrine, phenylpropanolamine, pimozide, procainamide, protriptyline, pseudoephedrine, quetiapine, quinidine, risperidone, ritodrine, salmeterol, sertraline, sibutramine, sotalol, sparfioxacin, tacrolimus, tamoxifen, telithromycin, terbutaline, thioridazine, tizanidine, trimethoprim-sulfa, trimipramine, vardenafil, venlafaxine, voriconazole, and ziprasidone.

* * * * *

UNITED STATES PATENT AND TRADEMARK OFFICE
CERTIFICATE OF CORRECTION

| | | |
|---|---|---|
| PATENT NO. | : 7,674,820 B2 | Page 1 of 1 |
| APPLICATION NO. | : 10/914864 | |
| DATED | : March 9, 2010 | |
| INVENTOR(S) | : David Fedida et al. | |

It is certified that error appears in the above-identified patent and that said Letters Patent is hereby corrected as shown below:

Column 116
Claim 8, Line 22, "sotalol, sparfioxacin, tacrolimus, tamoxifen, telithroycin" should read as --sotalol, sparfloxacin, tacrolimus, tamoxifen, telithroycin--.

Signed and Sealed this
Tenth Day of May, 2011

David J. Kappos
*Director of the United States Patent and Trademark Office*